United States Patent
Zhu et al.

(10) Patent No.: US 11,447,551 B2
(45) Date of Patent: Sep. 20, 2022

(54) BINDING MOLECULES SPECIFIC FOR CLAUDIN 18.2, COMPOSITIONS AND METHODS THEREOF, FOR THE TREATMENT OF CANCER AND OTHER DISEASES

(71) Applicant: Sparx Therapeutics Inc., Mt. Prospect, IL (US)

(72) Inventors: Guidong Zhu, Gurnee, IL (US); Jingdong Ye, Vernon Hills, IL (US); Jingdong Qin, Woodridge, IL (US); Jichun Ma, Germantown, MD (US)

(73) Assignee: SparX Bioscience Limited, Tortola (VG)

( * ) Notice: Subject to any disclaimer, the term of this patent is extended or adjusted under 35 U.S.C. 154(b) by 206 days.

(21) Appl. No.: 16/727,554

(22) Filed: Dec. 26, 2019

(65) Prior Publication Data

US 2020/0207857 A1 Jul. 2, 2020

Related U.S. Application Data

(60) Provisional application No. 62/786,012, filed on Dec. 28, 2018.

(51) Int. Cl.
  *C07K 16/00* (2006.01)
  *C07K 16/28* (2006.01)
  *C12N 15/85* (2006.01)

(52) U.S. Cl.
  CPC .......... *C07K 16/2827* (2013.01); *C12N 15/85* (2013.01); *C07K 2317/51* (2013.01); *C07K 2317/515* (2013.01); *C07K 2317/54* (2013.01); *C07K 2317/55* (2013.01); *C07K 2317/622* (2013.01); *C07K 2317/732* (2013.01); *C07K 2317/734* (2013.01); *C12N 2015/8518* (2013.01)

(58) Field of Classification Search
  CPC ............ C12N 15/85; C12N 2015/8518; C07K 2317/51; C07K 2317/515; C07K 2317/54; C07K 2317/55; C07K 2317/622; C07K 2317/734; A01K 2207/12
  See application file for complete search history.

(56) References Cited

U.S. PATENT DOCUMENTS

| | | |
|---|---|---|
| 4,683,195 A | 7/1987 | Mullis et al. |
| 4,816,567 A | 3/1989 | Cabilly et al. |
| 4,946,778 A | 8/1990 | Ladner et al. |
| 5,545,806 A | 8/1996 | Lonberg et al. |
| 5,545,807 A | 8/1996 | Surani et al. |
| 5,569,825 A | 10/1996 | Lonberg et al. |
| 5,624,821 A | 4/1997 | Winter et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,260 A | 7/1997 | Winter et al. |
| 5,661,016 A | 8/1997 | Lonberg et al. |
| 5,750,373 A | 5/1998 | Garrard et al. |
| 5,885,793 A | 3/1999 | Griffiths et al. |
| 5,969,108 A | 10/1999 | McCafferty et al. |
| 6,172,197 B1 | 1/2001 | McCafferty et al. |
| 6,300,064 B1 | 10/2001 | Knappik et al. |
| 6,413,746 B1 | 7/2002 | Field |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,653,068 B2 | 11/2003 | Frisch et al. |
| 6,660,501 B2 | 12/2003 | Field |
| 6,682,736 B1 | 1/2004 | Hanson et al. |
| 6,706,484 B1 | 3/2004 | Knappik et al. |
| 6,737,056 B1 | 5/2004 | Presta |
| 7,083,784 B2 | 8/2006 | Dall'Acqua et al. |
| 7,109,003 B2 | 9/2006 | Hanson et al. |
| 7,123,281 B2 | 10/2006 | Okada |
| 7,264,963 B1 | 9/2007 | Knappik et al. |
| 7,332,581 B2 | 2/2008 | Presta |
| 7,371,826 B2 | 5/2008 | Presta |
| 7,411,057 B2 | 8/2008 | Hanson et al. |
| 7,597,889 B1 | 10/2009 | Armour et al. |
| 7,658,921 B2 | 2/2010 | Dall'Acqua et al. |
| 7,785,791 B2 | 8/2010 | Presta |
| 7,790,858 B2 | 9/2010 | Presta |
| 7,807,797 B2 | 10/2010 | Hanson et al. |
| 7,824,679 B2 | 11/2010 | Hanson et al. |
| 7,932,087 B2 | 4/2011 | Kallmeier et al. |
| 8,143,379 B2 | 3/2012 | Hanson et al. |
| 8,168,427 B2 | 5/2012 | Sahin et al. |
| 8,491,895 B2 | 7/2013 | Hanson et al. |
| 8,779,108 B2 | 7/2014 | Queva et al. |
| 8,961,967 B2 | 2/2015 | Strohl et al. |
| 9,770,487 B2 * | 9/2017 | Sahin ..................... A61P 35/04 |

(Continued)

FOREIGN PATENT DOCUMENTS

WO    2014/047624    3/2014

OTHER PUBLICATIONS

Rawla, P., et al., "Epidemiology of gastric cancer: global trends, risk factors and Prevention," *Gastroenterology Rev.*, 14(1):26-38 (2019).

(Continued)

*Primary Examiner* — Lei Yao
(74) *Attorney, Agent, or Firm* — ivicLErmott Will & Emery LLP

(57) ABSTRACT

Compositions and methods of making isolated binding molecules (e.g. an antibodies) or antigen-binding fragment thereof useful as therapeutics for treating and/or preventing diseases associated with cells expressing claudin18.2, including tumor-related diseases such as gastric cancer, esophageal cancer, pancreatic cancer, lung cancer, ovarian cancer, colon cancer, hepatic cancer, head-neck cancer, and cancer of the gallbladder are described. Also, described are pharmaceutical formulations comprising the described compositions for the treatment of diseases either as single agent (e.g., naked antibodies) or as adjuvant therapy with other antigen-binding anticancer agents such as immune checkpoint inhibitors (e.g., anti-CTLA-4 and anti-PD-1/PD-L1 monoclonal antibodies), and/or by combination therapies where the anti-claudin18.2 antibodies are administered before, after, or concurrently with chemotherapy.

10 Claims, 25 Drawing Sheets

Specification includes a Sequence Listing.

(56) References Cited

U.S. PATENT DOCUMENTS

| | | |
|---|---|---|
| 2006/0024296 A1 | 2/2006 | Williams et al. |
| 2006/0194290 A1 | 8/2006 | Presta |
| 2006/0194291 A1 | 8/2006 | Presta |
| 2008/0177048 A1 | 7/2008 | Gagnon |
| 2008/0187954 A1 | 8/2008 | Kallmeier et al. |
| 2008/0274105 A1 | 11/2008 | Presta |
| 2008/0274506 A1 | 11/2008 | Presta |
| 2008/0312425 A1 | 12/2008 | Bonnerjea et al. |
| 2009/0187005 A1 | 7/2009 | Gagnon |
| 2011/0212087 A1 | 9/2011 | Strohl et al. |
| 2013/0034559 A1 | 2/2013 | Queva et al. |
| 2013/0071390 A1 | 3/2013 | Stadheim et al. |
| 2013/0089541 A1 | 4/2013 | D'Angelo et al. |
| 2013/0108623 A1 | 5/2013 | D'Angelo et al. |
| 2014/0356353 A1 | 12/2014 | Queva et al. |
| 2014/0378663 A1 | 12/2014 | Fontayne et al. |
| 2015/0098955 A1 | 4/2015 | Coyle et al. |
| 2015/0118227 A1 | 4/2015 | Strohl et al. |
| 2016/0108123 A1* | 4/2016 | Freeman ............ A61K 39/3955 424/85.2 |
| 2017/0122944 A1 | 3/2017 | Orren et al. |
| 2018/0319891 A1 | 11/2018 | Sahin et al. |

OTHER PUBLICATIONS

Etemadi, A., et al., "The global, regional, and national burden of stomach cancer in 195 countries, 1990-2017: a systematic analysis for the Global Burden of Disease study 2017," *Lancet Gastroenterol Hepatol*, 5:42-54 (2020).

Furuse, M., et al., "Claudin-1 and -2: Novel Integral Membrane Proteins Localizing at Tight Junctions with No Sequence Similarity to Occludin," *J. Cell Biol.*, 141(7), 1539-1550 (1998).

Sanada, Y., et al., "Down-regulation of the claudin-18 gene, identified through serial analysis of gene expression data analysis, in gastric cancer with an intestinal phenotype," *J. Pathol.*, 208:633-642 (2006).

Sahin, U., et al., "Claudin-18 Splice Variant 2 Is a Pan-Cancer Target Suitable for Therapeutic Antibody Development," *Clin Cancer Res.*, 14(23):7624-7634 (2008).

Takasawa, K., et al., "Claudin-18 coupled with EGFR/ERK signaling contributes to the malignant potentials of bile duct cancer," *Cancer Letters*, 403:66-73 (2017).

Shimobaba, S., et al., "Claudin-18 inhibits cell proliferation and motility mediated by inhibition of phosphorylation of PDK1 and Akt in human long adenocarcinoma A549 cells," *Biochimica et Biophysica Acta 1863*, 1170-1178 (2016).

Hayashi, D., et al., "Deficiency of Caudin-18 Causes Paracelluar H+ Leakage, Up-regulation of Interleukin-1β, and Atrophic Gastritis in Mice," *Gastroenterology*, 142:292-304 (2012).

Micke, P., et al., "Aberrantly activated claudin 6 and 18.2 as potential therapy targets in non-small-cell lung cancer," *Int. J. Cancer*, 135:2206-2214 (2014).

Jiang, H., et al., "Claudin18.2-Specific Chimeric Antigen Receptor Engineered T Cells for the Treatment of Gastric Cancer," *J Natl Cancer Inst.*, 111(4):409-418 (2019).

Dall'Acqua, W., et al., Properties of Human IgG1s Engineered for Enhanced Binding to the Neonatal Fc Receptor (FcRn), *J. Biol. Chem.* 281 (33):23514-23524 (2006).

Rothe, C., et al., "The Human Combinatorial Antibody Library HuCAL GOLD Combines Diversification of All Six CDRs According to the Natural Immune System with a Novel Display Method for Efficient Selection of High-Affinity Antibodies," *J. Mol. Biol.*, 376:1182-1200 (2008).

Kang, A., et al., "Linkage of recognition and replication functions by assembling combinatorial antibody Fab libraries along phage surfaces," *Proc. Natl. Acad. Sci. USA*, 88:4363-4366 (1991).

Sidhu, S.S., and Fellouse, F.A., "Synthetic therapeutic antibodies," *Nat. Chem. Biol.*, 2(12):682-688 (2006).

Winter, G., "Synthetic human antibodies and a strategy for protein engineering," *FEBS Letters*, 430:92-94 (1998).

Lerner, R.A., "Manufacturing Immunity to Disease in a Test Tube: The Magic Bullet Realized," *Angew. Chem. Int. Ed.*, 45:8106-8125 (2006).

Fellouse, F., et al., "High-throughput Generation of Synthetic Antibodies from Highly Functional Minimalist Phage-displayed Libraries," *J. Mol. Biol.*, 373:924-940 (2007).

Fellouse, F., et al., "Molecular Recognition by a Binary Code," *J. Mol. Biol.*, 348 1153-1162 (2005).

Liu, Y., et al., "Synthetic Fab fragments that bind the HIV-1 gp41 heptad repeat regions," *Biochem. Biophys. Res. Commun.*, 413:611-615 (2011).

Ye, J.-D., et al., "Synthetic antibodies for specific recognition and crystallization of structured RNA," *PNAS*, 105(1):82-87 (2008).

Gao, J., et al., "Two-state selection of conformation-specific antibodies," *PNAS*, 106(9):3071-3076 (2009).

Marks, J.D., et al., "By-Passing Immunization: Building High Affinity Human Antibodies By Chain Shuffling," *Bio/Technology*, 10:779-783 (1992).

Morimoto, K. and Inoue, K., "Single-step purification of F(ab')$_2$ fragments of mouse monoclonal antibodies (immunoglobulins G1) by hydrophobic interaction high performance liquid chromatography using TSKgel Phenyl-5PW," *J. of Biochem. Biophysical Methods*, 24:107-117 (1992).

Brennan, M., et al., "Preparation of Bispecific Antibodies by Chemical Recombination of Monoclonal Immunoglobulin G$_1$ Fragments," *Science*, 229:81-83 (1985).

Skerra, A., "Alternative non-antibody scaffolds for molecular recognition," *Current Opinion in Biotechnology*, 18:295-304 (2007).

Hosse, R.J., et al., "A new generation of protein display scaffolds for molecular recognition," *Protein Science*, 15:14-27 (2006).

Gill, D.S., and Damle, N.K., "Biopharmaceutical drug discovery using novel protein scaffolds," *Curr. Opin. in Biotechnol.*, 17:653-658 (2006).

Nygren, P.-A., "Alternative binding proteins: Affibody binding proteins developed from a small three-helix bundle scaffold," *FEBS*, 275:2668-2676 (2008).

Skerra, A., "Alternative binding proteins: Anticalins—harnessing the structural plasticity of the lipocalin ligand pocket to engineer novel binding activities," *FEBS J.*, 275:2677-2683 (2008).

Sambrook, et al., ed. "Molecular Cloning: A Laboratory Manual," vols. 1-3, 2$^{nd}$ ed., Cold Springs Harbor Laboratory Press, NY (1989)—entire book.

Glover, D.N. ed., DNA Cloning, vols. I and II, IRL Press, Oxford; Washington, DC (1985)—entire book.

Hames, B.D., and Higgins, S.J., eds., Nucleic Acid Hybridization: a practical approach; vol. 14 of Practical approach series, IRL Press (1985)—entire book.

Hames, B.D., and Higgins, S.J., eds., Transcription And Translation: a practical approach, IRL Press, Oxford; Washington, DC, (1984)—entire book.

Freshney, R.I., Culture Of Animal Cells. A Manual of Basic Technique and Specialized Applications, 7$^{th}$ Edition, Alan R. Liss, Inc., (1987)—entire book.

Woodward, J., ed., Immobilised cells and enzymes: a practical approach, Oxford University Press (1985)—entire book.

Perbal, B., ed., Practical Guide To Molecular Cloning, Methods In Enzymology, Wiley, New York, (1984)—entire book.

Miller, J., ed., Gene Transfer Vectors For Mammalian Cells (Current Communications in Cell and Molecular Biology, Cold Spring Harbor Laboratory (1987)—entire book.

Wu and Grossman eds., Methods in enzymology vol. 154, Recombinant DNA. Part E, Academic, San Diego (1987)—entire book.

Mayer, R.J, and Walker, J.H, eds. Immunochemical Methods In Cell And Molecular Biology, Academic Press, London; San Diego (1987)—entire book.

Weir, ed., Handbook Of Experimental Immunology, vols. I-IV, Blackwell, Oxford, London (1986)—entire book.

Hogan, B., ed., Manipulating the mouse embryo: A laboratory manual, Cold Spring Harbor Laboratory Press, Cold Spring Harbor, N.Y., (1986)—entire book.

Ausubel, et al., Current protocols in molecular biology, John Wiley and Sons, New York (1989)—entire book.

(56) References Cited

OTHER PUBLICATIONS

Borrebaeck, C.A.K., ed., Antibody Engineering, 2nd ed., Oxford Univ. Press, New York (1995)—entire book.
Rees, A.R., et al., eds., Protein Engineering, A Practical Approach (Book 108), Oxford Univ. Press; Spi edition, Oxford, Eng. (1993)—entire book.
Nisonoff, A., ed., Introduction to Molecular Immunology, 2nd ed., Sinauer Associates, Sunderland, Mass. (1984)—entire book.
Steward, M.W., ed., Outline Studies in Biology. Antibodies: Their structure and function, Chapman and Hall, London; New York (1984)—entire book.
Coligan, J.E., et al., eds., Current Protocols in Immunology, John Wiley & Sons, New York (2004)—entire book.
Stites, D.P., et al., ed., Basic and Clinical Immunology, 8th ed, Appleton & Lange, Norwalk, Conn. (1994).
Mishell, B., and Shilgi, S.M. eds., Selected Methods in Cellular Immunology, W.H. Freeman, San Francisco (1980).
Dondelinger, M., et al., "Understanding the Significance and Implications of Antibody Numbering and Antigen-Binding Surface/Residue Definition," *Frontiers in Immunology*, 9, 15 pages (2018).
Kabat, et al., Sequences of Proteins of Immunological Interest, vol. II, $5^{th}$ Ed., Diane Pub. Co (1992)—entire book.
Klein, J., ed., Immunology: The Science of Self-Nonself Discrimination, John Wiley & Sons Inc, (1984)—entire book.
Kennett, R.H., et al., eds., Monoclonal Antibodies, Hybridomas: A New Dimension in Biological Analyses, Springer, Boston, MA (1980)—entire book.
Campbell, A.M., ed., Laboratory Techniques in Biochemistry and Molecular Biology, 13: Monoclonal Antibody Technology, , Elsevier, Burlington (1984)—entire book.
Goldsby, R.A., et al.,eds., Kuby Immunology, $4^{th}$ ed., H. Freemand & Co. (2000)—entire book.
Roitt, et al., Immunology, 6ed., London: Mosby (2001)—entire book.
Abbas, A.K., et al., Cellular and Molecular Immunology, $7^{th}$ ed., Elsevier Health Sciences Division (2012).
Kontermann, R., and Dubel, S., eds., Antibody Engineering vol. 2, Springer-Verlag (2010)—entire book.
Sambrook, J., and Russell, D.W., Molecular Cloning: A Laboratory Manual Third Edition, Cold Spring Harbor Laboratory Press (2001)—entire book.
Harlow, E., and Lane, D., eds., Antibodies: A Laboratory Manual, Cold Spring Harbor Laboratory Press (1988)—entire book.
Dieffenbach, C., ed., PCR Primer: A Laboratory Manual, Cold Spring Harbor Laboratory Press (1995).
Niimi, T., "*claudin-18*, a Novel Downstream Target Gene for the T/EBP/NKX2.1 Homeodomain Transcription Factor, Encodes Lung- and Stomach-Specific Isoforms through Alternative Splicing," *Mol. Cell. Biol.*, 21(21):7380-90 (2001).
Kohler, G., and Milstein, C., "Continuous cultures of fused cells secreting antibody of predefined specificity," *Nature*, 256:495-497 (1975).
Babcock, J.S., et al., "A novel strategy for generating monoclonal antibodies from single, isolated lymphocytes producing antibodies of defined specificities," *Proc. Natl. Acad. Sci. USA*, 93(15): 7843-7848 (1996).
Welschof, M., and Krauss, J., eds., Recombinant Antibodies for Cancer Therapy. Methods and Protocols, Totowa, N.J.: Humana Press (2003)—entire book.
Benny, K.C., ed., Antibody Engineering. Methods and Protocols, Humana Press, Totowa, New Jersey (2004).

Miller, K., et al., "T Cell Receptor-Like Recognition of Tumor In Vivo by Synthetic Antibody Fragment," *PLOS ONE*, 7(8):e43746, 14 pages (2012).
Sherman, E., et al., "Specific RNA-Binding Antibodies with a Four-Amino-Acid Code," *J. Mol. Biol.*, 426:2145-2157 (2014).
Carter, P., et al., "Humanization of an anti-p185$^{HER2}$ antibody for human cancer therapy," *Proc. Natl. Acad. Sci. USA*, 89:4285-4289 (1992).
Presta, L.G., et al., "Humanization of an antibody directed against IgE," *J. Immunol*, 151:2623-2632 (1993).
Kabat, E.A., et al., eds, "Sequences of Proteins of Immunological Interest," 5th ed., *Public Health Service, National Institutes of Health*, Bethesda, MD (1991).
Kunkel, T., "Rapid and efficient site-specific mutagenesis without phenotypic selection," *Proc. Natl. Acad. Sci. USA*, 82:488-492 (1985).
Sidhu, S.S., et al., "Phage Display for Selection of Novel Binding Peptides," *Methods in Enzymology*, 328:333-363 (2000).
Baca, M., et al., "Antibody Humanization Using Monovalent Phage Display," *J. Biol. Chem.*, 272(16): 10678-10684 (1997).
Lee, C.V., et al., "High-affinity Human Antibodies from Phage-displayed Synthetic Fab Libraries with a Single Framework Scaffold," *J. Mol. Biol.*, 340:1073-1093 (2004).
Yang, W.-P., et al., "CDR Walking Mutagenesis for the Affinity Maturation of a Potent Human Anti-HIV-1 Antibody into the Picomolar Range," *J. Mol. Biol.*, 254:392-403 (1995).
Selim, J.H., et al., "Targeted and novel therapy in advanced gastric cancer," *Exp Hematol Oncol*, 8, 25 pages (2019).
Daneschdar, M., et al., "Rapid Mimotope Optimization for Pharmacokinetic Analysis of the Novel Therapeutic Antibody IMAB362," *Immunology*, 2 pages (2014).
Dottermusch, M., et al., "Expression of the potential therapeutic target claudin-18.2 is frequently decreased in gastric cancer: results from a large Caucasian cohort study," *Virchows Archiv*, 475:563-571 (2019).
Türeci, O., et al., "A multicentre, phase IIa study of zolbetuximab as a single agent in patients with recurrent or refractory advanced adenocarcinoma of the stomach or lower oesophagus: the MONO study," *Annals of Oncology*, 30:1487-1495 (2019).
Türeci, O., et al., "Claudin-18 gene structure, regulation, and expression is evolutionary conserved in mammals" *Gene*, 481:83-92 (2011).
Klamp, T., et al., "Highly Specific Auto-Antibodies against Claudin-18 Isoform 2 Induced by a Chimeric HBcAg Virus-Like Particle Vaccine Kill Tumor Cells and Inhibit the Growth of Lung Metastases," *Cancer Res*, 71 (2):516-527 (2011).
Sahin, U., et al., "A phase I dose-escalation study of IMAB362 (Zolbetuximab) in patients with advanced gastric and gastro-oesophageal junction cancer," *European Journal of Cancer*, 100:17-26 (2018).
Hashimoto, Y., et al., "Current progress in a second-generation claudin binder, anti-claudin antibody, for clinical applications," *Drug Discovery Today*, 21(10):1711-1718 (2016).
Türeci, O., et al., "Characterization of zolbetuximab in pancreatic cancer models," *Oncoimmunology*, 8(1):e1523096, 10 pages (2019).
Gait, M.J., "Oligonucleotide Synthesis: A Practical Approach, 'The Practical Approach Series,'" *IRL Press*, 210 pages, (1984)—entire book.
Lewin, "Genes VIII," *Pearson Prentice Hall* (2004)—entire book.
Search Report and Written Opinion of PCT/US2019/068591, dated May 6, 2020, 13 pp.

\* cited by examiner

|    | 14D7   | 4G3    | 5H7    | 5H8    | 14B7   | 5H1-2  | 15B5   | 5G7    |
|----|--------|--------|--------|--------|--------|--------|--------|--------|
| Kd | 0.1000 | 0.3427 | 0.1364 | 0.2281 | 0.2004 | 0.2036 | 0.2759 | 0.2929 |

|    | h5C9o  | h5C9a  | h5C9n  |
|----|--------|--------|--------|
| Kd | 0.1280 | 0.2783 | 0.3232 |

|    | h5C9o | h5C9o_Fc mu | h5C9ob | h5C9oae | h5C9oan | h5C9oao |
|----|-------|-------------|--------|---------|---------|---------|
| Kd | 0.1396 | 0.1622 | 0.1295 | 0.1091 | 0.1198 | 0.1023 |

|    | h5C9oa | h5C9ob | h5C9oc | h5C9od | h5C9oe | h5C9of | h5C9og | h5C9oh | h5C9oi | h5C9oj | H5C9o |
|----|--------|--------|--------|--------|--------|--------|--------|--------|--------|--------|-------|
| Kd | 0.08942 | 0.08634 | 0.08484 | 0.08756 | 0.08784 | 0.1034 | 0.08840 | 0.08019 | 0.08682 | 0.07768 | 0.08917 |

| | h5C9ok | h5C9ol | h5C9om | h5C9on | h5C9oo | h5C9op | h5C9oq | h5C9os |
|---|---|---|---|---|---|---|---|---|
| Kd | 0.1078 | 0.1188 | 0.1000 | 0.1311 | 0.1216 | 0.1094 | 0.1070 | 0.1342 |

| | h5C9or | h5C9ot | h5C9ou | h5C9ov | h5C9ow | h5C9ox | h5C9oy | h5C9oz | h5C9oaa |
|---|---|---|---|---|---|---|---|---|---|
| Kd | 0.07146 | 0.09870 | 0.09187 | 0.1069 | 0.08815 | 0.07896 | 0.1032 | 0.07777 | 0.08151 |

| | h5C9ob | h5C9oab | h5C9oad | h5C9oaf | h5C9oaj | h5C9oak | h5C9oal | h5C9oam |
|---|---|---|---|---|---|---|---|---|
| Kd | 0.1604 | 0.1642 | 0.1746 | 0.1621 | 0.1727 | 0.1614 | 0.1978 | 0.1717 |

| | h5C9ob | h5C9oh | h5C9oi | h5C9oj | h5C9oae | h5C9oag | h5C9oah | h5C9oai |
|---|---|---|---|---|---|---|---|---|
| Kd | 0.2126 | 0.2013 | 0.3156 | 0.2764 | 0.1830 | 0.1961 | 0.2364 | 0.1961 |

|    | h5C9o Fc | h5C9ob | h5C9oap | h5C9oaq | h5C9oao | h5C9oae |
|----|----------|--------|---------|---------|---------|---------|
| Kd | 0.1301   | 0.1389 | 0.1862  | 0.2134  | 0.1696  | 0.1612  |

|    | h5C9o Fc | h5C9ob | h5C9oap | h5C9oaq | h5C9oao | h5C9oae | h5C9oar |
|----|----------|--------|---------|---------|---------|---------|---------|
| Kd | 0.1142   | 0.1288 | 0.1892  | 0.2026  | 0.1338  | 0.1398  | 0.1492  |

| | h5C9o | h5C9o Fc mu | h5C9ob | h5C9oae | h5C9oan | h5C9oao |
|---|---|---|---|---|---|---|
| Kd | 0.1262 | 0.2127 | 0.1531 | 0.1229 | 0.1675 | 0.1489 |

| | h5C9o Fc mu | h5C9ob | h5C9oae | h5C9oag | h5C9oai | h5C9oan | h5C9oao |
|---|---|---|---|---|---|---|---|
| Kd | 0.2248 | 0.2063 | 0.1837 | 0.1909 | 0.1801 | 0.1939 | 0.1539 |

|      | h5C9o Fc mu | h5C9ob | h5C9oap | h5C9oaq | h5C9oao | h5C9oae |
|------|-------------|--------|---------|---------|---------|---------|
| Top  | 1977        | 2506   | 2809    | 2742    | 2553    | 1933    |
| EC50 | 0.8049      | 0.7750 | 1.104   | 1.245   | 0.7207  | 0.5512  |

|      | ch5C9   | ch15G11 | ch9A1   |
|------|---------|---------|---------|
| EC50 | 0.02023 | 0.01300 | 0.01312 |

| | zol | oab | oaf | oag | oaj | oak | oam |
|---|---|---|---|---|---|---|---|
| EC50 | 0.03819 | 0.03000 | 0.03055 | 0.02275 | 0.03585 | 0.01749 | 0.02650 |

| | oab | oaf | oag | oaj | oan | oh |
|---|---|---|---|---|---|---|
| EC50 | 0.02673 | 0.003789 | 0.01428 | 0.01340 | 0.02745 | 0.03901 |

|  | oao | oaq | oar | oai | oae |
|---|---|---|---|---|---|
| EC50 | 0.01452 | 0.01852 | 0.02186 | 0.02581 | 0.03005 |

|  | oaq | h5C9o Fc | h5C9ob | oae | oap | oao |
|---|---|---|---|---|---|---|
| EC50 | 0.03794 | 0.01746 | 0.02594 | 0.02477 | 0.02833 | 0.02420 |

SEQUENCE LISTING

```
<160> NUMBER OF SEQ ID NOS: 421

<210> SEQ ID NO 1
<211> LENGTH: 42
<212> TYPE: PRT
<213> ORGANISM: Artificial Sequence
<220> FEATURE:
<223> OTHER INFORMATION: Extracellular Loop 1 of claudin 18.2
      (CLDN18.2-ECL1)

<400> SEQUENCE: 1

Asp Gln Trp Ser Thr Gln Asp Leu Tyr Asn Asn Pro Val Thr Ala Val
1               5                   10                  15

Phe Asn Tyr Gln Gly Leu Trp Arg Ser Cys Val Arg Glu Ser Ser Gly
            20                  25                  30

Phe Thr Glu Cys Arg Gly Tyr Phe Thr Leu
        35                  40

<210> SEQ ID NO 2
<211> LENGTH: 261
<212> TYPE: PRT
<213> ORGANISM: Artificial Sequence
<220> FEATURE:
<223> OTHER INFORMATION: Full Length Protein of claudin 18.2 (CLDN18.2)
```

-continued

```
<400> SEQUENCE: 2

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 3
<211> LENGTH: 200
<212> TYPE: PRT
<213> ORGANISM: Artificial Sequence
<220> FEATURE:
<223> OTHER INFORMATION: C-terminal Deleted Domain of claudin 18.2
      (del-CLDN18.2)

<400> SEQUENCE: 3

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80
```

```
Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala
        195                 200

<210> SEQ ID NO 4
<211> LENGTH: 42
<212> TYPE: PRT
<213> ORGANISM: Artificial Sequence
<220> FEATURE:
<223> OTHER INFORMATION: Extracellular Loop 1 of Claudin 18.1
      (CLDN18.1-ECL1)

<400> SEQUENCE: 4

Asp Met Trp Ser Thr Gln Asp Leu Tyr Asp Asn Pro Val Thr Ser Val
1               5                   10                  15

Phe Gln Tyr Glu Gly Leu Trp Arg Ser Cys Val Arg Gln Ser Ser Gly
                20                  25                  30

Phe Thr Glu Cys Arg Pro Tyr Phe Thr Ile
            35                  40

<210> SEQ ID NO 5
<211> LENGTH: 261
<212> TYPE: PRT
<213> ORGANISM: Artificial Sequence
<220> FEATURE:
<223> OTHER INFORMATION: Full Length Protein of Claudin 18.1 (CLDN18.1)

<400> SEQUENCE: 5

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
                20                  25                  30

Gln Asp Leu Tyr Asp Asn Pro Val Thr Ser Val Phe Gln Tyr Glu Gly
            35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
```

```
                    130                 135                 140
Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
                180                 185                 190

Cys Ile Ala Cys Arg Gly Leu Ala Pro Glu Glu Thr Asn Tyr Lys Ala
                195                 200                 205

Val Ser Tyr His Ala Ser Gly His Ser Val Ala Tyr Lys Pro Gly Gly
                210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
                260

<210> SEQ ID NO 6
<211> LENGTH: 112
<212> TYPE: PRT
<213> ORGANISM: Artificial Sequence
<220> FEATURE:
<223> OTHER INFORMATION: Antibody 3B8 Light Chain Variable Region (VL)

<400> SEQUENCE: 6

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Gln Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
                100                 105                 110

<210> SEQ ID NO 7
<211> LENGTH: 16
<212> TYPE: PRT
<213> ORGANISM: Artificial Sequence
<220> FEATURE:
<223> OTHER INFORMATION: Antibody 3B8 VL-CDR1

<400> SEQUENCE: 7

Arg Ser Ser Gln Ser Ile Val His Ser Asn Gly Asn Thr Tyr Leu Gln
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Antibody 3B8 VL-CDR2

<400> SEQUENCE: 8
```

Lys Val Ser Asn Arg Phe Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Antibody 3B8 VL-CDR3

<400> SEQUENCE: 9

Phe Gln Gly Ser His Val Pro Phe Thr
1               5

<210> SEQ ID NO 10
<211> LENGTH: 117
<212> TYPE: PRT
<213> ORGANISM: Artificial Sequence
<220> FEATURE:
<223> OTHER INFORMATION: Antibody 3B8 Heavy Chain Variable Region (VH)

<400> SEQUENCE: 10

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Ser Phe Gly Tyr Asp Val Ala Met Asp Tyr Trp Gly Gln Gly Thr Ser
            100                 105                 110

Val Thr Val Ser Ser
        115

<210> SEQ ID NO 11
<211> LENGTH: 10
<212> TYPE: PRT
<213> ORGANISM: Artificial Sequence
<220> FEATURE:
<223> OTHER INFORMATION: Antibody 3B8 VH-CDR1

<400> SEQUENCE: 11

Gly Phe Thr Phe Ser Ser Tyr Ala Met Ser
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Antibody 3B8 VH-CDR2

<400> SEQUENCE: 12

Ser Ile Ser Ser Gly Gly Ser Thr Tyr
1               5

<210> SEQ ID NO 13

```
<211> LENGTH: 9
<212> TYPE: PRT
<213> ORGANISM: Artificial Sequence
<220> FEATURE:
<223> OTHER INFORMATION: Antibody 3B8 VH-CDR3

<400> SEQUENCE: 13

Phe Gly Tyr Asp Val Ala Met Asp Tyr
1               5

<210> SEQ ID NO 14
<211> LENGTH: 113
<212> TYPE: PRT
<213> ORGANISM: Artificial Sequence
<220> FEATURE:
<223> OTHER INFORMATION: Antibody 15G11Light Chain Variable Region (VL)

<400> SEQUENCE: 14

Asp Ile Met Met Thr Gln Ser Pro Leu Ser Leu Thr Val Thr Ala Gly
1               5                   10                  15

Glu Lys Val Thr Met Asn Cys Lys Ser Ser Gln Ser Leu Leu Asn Gly
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Ala Arg Phe Thr Gly Ser Gly Ser Gly Thr Asp Phe Thr Leu Thr
65                  70                  75                  80

Ile Asn Thr Val Gln Ala Glu Asp Leu Ala Val Tyr Tyr Cys Gln Asn
                85                  90                  95

Asp Tyr Phe Tyr Pro Leu Thr Phe Gly Thr Gly Thr Lys Leu Glu Leu
            100                 105                 110

Lys

<210> SEQ ID NO 15
<211> LENGTH: 17
<212> TYPE: PRT
<213> ORGANISM: Artificial Sequence
<220> FEATURE:
<223> OTHER INFORMATION: Antibody 15G11 VL-CDR1

<400> SEQUENCE: 15

Lys Ser Ser Gln Ser Leu Leu Asn Gly Gly Asn Gln Lys Asn Tyr Leu
1               5                   10                  15

Ala

<210> SEQ ID NO 16
<211> LENGTH: 7
<212> TYPE: PRT
<213> ORGANISM: Artificial Sequence
<220> FEATURE:
<223> OTHER INFORMATION: Antibody 15G11 VL-CDR2

<400> SEQUENCE: 16

Trp Ala Ser Thr Arg Glu Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Antibody 15G11 VL-CDR3
```

```
<400> SEQUENCE: 17

Gln Asn Asp Tyr Phe Tyr Pro Leu Thr
1               5

<210> SEQ ID NO 18
<211> LENGTH: 117
<212> TYPE: PRT
<213> ORGANISM: Artificial Sequence
<220> FEATURE:
<223> OTHER INFORMATION: Antibody 15G11 Heavy Chain Variable Region (VH)

<400> SEQUENCE: 18

Val Gln Leu Gln Glu Ser Gly Gly Gly Leu Val Gln Pro Gly Gly Ser
1               5                   10                  15

Arg Lys Leu Ser Cys Ala Ala Ser Gly Phe Ser Phe Ser Phe Gly
            20                  25                  30

Met His Trp Val Arg Gln Ala Pro Glu Lys Gly Leu Glu Trp Val Ala
        35                  40                  45

Phe Ile Ser Ser Gly Ser Ser Pro Ile Tyr Tyr Ala Asp Thr Val Lys
    50                  55                  60

Gly Arg Phe Thr Val Ser Arg Asp Asn Pro Lys Asn Thr Leu Phe Leu
65                  70                  75                  80

Gln Met Thr Ser Leu Arg Ser Glu Asp Thr Ala Met Tyr Phe Cys Ala
                85                  90                  95

Arg Asn Tyr Tyr Gly Asn Ala Met Asp Tyr Trp Gly Gln Gly Ser Ser
            100                 105                 110

Val Thr Val Ser Ser
        115

<210> SEQ ID NO 19
<211> LENGTH: 10
<212> TYPE: PRT
<213> ORGANISM: Artificial Sequence
<220> FEATURE:
<223> OTHER INFORMATION: Antibody 15G11 VH-CDR1

<400> SEQUENCE: 19

Gly Phe Ser Phe Ser Ser Phe Gly Met His
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Antibody 15G11 VH-CDR2

<400> SEQUENCE: 20

Phe Ile Ser Ser Gly Ser Ser Pro Ile Tyr Tyr Ala Asp Thr Val Lys
1               5                   10                  15

Gly

<210> SEQ ID NO 21
<211> LENGTH: 9
<212> TYPE: PRT
<213> ORGANISM: Artificial Sequence
<220> FEATURE:
<223> OTHER INFORMATION: Antibody 15G11 VH-CDR3

<400> SEQUENCE: 21

Asn Tyr Tyr Gly Asn Ala Met Asp Tyr
```

-continued

<210> SEQ ID NO 22
<211> LENGTH: 113
<212> TYPE: PRT
<213> ORGANISM: Artificial Sequence
<220> FEATURE:
<223> OTHER INFORMATION: Antibody 9A1Light Chain Variable Region (VL)

<400> SEQUENCE: 22

Asp Ile Leu Leu Thr Gln Ser Pro Leu Ser Leu Thr Val Thr Ala Gly
1               5                   10                  15

Glu Lys Val Thr Met Ser Cys Lys Ser Ser Gln Ser Leu Leu Asn Gly
            20                  25                  30

Gly Asn Leu Lys Asn Tyr Leu Thr Trp Tyr Gln Gln Lys Pro Gly Gln
        35                  40                  45

Pro Pro Lys Leu Leu Thr Tyr Trp Ala Ser Thr Arg Glu Ser Gly Val
    50                  55                  60

Pro Val Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Gly Tyr Phe Tyr Pro Tyr Thr Phe Gly Gly Gly Thr Lys Leu Glu Ile
            100                 105                 110

Lys

<210> SEQ ID NO 23
<211> LENGTH: 17
<212> TYPE: PRT
<213> ORGANISM: Artificial Sequence
<220> FEATURE:
<223> OTHER INFORMATION: Antibody 9A1 VL-CDR1

<400> SEQUENCE: 23

Lys Ser Ser Gln Ser Leu Leu Asn Gly Gly Asn Leu Lys Asn Tyr Leu
1               5                   10                  15

Thr

<210> SEQ ID NO 24
<211> LENGTH: 9
<212> TYPE: PRT
<213> ORGANISM: Artificial Sequence
<220> FEATURE:
<223> OTHER INFORMATION: Antibody 9A1 VL-CDR3

<400> SEQUENCE: 24

Gln Asn Gly Tyr Phe Tyr Pro Tyr Thr
1               5

<210> SEQ ID NO 25
<211> LENGTH: 117
<212> TYPE: PRT
<213> ORGANISM: Artificial Sequence
<220> FEATURE:
<223> OTHER INFORMATION: Antibody 9A1 Heavy Chain Variable Region (VH)

<400> SEQUENCE: 25

Val Gln Leu Gln Gln Ser Gly Ala Glu Leu Val Arg Pro Gly Thr Ser
1               5                   10                  15

Val Lys Val Ser Cys Lys Ala Ser Arg Tyr Ala Phe Thr Asn Tyr Leu
            20                  25                  30

```
Ile Glu Trp Val Lys Gln Arg Pro Gly Gln Gly Leu Glu Trp Ile Gly
        35                  40                  45

Met Ile Asn Pro Gly Ser Gly Gly Thr His Tyr Asn Glu Lys Phe Lys
 50                  55                  60

Val Lys Ala Thr Leu Thr Ala Asp Lys Ser Ser Thr Ala Tyr Met
 65                  70                  75                  80

Gln Leu Ser Ser Leu Thr Ser Asp Asp Ser Ala Val Tyr Phe Cys Ala
                85                  90                  95

Arg Gly Gly Phe Gly Asn Ser Phe Ala Tyr Trp Gly Gln Gly Thr Leu
            100                 105                 110

Val Thr Val Ser Ala
        115
```

<210> SEQ ID NO 26
<211> LENGTH: 10
<212> TYPE: PRT
<213> ORGANISM: Artificial Sequence
<220> FEATURE:
<223> OTHER INFORMATION: Antibody 9A1 VH-CDR1

<400> SEQUENCE: 26

```
Arg Tyr Ala Phe Thr Asn Tyr Leu Ile Glu
 1               5                  10
```

<210> SEQ ID NO 27
<211> LENGTH: 17
<212> TYPE: PRT
<213> ORGANISM: Artificial Sequence
<220> FEATURE:
<223> OTHER INFORMATION: Antibody 9A1 VH-CDR2

<400> SEQUENCE: 27

```
Met Ile Asn Pro Gly Ser Gly Gly Thr His Tyr Asn Glu Lys Phe Lys
 1               5                  10                  15

Val
```

<210> SEQ ID NO 28
<211> LENGTH: 9
<212> TYPE: PRT
<213> ORGANISM: Artificial Sequence
<220> FEATURE:
<223> OTHER INFORMATION: Antibody 9A1 VH-CDR3

<400> SEQUENCE: 28

```
Gly Gly Phe Gly Asn Ser Phe Ala Tyr
 1               5
```

<210> SEQ ID NO 29
<211> LENGTH: 113
<212> TYPE: PRT
<213> ORGANISM: Artificial Sequence
<220> FEATURE:
<223> OTHER INFORMATION: Antibody 5C9 Light Chain Variable Region (VL)

<400> SEQUENCE: 29

```
Asp Ile Leu Leu Thr Gln Ser Pro Leu Ser Leu Thr Val Thr Ala Gly
 1               5                  10                  15

Glu Lys Val Thr Met Ser Cys Lys Ser Ser Gln Ser Leu Leu Asn Ser
                20                  25                  30

Gly Asn Gln Lys Ser Tyr Leu Thr Trp Tyr Gln Gln Lys Pro Gly Gln
            35                  40                  45

Pro Pro Lys Leu Leu Leu Tyr Trp Ala Ser Thr Arg Glu Ser Gly Val
```

-continued

```
                 50                  55                  60
Pro Ala Arg Phe Thr Gly Ser Gly Ser Gly Thr Asp Phe Ser Leu Thr
 65                  70                  75                  80

Ile Ser Ser Val Gln Thr Glu Asp Leu Ala Val Tyr Tyr Cys Gln Asn
                 85                  90                  95

Ala Tyr Ser Phe Pro Phe Thr Phe Gly Ser Gly Thr Lys Leu Glu Ile
                100                 105                 110

Asn

<210> SEQ ID NO 30
<211> LENGTH: 17
<212> TYPE: PRT
<213> ORGANISM: Artificial Sequence
<220> FEATURE:
<223> OTHER INFORMATION: Antibody 5C9 VL-CDR1

<400> SEQUENCE: 30

Lys Ser Ser Gln Ser Leu Leu Asn Ser Gly Asn Gln Lys Ser Tyr Leu
 1               5                  10                  15

Thr

<210> SEQ ID NO 31
<211> LENGTH: 9
<212> TYPE: PRT
<213> ORGANISM: Artificial Sequence
<220> FEATURE:
<223> OTHER INFORMATION: Antibody 5C9 VL-CDR3

<400> SEQUENCE: 31

Gln Asn Ala Tyr Ser Phe Pro Phe Thr
 1               5

<210> SEQ ID NO 32
<211> LENGTH: 117
<212> TYPE: PRT
<213> ORGANISM: Artificial Sequence
<220> FEATURE:
<223> OTHER INFORMATION: Antibody 5C9 Heavy Chain Variable Region (VH)

<400> SEQUENCE: 32

Val Lys Leu Gln Glu Ser Gly Pro Glu Leu Lys Lys Pro Gly Glu Thr
 1               5                  10                  15

Val Lys Ile Ser Cys Lys Ala Ser Gly Tyr Thr Phe Thr Asn Tyr Gly
                 20                  25                  30

Met Asn Trp Val Lys Gln Ala Pro Gly Lys Gly Leu Lys Trp Met Gly
             35                  40                  45

Trp Ile Asn Met Tyr Thr Gly Glu Pro Thr Tyr Ala Asp Asp Phe Lys
     50                  55                  60

Gly Arg Phe Ala Phe Ser Leu Glu Thr Ser Ala Ser Thr Ala Tyr Leu
 65                  70                  75                  80

Gln Ile Asn Asn Leu Lys Asn Glu Asp Thr Ala Thr Tyr Phe Cys Ser
                 85                  90                  95

Arg Leu Tyr Asn Gly Asn Ser Leu Asp Tyr Trp Gly Gln Gly Thr Ser
                100                 105                 110

Leu Thr Val Ser Ser
            115

<210> SEQ ID NO 33
<211> LENGTH: 10
<212> TYPE: PRT
```

<213> ORGANISM: Artificial Sequence
<220> FEATURE:
<223> OTHER INFORMATION: Antibody 5C9 VH-CDR1

<400> SEQUENCE: 33

Gly Tyr Thr Phe Thr Asn Tyr Gly Met Asn
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Antibody 5C9 VH-CDR2

<400> SEQUENCE: 34

Trp Ile Asn Met Tyr Thr Gly Glu Pro Thr Tyr Ala Asp Asp Phe Lys
1               5                   10                  15

Gly

<210> SEQ ID NO 35
<211> LENGTH: 9
<212> TYPE: PRT
<213> ORGANISM: Artificial Sequence
<220> FEATURE:
<223> OTHER INFORMATION: Antibody 5C9 VH-CDR3

<400> SEQUENCE: 35

Leu Tyr Asn Gly Asn Ser Leu Asp Tyr
1               5

<210> SEQ ID NO 36
<211> LENGTH: 13
<212> TYPE: PRT
<213> ORGANISM: Artificial Sequence
<220> FEATURE:
<223> OTHER INFORMATION: Antibody

<400> SEQUENCE: 36

Asp Gln Trp Ser Thr Gln Asp Leu Tyr Asn Asn Pro Val
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Antibody

<400> SEQUENCE: 37

Asn Asn Pro Val Thr Ala Val Phe Asn Tyr Gln Gly Leu
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Antibody

<400> SEQUENCE: 38

Tyr Gln Gly Leu Trp Arg Ser Cys Val Arg Glu Ser Ser Gly
1               5                   10

<210> SEQ ID NO 39
<211> LENGTH: 14

```
<212> TYPE: PRT
<213> ORGANISM: Artificial Sequence
<220> FEATURE:
<223> OTHER INFORMATION: Antibody

<400> SEQUENCE: 39

Glu Ser Ser Gly Phe Thr Glu Cys Arg Gly Tyr Phe Thr Leu
1               5                   10

<210> SEQ ID NO 40
<211> LENGTH: 223
<212> TYPE: PRT
<213> ORGANISM: Artificial Sequence
<220> FEATURE:
<223> OTHER INFORMATION: CTLA4 polypeptide sequence

<400> SEQUENCE: 40

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
        210                 215                 220

<210> SEQ ID NO 41
<211> LENGTH: 288
<212> TYPE: PRT
<213> ORGANISM: Artificial Sequence
<220> FEATURE:
<223> OTHER INFORMATION: PD-1 polypeptide sequence

<400> SEQUENCE: 41

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
```

```
            35                  40                  45
Asn Ala Thr Phe Thr Cys Ser Phe Ser Asn Thr Ser Glu Ser Phe Val
 50                  55                  60
Ile Asn Trp Tyr Arg Met Ser Pro Ser Asn Gln Thr Asp Lys Leu Ala
 65                  70                  75                  80
Ala Phe Pro Glu Asp Arg Ser Gln Pro Gly Gln Asp Cys Arg Phe Arg
                 85                  90                  95
Val Thr Gln Leu Pro Asn Gly Arg Asp Phe His Met Ser Val Val Arg
                100                 105                 110
Ala Arg Arg Asn Asp Ser Gly Thr Tyr Leu Cys Gly Ala Ile Ser Leu
                115                 120                 125
Ala Pro Lys Ala Gln Ile Lys Glu Ser Leu Arg Ala Glu Leu Arg Val
130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Ile Val Val Gly Val Val Gly Gly
                165                 170                 175
Leu Leu Gly Ser Leu Val Leu Leu Val Trp Val Leu Ala Val Ile Cys
                180                 185                 190
Ser Arg Ala Ala Arg Gly Thr Ile Gly Ala Arg Arg Thr Gly Gln Pro
                195                 200                 205
Leu Lys Glu Asp Pro Ser Ala Val Pro Val Phe Ser Val Asp Tyr Gly
210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
                260                 265                 270
Ser Ala Gly Pro Leu Arg Pro Glu Asp Gly His Cys Ser Trp Pro Leu
                275                 280                 285
```

<210> SEQ ID NO 42
<211> LENGTH: 177
<212> TYPE: PRT
<213> ORGANISM: Artificial Sequence
<220> FEATURE:
<223> OTHER INFORMATION: PD-L1 polypeptide sequence

<400> SEQUENCE: 42

```
Met Arg Ile Phe Ala Val Phe Ile Phe Met Thr Tyr Trp His Leu Leu
 1                   5                  10                  15
Asn Ala Pro Tyr Asn Lys Ile Asn Gly Arg Ile Leu Val Val Asp Pro
                 20                  25                  30
Val Thr Ser Glu His Glu Leu Thr Cys Gln Leu Ala Glu Gly Tyr Pro
                 35                  40                  45
Lys Ala Glu Val Ile Trp Thr Ser Ser Asp His Gln Val Leu Ser Gly
 50                  55                  60
Lys Thr Thr Thr Thr Asn Ser Lys Arg Glu Glu Lys Leu Phe Asn Val
 65                  70                  75                  80
Thr Ser Thr Leu Arg Ile Asn Thr Thr Asn Glu Ile Phe Tyr Cys
                 85                  90                  95
Thr Phe Arg Arg Leu Asp Pro Glu Glu Asn His Thr Ala Glu Leu Val
                100                 105                 110
Ile Pro Glu Leu Pro Leu Ala His Pro Pro Asn Glu Arg Thr His Leu
```

```
                115                 120                 125
Val Ile Leu Gly Ala Ile Leu Leu Cys Leu Gly Val Ala Leu Thr Phe
            130                 135                 140

Ile Phe Arg Leu Arg Lys Gly Arg Met Met Asp Val Lys Lys Cys Gly
145                 150                 155                 160

Ile Gln Asp Thr Asn Ser Lys Lys Gly Ser Asp Thr His Leu Glu Glu
                165                 170                 175

Thr

<210> SEQ ID NO 43
<211> LENGTH: 113
<212> TYPE: PRT
<213> ORGANISM: Artificial Sequence
<220> FEATURE:
<223> OTHER INFORMATION: Antibody 5H1 Light Chain Variable Region (VL)

<400> SEQUENCE: 43

Asp Ile Met Met Thr Gln Ser Pro Leu Ser Leu Thr Val Thr Ala Gly
1               5                   10                  15

Glu Lys Val Thr Met Thr Cys Lys Ser Ser Gln Ser Leu Leu Asn Ser
            20                  25                  30

Gly Asn Leu Lys Asn Tyr Leu Thr Trp Tyr Gln Gln Lys Pro Gly Gln
        35                  40                  45

Pro Pro Lys Leu Leu Thr Tyr Trp Ala Ser Thr Arg Glu Ser Gly Val
    50                  55                  60

Pro Thr Arg Phe Thr Gly Ser Gly Ser Ala Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Phe Tyr Pro Tyr Thr Phe Gly Gly Gly Thr Lys Leu Glu Ile
            100                 105                 110

Lys

<210> SEQ ID NO 44
<211> LENGTH: 17
<212> TYPE: PRT
<213> ORGANISM: Artificial Sequence
<220> FEATURE:
<223> OTHER INFORMATION: Antibody 5H1 VL-CDR1

<400> SEQUENCE: 44

Lys Ser Ser Gln Ser Leu Leu Asn Ser Gly Asn Leu Lys Asn Tyr Leu
1               5                   10                  15

Thr

<210> SEQ ID NO 45
<211> LENGTH: 7
<212> TYPE: PRT
<213> ORGANISM: Artificial Sequence
<220> FEATURE:
<223> OTHER INFORMATION: Antibody 5H1 VL-CDR2

<400> SEQUENCE: 45

Trp Ala Ser Thr Arg Glu Ser
1               5

<210> SEQ ID NO 46
<211> LENGTH: 9
<212> TYPE: PRT
<213> ORGANISM: Artificial Sequence
```

<220> FEATURE:
<223> OTHER INFORMATION: Antibody 5H1 VL-CDR3

<400> SEQUENCE: 46

Gln Asn Ala Tyr Phe Tyr Pro Tyr Thr
1               5

<210> SEQ ID NO 47
<211> LENGTH: 117
<212> TYPE: PRT
<213> ORGANISM: Artificial Sequence
<220> FEATURE:
<223> OTHER INFORMATION: Antibody 5H1 VH

<400> SEQUENCE: 47

Val Gln Leu Gln Glu Ser Gly Ala Glu Leu Val Arg Pro Gly Thr Ser
1               5                   10                  15

Val Lys Val Ser Cys Lys Ala Ser Gly Tyr Ala Phe Thr Asn Tyr Leu
            20                  25                  30

Ile Glu Trp Ile Lys Gln Arg Pro Gly Gln Gly Leu Glu Trp Ile Gly
        35                  40                  45

Met Ile Asn Pro Gly Ser Gly Gly Thr Lys Tyr Asn Glu Lys Phe Lys
    50                  55                  60

Gly Lys Ala Ser Leu Thr Ala Asp Lys Thr Ser Ser Thr Ala Tyr Met
65                  70                  75                  80

Gln Leu Ser Ser Leu Thr Ser Asp Asp Ser Ala Val Tyr Phe Cys Ala
                85                  90                  95

Arg Gly Gly Phe Gly Asn Ser Phe Ala Tyr Trp Gly Gln Gly Thr Leu
            100                 105                 110

Val Thr Val Ser Ala
        115

<210> SEQ ID NO 48
<211> LENGTH: 10
<212> TYPE: PRT
<213> ORGANISM: Artificial Sequence
<220> FEATURE:
<223> OTHER INFORMATION: Antibody 5H1 VH-CDR1

<400> SEQUENCE: 48

Gly Tyr Ala Phe Thr Asn Tyr Leu Ile Glu
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Antibody 5H1 VH-CDR2

<400> SEQUENCE: 49

Met Ile Asn Pro Gly Ser Gly Gly Thr Lys Tyr Asn Glu Lys Phe Lys
1               5                   10                  15

Gly

<210> SEQ ID NO 50
<211> LENGTH: 9
<212> TYPE: PRT
<213> ORGANISM: Artificial Sequence
<220> FEATURE:
<223> OTHER INFORMATION: Antibody 5H1 VH-CDR3

<400> SEQUENCE: 50

```
Gly Gly Phe Gly Asn Ser Phe Ala Tyr
1               5
```

<210> SEQ ID NO 51
<211> LENGTH: 113
<212> TYPE: PRT
<213> ORGANISM: Artificial Sequence
<220> FEATURE:
<223> OTHER INFORMATION: Antibody 1D5 VL

<400> SEQUENCE: 51

```
Asp Ile Met Met Thr Gln Thr Pro Leu Ser Leu Thr Val Thr Ala Gly
1               5                   10                  15

Glu Lys Val Thr Met Ser Cys Lys Ser Ser Gln Ser Leu Leu Asn Gly
            20                  25                  30

Gly Asn Leu Lys Asn Tyr Leu Thr Trp Tyr Gln Lys Pro Gly Gln
        35                  40                  45

Pro Pro Lys Leu Leu Thr Tyr Trp Ala Ser Thr Arg Glu Ser Gly Val
    50                  55                  60

Pro Ala Arg Phe Thr Gly Ser Gly Ser Gly Thr Asp Phe Thr Leu Thr
65              70                  75                  80

Ile Ser Ser Val Gln Ala Glu Asp Leu Ala Val Tyr Tyr Cys Gln Asn
                85                  90                  95

Gly Tyr Phe Tyr Pro Tyr Thr Phe Gly Gly Gly Thr Lys Leu Glu Ile
            100                 105                 110

Lys
```

<210> SEQ ID NO 52
<211> LENGTH: 17
<212> TYPE: PRT
<213> ORGANISM: Artificial Sequence
<220> FEATURE:
<223> OTHER INFORMATION: Antibody 1D5 VL-CDR1

<400> SEQUENCE: 52

```
Lys Ser Ser Gln Ser Leu Leu Asn Gly Gly Asn Leu Lys Asn Tyr Leu
1               5                   10                  15

Thr
```

<210> SEQ ID NO 53
<211> LENGTH: 9
<212> TYPE: PRT
<213> ORGANISM: Artificial Sequence
<220> FEATURE:
<223> OTHER INFORMATION: Antibody 1D5 VL-CDR3

<400> SEQUENCE: 53

```
Gln Asn Gly Tyr Phe Tyr Pro Tyr Thr
1               5
```

<210> SEQ ID NO 54
<211> LENGTH: 117
<212> TYPE: PRT
<213> ORGANISM: Artificial Sequence
<220> FEATURE:
<223> OTHER INFORMATION: Antibody 1D5 VH

<400> SEQUENCE: 54

```
Val Gln Leu Gln Glu Ser Gly Ala Glu Leu Val Arg Pro Gly Thr Ser
1               5                   10                  15

Val Lys Val Ser Cys Lys Ala Ser Arg Tyr Ala Phe Thr Asn Tyr Leu
```

```
                    20                  25                  30
Ile Glu Trp Val Lys Gln Arg Pro Gly Gln Gly Leu Glu Trp Ile Gly
            35                  40                  45

Met Ile Asn Pro Gly Ser Gly Gly Thr His Tyr Asn Glu Lys Phe Lys
        50                  55                  60

Val Lys Ala Thr Leu Thr Ala Asp Lys Ser Ser Thr Ala Tyr Met
65                  70                  75                  80

Gln Leu Asn Ser Leu Thr Ser Asp Asp Ser Ala Val Tyr Phe Cys Ala
                85                  90                  95

Arg Gly Gly Phe Gly Asn Ser Phe Ala Tyr Trp Gly Gln Gly Thr Leu
            100                 105                 110

Val Thr Val Ser Ala
        115

<210> SEQ ID NO 55
<211> LENGTH: 10
<212> TYPE: PRT
<213> ORGANISM: Artificial Sequence
<220> FEATURE:
<223> OTHER INFORMATION: Antibody 1D5 VH-CDR1

<400> SEQUENCE: 55

Arg Tyr Ala Phe Thr Asn Tyr Leu Ile Glu
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Antibody 1D5 VH-CDR2

<400> SEQUENCE: 56

Met Ile Asn Pro Gly Ser Gly Gly Thr His Tyr Asn Glu Lys Phe Lys
1               5                   10                  15

Val

<210> SEQ ID NO 57
<211> LENGTH: 107
<212> TYPE: PRT
<213> ORGANISM: Artificial Sequence
<220> FEATURE:
<223> OTHER INFORMATION: Antibody 8C5 VL

<400> SEQUENCE: 57

Asp Ile Val Leu Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Trp
                85                  90                  95

Thr Phe Gly Gly Gly Thr Lys Leu Glu Ile Lys
            100                 105
```

```
<210> SEQ ID NO 58
<211> LENGTH: 11
<212> TYPE: PRT
<213> ORGANISM: Artificial Sequence
<220> FEATURE:
<223> OTHER INFORMATION: Antibody 8C5 VL-CDR1

<400> SEQUENCE: 58

Ile Thr Ser Thr Asp Ile Asp Asp Met Asn
1               5                   10

<210> SEQ ID NO 59
<211> LENGTH: 6
<212> TYPE: PRT
<213> ORGANISM: Artificial Sequence
<220> FEATURE:
<223> OTHER INFORMATION: Antibody 8C5 VL-CDR2

<400> SEQUENCE: 59

Glu Gly Asn Thr Leu Arg
1               5

<210> SEQ ID NO 60
<211> LENGTH: 9
<212> TYPE: PRT
<213> ORGANISM: Artificial Sequence
<220> FEATURE:
<223> OTHER INFORMATION: Antibody 8C5 VL-CDR3

<400> SEQUENCE: 60

Leu Gln Ser Asp Asn Leu Pro Trp Thr
1               5

<210> SEQ ID NO 61
<211> LENGTH: 114
<212> TYPE: PRT
<213> ORGANISM: Artificial Sequence
<220> FEATURE:
<223> OTHER INFORMATION: Antibody 8C5 Heavy Chain Variable Region (VH)

<400> SEQUENCE: 61

Val Gln Leu Gln Glu Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
        35                  40                  45

Trp Ile Asn Thr Asn Thr Gly Glu Pro Thr Tyr Ala Glu Glu Phe Lys
    50                  55                  60

Gly Arg Phe Ala Phe Ser Leu Glu Thr Ser Ala Ser Thr Ala Tyr Leu
65                  70                  75                  80

Gln Ile Asn Asn Leu Lys Asn Glu Asp Thr Ala Thr Tyr Phe Cys Ala
                85                  90                  95

Arg Arg Met Thr Ala Gly Tyr Trp Gly Gln Gly Thr Thr Leu Thr Val
            100                 105                 110

Ser Ser

<210> SEQ ID NO 62
<211> LENGTH: 17
<212> TYPE: PRT
<213> ORGANISM: Artificial Sequence
<220> FEATURE:
<223> OTHER INFORMATION: Antibody 8C5 VH-DR2
```

-continued

<400> SEQUENCE: 62

Trp Ile Asn Thr Asn Thr Gly Glu Pro Thr Tyr Ala Glu Glu Phe Lys
1               5                   10                  15

Gly

<210> SEQ ID NO 63
<211> LENGTH: 6
<212> TYPE: PRT
<213> ORGANISM: Artificial Sequence
<220> FEATURE:
<223> OTHER INFORMATION: Antibody 8C5 VH-DR3

<400> SEQUENCE: 63

Arg Met Thr Ala Gly Tyr
1               5

<210> SEQ ID NO 64
<211> LENGTH: 106
<212> TYPE: PRT
<213> ORGANISM: Artificial Sequence
<220> FEATURE:
<223> OTHER INFORMATION: Antibody 9F1 Light Chain Variable Region (VL)

<400> SEQUENCE: 64

Asp Ile Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
                20                  25                  30

Tyr Trp Tyr Gln Gln Lys Ser Asp Ala Ser Pro Lys Leu Trp Ile Tyr
            35                  40                  45

Tyr Thr Ser Asn Leu Ala Pro Gly Val Pro Ala Arg Phe Ser Gly Ser
        50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys
            100                 105

<210> SEQ ID NO 65
<211> LENGTH: 10
<212> TYPE: PRT
<213> ORGANISM: Artificial Sequence
<220> FEATURE:
<223> OTHER INFORMATION: Antibody 9F1 VL-CDR1

<400> SEQUENCE: 65

Arg Ala Ser Ser Ser Val Asn Tyr Met Tyr
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Antibody 9F1 VL-CDR2

<400> SEQUENCE: 66

Tyr Thr Ser Asn Leu Ala Pro
1               5

```
<210> SEQ ID NO 67
<211> LENGTH: 9
<212> TYPE: PRT
<213> ORGANISM: Artificial Sequence
<220> FEATURE:
<223> OTHER INFORMATION: Antibody 9F1 VL-CDR3

<400> SEQUENCE: 67

Gln Gln Phe Thr Ser Ser Pro Tyr Thr
1               5

<210> SEQ ID NO 68
<211> LENGTH: 117
<212> TYPE: PRT
<213> ORGANISM: Artificial Sequence
<220> FEATURE:
<223> OTHER INFORMATION: Antibody 9F1 Heavy Chain Variable Region (VH)

<400> SEQUENCE: 68

Val Gln Leu Gln Glu Ser Gly Ala Glu Leu Met Lys Pro Gly Ala Ser
1               5                   10                  15

Val Lys Ile Ser Cys Lys Ala Thr Gly Tyr Thr Phe Ser Ser Tyr Trp
            20                  25                  30

Ile Glu Trp Val Lys Gln Arg Pro Gly His Gly Leu Glu Trp Ile Gly
        35                  40                  45

Glu Ile Leu Pro Gly Ser Gly Ser Thr Asn Tyr Asn Glu Lys Phe Lys
    50                  55                  60

Gly Lys Ala Thr Phe Thr Ala Asp Thr Ser Ser Asn Thr Ala Tyr Met
65                  70                  75                  80

Gln Leu Ser Ser Leu Thr Ser Glu Asp Ser Ala Val Tyr Tyr Cys Ala
                85                  90                  95

Glu Gly Ala Tyr Tyr Arg Ser Phe Asp Tyr Trp Gly Gln Gly Thr Thr
            100                 105                 110

Leu Thr Val Ser Ser
        115

<210> SEQ ID NO 69
<211> LENGTH: 10
<212> TYPE: PRT
<213> ORGANISM: Artificial Sequence
<220> FEATURE:
<223> OTHER INFORMATION: Antibody 9F1 VH-CDR1

<400> SEQUENCE: 69

Gly Tyr Thr Phe Ser Ser Tyr Trp Ile Glu
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Antibody 9F1 VH-CDR2

<400> SEQUENCE: 70

Glu Ile Leu Pro Gly Ser Gly Ser Thr Asn Tyr Asn Glu Lys Phe Lys
1               5                   10                  15

Gly

<210> SEQ ID NO 71
<211> LENGTH: 9
<212> TYPE: PRT
<213> ORGANISM: Artificial Sequence
```

```
<220> FEATURE:
<223> OTHER INFORMATION: Antibody 9F1 VH-CDR3

<400> SEQUENCE: 71

Gly Ala Tyr Tyr Arg Ser Phe Asp Tyr
1               5

<210> SEQ ID NO 72
<211> LENGTH: 113
<212> TYPE: PRT
<213> ORGANISM: Artificial Sequence
<220> FEATURE:
<223> OTHER INFORMATION: Antibody 7A10 Light Chain Variable Region (VL)

<400> SEQUENCE: 72

Asp Ile Met Met Thr Gln Ser Pro Leu Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Leu Lys Asn Tyr Leu Thr Trp Tyr Gln Gln Lys Pro Gly Gln
            35                  40                  45

Pro Pro Lys Leu Leu Thr Tyr Trp Ala Ser Thr Arg Asp Ser Gly Val
    50                  55                  60

Pro Ala Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Phe Tyr Pro Tyr Thr Phe Gly Gly Gly Thr Lys Leu Glu Ile
            100                 105                 110

Lys

<210> SEQ ID NO 73
<211> LENGTH: 17
<212> TYPE: PRT
<213> ORGANISM: Artificial Sequence
<220> FEATURE:
<223> OTHER INFORMATION: Antibody 7A10 VL-CDR1

<400> SEQUENCE: 73

Lys Ser Ser Gln Ser Leu Leu Asn Ser Gly Asn Leu Lys Asn Tyr Leu
1               5                   10                  15

Thr

<210> SEQ ID NO 74
<211> LENGTH: 7
<212> TYPE: PRT
<213> ORGANISM: Artificial Sequence
<220> FEATURE:
<223> OTHER INFORMATION: Antibody 7A10 VL-CDR2

<400> SEQUENCE: 74

Trp Ala Ser Thr Arg Asp Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Antibody 7A10 VL-CDR3

<400> SEQUENCE: 75
```

Gln Asn Asp Tyr Phe Tyr Pro Tyr Thr
1               5

<210> SEQ ID NO 76
<211> LENGTH: 117
<212> TYPE: PRT
<213> ORGANISM: Artificial Sequence
<220> FEATURE:
<223> OTHER INFORMATION: Antibody 7A10 Heavy Chain Variable Region (VH)

<400> SEQUENCE: 76

Val Gln Leu Gln Glu Ser Gly Ala Glu Leu Val Arg Pro Gly Thr Ser
1               5                   10                  15

Val Lys Val Ser Cys Lys Ala Ser Gly Tyr Ala Phe Thr Asn Tyr Leu
            20                  25                  30

Ile Glu Trp Val Lys Gln Arg Pro Gly Gln Gly Leu Glu Trp Ile Gly
        35                  40                  45

Met Ile Asn Pro Gly Ser Gly Gly Thr Asn Tyr Asn Glu Lys Phe Lys
    50                  55                  60

Gly Lys Ala Thr Leu Thr Ala Asp Lys Ser Ser Ser Thr Ala Tyr Met
65                  70                  75                  80

Gln Leu Ser Ser Leu Thr Ser Asp Asp Ser Ala Val Tyr Phe Cys Ala
                85                  90                  95

Arg Gly Gly Phe Gly Asn Ser Phe Ala Tyr Trp Gly Gln Gly Thr Leu
            100                 105                 110

Val Thr Val Ser Ala
        115

<210> SEQ ID NO 77
<211> LENGTH: 17
<212> TYPE: PRT
<213> ORGANISM: Artificial Sequence
<220> FEATURE:
<223> OTHER INFORMATION: Antibody 7A10 VH-CDR2

<400> SEQUENCE: 77

Met Ile Asn Pro Gly Ser Gly Gly Thr Asn Tyr Asn Glu Lys Phe Lys
1               5                   10                  15

Gly

<210> SEQ ID NO 78
<211> LENGTH: 105
<212> TYPE: PRT
<213> ORGANISM: Artificial Sequence
<220> FEATURE:
<223> OTHER INFORMATION: Antibody 8C12 Light Chain Variable Region (VL)

<400> SEQUENCE: 78

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Asp Thr Ser Asn Leu Ala Ser Gly Phe Pro Ala Arg Phe Ser Gly Ser
    50                  55                  60

Gly Ser Gly Thr Ser Tyr Ser Leu Ile Ile Ser Asn Met Glu Ala Glu
65                  70                  75                  80

Asp Ala Ala Thr Tyr Tyr Cys His Gln Arg Ser Ser Tyr Pro Thr Phe
                85                  90                  95

```
<210> SEQ ID NO 79
<211> LENGTH: 10
<212> TYPE: PRT
<213> ORGANISM: Artificial Sequence
<220> FEATURE:
<223> OTHER INFORMATION: Antibody 8C12 VL-CDR1

<400> SEQUENCE: 79

Ser Ala Ser Ser Ser Val Ser Tyr Met Tyr
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Antibody 8C12 VL-CDR2

<400> SEQUENCE: 80

Asp Thr Ser Asn Leu Ala Ser
1               5

<210> SEQ ID NO 81
<211> LENGTH: 8
<212> TYPE: PRT
<213> ORGANISM: Artificial Sequence
<220> FEATURE:
<223> OTHER INFORMATION: Antibody 8C12 VL-CDR3

<400> SEQUENCE: 81

His Gln Arg Ser Ser Tyr Pro Thr
1               5

<210> SEQ ID NO 82
<211> LENGTH: 119
<212> TYPE: PRT
<213> ORGANISM: Artificial Sequence
<220> FEATURE:
<223> OTHER INFORMATION: Antibody 8C12 Heavy Chain Variable Region (VH)

<400> SEQUENCE: 82

Glu Val Gln Leu Gln Gln Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Gly Met Ala Trp Val Arg Gln Ala Pro Gly Lys Gly Pro Glu Trp Val
        35                  40                  45

Ala Phe Ile Ser Asn Leu Ala Tyr Ser Ile Tyr Ser Thr Asp Thr Val
    50                  55                  60

Thr Gly Arg Phe Thr Ile Ser Arg Glu Asn Ala Lys Asn Thr Leu Tyr
65                  70                  75                  80

Leu Glu Met Ser Ser Leu Arg Ser Asp Asp Thr Ala Met Tyr Tyr Cys
                85                  90                  95

Ala Arg Gly Ser Tyr Tyr Gly Asn Ser Phe Asp Tyr Trp Gly Gln Gly
            100                 105                 110

Thr Thr Leu Thr Val Ser Ser
        115

<210> SEQ ID NO 83
```

Gly Thr Gly Thr Lys Leu Glu Leu Lys
            100                 105

```
<211> LENGTH: 10
<212> TYPE: PRT
<213> ORGANISM: Artificial Sequence
<220> FEATURE:
<223> OTHER INFORMATION: Antibody 8C12 VH-CDR1

<400> SEQUENCE: 83

Gly Phe Thr Phe Ser Asp Tyr Gly Met Ala
1               5                   10

<210> SEQ ID NO 84
<211> LENGTH: 17
<212> TYPE: PRT
<213> ORGANISM: Artificial Sequence
<220> FEATURE:
<223> OTHER INFORMATION: Antibody 8C12 VH-CDR2

<400> SEQUENCE: 84

Phe Ile Ser Asn Leu Ala Tyr Ser Ile Tyr Ser Thr Asp Thr Val Thr
1               5                   10                  15

Gly

<210> SEQ ID NO 85
<211> LENGTH: 10
<212> TYPE: PRT
<213> ORGANISM: Artificial Sequence
<220> FEATURE:
<223> OTHER INFORMATION: Antibody 8C12 VH-CDR3

<400> SEQUENCE: 85

Gly Ser Tyr Tyr Gly Asn Ser Phe Asp Tyr
1               5                   10

<210> SEQ ID NO 86
<211> LENGTH: 110
<212> TYPE: PRT
<213> ORGANISM: Artificial Sequence
<220> FEATURE:
<223> OTHER INFORMATION: Antibody 14D7 Light Chain Variable Region (VL)

<400> SEQUENCE: 86

Met Thr Gln Asp Glu Leu Ser Leu Thr Val Thr Ala Gly Glu Lys Val
1               5                   10                  15

Thr Met Ser Cys Lys Ser Ser Gln Ser Leu Leu Asn Ser Gly Asn Gln
            20                  25                  30

Arg Asn Tyr Leu Thr Trp Tyr Gln Gln Lys Pro Gly Gln Pro Pro Lys
        35                  40                  45

Leu Leu Ile Tyr Trp Ala Ser Thr Arg Glu Ser Gly Val Pro Asn Arg
    50                  55                  60

Phe Thr Gly Ser Gly Ser Gly Thr Asp Phe Thr Leu Thr Ile Ser Ser
65                  70                  75                  80

Val Gln Ala Val Asp Leu Ala Val Tyr Tyr Cys Gln Asn Asn Tyr Phe
                85                  90                  95

Tyr Pro Leu Thr Phe Gly Ser Gly Thr Lys Leu Glu Leu Lys
            100                 105                 110

<210> SEQ ID NO 87
<211> LENGTH: 17
<212> TYPE: PRT
<213> ORGANISM: Artificial Sequence
<220> FEATURE:
<223> OTHER INFORMATION: Antibody 14D7 VL-CDR1

<400> SEQUENCE: 87
```

```
Lys Ser Ser Gln Ser Leu Leu Asn Ser Gly Asn Gln Arg Asn Tyr Leu
1               5                   10                  15

Thr

<210> SEQ ID NO 88
<211> LENGTH: 9
<212> TYPE: PRT
<213> ORGANISM: Artificial Sequence
<220> FEATURE:
<223> OTHER INFORMATION: Antibody 14D7 VL-CDR3

<400> SEQUENCE: 88

Gln Asn Asn Tyr Phe Tyr Pro Leu Thr
1               5

<210> SEQ ID NO 89
<211> LENGTH: 118
<212> TYPE: PRT
<213> ORGANISM: Artificial Sequence
<220> FEATURE:
<223> OTHER INFORMATION: Antibody 14D7 Heavy Chain Variable Region (VH)

<400> SEQUENCE: 89

Val Gln Leu Gln Gln Ser Gly Gly Gly Leu Val Gln Pro Gly Gly Ser
1               5                   10                  15

Arg Lys Leu Ser Cys Ala Ala Ser Gly Phe Thr Phe Ser Ser Phe Gly
            20                  25                  30

Met His Trp Val Arg Gln Ala Pro Glu Lys Gly Leu Glu Trp Val Gly
        35                  40                  45

Tyr Ile Asn Ser Gly Ser Ser Thr Ile Tyr Tyr Ala Asp Thr Val Lys
    50                  55                  60

Gly Arg Phe Thr Ile Ser Arg Asp Asn Pro Arg Asn Thr Leu Phe Leu
65                  70                  75                  80

Gln Met Thr Ser Leu Arg Ser Glu Asp Thr Ala Met Tyr Tyr Cys Ala
                85                  90                  95

Ser Gly Ala Tyr Tyr Gly Asn Ala Met Asp Tyr Trp Gly Gln Gly Thr
            100                 105                 110

Ser Val Thr Val Ser Ser
            115

<210> SEQ ID NO 90
<211> LENGTH: 10
<212> TYPE: PRT
<213> ORGANISM: Artificial Sequence
<220> FEATURE:
<223> OTHER INFORMATION: Antibody 14D7 VH-CDR1

<400> SEQUENCE: 90

Gly Phe Thr Phe Ser Ser Phe Gly Met His
1               5                   10

<210> SEQ ID NO 91
<211> LENGTH: 17
<212> TYPE: PRT
<213> ORGANISM: Artificial Sequence
<220> FEATURE:
<223> OTHER INFORMATION: Antibody 14D7 VH-CDR2

<400> SEQUENCE: 91

Tyr Ile Asn Ser Gly Ser Ser Thr Ile Tyr Tyr Ala Asp Thr Val Lys
1               5                   10                  15
```

Gly

<210> SEQ ID NO 92
<211> LENGTH: 10
<212> TYPE: PRT
<213> ORGANISM: Artificial Sequence
<220> FEATURE:
<223> OTHER INFORMATION: Antibody 14D7 VH-CDR3

<400> SEQUENCE: 92

Gly Ala Tyr Tyr Gly Asn Ala Met Asp Tyr
1               5                   10

<210> SEQ ID NO 93
<211> LENGTH: 113
<212> TYPE: PRT
<213> ORGANISM: Artificial Sequence
<220> FEATURE:
<223> OTHER INFORMATION: Antibody 5H7 Light Chain Variable Region (VL)

<400> SEQUENCE: 93

Asp Ile Val Met Thr Gln Asp Glu Leu Ser Leu Thr Val Thr Ala Arg
1               5                   10                  15

Glu Lys Val Thr Met Ser Cys Lys Ser Ser Gln Thr Leu Phe Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ile Phe Pro Tyr Thr Phe Gly Gly Gly Thr Lys Leu Glu Ile
            100                 105                 110

Lys

<210> SEQ ID NO 94
<211> LENGTH: 17
<212> TYPE: PRT
<213> ORGANISM: Artificial Sequence
<220> FEATURE:
<223> OTHER INFORMATION: Antibody 5H7 VL-CDR1

<400> SEQUENCE: 94

Lys Ser Ser Gln Thr Leu Phe Asn Ser Gly Asn Gln Lys Asn Tyr Leu
1               5                   10                  15

Thr

<210> SEQ ID NO 95
<211> LENGTH: 9
<212> TYPE: PRT
<213> ORGANISM: Artificial Sequence
<220> FEATURE:
<223> OTHER INFORMATION: Antibody 5H7 VL-CDR3

<400> SEQUENCE: 95

Gln Asn Asp Tyr Ile Phe Pro Tyr Thr
1               5

<210> SEQ ID NO 96
<211> LENGTH: 118

-continued

```
<212> TYPE: PRT
<213> ORGANISM: Artificial Sequence
<220> FEATURE:
<223> OTHER INFORMATION: Antibody 5H7 Heavy Chain Variable Region (VH)

<400> SEQUENCE: 96

Glu Val Lys Leu Gln Glu Ser Gly Pro Ser Leu Val Lys Pro Phe Gln
1               5                   10                  15

Ser Leu Ser Leu Thr Cys Thr Val Thr Asp Tyr Ser Ile Thr Arg Gly
            20                  25                  30

Tyr Asn Trp His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Asp Tyr Tyr Gly Asn Ser Phe Ala Tyr Trp Gly Gln Gly Thr
            100                 105                 110

Leu Val Thr Val Phe Cys
            115

<210> SEQ ID NO 97
<211> LENGTH: 11
<212> TYPE: PRT
<213> ORGANISM: Artificial Sequence
<220> FEATURE:
<223> OTHER INFORMATION: Antibody 5H7 VH-CDR1

<400> SEQUENCE: 97

Asp Tyr Ser Ile Thr Arg Gly Tyr Asn Trp His
1               5                   10

<210> SEQ ID NO 98
<211> LENGTH: 16
<212> TYPE: PRT
<213> ORGANISM: Artificial Sequence
<220> FEATURE:
<223> OTHER INFORMATION: Antibody 5H7 VH-CDR2

<400> SEQUENCE: 98

Tyr Ile His Tyr Ser Gly Ser Thr Asn Tyr Asn Pro Ser Leu Lys Ser
1               5                   10                  15

<210> SEQ ID NO 99
<211> LENGTH: 9
<212> TYPE: PRT
<213> ORGANISM: Artificial Sequence
<220> FEATURE:
<223> OTHER INFORMATION: Antibody 5H7 VH-CDR3

<400> SEQUENCE: 99

Asp Tyr Tyr Gly Asn Ser Phe Ala Tyr
1               5

<210> SEQ ID NO 100
<211> LENGTH: 110
<212> TYPE: PRT
<213> ORGANISM: Artificial Sequence
<220> FEATURE:
<223> OTHER INFORMATION: Antibody 5G7 Light Chain Variable Region (VL)

<400> SEQUENCE: 100
```

```
Met Thr Gln Asp Glu Leu Ser Leu Thr Val Thr Ala Gly Glu Lys Val
1               5                   10                  15

Thr Leu Ser Cys Lys Ser Ser Gln Ser Leu Leu Asn Ser Gly Asn Gln
            20                  25                  30

Arg Asn Tyr Leu Thr Trp Tyr Gln Gln Lys Gly Gln Pro Pro Lys
        35                  40                  45

Leu Leu Ile Tyr Trp Ala Ser Thr Arg Glu Ser Gly Val Pro Asp Arg
    50                  55                  60

Leu Thr Gly Ser Gly Ser Gly Thr Asp Phe Thr Leu Thr Ile Ser Gly
65                  70                  75                  80

Val Gln Ala Glu Asp Leu Ala Val Tyr Tyr Cys Gln Asn Ala Tyr Tyr
                85                  90                  95

Tyr Pro Phe Thr Phe Gly Ser Gly Thr Lys Leu Glu Ile Lys
            100                 105                 110
```

<210> SEQ ID NO 101
<211> LENGTH: 9
<212> TYPE: PRT
<213> ORGANISM: Artificial Sequence
<220> FEATURE:
<223> OTHER INFORMATION: Antibody 5G7 VL-CDR3

<400> SEQUENCE: 101

```
Gln Asn Ala Tyr Tyr Tyr Pro Phe Thr
1               5
```

<210> SEQ ID NO 102
<211> LENGTH: 118
<212> TYPE: PRT
<213> ORGANISM: Artificial Sequence
<220> FEATURE:
<223> OTHER INFORMATION: Antibody 5G7 Heavy Chain Variable Region (VH)

<400> SEQUENCE: 102

```
Lys Val Gln Leu Gln Glu Ser Gly Pro Glu Leu Val Arg Pro Gly Thr
1               5                   10                  15

Ser Val Lys Val Ser Cys Lys Ala Ser Lys Tyr Ala Phe Thr Asn Tyr
            20                  25                  30

Leu Ile Glu Trp Ile Lys Gln Arg Pro Gly Gln Gly Leu Glu Trp Ile
        35                  40                  45

Gly Met Ile Asn Pro Gly Ser Asp Gly Ser His Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Val Gly Tyr Gly Asn Ser Phe Ala Tyr Trp Gly Gln Gly Thr
            100                 105                 110

Leu Val Thr Val Ser Ala
        115
```

<210> SEQ ID NO 103
<211> LENGTH: 10
<212> TYPE: PRT
<213> ORGANISM: Artificial Sequence
<220> FEATURE:
<223> OTHER INFORMATION: Antibody 5G7 VH-CDR1

<400> SEQUENCE: 103

Lys Tyr Ala Phe Thr Asn Tyr Leu Ile Glu
1               5                   10

<210> SEQ ID NO 104
<211> LENGTH: 17
<212> TYPE: PRT
<213> ORGANISM: Artificial Sequence
<220> FEATURE:
<223> OTHER INFORMATION: Antibody 5G7 VH-CDR2

<400> SEQUENCE: 104

Met Ile Asn Pro Gly Ser Asp Gly Ser His Tyr Asn Glu Lys Phe Lys
1               5                   10                  15

Gly

<210> SEQ ID NO 105
<211> LENGTH: 9
<212> TYPE: PRT
<213> ORGANISM: Artificial Sequence
<220> FEATURE:
<223> OTHER INFORMATION: Antibody 5G7 VH-CDR3

<400> SEQUENCE: 105

Val Gly Tyr Gly Asn Ser Phe Ala Tyr
1               5

<210> SEQ ID NO 106
<211> LENGTH: 113
<212> TYPE: PRT
<213> ORGANISM: Artificial Sequence
<220> FEATURE:
<223> OTHER INFORMATION: Antibody 4G3 LIGHT CHAIN VARIABLE REGION (VL)

<400> SEQUENCE: 106

Asp Ile Val Met Thr Gln Asp Glu Leu Ser Leu Thr Val Thr Val Gly
1               5                   10                  15

Asp Lys Val Thr Met Asn Cys Arg Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Val Tyr Phe Tyr Pro Leu Thr Phe Gly Thr Gly Thr Lys Leu Glu Leu
            100                 105                 110

Lys

<210> SEQ ID NO 107
<211> LENGTH: 17
<212> TYPE: PRT
<213> ORGANISM: Artificial Sequence
<220> FEATURE:
<223> OTHER INFORMATION: Antibody 4G3 VL-CDR1

<400> SEQUENCE: 107

Arg Ser Ser Gln Ser Leu Leu Asn Ser Gly Asn Gln Arg Asn Tyr Leu
1               5                   10                  15

Thr

```
<210> SEQ ID NO 108
<211> LENGTH: 9
<212> TYPE: PRT
<213> ORGANISM: Artificial Sequence
<220> FEATURE:
<223> OTHER INFORMATION: Antibody 4G3 VL-CDR3

<400> SEQUENCE: 108

Gln Asn Val Tyr Phe Tyr Pro Leu Thr
1               5

<210> SEQ ID NO 109
<211> LENGTH: 119
<212> TYPE: PRT
<213> ORGANISM: Artificial Sequence
<220> FEATURE:
<223> OTHER INFORMATION: Antibody 4G3 Heavy Chain Variable Region (VH)

<400> SEQUENCE: 109

Lys Val Gln Leu Gln Gln Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Gly Tyr Ile Asn Ser Gly Ser Ser Thr Ile Tyr Ala Asp Thr Val
    50                  55                  60

Lys Gly Arg Phe Thr Ile Ser Arg Asp Asn Pro Arg Asn Thr Leu Phe
65                  70                  75                  80

Leu Gln Met Thr Ser Leu Arg Ser Glu Asp Thr Ala Met Tyr Tyr Cys
                85                  90                  95

Ala Ser Gly Ala Tyr Tyr Gly Asn Ala Met Asp Tyr Trp Gly Gln Gly
            100                 105                 110

Thr Ser Val Thr Val Ser Ser
        115

<210> SEQ ID NO 110
<211> LENGTH: 113
<212> TYPE: PRT
<213> ORGANISM: Artificial Sequence
<220> FEATURE:
<223> OTHER INFORMATION: Antibody 14B7 Light Chain Variable Region (VL)

<400> SEQUENCE: 110

Asp Ile Val Met Thr Gln Asp Glu Leu Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Leu
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Ile Tyr Pro Leu Thr Phe Gly Ala Gly Thr Lys Leu Glu Leu
            100                 105                 110

Lys
```

<210> SEQ ID NO 111
<211> LENGTH: 17
<212> TYPE: PRT
<213> ORGANISM: Artificial Sequence
<220> FEATURE:
<223> OTHER INFORMATION: Antibody 14B7 VL-CDR1

<400> SEQUENCE: 111

Lys Ser Ser Gln Ser Leu Leu Asn Ser Gly Asn Gln Lys Asn Tyr Leu
1               5                   10                  15

Thr

<210> SEQ ID NO 112
<211> LENGTH: 9
<212> TYPE: PRT
<213> ORGANISM: Artificial Sequence
<220> FEATURE:
<223> OTHER INFORMATION: Antibody 14B7 VL-CDR3

<400> SEQUENCE: 112

Gln Asn Asn Tyr Ile Tyr Pro Leu Thr
1               5

<210> SEQ ID NO 113
<211> LENGTH: 118
<212> TYPE: PRT
<213> ORGANISM: Artificial Sequence
<220> FEATURE:
<223> OTHER INFORMATION: Antibody 14B7 Heavy Chain Variable Region (VH)

<400> SEQUENCE: 113

Lys Val Lys Leu Gln Glu Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
                20                  25                  30

Lys Met Asp Trp Val Lys Gln Ser His Gly Lys Ser Leu Glu Trp Ile
            35                  40                  45

Gly Asp Ile Asn Pro Asn Asn Gly Gly Thr Ile Tyr Asn Gln Lys Phe
        50                  55                  60

Lys Gly Lys Ala Thr Leu Thr Val Asp Arg Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Ser Tyr Tyr Gly Asn Ser Leu Ala Tyr Trp Gly Gln Gly Thr
            100                 105                 110

Leu Val Thr Val Ser Ala
        115

<210> SEQ ID NO 114
<211> LENGTH: 10
<212> TYPE: PRT
<213> ORGANISM: Artificial Sequence
<220> FEATURE:
<223> OTHER INFORMATION: Antibody 14B7 VH-CDR1

<400> SEQUENCE: 114

Gly Tyr Thr Phe Thr Asp Tyr Lys Met Asp
1               5                   10

<210> SEQ ID NO 115
<211> LENGTH: 17

```
<212> TYPE: PRT
<213> ORGANISM: Artificial Sequence
<220> FEATURE:
<223> OTHER INFORMATION: Antibody 14B7 VH-CDR2

<400> SEQUENCE: 115

Asp Ile Asn Pro Asn Asn Gly Gly Thr Ile Tyr Asn Gln Lys Phe Lys
1               5                   10                  15

Gly

<210> SEQ ID NO 116
<211> LENGTH: 9
<212> TYPE: PRT
<213> ORGANISM: Artificial Sequence
<220> FEATURE:
<223> OTHER INFORMATION: Antibody 14B7 VH-CDR3

<400> SEQUENCE: 116

Ser Tyr Tyr Gly Asn Ser Leu Ala Tyr
1               5

<210> SEQ ID NO 117
<211> LENGTH: 106
<212> TYPE: PRT
<213> ORGANISM: Artificial Sequence
<220> FEATURE:
<223> OTHER INFORMATION: Antibody 7H1 Light Chain Variable Region (VL)

<400> SEQUENCE: 117

Asp Ile Val Leu Thr Gln Ser Pro Ala Ile Leu Ser Val Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Gly Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Thr Gly Thr Lys Leu Glu Leu Lys
            100                 105

<210> SEQ ID NO 118
<211> LENGTH: 10
<212> TYPE: PRT
<213> ORGANISM: Artificial Sequence
<220> FEATURE:
<223> OTHER INFORMATION: Antibody 7H1 VL-CDR1

<400> SEQUENCE: 118

Arg Ala Ser Ser Ser Val Ser Tyr Met His
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Antibody 7H1 VL-CDR2

<400> SEQUENCE: 119
```

Gly Thr Ser Asn Leu Ala Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Antibody 7H1 VL-CDR3

<400> SEQUENCE: 120

Gln Gln Trp Ser Ser Asn Pro Leu Thr
1               5

<210> SEQ ID NO 121
<211> LENGTH: 119
<212> TYPE: PRT
<213> ORGANISM: Artificial Sequence
<220> FEATURE:
<223> OTHER INFORMATION: Antibody 7H1 Heavy Chain Variable Region (VH)

<400> SEQUENCE: 121

Lys Val Gln Leu Gln Glu Ser Gly Gly Gly Ser Val Gln Pro Gly Gly
1               5                   10                  15

Ser Leu Lys Leu Ser Cys Ala Ala Ser Gly Phe Thr Phe Ser Ser Tyr
            20                  25                  30

Ser Met Ser Trp Val Arg Gln Thr Pro Glu Lys Arg Leu Glu Trp Val
        35                  40                  45

Ala Tyr Ile Ser Asn Leu Gly Gly Ala Thr Tyr Tyr Pro Asp Thr Val
    50                  55                  60

Lys Gly Arg Phe Thr Val Ser Arg Asp Asn Ala Arg Asn Ser Leu Tyr
65                  70                  75                  80

Leu Gln Met Thr Ser Leu Lys Ser Asp Asp Thr Ala Met Tyr Tyr Cys
                85                  90                  95

Thr Arg His Asn Tyr Gly Tyr Asp Gly Phe Ala Asp Trp Gly Gln Gly
            100                 105                 110

Thr Leu Ala Thr Val Ser Ala
        115

<210> SEQ ID NO 122
<211> LENGTH: 10
<212> TYPE: PRT
<213> ORGANISM: Artificial Sequence
<220> FEATURE:
<223> OTHER INFORMATION: Antibody 7H1 VH-CDR1

<400> SEQUENCE: 122

Gly Phe Thr Phe Ser Ser Tyr Ser Met Ser
1               5                   10

<210> SEQ ID NO 123
<211> LENGTH: 17
<212> TYPE: PRT
<213> ORGANISM: Artificial Sequence
<220> FEATURE:
<223> OTHER INFORMATION: Antibody 7H1 VH-CDR2

<400> SEQUENCE: 123

Tyr Ile Ser Asn Leu Gly Gly Ala Thr Tyr Tyr Pro Asp Thr Val Lys
1               5                   10                  15

Gly

```
<210> SEQ ID NO 124
<211> LENGTH: 10
<212> TYPE: PRT
<213> ORGANISM: Artificial Sequence
<220> FEATURE:
<223> OTHER INFORMATION: Antibody 7H1 VH-CDR3

<400> SEQUENCE: 124

His Asn Tyr Gly Tyr Asp Gly Phe Ala Asp
1               5                   10

<210> SEQ ID NO 125
<211> LENGTH: 113
<212> TYPE: PRT
<213> ORGANISM: Artificial Sequence
<220> FEATURE:
<223> OTHER INFORMATION: Antibody 5H1 Light Chain Variable Region (VL)

<400> SEQUENCE: 125

Asp Ile Val Met Thr Gln Asp Glu Leu Ser Leu Thr Val Thr Ala Gly
1               5                   10                  15

Lys Lys Val Thr Met Asn Cys Lys Ser Ser Gln Ser Leu Leu Asn Ser
                20                  25                  30

Gly Asn Gln Lys Ser Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Leu Tyr Tyr Cys Gln Asn
                85                  90                  95

Ala Tyr Phe Tyr Pro Leu Thr Phe Gly Ala Gly Thr Lys Leu Glu Gln
            100                 105                 110

Lys

<210> SEQ ID NO 126
<211> LENGTH: 9
<212> TYPE: PRT
<213> ORGANISM: Artificial Sequence
<220> FEATURE:
<223> OTHER INFORMATION: Antibody 5H1 VL-CDR3

<400> SEQUENCE: 126

Gln Asn Ala Tyr Phe Tyr Pro Leu Thr
1               5

<210> SEQ ID NO 127
<211> LENGTH: 119
<212> TYPE: PRT
<213> ORGANISM: Artificial Sequence
<220> FEATURE:
<223> OTHER INFORMATION: Antibody 5H1 Heavy Chain Variable Region (VH)

<400> SEQUENCE: 127

Lys Val Lys Leu Gln Gln Ser Gly Glu Gly Leu Val Gln Pro Gly Gly
1               5                   10                  15

Ser Arg Glu Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Phe Tyr Ala Asp Thr Val
        50                  55                  60
```

```
Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Ser Gly Ala Tyr Tyr Gly Asn Ala Met Asp Tyr Trp Gly Gln Gly
            100                 105                 110

Thr Ser Val Thr Val Ser Ser
        115
```

<210> SEQ ID NO 128
<211> LENGTH: 17
<212> TYPE: PRT
<213> ORGANISM: Artificial Sequence
<220> FEATURE:
<223> OTHER INFORMATION: Antibody 5H1 VH-CDR2

<400> SEQUENCE: 128

```
Tyr Ile Ser Ser Gly Ser Ser Thr Ile Phe Tyr Ala Asp Thr Val Lys
  1               5                  10                  15

Gly
```

<210> SEQ ID NO 129
<211> LENGTH: 10
<212> TYPE: PRT
<213> ORGANISM: Artificial Sequence
<220> FEATURE:
<223> OTHER INFORMATION: Antibody 5H1 VH-CDR3

<400> SEQUENCE: 129

```
Gly Ala Tyr Tyr Gly Asn Ala Met Asp Tyr
  1               5                  10
```

<210> SEQ ID NO 130
<211> LENGTH: 113
<212> TYPE: PRT
<213> ORGANISM: Artificial Sequence
<220> FEATURE:
<223> OTHER INFORMATION: Antibody 15B5 Light Chain Variable Region (VL)

<400> SEQUENCE: 130

```
Asp Ile Val Met Thr Gln Asp Glu Leu Ser Leu Thr Val Thr Val Gly
  1               5                  10                  15

Glu Lys Val Thr Met Thr Cys Lys Ser Ser Gln Ser Leu Leu Asn Ser
                 20                  25                  30

Gly Asn Gln Arg Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Val Tyr Phe Tyr Pro Leu Thr Phe Gly Thr Gly Thr Lys Leu Glu Leu
            100                 105                 110

Lys
```

<210> SEQ ID NO 131
<211> LENGTH: 113
<212> TYPE: PRT
<213> ORGANISM: Artificial Sequence
<220> FEATURE:
<223> OTHER INFORMATION: Antibody h5C9a Light Chain Variable Region (VL)

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 132
<211> LENGTH: 7
<212> TYPE: PRT
<213> ORGANISM: Artificial Sequence
<220> FEATURE:
<223> OTHER INFORMATION: Antibody h5C9a VL-CDR2

<400> SEQUENCE: 132

Trp Ala Ser Thr Leu Glu Ser
1               5

<210> SEQ ID NO 133
<211> LENGTH: 9
<212> TYPE: PRT
<213> ORGANISM: Artificial Sequence
<220> FEATURE:
<223> OTHER INFORMATION: Antibody h5C9a VL-CDR3

<400> SEQUENCE: 133

Gln Asn Ala Tyr Ser Phe Pro Phe Thr
1               5

<210> SEQ ID NO 134
<211> LENGTH: 118
<212> TYPE: PRT
<213> ORGANISM: Artificial Sequence
<220> FEATURE:
<223> OTHER INFORMATION: Antibody h5C9a Heavy Chain Variable Region (VH)

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Ala Trp Ile Asn Met Tyr Thr Gly Glu Pro Thr Tyr Ala Asp Asp Phe
    50                  55                  60

Lys Gly Arg Phe Thr Ile Ser Arg Asp Asp Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
            100                 105                 110

Leu Val Thr Val Ser Ser
        115

<210> SEQ ID NO 135
<211> LENGTH: 9
<212> TYPE: PRT
<213> ORGANISM: Artificial Sequence
<220> FEATURE:
<223> OTHER INFORMATION: Antibody h5C9a VH-CDR3

<400> SEQUENCE: 135

Leu Tyr Asn Gly Asn Ser Leu Asp Tyr
1               5

<210> SEQ ID NO 136
<211> LENGTH: 113
<212> TYPE: PRT
<213> ORGANISM: Artificial Sequence
<220> FEATURE:
<223> OTHER INFORMATION: Antibody h5C9b Light Chain Variable Region (VL)

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 137
<211> LENGTH: 118
<212> TYPE: PRT
<213> ORGANISM: Artificial Sequence
<220> FEATURE:
<223> OTHER INFORMATION: Antibody h5C9b Heavy Chain Variable Region (VH)

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Ala Trp Ile Asn Met Tyr Thr Gly Glu Pro Tyr Ala Asp Asp Phe
    50                  55                  60

Lys Gly Arg Phe Thr Ile Ser Arg Asp Asp Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
            100                 105                 110

Leu Val Thr Val Ser Ser
        115

<210> SEQ ID NO 138
<211> LENGTH: 113
<212> TYPE: PRT
<213> ORGANISM: Artificial Sequence
<220> FEATURE:
<223> OTHER INFORMATION: Antibody h5C9c Light Chain Variable Region (VL)

<400> SEQUENCE: 138

Asp Ile Gln Leu Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 139
<211> LENGTH: 118
<212> TYPE: PRT
<213> ORGANISM: Artificial Sequence
<220> FEATURE:
<223> OTHER INFORMATION: Antibody h5C9c Heavy Chain Variable Region (VH)

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Ala Trp Ile Asn Met Tyr Thr Gly Glu Pro Thr Tyr Ala Asp Asp Phe
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
            100                 105                 110

Leu Val Thr Val Ser Ser
        115

<210> SEQ ID NO 140

<211> LENGTH: 113
<212> TYPE: PRT
<213> ORGANISM: Artificial Sequence
<220> FEATURE:
<223> OTHER INFORMATION: Antibody h5C9f Light Chain Variable Region (VL)

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 141
<211> LENGTH: 118
<212> TYPE: PRT
<213> ORGANISM: Artificial Sequence
<220> FEATURE:
<223> OTHER INFORMATION: Antibody h5C9f Heavy Chain Variable Region (VH)

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Ala Trp Ile Asn Met Tyr Thr Gly Glu Pro Thr Tyr Ala Asp Asp Phe
    50                  55                  60

Lys Gly Arg Phe Thr Ile Ser Leu Asp Asp Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
            100                 105                 110

Leu Val Thr Val Ser Ser
        115

<210> SEQ ID NO 142
<211> LENGTH: 113
<212> TYPE: PRT
<213> ORGANISM: Artificial Sequence
<220> FEATURE:
<223> OTHER INFORMATION: Antibody h5C9g Light Chain Variable Region (VL)

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser

```
                20                  25                  30
Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 143
<211> LENGTH: 118
<212> TYPE: PRT
<213> ORGANISM: Artificial Sequence
<220> FEATURE:
<223> OTHER INFORMATION: Antibody h5C9g Heavy Chain Variable Region (VH)

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Ala Trp Ile Asn Met Tyr Thr Gly Glu Pro Thr Tyr Ala Asp Asp Phe
    50                  55                  60

Lys Gly Arg Phe Thr Phe Ser Arg Asp Asn Ser Lys Ser Thr Val Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
            100                 105                 110

Leu Val Thr Val Ser Ser
        115

<210> SEQ ID NO 144
<211> LENGTH: 113
<212> TYPE: PRT
<213> ORGANISM: Artificial Sequence
<220> FEATURE:
<223> OTHER INFORMATION: Antibody h5C9i Light Chain Variable Region (VL)

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Asn
```

85                  90                  95

Ala Tyr Ser Phe Pro Phe Thr Phe Gly Gln Gly Thr Lys Val Glu Ile
            100                 105                 110

Lys

<210> SEQ ID NO 145
<211> LENGTH: 118
<212> TYPE: PRT
<213> ORGANISM: Artificial Sequence
<220> FEATURE:
<223> OTHER INFORMATION: Antibody h5C9i Heavy Chain Variable Region (VH)

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Ala Trp Ile Asn Met Tyr Thr Gly Glu Pro Thr Tyr Ala Asp Asp Phe
    50                  55                  60

Lys Gly Arg Phe Thr Ile Ser Arg Asp Asp Ser Ala Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
            100                 105                 110

Leu Val Thr Val Ser Ser
        115

<210> SEQ ID NO 146
<211> LENGTH: 113
<212> TYPE: PRT
<213> ORGANISM: Artificial Sequence
<220> FEATURE:
<223> OTHER INFORMATION: Antibody h5C9j Light Chain Variable Region (VL)

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 147
<211> LENGTH: 118
<212> TYPE: PRT
<213> ORGANISM: Artificial Sequence

```
<220> FEATURE:
<223> OTHER INFORMATION: Antibody h5C9j Heavy Chain Variable Region (VH)

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Ala Trp Ile Asn Met Tyr Thr Gly Glu Pro Thr Tyr Ala Asp Asp Phe
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
            100                 105                 110

Leu Val Thr Val Ser Ser
        115

<210> SEQ ID NO 148
<211> LENGTH: 113
<212> TYPE: PRT
<213> ORGANISM: Artificial Sequence
<220> FEATURE:
<223> OTHER INFORMATION: Antibody h5C9l Light Chain Variable Region (VL)

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 149
<211> LENGTH: 118
<212> TYPE: PRT
<213> ORGANISM: Artificial Sequence
<220> FEATURE:
<223> OTHER INFORMATION: Antibody h5C9l Heavy Chain Variable Region (VH)

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Thr Ser Gly Tyr Thr Phe Thr Asn Tyr
            20                  25                  30

Gly Met Asn Trp Val Arg Gln Ala Pro Gly Lys Gly Leu Glu Trp Val
```

```
                35                  40                  45

Ala Trp Ile Asn Met Tyr Thr Gly Glu Pro Thr Tyr Ala Asp Asp Phe
 50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Tyr Asn Gly Asn Ser Leu Asp Tyr Trp Gly Gln Gly Thr
            100                 105                 110

Leu Val Thr Val Ser Ser
            115

<210> SEQ ID NO 150
<211> LENGTH: 113
<212> TYPE: PRT
<213> ORGANISM: Artificial Sequence
<220> FEATURE:
<223> OTHER INFORMATION: Antibody h5C9m Light Chain Variable Region (VL)

<400> SEQUENCE: 150

Asp Ile Gln Leu Thr Gln Ser Pro Ser Ser Leu Ser Ala Ser Val Gly
 1               5                  10                  15

Asp Arg Val Thr Ile Thr Cys Lys Ser Ser Gln Ser Leu Leu Asn Ser
             20                  25                  30

Gly Asn Gln Lys Ser Tyr Leu Thr Trp Tyr Gln Gln Lys Pro Gly Lys
         35                  40                  45

Ala Pro Lys Leu Leu Ile Tyr Trp Ala Ser Thr Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Ser Phe Pro Phe Thr Phe Gly Gln Gly Thr Lys Val Glu Ile
            100                 105                 110

Lys

<210> SEQ ID NO 151
<211> LENGTH: 118
<212> TYPE: PRT
<213> ORGANISM: Artificial Sequence
<220> FEATURE:
<223> OTHER INFORMATION: Antibody h5C9m Heavy Chain Variable Region (VH)

<400> SEQUENCE: 151

Glu Val Gln Leu Val Glu Ser Gly Gly Gly Leu Val Gln Pro Gly Gly
 1               5                  10                  15

Ser Leu Arg Leu Ser Cys Ala Thr Ser Gly Tyr Thr Phe Thr Asn Tyr
             20                  25                  30

Gly Met Asn Trp Val Arg Gln Ala Pro Gly Lys Gly Leu Glu Trp Val
         35                  40                  45

Ala Trp Ile Asn Met Tyr Thr Gly Glu Pro Thr Tyr Ala Asp Asp Phe
 50                  55                  60

Lys Gly Arg Phe Thr Ile Ser Arg Asp Asp Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Arg Leu Tyr Asn Gly Asn Ser Leu Asp Tyr Trp Gly Gln Gly Thr
```

Leu Val Thr Val Ser Ser
        115

<210> SEQ ID NO 152
<211> LENGTH: 113
<212> TYPE: PRT
<213> ORGANISM: Artificial Sequence
<220> FEATURE:
<223> OTHER INFORMATION: Antibody h5C9n Light Chain Variable Region (VL)

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 153
<211> LENGTH: 118
<212> TYPE: PRT
<213> ORGANISM: Artificial Sequence
<220> FEATURE:
<223> OTHER INFORMATION: Antibody h5C9n Heavy Chain Variable Region (VH)

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Ala Trp Ile Asn Met Tyr Thr Gly Glu Pro Thr Tyr Ala Asp Asp Phe
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
            100                 105                 110

Leu Val Thr Val Ser Ser
        115

<210> SEQ ID NO 154
<211> LENGTH: 113
<212> TYPE: PRT
<213> ORGANISM: Artificial Sequence
<220> FEATURE:
<223> OTHER INFORMATION: Antibody h5C9o Light Chain Variable Region (VL)

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 155
<211> LENGTH: 115
<212> TYPE: PRT
<213> ORGANISM: Artificial Sequence
<220> FEATURE:
<223> OTHER INFORMATION: Antibody h5C9o Heavy Chain Variable Region (VH)

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 156
<211> LENGTH: 7
<212> TYPE: PRT
<213> ORGANISM: Artificial Sequence
<220> FEATURE:
<223> OTHER INFORMATION: Antibody h5C9o VH-CDR1

<400> SEQUENCE: 156

Gly Tyr Thr Phe Ser Met Asn
1               5

<210> SEQ ID NO 157
<211> LENGTH: 113
<212> TYPE: PRT
<213> ORGANISM: Artificial Sequence
<220> FEATURE:

<223> OTHER INFORMATION: Antibody h5C9oa Light Chain Variable Region
      (VL)

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ala Phe Pro Phe Thr Phe Gly Gln Gly Thr Lys Val Glu Ile
            100                 105                 110

Lys

<210> SEQ ID NO 158
<211> LENGTH: 9
<212> TYPE: PRT
<213> ORGANISM: Artificial Sequence
<220> FEATURE:
<223> OTHER INFORMATION: Antibody h5C9oa VL-CDR3

<400> SEQUENCE: 158

Gln Asn Ala Tyr Ala Phe Pro Phe Thr
1               5

<210> SEQ ID NO 159
<211> LENGTH: 115
<212> TYPE: PRT
<213> ORGANISM: Artificial Sequence
<220> FEATURE:
<223> OTHER INFORMATION: Antibody h5C9oa Heavy Chain Variable Region
      (VH)

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 160
<211> LENGTH: 113

```
<212> TYPE: PRT
<213> ORGANISM: Artificial Sequence
<220> FEATURE:
<223> OTHER INFORMATION: Antibody h5C9ob Light Chain Variable Region
      (VL)

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
                100                 105                 110

Lys

<210> SEQ ID NO 161
<211> LENGTH: 9
<212> TYPE: PRT
<213> ORGANISM: Artificial Sequence
<220> FEATURE:
<223> OTHER INFORMATION: Antibody h5C9ob VL-CDR3

<400> SEQUENCE: 161

Gln Asn Ala Tyr Phe Phe Pro Phe Thr
1               5

<210> SEQ ID NO 162
<211> LENGTH: 115
<212> TYPE: PRT
<213> ORGANISM: Artificial Sequence
<220> FEATURE:
<223> OTHER INFORMATION: Antibody h5C9ob Heavy Chain Variable Region
      (VH)

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
                100                 105                 110

Val Ser Ser
        115
```

```
<210> SEQ ID NO 163
<211> LENGTH: 113
<212> TYPE: PRT
<213> ORGANISM: Artificial Sequence
<220> FEATURE:
<223> OTHER INFORMATION: Antibody h5C9oc Light Chain Variable Region
      (VL)

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Gly Tyr Ser Phe Pro Phe Thr Phe Gly Gln Gly Thr Lys Val Glu Ile
            100                 105                 110

Lys

<210> SEQ ID NO 164
<211> LENGTH: 9
<212> TYPE: PRT
<213> ORGANISM: Artificial Sequence
<220> FEATURE:
<223> OTHER INFORMATION: Antibody h5C9oc VL-CDR3

<400> SEQUENCE: 164

Gln Asn Gly Tyr Ser Phe Pro Phe Thr
1               5

<210> SEQ ID NO 165
<211> LENGTH: 115
<212> TYPE: PRT
<213> ORGANISM: Artificial Sequence
<220> FEATURE:
<223> OTHER INFORMATION: Antibody h5C9oc Heavy Chain Variable Region
      (VH)

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110
```

Val Ser Ser
        115

<210> SEQ ID NO 166
<211> LENGTH: 113
<212> TYPE: PRT
<213> ORGANISM: Artificial Sequence
<220> FEATURE:
<223> OTHER INFORMATION: Antibody h5C9od Light Chain Variable Region
      (VL)

<400> SEQUENCE: 166

Asp Ile Gln Met Thr Gln Ser Pro Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Trp Phe Pro Phe Thr Phe Gly Gln Gly Thr Lys Val Glu Ile
            100                 105                 110

Lys

<210> SEQ ID NO 167
<211> LENGTH: 9
<212> TYPE: PRT
<213> ORGANISM: Artificial Sequence
<220> FEATURE:
<223> OTHER INFORMATION: Antibody h5C9od VL-CDR3

<400> SEQUENCE: 167

Gln Asn Ala Tyr Trp Phe Pro Phe Thr
1               5

<210> SEQ ID NO 168
<211> LENGTH: 115
<212> TYPE: PRT
<213> ORGANISM: Artificial Sequence
<220> FEATURE:
<223> OTHER INFORMATION: Antibody h5C9od Heavy Chain Variable Region
      (VH)

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
                20                  25                  30

Trp Val Arg Gln Ala Pro Gly Lys Gly Leu Glu Trp Val Ala Trp Ile
            35                  40                  45

Asn Met Tyr Thr Gly Glu Pro Thr Tyr Ala Asp Asp Phe Lys Gly Arg
        50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

```
Tyr Asn Gly Asn Ser Leu Asp Tyr Trp Gly Gln Gly Thr Leu Val Thr
            100                 105                 110

Val Ser Ser
        115

<210> SEQ ID NO 169
<211> LENGTH: 113
<212> TYPE: PRT
<213> ORGANISM: Artificial Sequence
<220> FEATURE:
<223> OTHER INFORMATION: Antibody h5C9oe Light Chain Variable Region
      (VL)

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Arg Phe Pro Phe Thr Phe Gly Gln Gly Thr Lys Val Glu Ile
            100                 105                 110

Lys

<210> SEQ ID NO 170
<211> LENGTH: 9
<212> TYPE: PRT
<213> ORGANISM: Artificial Sequence
<220> FEATURE:
<223> OTHER INFORMATION: Antibody h5C9oeVL-CDR3

<400> SEQUENCE: 170

Gln Asn Ala Tyr Arg Phe Pro Phe Thr
1               5

<210> SEQ ID NO 171
<211> LENGTH: 115
<212> TYPE: PRT
<213> ORGANISM: Artificial Sequence
<220> FEATURE:
<223> OTHER INFORMATION: Antibody h5C9oe Heavy Chain Variable Region
      (VH)

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80
```

```
Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 172
<211> LENGTH: 113
<212> TYPE: PRT
<213> ORGANISM: Artificial Sequence
<220> FEATURE:
<223> OTHER INFORMATION: Antibody h5C9of Light Chain Variable Region
      (VL)

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ser Tyr Ser Phe Pro Phe Thr Phe Gly Gln Gly Thr Lys Val Glu Ile
            100                 105                 110

Lys

<210> SEQ ID NO 173
<211> LENGTH: 9
<212> TYPE: PRT
<213> ORGANISM: Artificial Sequence
<220> FEATURE:
<223> OTHER INFORMATION: Antibody h5C9of VL-CDR3

<400> SEQUENCE: 173

Gln Asn Ser Tyr Ser Phe Pro Phe Thr
1               5

<210> SEQ ID NO 174
<211> LENGTH: 115
<212> TYPE: PRT
<213> ORGANISM: Artificial Sequence
<220> FEATURE:
<223> OTHER INFORMATION: Antibody h5C9of Heavy Chain Variable Region
      (VH)

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60
```

```
Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Tyr Asn Gly Asn Ser Leu Asp Tyr Trp Gly Gln Gly Thr Leu Val Thr
            100                 105                 110

Val Ser Ser
        115
```

<210> SEQ ID NO 175
<211> LENGTH: 113
<212> TYPE: PRT
<213> ORGANISM: Artificial Sequence
<220> FEATURE:
<223> OTHER INFORMATION: Antibody h5C9og Light Chain Variable Region
      (VL)

<400> SEQUENCE: 175

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ser Tyr Ser Phe Pro Phe Thr Phe Gly Gln Gly Thr Lys Val Glu Ile
            100                 105                 110

Lys
```

<210> SEQ ID NO 176
<211> LENGTH: 115
<212> TYPE: PRT
<213> ORGANISM: Artificial Sequence
<220> FEATURE:
<223> OTHER INFORMATION: Antibody h5C9og Heavy Chain Variable Region
      (VH)

<400> SEQUENCE: 176

```
Glu Val Gln Leu Val Glu Ser Gly Gly Gly Leu Val Gln Pro Gly Gly
 1               5                  10                  15

Ser Leu Arg Leu Ser Cys Ala Val Ser Gly Tyr Thr Phe Ser Met Asn
                20                  25                  30

Trp Val Arg Gln Ala Pro Gly Lys Gly Leu Glu Trp Val Ala Trp Ile
            35                  40                  45

Asn Met Tyr Thr Gly Glu Pro Thr Tyr Ala Asp Asp Phe Lys Gly Arg
 50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Tyr Arg Gly Asn Ser Leu Asp Tyr Trp Gly Gln Gly Thr Leu Val Thr
            100                 105                 110

Val Ser Ser
```

```
                115

<210> SEQ ID NO 177
<211> LENGTH: 9
<212> TYPE: PRT
<213> ORGANISM: Artificial Sequence
<220> FEATURE:
<223> OTHER INFORMATION: Antibody h5C9og VH-CDR3

<400> SEQUENCE: 177

Leu Tyr Arg Gly Asn Ser Leu Asp Tyr
1               5

<210> SEQ ID NO 178
<211> LENGTH: 113
<212> TYPE: PRT
<213> ORGANISM: Artificial Sequence
<220> FEATURE:
<223> OTHER INFORMATION: Antibody h5C9oh Light Chain Variable Region
      (VL)

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Glu Phe Pro Phe Thr Phe Gly Gln Gly Thr Lys Val Glu Ile
            100                 105                 110

Lys

<210> SEQ ID NO 179
<211> LENGTH: 115
<212> TYPE: PRT
<213> ORGANISM: Artificial Sequence
<220> FEATURE:
<223> OTHER INFORMATION: Antibody h5C9oh Heavy Chain Variable Region
      (VH)

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
```

Val Ser Ser
    115

<210> SEQ ID NO 180
<211> LENGTH: 113
<212> TYPE: PRT
<213> ORGANISM: Artificial Sequence
<220> FEATURE:
<223> OTHER INFORMATION: Antibody h5C9oi Light Chain Variable Region
      (VL)

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ser Tyr Ser Phe Pro Phe Thr Phe Gly Gln Gly Thr Lys Val Glu Ile
            100                 105                 110

Lys

<210> SEQ ID NO 181
<211> LENGTH: 115
<212> TYPE: PRT
<213> ORGANISM: Artificial Sequence
<220> FEATURE:
<223> OTHER INFORMATION: Antibody h5C9oi Heavy Chain Variable Region
      (VH)

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Met
                85                  90                  95

Tyr Asn Gly Asn Ser Leu Asp Tyr Trp Gly Gln Gly Thr Leu Val Thr
            100                 105                 110

Val Ser Ser
    115

<210> SEQ ID NO 182
<211> LENGTH: 9
<212> TYPE: PRT
<213> ORGANISM: Artificial Sequence
<220> FEATURE:
<223> OTHER INFORMATION: Antibody h5C9oi VH-CDR3

<400> SEQUENCE: 182

Met Tyr Asn Gly Asn Ser Leu Asp Tyr
1               5

<210> SEQ ID NO 183
<211> LENGTH: 113
<212> TYPE: PRT
<213> ORGANISM: Artificial Sequence
<220> FEATURE:
<223> OTHER INFORMATION: Antibody h5C9oj Light Chain Variable Region
      (VL)

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys

<210> SEQ ID NO 184
<211> LENGTH: 115
<212> TYPE: PRT
<213> ORGANISM: Artificial Sequence
<220> FEATURE:
<223> OTHER INFORMATION: Antibody h5C9oj Heavy Chain Variable Region
      (VH)

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ala Leu Asp Tyr Trp Gly Gln Gly Thr Leu Val Thr
            100                 105                 110

Val Ser Ser
        115

<210> SEQ ID NO 185

```
<211> LENGTH: 9
<212> TYPE: PRT
<213> ORGANISM: Artificial Sequence
<220> FEATURE:
<223> OTHER INFORMATION: Antibody h5C9oj VH-CDR3

<400> SEQUENCE: 185

Leu Tyr Asn Gly Asn Ala Leu Asp Tyr
1               5

<210> SEQ ID NO 186
<211> LENGTH: 113
<212> TYPE: PRT
<213> ORGANISM: Artificial Sequence
<220> FEATURE:
<223> OTHER INFORMATION: Antibody h5C9ok VL

<400> SEQUENCE: 186

Asp Ile Gln Met Thr Gln Ser Pro Ser Ser Leu Ser Ala Ser Val Gly
1               5                  10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 187
<211> LENGTH: 115
<212> TYPE: PRT
<213> ORGANISM: Artificial Sequence
<220> FEATURE:
<223> OTHER INFORMATION: Antibody h5C9ok Heavy Chain Variable Region
      (VH)

<400> SEQUENCE: 187

Glu Val Gln Leu Val Glu Ser Gly Gly Gly Leu Val Gln Pro Gly Gly
1               5                  10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Thr Arg Gly Asn Ser Leu Asp Tyr Trp Gly Gln Gly Thr Leu Val Thr
            100                 105                 110

Val Ser Ser
        115
```

<210> SEQ ID NO 188
<211> LENGTH: 9
<212> TYPE: PRT
<213> ORGANISM: Artificial Sequence
<220> FEATURE:
<223> OTHER INFORMATION: Antibody h5C9ok VH-CDR3

<400> SEQUENCE: 188

Leu Thr Arg Gly Asn Ser Leu Asp Tyr
1               5

<210> SEQ ID NO 189
<211> LENGTH: 115
<212> TYPE: PRT
<213> ORGANISM: Artificial Sequence
<220> FEATURE:
<223> OTHER INFORMATION: Antibody h5C9ol Heavy Chain Variable Region
      (VH)

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Gly Pro Gly Asn Val Phe Asp Tyr Trp Gly Gln Gly Thr Leu Val Thr
            100                 105                 110

Val Ser Ser
        115

<210> SEQ ID NO 190
<211> LENGTH: 9
<212> TYPE: PRT
<213> ORGANISM: Artificial Sequence
<220> FEATURE:
<223> OTHER INFORMATION: Antibody h5C9ol VH-CDR3

<400> SEQUENCE: 190

Leu Gly Pro Gly Asn Val Phe Asp Tyr
1               5

<210> SEQ ID NO 191
<211> LENGTH: 115
<212> TYPE: PRT
<213> ORGANISM: Artificial Sequence
<220> FEATURE:
<223> OTHER INFORMATION: Antibody h5C9om Heavy Chain Variable Region
      (VH)

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile

```
                35                  40                  45

Asn Met Tyr Thr Gly Glu Pro Thr Tyr Ala Asp Asp Phe Lys Gly Arg
         50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Ala Arg Gly Asn Gly Phe Asp Tyr Trp Gly Gln Gly Thr Leu Val Thr
            100                 105                 110

Val Ser Ser
        115

<210> SEQ ID NO 192
<211> LENGTH: 9
<212> TYPE: PRT
<213> ORGANISM: Artificial Sequence
<220> FEATURE:
<223> OTHER INFORMATION: Antibody h5C9om VH-CDR3

<400> SEQUENCE: 192

Leu Ala Arg Gly Asn Gly Phe Asp Tyr
1               5

<210> SEQ ID NO 193
<211> LENGTH: 115
<212> TYPE: PRT
<213> ORGANISM: Artificial Sequence
<220> FEATURE:
<223> OTHER INFORMATION: Antibody h5C9on Heavy Chain Variable Region
      (VH)

<400> SEQUENCE: 193

Glu Val Gln Leu Val Glu Ser Gly Gly Gly Leu Val Gln Pro Gly Gly
1               5                  10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Thr
                85                  90                  95

Ala Pro Gly Asn Gly Phe Asp Tyr Trp Gly Gln Gly Thr Leu Val Thr
            100                 105                 110

Val Ser Ser
        115

<210> SEQ ID NO 194
<211> LENGTH: 9
<212> TYPE: PRT
<213> ORGANISM: Artificial Sequence
<220> FEATURE:
<223> OTHER INFORMATION: Antibody h5C9on VH-CDR3

<400> SEQUENCE: 194

Thr Ala Pro Gly Asn Gly Phe Asp Tyr
1               5
```

```
<210> SEQ ID NO 195
<211> LENGTH: 115
<212> TYPE: PRT
<213> ORGANISM: Artificial Sequence
<220> FEATURE:
<223> OTHER INFORMATION: Antibody h5C9oo Heavy Chain Variable Region
      (VH)

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Val Arg Gly Asn Gly Phe Asp Tyr Trp Gly Gln Gly Leu Val Thr
            100                 105                 110

Val Ser Ser
        115

<210> SEQ ID NO 196
<211> LENGTH: 9
<212> TYPE: PRT
<213> ORGANISM: Artificial Sequence
<220> FEATURE:
<223> OTHER INFORMATION: Antibody h5C9oo VH-CDR3

<400> SEQUENCE: 196

Leu Val Arg Gly Asn Gly Phe Asp Tyr
1               5

<210> SEQ ID NO 197
<211> LENGTH: 115
<212> TYPE: PRT
<213> ORGANISM: Artificial Sequence
<220> FEATURE:
<223> OTHER INFORMATION: Antibody h5C9op Heavy Chain Variable Region
      (VH)

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Thr
                85                  90                  95

Ser Arg Gly Asn Gly Met Asp Tyr Trp Gly Gln Gly Leu Val Thr
            100                 105                 110
```

-continued

Val Ser Ser
     115

<210> SEQ ID NO 198
<211> LENGTH: 9
<212> TYPE: PRT
<213> ORGANISM: Artificial Sequence
<220> FEATURE:
<223> OTHER INFORMATION: Antibody h5C9op VH-CDR3

<400> SEQUENCE: 198

Thr Ser Arg Gly Asn Gly Met Asp Tyr
1               5

<210> SEQ ID NO 199
<211> LENGTH: 115
<212> TYPE: PRT
<213> ORGANISM: Artificial Sequence
<220> FEATURE:
<223> OTHER INFORMATION: Antibody h5C9oq Heavy Chain Variable Region
      (VH)

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Val Met Asp Tyr Trp Gly Gln Gly Thr Leu Val Thr
            100                 105                 110

Val Ser Ser
     115

<210> SEQ ID NO 200
<211> LENGTH: 9
<212> TYPE: PRT
<213> ORGANISM: Artificial Sequence
<220> FEATURE:
<223> OTHER INFORMATION: Antibody h5C9oq VH-CDR3

<400> SEQUENCE: 200

Leu Tyr Arg Gly Asn Val Met Asp Tyr
1               5

<210> SEQ ID NO 201
<211> LENGTH: 115
<212> TYPE: PRT
<213> ORGANISM: Artificial Sequence
<220> FEATURE:
<223> OTHER INFORMATION: Antibody h5C9or Heavy Chain Variable Region
      (VH)

<400> SEQUENCE: 201

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn

```
                    20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Asn Arg Gly Asn Ser Met Asp Tyr Trp Gly Gln Gly Thr Leu Val Thr
            100                 105                 110

Val Ser Ser
        115

<210> SEQ ID NO 202
<211> LENGTH: 9
<212> TYPE: PRT
<213> ORGANISM: Artificial Sequence
<220> FEATURE:
<223> OTHER INFORMATION: Antibody h5C9or VH-CDR3

<400> SEQUENCE: 202

Leu Asn Arg Gly Asn Ser Met Asp Tyr
1               5

<210> SEQ ID NO 203
<211> LENGTH: 115
<212> TYPE: PRT
<213> ORGANISM: Artificial Sequence
<220> FEATURE:
<223> OTHER INFORMATION: Antibody h5C9os Heavy Chain Variable Region
      (VH)

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Thr
                85                  90                  95

Gly Thr Gly Asn Thr Met Asp Tyr Trp Gly Gln Gly Thr Leu Val Thr
            100                 105                 110

Val Ser Ser
        115

<210> SEQ ID NO 204
<211> LENGTH: 9
<212> TYPE: PRT
<213> ORGANISM: Artificial Sequence
<220> FEATURE:
<223> OTHER INFORMATION: Antibody h5C9os VH-CDR3

<400> SEQUENCE: 204

Thr Gly Thr Gly Asn Thr Met Asp Tyr
```

-continued

```
1               5
```

<210> SEQ ID NO 205
<211> LENGTH: 115
<212> TYPE: PRT
<213> ORGANISM: Artificial Sequence
<220> FEATURE:
<223> OTHER INFORMATION: Antibody h5C9ot Heavy Chain Variable Region
      (VH)

<400> SEQUENCE: 205

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Ser
                85                  90                  95

Ser Met Gly Asn Gly Phe Asp Tyr Trp Gly Gln Gly Thr Leu Val Thr
            100                 105                 110

Val Ser Ser
        115
```

<210> SEQ ID NO 206
<211> LENGTH: 9
<212> TYPE: PRT
<213> ORGANISM: Artificial Sequence
<220> FEATURE:
<223> OTHER INFORMATION: Antibody h5C9ot VH-CDR3

<400> SEQUENCE: 206

```
Ser Ser Met Gly Asn Gly Phe Asp Tyr
1               5
```

<210> SEQ ID NO 207
<211> LENGTH: 115
<212> TYPE: PRT
<213> ORGANISM: Artificial Sequence
<220> FEATURE:
<223> OTHER INFORMATION: Antibody h5C9ou Heavy Chain Variable Region
      (VH)

<400> SEQUENCE: 207

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95
```

```
Ser Lys Gly Asn Gly Met Asp Tyr Trp Gly Gln Gly Thr Leu Val Thr
            100                 105                 110
Val Ser Ser
        115

<210> SEQ ID NO 208
<211> LENGTH: 9
<212> TYPE: PRT
<213> ORGANISM: Artificial Sequence
<220> FEATURE:
<223> OTHER INFORMATION: Antibody h5C9ou VH-CDR3

<400> SEQUENCE: 208

Leu Ser Lys Gly Asn Gly Met Asp Tyr
1               5

<210> SEQ ID NO 209
<211> LENGTH: 115
<212> TYPE: PRT
<213> ORGANISM: Artificial Sequence
<220> FEATURE:
<223> OTHER INFORMATION: Antibody h5C9ov Heavy Chain Variable Region
      (VH)

<400> SEQUENCE: 209

Glu Val Gln Leu Val Glu Ser Gly Gly Gly Leu Val Gln Pro Gly Gly
1               5                   10                  15
Ser Leu Arg Leu Ser Cys Ala Val Ser Gly Tyr Thr Phe Ser Met Asn
            20                  25                  30
Trp Val Arg Gln Ala Pro Gly Lys Gly Leu Glu Trp Val Ala Trp Ile
        35                  40                  45
Asn Met Tyr Thr Gly Glu Pro Thr Tyr Ala Asp Asp Phe Lys Gly Arg
    50                  55                  60
Phe Thr Ile Ser Arg Asp Asp Ser Lys Asn Thr Leu Tyr Leu Gln Met
65                  70                  75                  80
Asn Ser Leu Arg Ala Glu Asp Thr Ala Val Tyr Tyr Cys Ala Arg Leu
                85                  90                  95
Val Lys Gly Asn Gly Phe Asp Tyr Trp Gly Gln Gly Thr Leu Val Thr
            100                 105                 110
Val Ser Ser
        115

<210> SEQ ID NO 210
<211> LENGTH: 9
<212> TYPE: PRT
<213> ORGANISM: Artificial Sequence
<220> FEATURE:
<223> OTHER INFORMATION: Antibody h5C9ov VH-CDR3

<400> SEQUENCE: 210

Leu Val Lys Gly Asn Gly Phe Asp Tyr
1               5

<210> SEQ ID NO 211
<211> LENGTH: 115
<212> TYPE: PRT
<213> ORGANISM: Artificial Sequence
<220> FEATURE:
<223> OTHER INFORMATION: Antibody h5C9ow Heavy Chain Variable Region
      (VH)

<400> SEQUENCE: 211

Glu Val Gln Leu Val Glu Ser Gly Gly Gly Leu Val Gln Pro Gly Gly
```

```
1               5                   10                  15
Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Pro Thr Tyr Ala Asp Asp Phe Lys Gly Arg
            50                  55                  60

Phe Thr Ile Ser Arg Asp Asp Ser Lys Asn Thr Leu Tyr Leu Gln Met
 65                 70                  75                  80

Asn Ser Leu Arg Ala Glu Asp Thr Ala Val Tyr Tyr Cys Ala Arg Leu
                85                  90                  95

Thr Lys Gly Asn Gly Met Asp Tyr Trp Gly Gln Gly Thr Leu Val Thr
            100                 105                 110

Val Ser Ser
        115

<210> SEQ ID NO 212
<211> LENGTH: 9
<212> TYPE: PRT
<213> ORGANISM: Artificial Sequence
<220> FEATURE:
<223> OTHER INFORMATION: Antibody h5C9ow VH-CDR3

<400> SEQUENCE: 212

Leu Thr Lys Gly Asn Gly Met Asp Tyr
 1               5

<210> SEQ ID NO 213
<211> LENGTH: 115
<212> TYPE: PRT
<213> ORGANISM: Artificial Sequence
<220> FEATURE:
<223> OTHER INFORMATION: Antibody h5C9ox Heavy Chain Variable Region
      (VH)

<400> SEQUENCE: 213

Glu Val Gln Leu Val Glu Ser Gly Gly Gly Leu Val Gln Pro Gly Gly
 1               5                  10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Pro Thr Tyr Ala Asp Asp Phe Lys Gly Arg
            50                  55                  60

Phe Thr Ile Ser Arg Asp Asp Ser Lys Asn Thr Leu Tyr Leu Gln Met
 65                 70                  75                  80

Asn Ser Leu Arg Ala Glu Asp Thr Ala Val Tyr Tyr Cys Ala Arg Ala
                85                  90                  95

Ser Arg Gly Asn Gly Met Asp Tyr Trp Gly Gln Gly Thr Leu Val Thr
            100                 105                 110

Val Ser Ser
        115

<210> SEQ ID NO 214
<211> LENGTH: 9
<212> TYPE: PRT
<213> ORGANISM: Artificial Sequence
<220> FEATURE:
<223> OTHER INFORMATION: Antibody h5C9ox VH-CDR3
```

-continued

```
<400> SEQUENCE: 214

Ala Ser Arg Gly Asn Gly Met Asp Tyr
1               5

<210> SEQ ID NO 215
<211> LENGTH: 115
<212> TYPE: PRT
<213> ORGANISM: Artificial Sequence
<220> FEATURE:
<223> OTHER INFORMATION: Antibody h5C9oy Heavy Chain Variable Region
      (VH)

<400> SEQUENCE: 215

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Ser
                85                  90                  95

Ser Lys Gly Asn Gly Leu Asp Tyr Trp Gly Gln Gly Thr Leu Val Thr
            100                 105                 110

Val Ser Ser
        115

<210> SEQ ID NO 216
<211> LENGTH: 9
<212> TYPE: PRT
<213> ORGANISM: Artificial Sequence
<220> FEATURE:
<223> OTHER INFORMATION: Antibody h5C9oy VH-CDR3

<400> SEQUENCE: 216

Ser Ser Lys Gly Asn Gly Leu Asp Tyr
1               5

<210> SEQ ID NO 217
<211> LENGTH: 115
<212> TYPE: PRT
<213> ORGANISM: Artificial Sequence
<220> FEATURE:
<223> OTHER INFORMATION: Antibody h5C9oz Heavy Chain Variable Region
      (VH)

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80
```

```
Asn Ser Leu Arg Ala Glu Asp Thr Ala Val Tyr Tyr Cys Ala Arg Leu
                85                  90                  95

Ser Arg Gly Asn Ser Leu Asp Tyr Trp Gly Gln Gly Thr Leu Val Thr
            100                 105                 110

Val Ser Ser
        115

<210> SEQ ID NO 218
<211> LENGTH: 9
<212> TYPE: PRT
<213> ORGANISM: Artificial Sequence
<220> FEATURE:
<223> OTHER INFORMATION: Antibody h5C9oz VH-CDR3

<400> SEQUENCE: 218

Leu Ser Arg Gly Asn Ser Leu Asp Tyr
1               5

<210> SEQ ID NO 219
<211> LENGTH: 115
<212> TYPE: PRT
<213> ORGANISM: Artificial Sequence
<220> FEATURE:
<223> OTHER INFORMATION: Antibody h5C9oaa Heavy Chain Variable Region
      (VH)

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Val Arg Gly Asn Gly Met Asp Tyr Trp Gly Gln Gly Thr Leu Val Thr
            100                 105                 110

Val Ser Ser
        115

<210> SEQ ID NO 220
<211> LENGTH: 9
<212> TYPE: PRT
<213> ORGANISM: Artificial Sequence
<220> FEATURE:
<223> OTHER INFORMATION: Antibody h5C9oaa VH-CDR3

<400> SEQUENCE: 220

Leu Val Arg Gly Asn Gly Met Asp Tyr
1               5

<210> SEQ ID NO 221
<211> LENGTH: 113
<212> TYPE: PRT
<213> ORGANISM: Artificial Sequence
<220> FEATURE:
<223> OTHER INFORMATION: Antibody h5C9oab Light Chain Variable Region
      (VL)
```

-continued

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Tyr Phe Pro Phe Thr Phe Gly Gln Gly Thr Lys Val Glu Ile
            100                 105                 110

Lys

<210> SEQ ID NO 222
<211> LENGTH: 115
<212> TYPE: PRT
<213> ORGANISM: Artificial Sequence
<220> FEATURE:
<223> OTHER INFORMATION: Antibody h5C9oab Heavy Chain Variable Region
      (VH)

<400> SEQUENCE: 222

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 223
<211> LENGTH: 115
<212> TYPE: PRT
<213> ORGANISM: Artificial Sequence
<220> FEATURE:
<223> OTHER INFORMATION: Antibody h5C9oad Heavy Chain Variable Region
      (VH)

<400> SEQUENCE: 223

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
            50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser
        115

<210> SEQ ID NO 224
<211> LENGTH: 113
<212> TYPE: PRT
<213> ORGANISM: Artificial Sequence
<220> FEATURE:
<223> OTHER INFORMATION: Antibody h5C9oae Light Chain Variable Region
      (VL)

<400> SEQUENCE: 224

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
        50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys

<210> SEQ ID NO 225
<211> LENGTH: 115
<212> TYPE: PRT
<213> ORGANISM: Artificial Sequence
<220> FEATURE:
<223> OTHER INFORMATION: Antibody h5C9oae Heavy Chain Variable Region
      (VH)

<400> SEQUENCE: 225

Glu Val Gln Leu Val Glu Ser Gly Gly Gly Leu Val Gln Pro Gly Gly
 1               5                  10                  15

Ser Leu Arg Leu Ser Cys Ala Val Ser Gly Tyr Thr Phe Ser Met Asn
                20                  25                  30

Trp Val Arg Gln Ala Pro Gly Lys Gly Leu Glu Trp Val Ala Trp Ile
            35                  40                  45

Asn Met Tyr Thr Gly Glu Pro Thr Tyr Ala Asp Asp Phe Lys Gly Arg
        50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser
        115

<210> SEQ ID NO 226
<211> LENGTH: 115
<212> TYPE: PRT
<213> ORGANISM: Artificial Sequence
<220> FEATURE:
<223> OTHER INFORMATION: Antibody h5C9oaf Heavy Chain Variable Region
      (VH)

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Phe Asn Gly Asn Ser Leu Asp Tyr Trp Gly Gln Gly Thr Leu Val Thr
            100                 105                 110

Val Ser Ser
        115

<210> SEQ ID NO 227
<211> LENGTH: 9
<212> TYPE: PRT
<213> ORGANISM: Artificial Sequence
<220> FEATURE:
<223> OTHER INFORMATION: Antibody h5C9oaf VH-CDR3

<400> SEQUENCE: 227

Leu Phe Asn Gly Asn Ser Leu Asp Tyr
1               5

<210> SEQ ID NO 228
<211> LENGTH: 113
<212> TYPE: PRT
<213> ORGANISM: Artificial Sequence
<220> FEATURE:
<223> OTHER INFORMATION: Antibody h5C9oag Light Chain Variable Region
      (VL)

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 229
<211> LENGTH: 115
<212> TYPE: PRT
<213> ORGANISM: Artificial Sequence
<220> FEATURE:
<223> OTHER INFORMATION: Antibody h5C9oag Heavy Chain Variable Region
      (VH)

<400> SEQUENCE: 229

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Ala Arg Gly Asn Ser Ile Asp Tyr Trp Gly Gln Gly Thr Leu Val Thr
            100                 105                 110

Val Ser Ser
        115

<210> SEQ ID NO 230
<211> LENGTH: 9
<212> TYPE: PRT
<213> ORGANISM: Artificial Sequence
<220> FEATURE:
<223> OTHER INFORMATION: Antibody h5C9oag VH-CDR3

<400> SEQUENCE: 230

Leu Ala Arg Gly Asn Ser Ile Asp Tyr
1               5

<210> SEQ ID NO 231
<211> LENGTH: 113
<212> TYPE: PRT
<213> ORGANISM: Artificial Sequence
<220> FEATURE:
<223> OTHER INFORMATION: Antibody h5C9oah Light Chain Variable Region
      (VL)

<400> SEQUENCE: 231

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
50                  55                  60

```
Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 232
<211> LENGTH: 115
<212> TYPE: PRT
<213> ORGANISM: Artificial Sequence
<220> FEATURE:
<223> OTHER INFORMATION: Antibody h5C9oah Heavy Chain Variable Region
      (VH)

<400> SEQUENCE: 232

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Ser
                85                  90                  95

Ser Arg Gly Asn Gly Phe Asp Tyr Trp Gly Gln Gly Thr Leu Val Thr
            100                 105                 110

Val Ser Ser
        115

<210> SEQ ID NO 233
<211> LENGTH: 9
<212> TYPE: PRT
<213> ORGANISM: Artificial Sequence
<220> FEATURE:
<223> OTHER INFORMATION: Antibody h5C9oah VH-CDR3

<400> SEQUENCE: 233

Ser Ser Arg Gly Asn Gly Phe Asp Tyr
1               5

<210> SEQ ID NO 234
<211> LENGTH: 113
<212> TYPE: PRT
<213> ORGANISM: Artificial Sequence
<220> FEATURE:
<223> OTHER INFORMATION: Antibody h5C9oai Light Chain Variable Region
      (VL)

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45
```

Ala Pro Lys Leu Leu Ile Tyr Trp Ala Ser Thr Leu Glu Ser Gly Val
         50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Ser Phe Pro Phe Thr Phe Gly Gln Gly Thr Lys Val Glu Ile
            100                 105                 110

Lys

<210> SEQ ID NO 235
<211> LENGTH: 115
<212> TYPE: PRT
<213> ORGANISM: Artificial Sequence
<220> FEATURE:
<223> OTHER INFORMATION: Antibody h5C9oai Heavy Chain Variable Region
      (VH)

<400> SEQUENCE: 235

Glu Val Gln Leu Val Glu Ser Gly Gly Gly Leu Val Gln Pro Gly Gly
 1               5                  10                  15

Ser Leu Arg Leu Ser Cys Ala Val Ser Gly Tyr Thr Phe Ser Met Asn
             20                  25                  30

Trp Val Arg Gln Ala Pro Gly Lys Gly Leu Glu Trp Val Ala Trp Ile
         35                  40                  45

Asn Met Tyr Thr Gly Glu Pro Thr Tyr Ala Asp Asp Phe Lys Gly Arg
 50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Ala Arg Gly Asn Ser Met Asp Tyr Trp Gly Gln Gly Thr Leu Val Thr
            100                 105                 110

Val Ser Ser
        115

<210> SEQ ID NO 236
<211> LENGTH: 9
<212> TYPE: PRT
<213> ORGANISM: Artificial Sequence
<220> FEATURE:
<223> OTHER INFORMATION: Antibody h5C9oai VH-CDR3

<400> SEQUENCE: 236

Leu Ala Arg Gly Asn Ser Met Asp Tyr
 1               5

<210> SEQ ID NO 237
<211> LENGTH: 113
<212> TYPE: PRT
<213> ORGANISM: Artificial Sequence
<220> FEATURE:
<223> OTHER INFORMATION: Antibody h5C9oap Light Chain Variable Region
      (VL)

<400> SEQUENCE: 237

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Asn Trp
             20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Gln Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Ser Phe Pro Phe Thr Phe Gly Gln Gly Thr Lys Val Glu Ile
                100                 105                 110

Lys

<210> SEQ ID NO 238
<211> LENGTH: 17
<212> TYPE: PRT
<213> ORGANISM: Artificial Sequence
<220> FEATURE:
<223> OTHER INFORMATION: Antibody h5C9oap VL-CDR1

<400> SEQUENCE: 238

Lys Ser Ser Gln Ser Leu Leu Asn Trp Gly Asn Gln Lys Ser Tyr Leu
1               5                   10                  15

Thr

<210> SEQ ID NO 239
<211> LENGTH: 7
<212> TYPE: PRT
<213> ORGANISM: Artificial Sequence
<220> FEATURE:
<223> OTHER INFORMATION: Antibody h5C9oap VL-CDR2

<400> SEQUENCE: 239

Trp Ala Ser Thr Leu Gln Ser
1               5

<210> SEQ ID NO 240
<211> LENGTH: 115
<212> TYPE: PRT
<213> ORGANISM: Artificial Sequence
<220> FEATURE:
<223> OTHER INFORMATION: Antibody h5C9oap Heavy Chain Variable Region
      (VH)

<400> SEQUENCE: 240

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
                100                 105                 110

Val Ser Ser

```
            115

<210> SEQ ID NO 241
<211> LENGTH: 17
<212> TYPE: PRT
<213> ORGANISM: Artificial Sequence
<220> FEATURE:
<223> OTHER INFORMATION: Antibody h5C9oap VH-CDR2

<400> SEQUENCE: 241

Trp Ile Asn Met Tyr Thr Gly Glu Pro Thr Tyr Ala Asp Asp Phe Lys
1               5                   10                  15

Gly

<210> SEQ ID NO 242
<211> LENGTH: 113
<212> TYPE: PRT
<213> ORGANISM: Artificial Sequence
<220> FEATURE:
<223> OTHER INFORMATION: Antibody h5C9oaq Light Chain Variable Region
      (VL)

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Phe Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 243
<211> LENGTH: 7
<212> TYPE: PRT
<213> ORGANISM: Artificial Sequence
<220> FEATURE:
<223> OTHER INFORMATION: Antibody h5C9oaq VL-CDR2

<400> SEQUENCE: 243

Trp Ala Ser Thr Leu Phe Ser
1               5

<210> SEQ ID NO 244
<211> LENGTH: 115
<212> TYPE: PRT
<213> ORGANISM: Artificial Sequence
<220> FEATURE:
<223> OTHER INFORMATION: Antibody h5C9oaq Heavy Chain Variable Region
      (VH)

<400> SEQUENCE: 244

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
```

```
                    20                  25                  30
Trp Val Arg Gln Ala Pro Gly Lys Gly Leu Glu Trp Val Ala Trp Ile
        35                  40                  45

Asn Met Tyr Thr Gly Glu Gln Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 245
<211> LENGTH: 17
<212> TYPE: PRT
<213> ORGANISM: Artificial Sequence
<220> FEATURE:
<223> OTHER INFORMATION: Antibody h5C9oaq VH-CDR2

<400> SEQUENCE: 245

Trp Ile Asn Met Tyr Thr Gly Glu Pro Thr Tyr Ala Asp Asp Phe Lys
1               5                   10                  15

Gly

<210> SEQ ID NO 246
<211> LENGTH: 113
<212> TYPE: PRT
<213> ORGANISM: Artificial Sequence
<220> FEATURE:
<223> OTHER INFORMATION: Antibody h5C9oar Light Chain Variable Region
      (VL)

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Trp Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys

<210> SEQ ID NO 247
<211> LENGTH: 7
<212> TYPE: PRT
<213> ORGANISM: Artificial Sequence
<220> FEATURE:
<223> OTHER INFORMATION: Antibody h5C9oar VL-CDR2

<400> SEQUENCE: 247
```

Trp Ala Ser Thr Leu Trp Ser
1               5

<210> SEQ ID NO 248
<211> LENGTH: 115
<212> TYPE: PRT
<213> ORGANISM: Artificial Sequence
<220> FEATURE:
<223> OTHER INFORMATION: Antibody h5C9oar Heavy Chain Variable Region
      (VH)

<400> SEQUENCE: 248

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Asn Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser
        115

<210> SEQ ID NO 249
<211> LENGTH: 17
<212> TYPE: PRT
<213> ORGANISM: Artificial Sequence
<220> FEATURE:
<223> OTHER INFORMATION: Antibody h5C9oar VH-CDR2

<400> SEQUENCE: 249

Trp Ile Asn Met Tyr Thr Gly Glu Pro Thr Tyr Ala Asp Asp Phe Lys
1               5                   10                  15

Gly

<210> SEQ ID NO 250
<211> LENGTH: 220
<212> TYPE: PRT
<213> ORGANISM: Artificial Sequence
<220> FEATURE:
<223> OTHER INFORMATION: Antibody h5C9o Light Chain

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn

```
                     85                  90                  95

Ala Tyr Ser Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 251
<211> LENGTH: 445
<212> TYPE: PRT
<213> ORGANISM: Artificial Sequence
<220> FEATURE:
<223> OTHER INFORMATION: Antibody h5C9o heavy Chain

<400> SEQUENCE: 251

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
```

```
                  225                 230                 235                 240

Phe Pro Pro Lys Pro Lys Asp Thr Leu Met Ile Ser Arg Thr Pro Glu
                        245                 250                 255

Val Thr Cys Val Val Val Asp Val Ser His Glu Asp Pro Glu Val Lys
                        260                 265                 270

Phe Asn Trp Tyr Val Asp Gly Val Glu Val His Asn Ala Lys Thr Lys
                        275                 280                 285

Pro Arg Glu Glu Gln Tyr Asn Ser Thr Tyr Arg Val Val Ser Val Leu
                        290                 295                 300

Thr Val Leu His Gln Asp Trp Leu Asn Gly Lys Glu Tyr Lys Cys Lys
        305                 310                 315                 320

Val Ser Asn Lys Ala Leu Pro Ala Pro Ile Glu Lys Thr Ile Ser Lys
                        325                 330                 335

Ala Lys Gly Gln Pro Arg Glu Pro Gln Val Tyr Thr Leu Pro Pro Ser
                        340                 345                 350

Arg Asp Glu Leu Thr Lys Asn Gln Val Ser Leu Thr Cys Leu Val Lys
                        355                 360                 365

Gly Phe Tyr Pro Ser Asp Ile Ala Val Glu Trp Glu Ser Asn Gly Gln
                        370                 375                 380

Pro Glu Asn Asn Tyr Lys Thr Thr Pro Pro Val Leu Asp Ser Asp Gly
        385                 390                 395                 400

Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                        420                 425                 430

His Tyr Thr Gln Lys Ser Leu Ser Leu Ser Pro Gly Lys
                        435                 440                 445

<210> SEQ ID NO 252
<211> LENGTH: 220
<212> TYPE: PRT
<213> ORGANISM: Artificial Sequence
<220> FEATURE:
<223> OTHER INFORMATION: Antibody h5C9a Light Chain

<400> SEQUENCE: 252

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
```

```
                145                 150                 155                 160
Gln Ser Gly Asn Ser Gln Glu Ser Val Thr Glu Gln Asp Ser Lys Asp
                    165                 170                 175

Ser Thr Tyr Ser Leu Ser Ser Thr Leu Thr Leu Ser Lys Ala Asp Tyr
                    180                 185                 190

Glu Lys His Lys Val Tyr Ala Cys Glu Val Thr His Gln Gly Leu Ser
                    195                 200                 205

Ser Pro Val Thr Lys Ser Phe Asn Arg Gly Glu Cys
                    210                 215                 220

<210> SEQ ID NO 253
<211> LENGTH: 448
<212> TYPE: PRT
<213> ORGANISM: Artificial Sequence
<220> FEATURE:
<223> OTHER INFORMATION: Antibody h5C9a heavy Chain

<400> SEQUENCE: 253

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
                35                  40                  45

Ala Trp Ile Asn Met Tyr Thr Gly Glu Pro Thr Tyr Ala Asp Asp Phe
            50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
```

```
            290                 295                 300
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 254
<211> LENGTH: 220
<212> TYPE: PRT
<213> ORGANISM: Artificial Sequence
<220> FEATURE:
<223> OTHER INFORMATION: Antibody h5C9n Light Chain

<400> SEQUENCE: 254

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
```

<210> SEQ ID NO 255
<211> LENGTH: 448
<212> TYPE: PRT
<213> ORGANISM: Artificial Sequence
<220> FEATURE:
<223> OTHER INFORMATION: Antibody h5C9n heavy Chain

<400> SEQUENCE: 255

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Ala Trp Ile Asn Met Tyr Thr Gly Glu Pro Thr Tyr Ala Asp Asp Phe
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Gly Asn Ser Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
```

-continued

```
                355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
                435                 440                 445

<210> SEQ ID NO 256
<211> LENGTH: 220
<212> TYPE: PRT
<213> ORGANISM: Artificial Sequence
<220> FEATURE:
<223> OTHER INFORMATION: Antibody h5C9oa Light Chain

<400> SEQUENCE: 256

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ala Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 257
<211> LENGTH: 445
<212> TYPE: PRT
<213> ORGANISM: Artificial Sequence
<220> FEATURE:
<223> OTHER INFORMATION: Antibody h5C9oa heavy Chain

<400> SEQUENCE: 257
```

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
    195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
```

His Tyr Thr Gln Lys Ser Leu Ser Leu Ser Pro Gly Lys
            420                 425                 430
                435                 440                 445

<210> SEQ ID NO 258
<211> LENGTH: 220
<212> TYPE: PRT
<213> ORGANISM: Artificial Sequence
<220> FEATURE:
<223> OTHER INFORMATION: Antibody h5C9ob Light Chain

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 259
<211> LENGTH: 445
<212> TYPE: PRT
<213> ORGANISM: Artificial Sequence
<220> FEATURE:
<223> OTHER INFORMATION: Antibody h5C9ob heavy Chain

<400> SEQUENCE: 259

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

```
Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
             85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 260
<211> LENGTH: 220
<212> TYPE: PRT
<213> ORGANISM: Artificial Sequence
<220> FEATURE:
<223> OTHER INFORMATION: Antibody h5C9oc Light Chain
```

```
<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Gly Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 261
<211> LENGTH: 445
<212> TYPE: PRT
<213> ORGANISM: Artificial Sequence
<220> FEATURE:
<223> OTHER INFORMATION: Antibody h5C9oc heavy Chain

<400> SEQUENCE: 261

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125
```

```
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 262
<211> LENGTH: 220
<212> TYPE: PRT
<213> ORGANISM: Artificial Sequence
<220> FEATURE:
<223> OTHER INFORMATION: Antibody h5C9od Light Chain

<400> SEQUENCE: 262

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45
```

```
Ala Pro Lys Leu Leu Ile Tyr Trp Ala Ser Thr Leu Glu Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Trp Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
210                 215                 220

<210> SEQ ID NO 263
<211> LENGTH: 445
<212> TYPE: PRT
<213> ORGANISM: Artificial Sequence
<220> FEATURE:
<223> OTHER INFORMATION: Antibody h5C9od heavy Chain

<400> SEQUENCE: 263

Glu Val Gln Leu Val Glu Ser Gly Gly Gly Leu Val Gln Pro Gly Gly
 1               5                  10                  15

Ser Leu Arg Leu Ser Cys Ala Val Ser Gly Tyr Thr Phe Ser Met Asn
                20                  25                  30

Trp Val Arg Gln Ala Pro Gly Lys Gly Leu Glu Trp Val Ala Trp Ile
            35                  40                  45

Asn Met Tyr Thr Gly Glu Pro Thr Tyr Ala Asp Asp Phe Lys Gly Arg
 50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Tyr Asn Gly Asn Ser Leu Asp Tyr Trp Gly Gln Gly Thr Leu Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
                130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190
```

```
Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 264
<211> LENGTH: 220
<212> TYPE: PRT
<213> ORGANISM: Artificial Sequence
<220> FEATURE:
<223> OTHER INFORMATION: Antibody h5C9oe Light Chain

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Arg Phe Pro Phe Thr Phe Gly Gln Gly Thr Lys Val Glu Ile
            100                 105                 110
```

Lys Arg Thr Val Ala Ala Pro Ser Val Phe Ile Phe Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 265
<211> LENGTH: 445
<212> TYPE: PRT
<213> ORGANISM: Artificial Sequence
<220> FEATURE:
<223> OTHER INFORMATION: Antibody h5C9oe heavy Chain

<400> SEQUENCE: 265

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

```
Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 266
<211> LENGTH: 220
<212> TYPE: PRT
<213> ORGANISM: Artificial Sequence
<220> FEATURE:
<223> OTHER INFORMATION: Antibody h5C9of Light Chain

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ser Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 267
<211> LENGTH: 445
<212> TYPE: PRT
<213> ORGANISM: Artificial Sequence
<220> FEATURE:
<223> OTHER INFORMATION: Antibody h5C9of heavy Chain

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

```
Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
    435                 440                 445

<210> SEQ ID NO 268
<211> LENGTH: 220
<212> TYPE: PRT
<213> ORGANISM: Artificial Sequence
<220> FEATURE:
<223> OTHER INFORMATION: Antibody h5C9og Light Chain

<400> SEQUENCE: 268

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ser Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 269
<211> LENGTH: 445
```

```
<212> TYPE: PRT
<213> ORGANISM: Artificial Sequence
<220> FEATURE:
<223> OTHER INFORMATION: Antibody h5C9og heavy Chain

<400> SEQUENCE: 269
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 |
| Ser | Leu | Arg | Leu | Ser | Cys | Ala | Val | Ser | Gly | Tyr | Thr | Phe | Ser | Met | Asn |
| | | | 20 | | | | | 25 | | | | | 30 | | |
| Trp | Val | Arg | Gln | Ala | Pro | Gly | Lys | Gly | Leu | Glu | Trp | Val | Ala | Trp | Ile |
| | | 35 | | | | | 40 | | | | | 45 | | | |
| Asn | Met | Tyr | Thr | Gly | Glu | Pro | Thr | Tyr | Ala | Asp | Asp | Phe | Lys | Gly | Arg |
| | 50 | | | | | 55 | | | | | 60 | | | | |
| Phe | Thr | Ile | Ser | Arg | Asp | Asp | Ser | Lys | Asn | Thr | Leu | Tyr | Leu | Gln | Met |
| 65 | | | | | 70 | | | | | 75 | | | | | 80 |
| Asn | Ser | Leu | Arg | Ala | Glu | Asp | Thr | Ala | Val | Tyr | Tyr | Cys | Ala | Arg | Leu |
| | | | | 85 | | | | | 90 | | | | | 95 | |
| Tyr | Arg | Gly | Asn | Ser | Leu | Asp | Tyr | Trp | Gly | Gln | Gly | Thr | Leu | Val | Thr |
| | | | 100 | | | | | 105 | | | | | 110 | | |
| Val | Ser | Ser | Ala | Ser | Thr | Lys | Gly | Pro | Ser | Val | Phe | Pro | Leu | Ala | Pro |
| | | 115 | | | | | 120 | | | | | 125 | | | |
| Ser | Ser | Lys | Ser | Thr | Ser | Gly | Gly | Thr | Ala | Ala | Leu | Gly | Cys | Leu | Val |
| | 130 | | | | | 135 | | | | | 140 | | | | |
| Lys | Asp | Tyr | Phe | Pro | Glu | Pro | Val | Thr | Val | Ser | Trp | Asn | Ser | Gly | Ala |
| 145 | | | | | 150 | | | | | 155 | | | | | 160 |
| Leu | Thr | Ser | Gly | Val | His | Thr | Phe | Pro | Ala | Val | Leu | Gln | Ser | Ser | Gly |
| | | | | 165 | | | | | 170 | | | | | 175 | |
| Leu | Tyr | Ser | Leu | Ser | Ser | Val | Val | Thr | Val | Pro | Ser | Ser | Ser | Leu | Gly |
| | | | 180 | | | | | 185 | | | | | 190 | | |
| Thr | Gln | Thr | Tyr | Ile | Cys | Asn | Val | Asn | His | Lys | Pro | Ser | Asn | Thr | Lys |
| | | 195 | | | | | 200 | | | | | 205 | | | |
| Val | Asp | Lys | Lys | Val | Glu | Pro | Lys | Ser | Cys | Asp | Lys | Thr | His | Thr | Cys |
| 210 | | | | | 215 | | | | | 220 | | | | | |
| Pro | Pro | Cys | Pro | Ala | Pro | Glu | Leu | Leu | Gly | Gly | Pro | Ser | Val | Phe | Leu |
| 225 | | | | | 230 | | | | | 235 | | | | | 240 |
| Phe | Pro | Pro | Lys | Pro | Lys | Asp | Thr | Leu | Met | Ile | Ser | Arg | Thr | Pro | Glu |
| | | | | 245 | | | | | 250 | | | | | 255 | |
| Val | Thr | Cys | Val | Val | Val | Asp | Val | Ser | His | Glu | Asp | Pro | Glu | Val | Lys |
| | | | 260 | | | | | 265 | | | | | 270 | | |
| Phe | Asn | Trp | Tyr | Val | Asp | Gly | Val | Glu | Val | His | Asn | Ala | Lys | Thr | Lys |
| | | 275 | | | | | 280 | | | | | 285 | | | |
| Pro | Arg | Glu | Glu | Gln | Tyr | Asn | Ser | Thr | Tyr | Arg | Val | Val | Ser | Val | Leu |
| 290 | | | | | 295 | | | | | 300 | | | | | |
| Thr | Val | Leu | His | Gln | Asp | Trp | Leu | Asn | Gly | Lys | Glu | Tyr | Lys | Cys | Lys |
| 305 | | | | | 310 | | | | | 315 | | | | | 320 |
| Val | Ser | Asn | Lys | Ala | Leu | Pro | Ala | Pro | Ile | Glu | Lys | Thr | Ile | Ser | Lys |
| | | | | 325 | | | | | 330 | | | | | 335 | |
| Ala | Lys | Gly | Gln | Pro | Arg | Glu | Pro | Gln | Val | Tyr | Thr | Leu | Pro | Pro | Ser |
| | | | 340 | | | | | 345 | | | | | 350 | | |
| Arg | Asp | Glu | Leu | Thr | Lys | Asn | Gln | Val | Ser | Leu | Thr | Cys | Leu | Val | Lys |
| | | 355 | | | | | 360 | | | | | 365 | | | |
| Gly | Phe | Tyr | Pro | Ser | Asp | Ile | Ala | Val | Glu | Trp | Glu | Ser | Asn | Gly | Gln |
| 370 | | | | | 375 | | | | | 380 | | | | | |

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 270
<211> LENGTH: 220
<212> TYPE: PRT
<213> ORGANISM: Artificial Sequence
<220> FEATURE:
<223> OTHER INFORMATION: Antibody h5C9oh Light Chain

<400> SEQUENCE: 270

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Glu Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 271
<211> LENGTH: 445
<212> TYPE: PRT
<213> ORGANISM: Artificial Sequence
<220> FEATURE:
<223> OTHER INFORMATION: Antibody h5C9oh heavy Chain

<400> SEQUENCE: 271

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

-continued

Trp Val Arg Gln Ala Pro Gly Lys Gly Leu Glu Trp Val Ala Trp Ile
    35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 272
<211> LENGTH: 220
<212> TYPE: PRT
<213> ORGANISM: Artificial Sequence
<220> FEATURE:
<223> OTHER INFORMATION: Antibody h5C9oi Light Chain

<400> SEQUENCE: 272

```
Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ser Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 273
<211> LENGTH: 445
<212> TYPE: PRT
<213> ORGANISM: Artificial Sequence
<220> FEATURE:
<223> OTHER INFORMATION: Antibody h5C9oi heavy Chain

<400> SEQUENCE: 273

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Met
                85                  90                  95
```

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 274
<211> LENGTH: 220
<212> TYPE: PRT
<213> ORGANISM: Artificial Sequence
<220> FEATURE:
<223> OTHER INFORMATION: Antibody h5C9oj Light Chain

<400> SEQUENCE: 274

Asp Ile Gln Met Thr Gln Ser Pro Ser Ser Leu Ser Ala Ser Val Gly
1               5                   10                  15

```
Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 275
<211> LENGTH: 445
<212> TYPE: PRT
<213> ORGANISM: Artificial Sequence
<220> FEATURE:
<223> OTHER INFORMATION: Antibody h5C9oj heavy Chain

<400> SEQUENCE: 275

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ala Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160
```

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 276
<211> LENGTH: 220
<212> TYPE: PRT
<213> ORGANISM: Artificial Sequence
<220> FEATURE:
<223> OTHER INFORMATION: Antibody h5C9ok Light Chain

<400> SEQUENCE: 276

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
            50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
              85                  90                  95

Ala Tyr Ser Phe Pro Phe Thr Phe Gly Gln Gly Thr Lys Val Glu Ile
             100                 105                 110

Lys Arg Thr Val Ala Ala Pro Ser Val Phe Ile Phe Pro Pro Ser Asp
             115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
             165                 170                 175

Ser Thr Tyr Ser Leu Ser Ser Thr Leu Thr Leu Ser Lys Ala Asp Tyr
             180                 185                 190

Glu Lys His Lys Val Tyr Ala Cys Glu Val Thr His Gln Gly Leu Ser
             195                 200                 205

Ser Pro Val Thr Lys Ser Phe Asn Arg Gly Glu Cys
             210                 215                 220

<210> SEQ ID NO 277
<211> LENGTH: 445
<212> TYPE: PRT
<213> ORGANISM: Artificial Sequence
<220> FEATURE:
<223> OTHER INFORMATION: Antibody h5C9ok heavy Chain

<400> SEQUENCE: 277

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
             20                  25                  30

Trp Val Arg Gln Ala Pro Gly Lys Gly Leu Glu Trp Val Ala Trp Ile
             35                  40                  45

Asn Met Tyr Thr Gly Glu Pro Thr Tyr Ala Asp Asp Phe Lys Gly Arg
50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
             85                  90                  95

Thr Arg Gly Asn Ser Leu Asp Tyr Trp Gly Gln Gly Thr Leu Val Thr
             100                 105                 110

Val Ser Ser Ala Ser Thr Lys Gly Pro Ser Val Phe Pro Leu Ala Pro
             115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
             165                 170                 175

Leu Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
             195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 278
<211> LENGTH: 220
<212> TYPE: PRT
<213> ORGANISM: Artificial Sequence
<220> FEATURE:
<223> OTHER INFORMATION: Antibody h5C9o1 Light Chain

<400> SEQUENCE: 278

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 279
<211> LENGTH: 445
<212> TYPE: PRT
<213> ORGANISM: Artificial Sequence
<220> FEATURE:
<223> OTHER INFORMATION: Antibody h5C9ol heavy Chain

<400> SEQUENCE: 279

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
            85                  90                  95

Gly Pro Gly Asn Val Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285
```

```
Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 280
<211> LENGTH: 220
<212> TYPE: PRT
<213> ORGANISM: Artificial Sequence
<220> FEATURE:
<223> OTHER INFORMATION: Antibody h5C9om Light Chain

<400> SEQUENCE: 280

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205
```

-continued

```
Ser Pro Val Thr Lys Ser Phe Asn Arg Gly Glu Cys
    210                 215                 220

<210> SEQ ID NO 281
<211> LENGTH: 445
<212> TYPE: PRT
<213> ORGANISM: Artificial Sequence
<220> FEATURE:
<223> OTHER INFORMATION: Antibody h5C9om heavy Chain

<400> SEQUENCE: 281

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Ala Arg Gly Asn Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

```
Arg Asp Glu Leu Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 282
<211> LENGTH: 220
<212> TYPE: PRT
<213> ORGANISM: Artificial Sequence
<220> FEATURE:
<223> OTHER INFORMATION: Antibody h5C9on Light Chain

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 283
<211> LENGTH: 445
<212> TYPE: PRT
<213> ORGANISM: Artificial Sequence
<220> FEATURE:
<223> OTHER INFORMATION: Antibody h5C9on heavy Chain
```

```
<400> SEQUENCE: 283

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Thr
                85                  90                  95

Ala Pro Gly Asn Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

```
Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 284
<211> LENGTH: 220
<212> TYPE: PRT
<213> ORGANISM: Artificial Sequence
<220> FEATURE:
<223> OTHER INFORMATION: Antibody h5C9oo Light Chain

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
            85                  90                  95

Ala Tyr Ser Phe Pro Phe Thr Phe Gly Gln Gly Thr Lys Val Glu Ile
        100                 105                 110

Lys Arg Thr Val Ala Ala Pro Ser Val Phe Ile Phe Pro Pro Ser Asp
    115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
    210                 215                 220

<210> SEQ ID NO 285
<211> LENGTH: 445
<212> TYPE: PRT
<213> ORGANISM: Artificial Sequence
<220> FEATURE:
<223> OTHER INFORMATION: Antibody h5C9oo heavy Chain

<400> SEQUENCE: 285

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
```

```
             50                  55                  60
Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Val Arg Gly Asn Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
            210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 286
<211> LENGTH: 220
<212> TYPE: PRT
<213> ORGANISM: Artificial Sequence
```

```
<220> FEATURE:
<223> OTHER INFORMATION: Antibody h5C9op Light Chain

<400> SEQUENCE: 286

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 287
<211> LENGTH: 445
<212> TYPE: PRT
<213> ORGANISM: Artificial Sequence
<220> FEATURE:
<223> OTHER INFORMATION: Antibody h5C9op heavy Chain

<400> SEQUENCE: 287

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Thr
                85                  90                  95

Ser Arg Gly Asn Gly Met Asp Tyr Trp Gly Gln Gly Thr Leu Val Thr
            100                 105                 110

Val Ser Ser Ala Ser Thr Lys Gly Pro Ser Val Phe Pro Leu Ala Pro
```

```
                115                 120                 125
    Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
    145                 150                 155                 160

Leu Thr Ser Gly Val His Thr Phe Pro Ala Val Leu Gln Ser Ser Gly
                    165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
    225                 230                 235                 240

Phe Pro Pro Lys Pro Lys Asp Thr Leu Met Ile Ser Arg Thr Pro Glu
                    245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
    305                 310                 315                 320

Val Ser Asn Lys Ala Leu Pro Ala Pro Ile Glu Lys Thr Ile Ser Lys
                    325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
    385                 390                 395                 400

Ser Phe Phe Leu Tyr Ser Lys Leu Thr Val Asp Lys Ser Arg Trp Gln
                    405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 288
<211> LENGTH: 220
<212> TYPE: PRT
<213> ORGANISM: Artificial Sequence
<220> FEATURE:
<223> OTHER INFORMATION: Antibody h5C9oq Light Chain

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
```

```
            35                  40                  45
Ala Pro Lys Leu Leu Ile Tyr Trp Ala Ser Thr Leu Glu Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 289
<211> LENGTH: 445
<212> TYPE: PRT
<213> ORGANISM: Artificial Sequence
<220> FEATURE:
<223> OTHER INFORMATION: Antibody h5C9oq heavy Chain

<400> SEQUENCE: 289

Glu Val Gln Leu Val Glu Ser Gly Gly Gly Leu Val Gln Pro Gly Gly
 1               5                  10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
 50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                 85                  90                  95

Tyr Arg Gly Asn Val Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
```

```
                   180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
        210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 290
<211> LENGTH: 220
<212> TYPE: PRT
<213> ORGANISM: Artificial Sequence
<220> FEATURE:
<223> OTHER INFORMATION: Antibody h5C9or Light Chain

<400> SEQUENCE: 290

Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Asn Ser
            20                  25                  30
Gly Asn Gln Lys Ser Tyr Leu Thr Trp Tyr Gln Gln Lys Pro Gly Lys
        35                  40                  45
Ala Pro Lys Leu Leu Ile Tyr Trp Ala Ser Thr Leu Glu Ser Gly Val
    50                  55                  60
Pro Ser Arg Phe Ser Gly Ser Gly Ser Gly Thr Asp Tyr Thr Leu Thr
65                  70                  75                  80
Ile Ser Ser Leu Gln Pro Glu Asp Phe Ala Thr Tyr Tyr Cys Gln Asn
                85                  90                  95
Ala Tyr Ser Phe Pro Phe Thr Phe Gly Gln Gly Thr Lys Val Glu Ile
```

|  |  | 100 |  |  |  | 105 |  |  |  | 110 |  |
|--|--|--|--|--|--|--|--|--|--|--|--|

Lys Arg Thr Val Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 291
<211> LENGTH: 445
<212> TYPE: PRT
<213> ORGANISM: Artificial Sequence
<220> FEATURE:
<223> OTHER INFORMATION: Antibody h5C9or heavy Chain

<400> SEQUENCE: 291

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
            85                  90                  95

Asn Arg Gly Asn Ser Met Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
            210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu

-continued

```
                245                 250                 255
Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 292
<211> LENGTH: 220
<212> TYPE: PRT
<213> ORGANISM: Artificial Sequence
<220> FEATURE:
<223> OTHER INFORMATION: Antibody h5C9os Light Chain

<400> SEQUENCE: 292

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
```

```
                    165                 170                 175
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 293
<211> LENGTH: 445
<212> TYPE: PRT
<213> ORGANISM: Artificial Sequence
<220> FEATURE:
<223> OTHER INFORMATION: Antibody h5C9os heavy Chain

<400> SEQUENCE: 293

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Thr
                85                  90                  95

Gly Thr Gly Asn Thr Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
305                 310                 315                 320
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 294
<211> LENGTH: 220
<212> TYPE: PRT
<213> ORGANISM: Artificial Sequence
<220> FEATURE:
<223> OTHER INFORMATION: Antibody h5C9ot Light Chain

<400> SEQUENCE: 294

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220
```

<210> SEQ ID NO 295
<211> LENGTH: 445
<212> TYPE: PRT
<213> ORGANISM: Artificial Sequence
<220> FEATURE:
<223> OTHER INFORMATION: Antibody h5C9ot heavy Chain

<400> SEQUENCE: 295

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Ser
                85                  90                  95

Ser Met Gly Asn Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
```

```
                370              375              380
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 296
<211> LENGTH: 220
<212> TYPE: PRT
<213> ORGANISM: Artificial Sequence
<220> FEATURE:
<223> OTHER INFORMATION: Antibody h5C9ou Light Chain

<400> SEQUENCE: 296

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 297
<211> LENGTH: 445
<212> TYPE: PRT
<213> ORGANISM: Artificial Sequence
<220> FEATURE:
<223> OTHER INFORMATION: Antibody h5C9ou heavy Chain

<400> SEQUENCE: 297

Glu Val Gln Leu Val Glu Ser Gly Gly Gly Leu Val Gln Pro Gly Gly
1               5                   10                  15
```

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Pro Thr Tyr Ala Asp Asp Phe Lys Gly Arg
 50                      55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
            85                  90                  95

Ser Lys Gly Asn Gly Met Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys

<210> SEQ ID NO 298
<211> LENGTH: 220
<212> TYPE: PRT
<213> ORGANISM: Artificial Sequence
<220> FEATURE:
<223> OTHER INFORMATION: Antibody h5C9ov Light Chain

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 299
<211> LENGTH: 445
<212> TYPE: PRT
<213> ORGANISM: Artificial Sequence
<220> FEATURE:
<223> OTHER INFORMATION: Antibody h5C9ov heavy Chain

<400> SEQUENCE: 299

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

-continued

Asn Ser Leu Arg Ala Glu Asp Thr Ala Val Tyr Tyr Cys Ala Arg Leu
            85                  90                  95

Val Lys Gly Asn Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Val Leu Asp Ser Asp Gly Ser
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 300
<211> LENGTH: 220
<212> TYPE: PRT
<213> ORGANISM: Artificial Sequence
<220> FEATURE:
<223> OTHER INFORMATION: Antibody h5C9ow Light Chain

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 301
<211> LENGTH: 445
<212> TYPE: PRT
<213> ORGANISM: Artificial Sequence
<220> FEATURE:
<223> OTHER INFORMATION: Antibody h5C9ow heavy Chain

<400> SEQUENCE: 301

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Thr Lys Gly Asn Gly Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 302
<211> LENGTH: 220
<212> TYPE: PRT
<213> ORGANISM: Artificial Sequence
<220> FEATURE:
<223> OTHER INFORMATION: Antibody h5C9ox Light Chain

<400> SEQUENCE: 302

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
                35                  40                  45

Ala Pro Lys Leu Leu Ile Tyr Trp Ala Ser Thr Leu Glu Ser Gly Val
50                  55                  60
```

```
Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 303
<211> LENGTH: 445
<212> TYPE: PRT
<213> ORGANISM: Artificial Sequence
<220> FEATURE:
<223> OTHER INFORMATION: Antibody h5C9ox heavy Chain

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
 65                 70                  75                  80

Asn Ser Leu Arg Ala Glu Asp Thr Ala Val Tyr Tyr Cys Ala Arg Ala
                85                  90                  95

Ser Arg Gly Asn Gly Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205
```

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 304
<211> LENGTH: 220
<212> TYPE: PRT
<213> ORGANISM: Artificial Sequence
<220> FEATURE:
<223> OTHER INFORMATION: Antibody h5C9oy Light Chain

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 305
<211> LENGTH: 445
<212> TYPE: PRT
<213> ORGANISM: Artificial Sequence
<220> FEATURE:
<223> OTHER INFORMATION: Antibody h5C9oy heavy Chain

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Ser
                85                  90                  95

Ser Lys Gly Asn Gly Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 306
<211> LENGTH: 220
<212> TYPE: PRT
<213> ORGANISM: Artificial Sequence
<220> FEATURE:
<223> OTHER INFORMATION: Antibody h5C9oz Light Chain

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220

<210> SEQ ID NO 307
<211> LENGTH: 445
<212> TYPE: PRT
<213> ORGANISM: Artificial Sequence
<220> FEATURE:
<223> OTHER INFORMATION: Antibody h5C9oz heavy Chain

<400> SEQUENCE: 307

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Ser Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 308
<211> LENGTH: 220
<212> TYPE: PRT
<213> ORGANISM: Artificial Sequence
<220> FEATURE:
<223> OTHER INFORMATION: Antibody h5C9oaa Light Chain

<400> SEQUENCE: 308

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 309
<211> LENGTH: 445
<212> TYPE: PRT
<213> ORGANISM: Artificial Sequence
<220> FEATURE:

<223> OTHER INFORMATION: Antibody h5C9oaa heavy Chain

<400> SEQUENCE: 309

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Val Arg Gly Asn Gly Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
        435                 440                 445

<210> SEQ ID NO 310
<211> LENGTH: 220
<212> TYPE: PRT
<213> ORGANISM: Artificial Sequence
<220> FEATURE:
<223> OTHER INFORMATION: Antibody h5C9o Light Chain

<400> SEQUENCE: 310

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 311
<211> LENGTH: 445
<212> TYPE: PRT
<213> ORGANISM: Artificial Sequence
<220> FEATURE:
<223> OTHER INFORMATION: Antibody h5C9o heavy Chain with Fc mutations

<400> SEQUENCE: 311

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
            50                  55                  60

Phe Thr Ile Ser Arg Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 312
<211> LENGTH: 220

<212> TYPE: PRT
<213> ORGANISM: Artificial Sequence
<220> FEATURE:
<223> OTHER INFORMATION: Antibody h5C9oab Light Chain

<400> SEQUENCE: 312

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Tyr Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 313
<211> LENGTH: 445
<212> TYPE: PRT
<213> ORGANISM: Artificial Sequence
<220> FEATURE:
<223> OTHER INFORMATION: Antibody h5C9oab heavy Chain

<400> SEQUENCE: 313

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 314
<211> LENGTH: 220
<212> TYPE: PRT
<213> ORGANISM: Artificial Sequence
<220> FEATURE:
<223> OTHER INFORMATION: Antibody h5C9oad Light Chain

<400> SEQUENCE: 314

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

```
Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Tyr Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 315
<211> LENGTH: 445
<212> TYPE: PRT
<213> ORGANISM: Artificial Sequence
<220> FEATURE:
<223> OTHER INFORMATION: Antibody h5C9oad heavy Chain

<400> SEQUENCE: 315

Glu Val Gln Leu Val Glu Ser Gly Gly Gly Leu Val Gln Pro Gly Gly
1               5                  10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
 50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Thr Val Pro Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 316
<211> LENGTH: 220
<212> TYPE: PRT
<213> ORGANISM: Artificial Sequence
<220> FEATURE:
<223> OTHER INFORMATION: Antibody h5C9oae Light Chain

<400> SEQUENCE: 316

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95
```

```
Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 317
<211> LENGTH: 445
<212> TYPE: PRT
<213> ORGANISM: Artificial Sequence
<220> FEATURE:
<223> OTHER INFORMATION: Antibody h5C9oae heavy Chain

<400> SEQUENCE: 317

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Arg Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 318
<211> LENGTH: 220
<212> TYPE: PRT
<213> ORGANISM: Artificial Sequence
<220> FEATURE:
<223> OTHER INFORMATION: Antibody h5C9oaf Light Chain

<400> SEQUENCE: 318

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Tyr Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

Gln Ser Gly Asn Ser Gln Glu Ser Val Thr Glu Gln Asp Ser Lys Asp
              165                 170                 175

Ser Thr Tyr Ser Leu Ser Ser Thr Leu Thr Leu Ser Lys Ala Asp Tyr
              180                 185                 190

Glu Lys His Lys Val Tyr Ala Cys Glu Val Thr His Gln Gly Leu Ser
              195                 200                 205

Ser Pro Val Thr Lys Ser Phe Asn Arg Gly Glu Cys
              210                 215                 220

<210> SEQ ID NO 319
<211> LENGTH: 445
<212> TYPE: PRT
<213> ORGANISM: Artificial Sequence
<220> FEATURE:
<223> OTHER INFORMATION: Antibody h5C9oaf heavy Chain with Fc mutations

<400> SEQUENCE: 319

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
              20                  25                  30

Trp Val Arg Gln Ala Pro Gly Lys Gly Leu Glu Trp Val Ala Trp Ile
          35                  40                  45

Asn Met Tyr Thr Gly Glu Pro Thr Tyr Ala Asp Asp Phe Lys Gly Arg
  50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
              85                  90                  95

Phe Asn Gly Asn Ser Leu Asp Tyr Trp Gly Gln Gly Thr Leu Val Thr
              100                 105                 110

Val Ser Ser Ala Ser Thr Lys Gly Pro Ser Val Phe Pro Leu Ala Pro
          115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
              165                 170                 175

Leu Tyr Ser Leu Ser Ser Val Val Thr Val Pro Ser Ser Ser Leu Gly
              180                 185                 190

Thr Gln Thr Tyr Ile Cys Asn Val Asn His Lys Pro Ser Asn Thr Lys
          195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
              245                 250                 255

Val Thr Cys Val Val Val Asp Val Ser His Glu Asp Pro Glu Val Lys
              260                 265                 270

Phe Asn Trp Tyr Val Asp Gly Val Glu Val His Asn Ala Lys Thr Lys
          275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 320
<211> LENGTH: 220
<212> TYPE: PRT
<213> ORGANISM: Artificial Sequence
<220> FEATURE:
<223> OTHER INFORMATION: Antibody h5C9oag Light Chain

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 321
<211> LENGTH: 445
<212> TYPE: PRT
<213> ORGANISM: Artificial Sequence
<220> FEATURE:
<223> OTHER INFORMATION: Antibody h5C9oag heavy Chain with Fc mutations

<400> SEQUENCE: 321

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Ala Arg Gly Asn Ser Ile Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365
```

-continued

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 322
<211> LENGTH: 220
<212> TYPE: PRT
<213> ORGANISM: Artificial Sequence
<220> FEATURE:
<223> OTHER INFORMATION: Antibody h5C9oah Light Chain

<400> SEQUENCE: 322

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 323
<211> LENGTH: 445
<212> TYPE: PRT
<213> ORGANISM: Artificial Sequence
<220> FEATURE:
<223> OTHER INFORMATION: Antibody h5C9oah heavy Chain

<400> SEQUENCE: 323

Glu Val Gln Leu Val Glu Ser Gly Gly Gly Leu Val Gln Pro Gly Gly

-continued

```
1               5                   10                  15
Ser Leu Arg Leu Ser Cys Ala Val Ser Gly Tyr Thr Phe Ser Met Asn
                20                  25                  30
Trp Val Arg Gln Ala Pro Gly Lys Gly Leu Glu Trp Val Ala Trp Ile
                35                  40                  45
Asn Met Tyr Thr Gly Glu Pro Thr Tyr Ala Asp Asp Phe Lys Gly Arg
 50                  55                  60
Phe Thr Ile Ser Arg Asp Asp Ser Lys Asn Thr Leu Tyr Leu Gln Met
 65                  70                  75                  80
Asn Ser Leu Arg Ala Glu Asp Thr Ala Val Tyr Tyr Cys Ala Arg Ser
                85                  90                  95
Ser Arg Gly Asn Gly Phe Asp Tyr Trp Gly Gln Gly Thr Leu Val Thr
                100                 105                 110
Val Ser Ser Ala Ser Thr Lys Gly Pro Ser Val Phe Pro Leu Ala Pro
                115                 120                 125
Ser Ser Lys Ser Thr Ser Gly Gly Thr Ala Ala Leu Gly Cys Leu Val
                130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                195                 200                 205
Val Asp Lys Lys Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
                275                 280                 285
Pro Arg Glu Glu Gln Tyr Asn Ser Thr Tyr Arg Val Val Ser Val Leu
                290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
                370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
```

His Tyr Thr Gln Lys Ser Leu Ser Leu Ser Pro Gly Lys
        435                 440                 445

<210> SEQ ID NO 324
<211> LENGTH: 220
<212> TYPE: PRT
<213> ORGANISM: Artificial Sequence
<220> FEATURE:
<223> OTHER INFORMATION: Antibody h5C9oai Light Chain

<400> SEQUENCE: 324

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 325
<211> LENGTH: 445
<212> TYPE: PRT
<213> ORGANISM: Artificial Sequence
<220> FEATURE:
<223> OTHER INFORMATION: Antibody h5C9oai heavy Chain with Fc mutations

<400> SEQUENCE: 325

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met 65                  70                  75                  80
Asn Ser Leu Arg Ala Glu Asp Thr Ala Val Tyr Tyr Cys Ala Arg Leu
                85                  90                  95
Ala Arg Gly Asn Ser Met Asp Tyr Trp Gly Gln Gly Thr Leu Val Thr
                100                 105                 110
Val Ser Ser Ala Ser Thr Lys Gly Pro Ser Val Phe Pro Leu Ala Pro
                115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                195                 200                 205
Val Asp Lys Lys Val Glu Pro Lys Ser Cys Asp Lys Thr His Thr Cys
        210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
                290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly Lys
                435                 440                 445

<210> SEQ ID NO 326
<211> LENGTH: 220
<212> TYPE: PRT
<213> ORGANISM: Artificial Sequence
<220> FEATURE:
<223> OTHER INFORMATION: Antibody h5C9oaj Light Chain -continued

<400> SEQUENCE: 326

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Tyr Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 327
<211> LENGTH: 445
<212> TYPE: PRT
<213> ORGANISM: Artificial Sequence
<220> FEATURE:
<223> OTHER INFORMATION: Antibody h5C9oaj heavy Chain

<400> SEQUENCE: 327

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Ala Arg Gly Asn Ser Ile Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
```

```
              130                 135                 140
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 328
<211> LENGTH: 220
<212> TYPE: PRT
<213> ORGANISM: Artificial Sequence
<220> FEATURE:
<223> OTHER INFORMATION: Antibody h5C9oak Light Chain

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
```

```
                50              55              60
Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                     85                  90                  95

Ala Tyr Tyr Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 329
<211> LENGTH: 445
<212> TYPE: PRT
<213> ORGANISM: Artificial Sequence
<220> FEATURE:
<223> OTHER INFORMATION: Antibody h5C9oak heavy Chain

<400> SEQUENCE: 329

Glu Val Gln Leu Val Glu Ser Gly Gly Gly Leu Val Gln Pro Gly Gly
  1               5                  10                  15

Ser Leu Arg Leu Ser Cys Ala Val Ser Gly Tyr Thr Phe Ser Met Asn
                 20                  25                  30

Trp Val Arg Gln Ala Pro Gly Lys Gly Leu Glu Trp Val Ala Trp Ile
             35                  40                  45

Asn Met Tyr Thr Gly Glu Pro Thr Tyr Ala Asp Asp Phe Lys Gly Arg
 50                  55                  60

Phe Thr Ile Ser Arg Asp Asp Ser Lys Asn Thr Leu Tyr Leu Gln Met
 65                  70                  75                  80

Asn Ser Leu Arg Ala Glu Asp Thr Ala Val Tyr Tyr Cys Ala Arg Ser
                 85                  90                  95

Ser Arg Gly Asn Gly Phe Asp Tyr Trp Gly Gln Gly Thr Leu Val Thr
                100                 105                 110

Val Ser Ser Ala Ser Thr Lys Gly Pro Ser Val Phe Pro Leu Ala Pro
             115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
```

-continued

```
                195                 200                 205
Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
                290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 330
<211> LENGTH: 220
<212> TYPE: PRT
<213> ORGANISM: Artificial Sequence
<220> FEATURE:
<223> OTHER INFORMATION: Antibody h5C9oa1 Light Chain

<400> SEQUENCE: 330

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
                35                  40                  45

Ala Pro Lys Leu Leu Ile Tyr Trp Ala Ser Thr Leu Glu Ser Gly Val
                50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Tyr Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
```

```
            115                 120                 125
Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 331
<211> LENGTH: 445
<212> TYPE: PRT
<213> ORGANISM: Artificial Sequence
<220> FEATURE:
<223> OTHER INFORMATION: Antibody h5C9oa1 heavy Chain with Fc mutations

<400> SEQUENCE: 331

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Ala Arg Gly Asn Ser Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
```

```
                    260                 265                 270
Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 332
<211> LENGTH: 220
<212> TYPE: PRT
<213> ORGANISM: Artificial Sequence
<220> FEATURE:
<223> OTHER INFORMATION: Antibody h5C9oam Light Chain

<400> SEQUENCE: 332

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
```

```
                180              185              190
Glu Lys His Lys Val Tyr Ala Cys Glu Val Thr His Gln Gly Leu Ser
            195              200              205

Ser Pro Val Thr Lys Ser Phe Asn Arg Gly Glu Cys
        210              215              220

<210> SEQ ID NO 333
<211> LENGTH: 445
<212> TYPE: PRT
<213> ORGANISM: Artificial Sequence
<220> FEATURE:
<223> OTHER INFORMATION: Antibody h5C9oam heavy Chain with Fc mutations

<400> SEQUENCE: 333

Glu Val Gln Leu Val Glu Ser Gly Gly Gly Leu Val Gln Pro Gly Gly
1               5                  10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Ala Arg Gly Asn Ser Ile Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
```

```
                    325                 330                 335
Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 334
<211> LENGTH: 220
<212> TYPE: PRT
<213> ORGANISM: Artificial Sequence
<220> FEATURE:
<223> OTHER INFORMATION: Antibody h5C9oan Light Chain

<400> SEQUENCE: 334

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 335
<211> LENGTH: 445
<212> TYPE: PRT
```

<213> ORGANISM: Artificial Sequence
<220> FEATURE:
<223> OTHER INFORMATION: Antibody h5C9oan heavy Chain with Fc mutations

<400> SEQUENCE: 335

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Ser
                85                  90                  95

Ser Arg Gly Asn Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

```
                385                 390                 395                 400
Ser Phe Phe Leu Tyr Ser Lys Leu Thr Val Asp Lys Ser Arg Trp Gln
                    405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445
```

<210> SEQ ID NO 336
<211> LENGTH: 220
<212> TYPE: PRT
<213> ORGANISM: Artificial Sequence
<220> FEATURE:
<223> OTHER INFORMATION: Antibody h5C9oao Light Chain

<400> SEQUENCE: 336

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
        50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 337
<211> LENGTH: 445
<212> TYPE: PRT
<213> ORGANISM: Artificial Sequence
<220> FEATURE:
<223> OTHER INFORMATION: Antibody h5C9oao heavy Chain

<400> SEQUENCE: 337

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
                20                  25                  30
```

```
Trp Val Arg Gln Ala Pro Gly Lys Gly Leu Glu Trp Val Ala Trp Ile
         35                  40                  45
Asn Met Tyr Thr Gly Glu Pro Thr Tyr Ala Asp Asp Phe Lys Gly Arg
 50                  55                  60
Phe Thr Ile Ser Arg Asp Asp Ser Lys Asn Thr Leu Tyr Leu Gln Met
 65                  70                  75                  80
Asn Ser Leu Arg Ala Glu Asp Thr Ala Val Tyr Tyr Cys Ala Arg Leu
                 85                  90                  95
Ala Arg Gly Asn Ser Met Asp Tyr Trp Gly Gln Gly Thr Leu Val Thr
                100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
        210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly Lys
        435                 440                 445
```

```
<210> SEQ ID NO 338
<211> LENGTH: 220
<212> TYPE: PRT
<213> ORGANISM: Artificial Sequence
<220> FEATURE:
<223> OTHER INFORMATION: Antibody h5C9oap Light Chain

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Gln Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 339
<211> LENGTH: 445
<212> TYPE: PRT
<213> ORGANISM: Artificial Sequence
<220> FEATURE:
<223> OTHER INFORMATION: Antibody h5C9oap heavy Chain with Fc mutations

<400> SEQUENCE: 339

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95
```

-continued

```
Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 340
<211> LENGTH: 220
<212> TYPE: PRT
<213> ORGANISM: Artificial Sequence
<220> FEATURE:
<223> OTHER INFORMATION: Antibody h5C9oaq Light Chain

<400> SEQUENCE: 340

Asp Ile Gln Met Thr Gln Ser Pro Ser Ser Leu Ser Ala Ser Val Gly
1               5                   10                  15
```

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Phe Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
            85                  90                  95

Ala Tyr Ser Phe Pro Phe Thr Phe Gly Gln Gly Thr Lys Val Glu Ile
        100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 341
<211> LENGTH: 445
<212> TYPE: PRT
<213> ORGANISM: Artificial Sequence
<220> FEATURE:
<223> OTHER INFORMATION: Antibody h5C9oaq heavy Chain

<400> SEQUENCE: 341

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Gln Thr Tyr Ala Asp Asp Phe Lys Gly Arg
 50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
            85                  90                  95

Tyr Asn Gly Asn Ser Leu Asp Tyr Trp Gly Gln Gly Thr Leu Val Thr
        100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 342
<211> LENGTH: 220
<212> TYPE: PRT
<213> ORGANISM: Artificial Sequence
<220> FEATURE:
<223> OTHER INFORMATION: Antibody h5C9oar Light Chain

<400> SEQUENCE: 342

Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Asn Trp
            20                  25                  30
Gly Asn Gln Lys Ser Tyr Leu Thr Trp Tyr Gln Gln Lys Pro Gly Lys
        35                  40                  45
Ala Pro Lys Leu Leu Ile Tyr Trp Ala Ser Thr Leu Trp Ser Gly Val
    50                  55                  60
Pro Ser Arg Phe Ser Gly Ser Gly Ser Gly Thr Asp Tyr Thr Leu Thr
65                  70                  75                  80

```
Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220

<210> SEQ ID NO 343
<211> LENGTH: 445
<212> TYPE: PRT
<213> ORGANISM: Artificial Sequence
<220> FEATURE:
<223> OTHER INFORMATION: Antibody h5C9oar heavy Chain with Fc mutations

<400> SEQUENCE: 343

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Asn Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220
```

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 344
<211> LENGTH: 220
<212> TYPE: PRT
<213> ORGANISM: Artificial Sequence
<220> FEATURE:
<223> OTHER INFORMATION: Antibody chimeric 5C9 Light Chain

<400> SEQUENCE: 344

Asp Ile Leu Leu Thr Gln Ser Pro Leu Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Ser Tyr Leu Thr Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Ala Arg Phe Thr Gly Ser Gly Ser Gly Thr Asp Phe Ser Leu Thr
65                  70                  75                  80

Ile Ser Ser Val Gln Thr Glu Asp Leu Ala Val Tyr Tyr Cys Gln Asn
                85                  90                  95

Ala Tyr Ser Phe Pro Phe Thr Phe Gly Ser Gly Thr Lys Leu Glu Ile
            100                 105                 110

Asn Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 345
<211> LENGTH: 448
<212> TYPE: PRT
<213> ORGANISM: Artificial Sequence
<220> FEATURE:
<223> OTHER INFORMATION: Antibody chimeric 5C9 heavy Chain

<400> SEQUENCE: 345

Glu Val Lys Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Met Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ser Arg Leu Tyr Asn Gly Asn Ser Leu Asp Tyr Trp Gly Gln Gly Thr
            100                 105                 110

Ser Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                    325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 346
<211> LENGTH: 220
<212> TYPE: PRT
<213> ORGANISM: Artificial Sequence
<220> FEATURE:
<223> OTHER INFORMATION: Antibody chimeric 9A1 Light Chain

<400> SEQUENCE: 346

```
Asp Ile Leu Leu Thr Gln Ser Pro Leu Ser Leu Thr Val Thr Ala Gly
1               5                   10                  15

Glu Lys Val Thr Met Ser Cys Lys Ser Ser Gln Ser Leu Leu Asn Gly
                20                  25                  30

Gly Asn Leu Lys Asn Tyr Leu Thr Trp Tyr Gln Gln Lys Pro Gly Gln
            35                  40                  45

Pro Pro Lys Leu Leu Thr Tyr Trp Ala Ser Thr Arg Glu Ser Gly Val
    50                  55                  60

Pro Val Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Gly Tyr Phe Tyr Pro Tyr Thr Phe Gly Gly Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205
```

Ser Pro Val Thr Lys Ser Phe Asn Arg Gly Glu Cys
    210                 215                 220

<210> SEQ ID NO 347
<211> LENGTH: 448
<212> TYPE: PRT
<213> ORGANISM: Artificial Sequence
<220> FEATURE:
<223> OTHER INFORMATION: Antibody chimeric 9A1 heavy Chain

<400> SEQUENCE: 347

Glu Val Gln Leu Gln Gln Ser Gly Ala Glu Leu Val Arg Pro Gly Thr
1               5                   10                  15

Ser Val Lys Val Ser Cys Lys Ala Ser Arg Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Met Ile Asn Pro Gly Ser Gly Gly Thr His Tyr Asn Glu Lys Phe
    50                  55                  60

Lys Val Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Gly Gly Phe Gly Asn Ser Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 348
<211> LENGTH: 220
<212> TYPE: PRT
<213> ORGANISM: Artificial Sequence
<220> FEATURE:
<223> OTHER INFORMATION: Antibody chimeric 15G11 Light Chain

<400> SEQUENCE: 348

Asp Ile Met Met Thr Gln Ser Pro Leu Ser Leu Thr Val Thr Ala Gly
1               5                   10                  15

Glu Lys Val Thr Met Asn Cys Lys Ser Ser Gln Ser Leu Leu Asn Gly
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Ala Arg Phe Thr Gly Ser Gly Ser Gly Thr Asp Phe Thr Leu Thr
65                  70                  75                  80

Ile Asn Thr Val Gln Ala Glu Asp Leu Ala Val Tyr Tyr Cys Gln Asn
                85                  90                  95

Asp Tyr Phe Tyr Pro Leu Thr Phe Gly Thr Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 349
<211> LENGTH: 448
<212> TYPE: PRT
<213> ORGANISM: Artificial Sequence
<220> FEATURE:
<223> OTHER INFORMATION: Antibody chimeric 15G11 heavy Chain

<400> SEQUENCE: 349

```
Glu Val Gln Leu Gln Glu Ser Gly Gly Leu Val Gln Pro Gly Gly
1               5                   10                  15

Ser Arg Lys Leu Ser Cys Ala Ala Ser Gly Phe Ser Phe Ser Ser Phe
            20                  25                  30

Gly Met His Trp Val Arg Gln Ala Pro Glu Lys Gly Leu Glu Trp Val
        35                  40                  45

Ala Phe Ile Ser Ser Gly Ser Ser Pro Ile Tyr Tyr Ala Asp Thr Val
50                  55                  60

Lys Gly Arg Phe Thr Val Ser Arg Asp Asn Pro Lys Asn Thr Leu Phe
65                  70                  75                  80

Leu Gln Met Thr Ser Leu Arg Ser Glu Asp Thr Ala Met Tyr Phe Cys
            85                  90                  95

Ala Arg Asn Tyr Tyr Gly Asn Ala Met Asp Tyr Trp Gly Gln Gly Ser
            100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415
```

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 350
<211> LENGTH: 213
<212> TYPE: PRT
<213> ORGANISM: Artificial Sequence
<220> FEATURE:
<223> OTHER INFORMATION: Antibody chimeric 7H1 Light Chain

<400> SEQUENCE: 350

Asp Ile Val Leu Thr Gln Ser Pro Ala Ile Leu Ser Val Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Gly Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Thr Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 351
<211> LENGTH: 449
<212> TYPE: PRT
<213> ORGANISM: Artificial Sequence
<220> FEATURE:
<223> OTHER INFORMATION: Antibody chimeric 7H1 heavy Chain

<400> SEQUENCE: 351

Lys Val Gln Leu Gln Glu Ser Gly Gly Gly Ser Val Gln Pro Gly Gly
1               5                   10                  15

Ser Leu Lys Leu Ser Cys Ala Ala Ser Gly Phe Thr Phe Ser Ser Tyr
            20                  25                  30

Ser Met Ser Trp Val Arg Gln Thr Pro Glu Lys Arg Leu Glu Trp Val
        35                  40                  45

Ala Tyr Ile Ser Asn Leu Gly Gly Ala Thr Tyr Tyr Pro Asp Thr Val
    50                  55                  60
```

```
Lys Gly Arg Phe Thr Val Ser Arg Asp Asn Ala Arg Asn Ser Leu Tyr
 65                  70                  75                  80

Leu Gln Met Thr Ser Leu Lys Ser Asp Asp Thr Ala Met Tyr Tyr Cys
                 85                  90                  95

Thr Arg His Asn Tyr Gly Tyr Asp Gly Phe Ala Asp Trp Gly Gln Gly
            100                 105                 110

Thr Leu Ala Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 352
<211> LENGTH: 220
<212> TYPE: PRT
```

<213> ORGANISM: Artificial Sequence
<220> FEATURE:
<223> OTHER INFORMATION: Antibody h5C9o Light Chain with CH1 mutation

<400> SEQUENCE: 352

```
Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Asn Ser
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Glu Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 353
<211> LENGTH: 445
<212> TYPE: PRT
<213> ORGANISM: Artificial Sequence
<220> FEATURE:
<223> OTHER INFORMATION: Antibody h5C9o heavy Chain with CH1 and Fc
      mutations

<400> SEQUENCE: 353

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110
```

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 354
<211> LENGTH: 220
<212> TYPE: PRT
<213> ORGANISM: Artificial Sequence
<220> FEATURE:
<223> OTHER INFORMATION: Antibody h5C9ob Light Chain with CH1 mutations

<400> SEQUENCE: 354

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

```
Gly Asn Gln Lys Ser Tyr Leu Thr Trp Tyr Gln Gln Lys Pro Gly Lys
            35                  40                  45

Ala Pro Lys Leu Leu Ile Tyr Trp Ala Ser Thr Leu Glu Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Asn
                 85                  90                  95

Ala Tyr Phe Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 355
<211> LENGTH: 445
<212> TYPE: PRT
<213> ORGANISM: Artificial Sequence
<220> FEATURE:
<223> OTHER INFORMATION: Antibody h5C9ob heavy Chain with CH1 and Fc
      mutations

<400> SEQUENCE: 355

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
            35                  40                  45

Asn Met Tyr Thr Gly Glu Pro Thr Tyr Ala Asp Asp Phe Lys Gly Arg
 50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
```

```
                    165                 170                 175
Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 356
<211> LENGTH: 220
<212> TYPE: PRT
<213> ORGANISM: Artificial Sequence
<220> FEATURE:
<223> OTHER INFORMATION: Antibody h5C9oap Light Chain with CH1 mutations

<400> SEQUENCE: 356

Asp Ile Gln Met Thr Gln Ser Pro Ser Ser Leu Ser Ala Ser Val Gly
1               5                   10                  15

Asp Arg Val Thr Ile Thr Cys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Gln Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
```

```
                  85                  90                  95
Ala Tyr Ser Phe Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 357
<211> LENGTH: 445
<212> TYPE: PRT
<213> ORGANISM: Artificial Sequence
<220> FEATURE:
<223> OTHER INFORMATION: Antibody h5C9oap heavy Chain with CH1 and Fc
      mutations

<400> SEQUENCE: 357

Glu Val Gln Leu Val Glu Ser Gly Gly Gly Leu Val Gln Pro Gly Gly
1               5                  10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Arg Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220
```

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 358
<211> LENGTH: 220
<212> TYPE: PRT
<213> ORGANISM: Artificial Sequence
<220> FEATURE:
<223> OTHER INFORMATION: Antibody h5C9oaq Light Chain with CH1 mutations

<400> SEQUENCE: 358

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Phe Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 359
<211> LENGTH: 445
<212> TYPE: PRT
<213> ORGANISM: Artificial Sequence
<220> FEATURE:
<223> OTHER INFORMATION: Antibody h5C9oaq heavy Chain with CH1 and Fc
      mutations

<400> SEQUENCE: 359

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Gln Thr Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285
```

```
Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 360
<211> LENGTH: 220
<212> TYPE: PRT
<213> ORGANISM: Artificial Sequence
<220> FEATURE:
<223> OTHER INFORMATION: Antibody h5C9oar Light Chain with CH1 mutation

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Trp
            20                  25                  30

Gly Asn Gln Lys Ser Tyr Leu Thr Trp Tyr Gln Gln Lys Pro Gly Lys
        35                  40                  45

Ala Pro Lys Leu Leu Ile Tyr Trp Ala Ser Thr Leu Trp Ser Gly Val
    50                  55                  60

Pro Ser Arg Phe Ser Gly Ser Gly Ser Gly Thr Asp Tyr Thr Leu Thr
65                  70                  75                  80

Ile Ser Ser Leu Gln Pro Glu Asp Phe Ala Thr Tyr Tyr Cys Gln Asn
                85                  90                  95

Ala Tyr Ser Phe Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205
```

```
Ser Pro Val Thr Lys Ser Phe Asn Arg Gly Glu Cys
        210                 215                 220

<210> SEQ ID NO 361
<211> LENGTH: 445
<212> TYPE: PRT
<213> ORGANISM: Artificial Sequence
<220> FEATURE:
<223> OTHER INFORMATION: Antibody h5C9oar heavy Chain with CH1 and Fc
      mutations

<400> SEQUENCE: 361

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Phe Ser Met Asn
            20                  25                  30

Trp Val Arg Gln Ala Pro Gly Lys Gly Leu Glu Trp Val Ala Trp Ile
        35                  40                  45

Asn Met Tyr Thr Gly Glu Pro Asn Tyr Ala Asp Asp Phe Lys Gly Arg
    50                  55                  60

Phe Thr Ile Ser Arg Asp Asp Ser Lys Asn Thr Leu Tyr Leu Gln Met
65                  70                  75                  80

Asn Ser Leu Arg Ala Glu Asp Thr Ala Val Tyr Tyr Cys Ala Arg Leu
                85                  90                  95

Tyr Asn Gly Asn Ser Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
```

-continued

```
                    340                 345                 350
Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
                435                 440                 445

<210> SEQ ID NO 362
<211> LENGTH: 33
<212> TYPE: PRT
<213> ORGANISM: Artificial Sequence
<220> FEATURE:
<223> OTHER INFORMATION: A general formula of light chain variable
      region (VL)
<220> FEATURE:
<221> NAME/KEY: MISC_FEATURE
<222> LOCATION: (1)..(1)
<223> OTHER INFORMATION: [FW1]; VL framework regions
<220> FEATURE:
<221> NAME/KEY: MISC_FEATURE
<222> LOCATION: (1)..(1)
<223> OTHER INFORMATION: X1 represents amino acid residues Isoleucine
      (I), Arginine (R), Serine (S), or Lysine (K)
<220> FEATURE:
<221> NAME/KEY: MISC_FEATURE
<222> LOCATION: (2)..(2)
<223> OTHER INFORMATION: X2 represents amino acid residues Threonine
      (T), Alanine (A), or Serine (S)
<220> FEATURE:
<221> NAME/KEY: MISC_FEATURE
<222> LOCATION: (4)..(4)
<223> OTHER INFORMATION: X3 represents amino acid residues Threonine
      (T), Serine (S), or Glutamine (Q)
<220> FEATURE:
<221> NAME/KEY: MISC_FEATURE
<222> LOCATION: (5)..(5)
<223> OTHER INFORMATION: X4 represents amino acid residues Aspartic acid
      (D), Serine (S), or Threonine (T)
<220> FEATURE:
<221> NAME/KEY: MISC_FEATURE
<222> LOCATION: (6)..(6)
<223> OTHER INFORMATION: X5 represents amino acid residues Isoleucine
      (I), Valine (V), or Leucine
<220> FEATURE:
<221> NAME/KEY: MISC_FEATURE
<222> LOCATION: (7)..(7)
<223> OTHER INFORMATION: X6 represents a bond or amino acid residues
      compromised Valine (V), Leucine (L), or Phenylalanine (F)
<220> FEATURE:
<221> NAME/KEY: MISC_FEATURE
<222> LOCATION: (8)..(8)
<223> OTHER INFORMATION: X7 represents a bond or amino acid residues
      compromised Histidine (H), Asparagine (N)
<220> FEATURE:
<221> NAME/KEY: MISC_FEATURE
<222> LOCATION: (9)..(9)
<223> OTHER INFORMATION: X8 represents a bond or amino acid residues
      compromised of Serine (S), Tryptophan (W), or Glycine (G)
<220> FEATURE:
<221> NAME/KEY: MISC_FEATURE
<222> LOCATION: (10)..(10)
<223> OTHER INFORMATION: X9 represents a bond or amino acid residues
      compromised of Glycine (G)
<220> FEATURE:
<221> NAME/KEY: MISC_FEATURE
```

```
<222> LOCATION: (11)..(11)
<223> OTHER INFORMATION: X10 represents a bond or amino acid residues
      compromised of Asparagine (N)
<220> FEATURE:
<221> NAME/KEY: MISC_FEATURE
<222> LOCATION: (12)..(12)
<223> OTHER INFORMATION: X11 represents a bond or amino acid residues
      compromised of Glycine (G), Glutamine (Q), or Leucine (L)
<220> FEATURE:
<221> NAME/KEY: MISC_FEATURE
<222> LOCATION: (13)..(13)
<223> OTHER INFORMATION: X12 represents a bond or amino acid residues
      compromised of Aspartic acid (D), Asparagine (N), Lysine (K), or
      Arginine (R)
<220> FEATURE:
<221> NAME/KEY: MISC_FEATURE
<222> LOCATION: (14)..(14)
<223> OTHER INFORMATION: X13 represents amino acid residues Aspartic
      acid (D), Asparagine (N), Serine (S), or Threonine (T)
<220> FEATURE:
<221> NAME/KEY: MISC_FEATURE
<222> LOCATION: (15)..(15)
<223> OTHER INFORMATION: X14 represents amino acid residues Aspartic
      acid (D), or Tyrosine (Y)
<220> FEATURE:
<221> NAME/KEY: MISC_FEATURE
<222> LOCATION: (16)..(16)
<223> OTHER INFORMATION: X15 represents amino acid residues Methionine
      (M), or Leucine (L)
<220> FEATURE:
<221> NAME/KEY: MISC_FEATURE
<222> LOCATION: (17)..(17)
<223> OTHER INFORMATION: X16 represents amino acid residues Asparagine
      (N), Tyrosine (Y), Histidine (H), Glutamine (Q), Threonine (T), or
      Alanine (A)
<220> FEATURE:
<221> NAME/KEY: MISC_FEATURE
<222> LOCATION: (17)..(18)
<223> OTHER INFORMATION: [FW2]; VL framework regions
<220> FEATURE:
<221> NAME/KEY: MISC_FEATURE
<222> LOCATION: (18)..(18)
<223> OTHER INFORMATION: X17 represents amino acid residues Glutamic
      acid (E), Tyrosine (Y), Aspartic acid (D), Glycine (G), Lysine
      (K), or Tryptophan (W)
<220> FEATURE:
<221> NAME/KEY: MISC_FEATURE
<222> LOCATION: (19)..(19)
<223> OTHER INFORMATION: X18 represents amino acid residues Glycine (G),
      Threonine (T), Valine (V), or Alanine (A)
<220> FEATURE:
<221> NAME/KEY: MISC_FEATURE
<222> LOCATION: (20)..(20)
<223> OTHER INFORMATION: X19 represents amino acid residues Asparagine
      (N), or Serine (S)
<220> FEATURE:
<221> NAME/KEY: MISC_FEATURE
<222> LOCATION: (21)..(21)
<223> OTHER INFORMATION: X20 represents amino acid residues Threonine
      (T), or Asparagine (N)
<220> FEATURE:
<221> NAME/KEY: MISC_FEATURE
<222> LOCATION: (22)..(22)
<223> OTHER INFORMATION: X21 represents amino acid residues Leucine (L),
      or Arginine (R)
<220> FEATURE:
<221> NAME/KEY: MISC_FEATURE
<222> LOCATION: (23)..(23)
<223> OTHER INFORMATION: X22 represents amino acid residues Arginine
      (R), Alanine (A), Phenylalanine (F), Tryptophan (W), Glutamine
      (Q), Glutamic acid (E), or Aspartic acid (D)
<220> FEATURE:
<221> NAME/KEY: MISC_FEATURE
<222> LOCATION: (24)..(24)
<223> OTHER INFORMATION: X23 represents amino acid residues Proline (P),
      or Serine (S)
<220> FEATURE:
<221> NAME/KEY: MISC_FEATURE
<222> LOCATION: (25)..(25)
```

-continued

```
<223> OTHER INFORMATION: X24 represents amino acid residues Leucine (L),
      Glutamine (Q), Histidine (H), or Phenylalanine (F)
<220> FEATURE:
<221> NAME/KEY: MISC_FEATURE
<222> LOCATION: (26)..(26)
<223> OTHER INFORMATION: X25 represents amino acid residues Glutamine
      (Q), or Asparagine (N)
<220> FEATURE:
<221> NAME/KEY: MISC_FEATURE
<222> LOCATION: (27)..(27)
<223> OTHER INFORMATION: X26 represents amino acid residues Serine (S),
      Phenylalanine (F), Arginine (R), Tryptophan (W), Glycine (G),
      Alanine (A), Aspartic acid (D), Asparagine (N), or Valine (V)
<220> FEATURE:
<221> NAME/KEY: MISC_FEATURE
<222> LOCATION: (28)..(28)
<223> OTHER INFORMATION: X27 represents amino acid residues Aspartic
      acid (D), Threonine (T), Serine (S), or Tyrosine (Y)
<220> FEATURE:
<221> NAME/KEY: MISC_FEATURE
<222> LOCATION: (29)..(29)
<223> OTHER INFORMATION: X28 represents amino acid residues Asparagine
      (N), Serine (S), Histidine (H), Arginine (R), Glutamic acid (E),
      Tyrosine (Y), Tryptophan (W), Phenylalanine (F), Alanine (A),
      Isoleucine (I)
<220> FEATURE:
<221> NAME/KEY: MISC_FEATURE
<222> LOCATION: (30)..(30)
<223> OTHER INFORMATION: X29 represents amino acid residues Leucine (L),
      Serine (S), Tyrosine (Y), Asparagine (N), Valine (V),
      Phenylalanine (F)
<220> FEATURE:
<221> NAME/KEY: MISC_FEATURE
<222> LOCATION: (32)..(32)
<223> OTHER INFORMATION: X30 represents a bond or amino acid residues
      compromised of Tryptophan (W), Tyrosine (Y), Leucine (L), or
      Phenylalanine (F)
<220> FEATURE:
<221> NAME/KEY: MISC_FEATURE
<222> LOCATION: (33)..(33)
<223> OTHER INFORMATION: [FW3]; VL framework regions

<400> SEQUENCE: 362

Xaa Xaa Ser Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Pro Xaa
            20                  25                  30

Thr

<210> SEQ ID NO 363
<211> LENGTH: 39
<212> TYPE: PRT
<213> ORGANISM: Artificial Sequence
<220> FEATURE:
<223> OTHER INFORMATION: A general formula of heavy chain variable
      region (VH)
<220> FEATURE:
<221> NAME/KEY: MISC_FEATURE
<222> LOCATION: (1)..(1)
<223> OTHER INFORMATION: [FW1], which represents VH framework region
<220> FEATURE:
<221> NAME/KEY: MISC_FEATURE
<222> LOCATION: (1)..(1)
<223> OTHER INFORMATION: X31 represents amino acid residues Aspartic
      acid (D), Glycine (G), Lysine (K), or Arginine (R)
<220> FEATURE:
<221> NAME/KEY: MISC_FEATURE
<222> LOCATION: (2)..(2)
<223> OTHER INFORMATION: X32 represents amino acid residues Tyrosine
      (Y), or Phenylalanine (F)
<220> FEATURE:
<221> NAME/KEY: MISC_FEATURE
<222> LOCATION: (3)..(3)
<223> OTHER INFORMATION: X33 represents amino acid residues Serine (S),
      Threonine (T), or Alanine (A)
```

```
<220> FEATURE:
<221> NAME/KEY: MISC_FEATURE
<222> LOCATION: (4)..(4)
<223> OTHER INFORMATION: X34 represents amino acid residues Isoleucine
      (I), or Phenylalanine (F)
<220> FEATURE:
<221> NAME/KEY: MISC_FEATURE
<222> LOCATION: (5)..(5)
<223> OTHER INFORMATION: X35 represents amino acid residues Threonine
      (T), or Serine (S)
<220> FEATURE:
<221> NAME/KEY: MISC_FEATURE
<222> LOCATION: (6)..(6)
<223> OTHER INFORMATION: X36 represents a bond or amino acid residues
      compromised Arginine (R)
<220> FEATURE:
<221> NAME/KEY: MISC_FEATURE
<222> LOCATION: (7)..(7)
<223> OTHER INFORMATION: X37 represents a bond or amino acid residues
      compromised Glycine (G), Aspartic acid (D), Serine (S), or
      Asparagine (N)
<220> FEATURE:
<221> NAME/KEY: MISC_FEATURE
<222> LOCATION: (8)..(8)
<223> OTHER INFORMATION: X38 represents a bond or amino acid residues
      compromised Phenylalanine (F), or Tyrosine (Y)
<220> FEATURE:
<221> NAME/KEY: MISC_FEATURE
<222> LOCATION: (9)..(9)
<223> OTHER INFORMATION: X39 represents a bond or amino acid residues
      compromised Asparagine (N), Lysine (K), Tryptophan (W), Leucine
      (L), Glycine (G), Serine (S), or Alanine (A)
<220> FEATURE:
<221> NAME/KEY: MISC_FEATURE
<222> LOCATION: (10)..(10)
<223> OTHER INFORMATION: X40 represents amino acid residues Tryptophan
      (W), Methionine (M), or Isoleucine (I)
<220> FEATURE:
<221> NAME/KEY: MISC_FEATURE
<222> LOCATION: (11)..(12)
<223> OTHER INFORMATION: [FW2], which represents VH framework region
<220> FEATURE:
<221> NAME/KEY: MISC_FEATURE
<222> LOCATION: (11)..(11)
<223> OTHER INFORMATION: X41 represents amino acid Histidine (H),
      Aspartic acid (D), Glutamic acid (E), Alanine (A), Serine (S), or
      Asparagine (N)
<220> FEATURE:
<221> NAME/KEY: MISC_FEATURE
<222> LOCATION: (12)..(12)
<223> OTHER INFORMATION: X42 represents amino acid residues Tyrosine
      (Y), Aspartic acid (D), Glutamic acid (E), Methionine (M),
      Phenylalanine (F), Serine (S), or Tryptophan (W)
<220> FEATURE:
<221> NAME/KEY: MISC_FEATURE
<222> LOCATION: (14)..(14)
<223> OTHER INFORMATION: X43 represents amino acid residues Histidine
      (H), Asparagine (N), Leucine (L), or Serine (S)
<220> FEATURE:
<221> NAME/KEY: MISC_FEATURE
<222> LOCATION: (15)..(15)
<223> OTHER INFORMATION: X44 represents a bond or amino acid residues
      compromised of Proline (P), Asparagine (N), Serine (S), Methionine
      (M), or Threonine (T)
<220> FEATURE:
<221> NAME/KEY: MISC_FEATURE
<222> LOCATION: (16)..(16)
<223> OTHER INFORMATION: X45 represents amino acid residues Tyrosine
      (Y), Asparagine (N), Glycine (G), or Leucine (L)
<220> FEATURE:
<221> NAME/KEY: MISC_FEATURE
<222> LOCATION: (17)..(17)
<223> OTHER INFORMATION: X46 represents a bond or amino acid residues
      compromised of Serine (S), Asparagine (N), Alanine (A), Glycine
      (G), or Threonine (T)
<220> FEATURE:
<221> NAME/KEY: MISC_FEATURE
<222> LOCATION: (18)..(18)
<223> OTHER INFORMATION: X47 represents amino acid residues Glycine (G),
```

-continued

```
      Aspartic acid (D), Tyrosine (Y), or Serine (S)
<220> FEATURE:
<221> NAME/KEY: MISC_FEATURE
<222> LOCATION: (19)..(19)
<223> OTHER INFORMATION: X48 represents amino acid residues Serine (S),
      Glycine (G), Proline (P), Threonine (T), Alanine (A), or Glutamic
      acid (E)
<220> FEATURE:
<221> NAME/KEY: MISC_FEATURE
<222> LOCATION: (20)..(20)
<223> OTHER INFORMATION: X49 represents amino acid residues Threonine
      (T), Serine (S), Isoleucine (I), Proline (P), Arginine (R), or
      Glutamine (Q)
<220> FEATURE:
<221> NAME/KEY: MISC_FEATURE
<222> LOCATION: (21)..(21)
<223> OTHER INFORMATION: X50 represents amino acid residues Asparagine
      (N), Isoleucine (I), Histidine (H), Lysine (K), Tyrosine (Y),
      Phenylalanine (F), Threonine (T)
<220> FEATURE:
<221> NAME/KEY: MISC_FEATURE
<222> LOCATION: (22)..(22)
<223> OTHER INFORMATION: X51 represents amino acid residues Tyrosine
      (Y), or Serine
<220> FEATURE:
<221> NAME/KEY: MISC_FEATURE
<222> LOCATION: (23)..(23)
<223> OTHER INFORMATION: X52 represents amino acid residues Asparagine
      (N), Threonine (T), Alanine (A), or Proline (P)
<220> FEATURE:
<221> NAME/KEY: MISC_FEATURE
<222> LOCATION: (24)..(24)
<223> OTHER INFORMATION: X53 represents amino acid residues Proline (P),
      Glutamine (Q), Glutamic acid (E), or Aspartic acid (D)
<220> FEATURE:
<221> NAME/KEY: MISC_FEATURE
<222> LOCATION: (25)..(25)
<223> OTHER INFORMATION: X54 represents amino acid residues Serine (S),
      Lysine (K), Threonine (T), Aspartic acid (D), or Glutamic acid (E)
<220> FEATURE:
<221> NAME/KEY: MISC_FEATURE
<222> LOCATION: (26)..(26)
<223> OTHER INFORMATION: X55 represents amino acid residues Leucine (L),
      Phenylalanine (F), or Valine (V)
<220> FEATURE:
<221> NAME/KEY: MISC_FEATURE
<222> LOCATION: (27)..(27)
<223> OTHER INFORMATION: X56 represents amino acid residues Lysine (K),
      or Threonine (T)
<220> FEATURE:
<221> NAME/KEY: MISC_FEATURE
<222> LOCATION: (28)..(29)
<223> OTHER INFORMATION: [FW3], which represents VH framework region
<220> FEATURE:
<221> NAME/KEY: MISC_FEATURE
<222> LOCATION: (28)..(28)
<223> OTHER INFORMATION: X57 represents amino acid residues Serine (S),
      Glycine (G), or Valine (V)
<220> FEATURE:
<221> NAME/KEY: MISC_FEATURE
<222> LOCATION: (29)..(29)
<223> OTHER INFORMATION: X58 represents amino acid residues Aspartic
      acid (D), Serine (S), Glycine (G), Valine (V), Asparagine (N),
      Histidine (H), Phenylalanine (F), Leucine (L), Threonine (T),
      Arginine (R), Alanine (A), or Methionine (M)
<220> FEATURE:
<221> NAME/KEY: MISC_FEATURE
<222> LOCATION: (30)..(30)
<223> OTHER INFORMATION: X59 represents amino acid residues Tyrosine
      (Y), Alanine (A), Glycine (G), Serine (S), Asparagine (N),
      Phenylalanine (F), Threonine (T), Valine (V), or Methionine (M)
<220> FEATURE:
<221> NAME/KEY: MISC_FEATURE
<222> LOCATION: (31)..(31)
<223> OTHER INFORMATION: X60 represents a bond or amino acid residues
      compromised Tyrosine (Y), or Threonine (T)
<220> FEATURE:
<221> NAME/KEY: MISC_FEATURE
<222> LOCATION: (32)..(32)
```

<223> OTHER INFORMATION: X61 represents amino acid residues Tyrosine
      (Y), Phenylalanine (F), Asparagine (N), Arginine (R), Threonine
      (T), Proline (P), Lysine (K), Alanine (A), or Methionine (M)
<220> FEATURE:
<221> NAME/KEY: MISC_FEATURE
<222> LOCATION: (33)..(33)
<223> OTHER INFORMATION: X62 represents amino acid residues Glycine (G),
      Tyrosine (Y), or Aspartic acid (D)
<220> FEATURE:
<221> NAME/KEY: MISC_FEATURE
<222> LOCATION: (34)..(34)
<223> OTHER INFORMATION: X63 represents a bond or amino acid residues
      compromised Tyrosine (Y)
<220> FEATURE:
<221> NAME/KEY: MISC_FEATURE
<222> LOCATION: (35)..(35)
<223> OTHER INFORMATION: X64 represents a bond or amino acid residues
      compromised of Asparagine (N), Arginine (R), Aspartic acid (D), or
      Valine (V)
<220> FEATURE:
<221> NAME/KEY: MISC_FEATURE
<222> LOCATION: (36)..(36)
<223> OTHER INFORMATION: X65 represents a bond or amino acid residues
      compromised of Serine (S), Alanine (A), Threonine (T), Valine (V),
      or Glycine (G)
<220> FEATURE:
<221> NAME/KEY: MISC_FEATURE
<222> LOCATION: (37)..(37)
<223> OTHER INFORMATION: X66 represents a bond or amino acid residues
      compromised of Phenylalanine (F), Leucine (L), Methionine (M), or
      Isoleucine (I)
<220> FEATURE:
<221> NAME/KEY: MISC_FEATURE
<222> LOCATION: (38)..(38)
<223> OTHER INFORMATION: X67 represents a bond or amino acid residues
      compromised of Alanine (A), or Aspartic acid (D)
<220> FEATURE:
<221> NAME/KEY: MISC_FEATURE
<222> LOCATION: (39)..(39)
<223> OTHER INFORMATION: [FW4], which represents VH framework region
<220> FEATURE:
<221> NAME/KEY: MISC_FEATURE
<222> LOCATION: (39)..(39)
<223> OTHER INFORMATION: X68 represents amino acid residues Tyrosine
      (Y), or Aspartic acid (D)

<400> SEQUENCE: 363

Xaa Xaa Xaa Xaa Xaa Xaa Xaa Xaa Xaa Xaa Xaa Xaa Ile Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 364
<211> LENGTH: 17
<212> TYPE: PRT
<213> ORGANISM: Artificial Sequence
<220> FEATURE:
<223> OTHER INFORMATION: A general formula of a light chain CDR1
<220> FEATURE:
<221> NAME/KEY: misc_feature
<222> LOCATION: (9)..(9)
<223> OTHER INFORMATION: Xaa can be any naturally occurring amino acid

<400> SEQUENCE: 364

Lys Ser Ser Gln Ser Leu Leu Asn Xaa Gly Asn Gln Lys Ser Tyr Leu
1               5                   10                  15

Thr

<210> SEQ ID NO 365
<211> LENGTH: 7

```
<212> TYPE: PRT
<213> ORGANISM: Artificial Sequence
<220> FEATURE:
<223> OTHER INFORMATION: A general formula of a light chain CDR2
<220> FEATURE:
<221> NAME/KEY: MISC_FEATURE
<222> LOCATION: (5)..(5)
<223> OTHER INFORMATION: X2 represents amino acid residues leucine (L)
      or Arginine (R)

<400> SEQUENCE: 365

Trp Ala Ser Thr Xaa Glu Ser
1               5

<210> SEQ ID NO 366
<211> LENGTH: 9
<212> TYPE: PRT
<213> ORGANISM: Artificial Sequence
<220> FEATURE:
<223> OTHER INFORMATION: A general formula of a light chain CDR3
<220> FEATURE:
<221> NAME/KEY: MISC_FEATURE
<222> LOCATION: (3)..(3)
<223> OTHER INFORMATION: X3 represents amino acid residues Asparagine
      (?), Glycine (G), Serine (S)
<220> FEATURE:
<221> NAME/KEY: MISC_FEATURE
<222> LOCATION: (5)..(5)
<223> OTHER INFORMATION: X4 represents amino acid residues Serine (S),
      Alanine (A), Phenylalanine (F)

<400> SEQUENCE: 366

Gln Asn Xaa Tyr Xaa Phe Pro Phe Thr
1               5

<210> SEQ ID NO 367
<211> LENGTH: 10
<212> TYPE: PRT
<213> ORGANISM: Artificial Sequence
<220> FEATURE:
<223> OTHER INFORMATION: A general formula of a heavy chain CDR1
<220> FEATURE:
<221> NAME/KEY: MISC_FEATURE
<222> LOCATION: (5)..(5)
<223> OTHER INFORMATION: X5 represents amino acid residues Serine (S) or
      Threonine (T)
<220> FEATURE:
<221> NAME/KEY: MISC_FEATURE
<222> LOCATION: (6)..(6)
<223> OTHER INFORMATION: X6 represents amino acid residues Asparagine
      (N) or a bond
<220> FEATURE:
<221> NAME/KEY: MISC_FEATURE
<222> LOCATION: (7)..(7)
<223> OTHER INFORMATION: X7 represents amino acid residues Tyrosine (Y)
      or a bond
<220> FEATURE:
<221> NAME/KEY: MISC_FEATURE
<222> LOCATION: (8)..(8)
<223> OTHER INFORMATION: X8 represents amino acid residues Glycine (G)
      or a bond

<400> SEQUENCE: 367

Gly Tyr Thr Phe Xaa Xaa Xaa Xaa Met Asn
1               5                   10

<210> SEQ ID NO 368
<211> LENGTH: 17
<212> TYPE: PRT
<213> ORGANISM: Artificial Sequence
<220> FEATURE:
<223> OTHER INFORMATION: A general formula of a heavy chain CDR2
<220> FEATURE:
```

```
<221> NAME/KEY: MISC_FEATURE
<222> LOCATION: (9)..(9)
<223> OTHER INFORMATION: X9 represents amino acid residues Proline (P),
      Arginine (R) or Glutamine (Q)
<220> FEATURE:
<221> NAME/KEY: MISC_FEATURE
<222> LOCATION: (10)..(10)
<223> OTHER INFORMATION: X10 represents amino acid residues Threonine
      (T) or Asparagine (N)

<400> SEQUENCE: 368

Trp Ile Asn Met Tyr Thr Gly Glu Xaa Xaa Tyr Ala Asp Asp Phe Lys
1               5                   10                  15

Gly

<210> SEQ ID NO 369
<211> LENGTH: 9
<212> TYPE: PRT
<213> ORGANISM: Artificial Sequence
<220> FEATURE:
<223> OTHER INFORMATION: A general formula of a heavy chain CDR3
<220> FEATURE:
<221> NAME/KEY: MISC_FEATURE
<222> LOCATION: (1)..(1)
<223> OTHER INFORMATION: X11 represents amino acid residues Leucine (L),
      Methionine (M), Threonine (T), Serine (S), or Alanine (A)
<220> FEATURE:
<221> NAME/KEY: MISC_FEATURE
<222> LOCATION: (2)..(2)
<223> OTHER INFORMATION: X12 represents amino acid residues Tyrosine
      (Y), Threonine (T), Glycine (G), Alanine (A), Serine (S), Valine
      (V), Asparagine (N), or Phenylalanine (F)
<220> FEATURE:
<221> NAME/KEY: MISC_FEATURE
<222> LOCATION: (3)..(3)
<223> OTHER INFORMATION: X13 represents amino acid residues Asparagine
      (N), Arginine (R), Proline (P), Threonine (T), Methionine (M),
      Lysine (K), or Histidine (H)
<220> FEATURE:
<221> NAME/KEY: MISC_FEATURE
<222> LOCATION: (6)..(6)
<223> OTHER INFORMATION: X14 represents amino acid residues Serine (S),
      Alanine (A), Valine (V), Glycine (G), Threonine (T)
<220> FEATURE:
<221> NAME/KEY: MISC_FEATURE
<222> LOCATION: (7)..(7)
<223> OTHER INFORMATION: X15 represents amino acid residues Leucine (L),
      Phenylalanine (F), Methionine (M), or Isoleucine (I)

<400> SEQUENCE: 369

Xaa Xaa Xaa Gly Asn Xaa Xaa Asp Tyr
1               5

<210> SEQ ID NO 370
<211> LENGTH: 33
<212> TYPE: PRT
<213> ORGANISM: Artificial Sequence
<220> FEATURE:
<223> OTHER INFORMATION: A general formula of light chain variable
      region (VL)
<220> FEATURE:
<221> NAME/KEY: MISC_FEATURE
<222> LOCATION: (1)..(1)
<223> OTHER INFORMATION: [FW1], which represents VL framework region
<220> FEATURE:
<221> NAME/KEY: MISC_FEATURE
<222> LOCATION: (9)..(9)
<223> OTHER INFORMATION: X1 represents amino acid residues Serine (S) or
      Tryptophan (W)
<220> FEATURE:
<221> NAME/KEY: MISC_FEATURE
<222> LOCATION: (17)..(18)
<223> OTHER INFORMATION: [FW2], which represents VL framework region
<220> FEATURE:
```

-continued

```
<221> NAME/KEY: MISC_FEATURE
<222> LOCATION: (22)..(22)
<223> OTHER INFORMATION: X2 represents amino acid residues leucine (L)
      or Arginine (R)
<220> FEATURE:
<221> NAME/KEY: MISC_FEATURE
<222> LOCATION: (24)..(25)
<223> OTHER INFORMATION: [FW3], which represents VL framework region
<220> FEATURE:
<221> NAME/KEY: MISC_FEATURE
<222> LOCATION: (27)..(27)
<223> OTHER INFORMATION: X3 represents amino acid residues Asparagine
      (?), Glycine (G), Serine (S)
<220> FEATURE:
<221> NAME/KEY: MISC_FEATURE
<222> LOCATION: (29)..(29)
<223> OTHER INFORMATION: X4 represents amino acid residues Serine (S),
      Alanine (A), Phenylalanine (F)
<220> FEATURE:
<221> NAME/KEY: MISC_FEATURE
<222> LOCATION: (33)..(33)
<223> OTHER INFORMATION: [FW4], which represents VL framework region

<400> SEQUENCE: 370

Lys Ser Ser Gln Ser Leu Leu Asn Xaa Gly Asn Gln Lys Ser Tyr Leu
1               5                   10                  15

Thr Trp Ala Ser Thr Xaa Glu Ser Gln Asn Xaa Tyr Xaa Phe Pro Phe
            20                  25                  30

Thr

<210> SEQ ID NO 371
<211> LENGTH: 36
<212> TYPE: PRT
<213> ORGANISM: Artificial Sequence
<220> FEATURE:
<223> OTHER INFORMATION: A general formula of heavy chain variable
      region (VH)
<220> FEATURE:
<221> NAME/KEY: MISC_FEATURE
<222> LOCATION: (1)..(1)
<223> OTHER INFORMATION: [FW5], which represents VH framework region
<220> FEATURE:
<221> NAME/KEY: MISC_FEATURE
<222> LOCATION: (5)..(5)
<223> OTHER INFORMATION: X5 represents amino acid residues Serine (S) or
      Threonine (T)
<220> FEATURE:
<221> NAME/KEY: MISC_FEATURE
<222> LOCATION: (6)..(6)
<223> OTHER INFORMATION: X6 represents amino acid residues Asparagine
      (N) or a bond
<220> FEATURE:
<221> NAME/KEY: MISC_FEATURE
<222> LOCATION: (7)..(7)
<223> OTHER INFORMATION: X7 represents amino acid residues Tyrosine (Y)
      or a bond
<220> FEATURE:
<221> NAME/KEY: MISC_FEATURE
<222> LOCATION: (8)..(8)
<223> OTHER INFORMATION: X8 represents amino acid residues Glycine (G)
      or a bond
<220> FEATURE:
<221> NAME/KEY: MISC_FEATURE
<222> LOCATION: (10)..(11)
<223> OTHER INFORMATION: [FW6], which represents VH framework region
<220> FEATURE:
<221> NAME/KEY: MISC_FEATURE
<222> LOCATION: (19)..(19)
<223> OTHER INFORMATION: X9 represents amino acid residues Proline (P),
      Arginine (R) or Glutamine (Q)
<220> FEATURE:
<221> NAME/KEY: MISC_FEATURE
<222> LOCATION: (20)..(20)
<223> OTHER INFORMATION: X10 represents amino acid residues Threonine
      (T) or Asparagine (N)
```

<220> FEATURE:
<221> NAME/KEY: MISC_FEATURE
<222> LOCATION: (27)..(28)
<223> OTHER INFORMATION: [FW7], which represents VH framework region
<220> FEATURE:
<221> NAME/KEY: MISC_FEATURE
<222> LOCATION: (28)..(28)
<223> OTHER INFORMATION: X11 represents amino acid residues Leucine (L), Methionine (M), Threonine (T), Serine (S), or Alanine (A)
<220> FEATURE:
<221> NAME/KEY: MISC_FEATURE
<222> LOCATION: (29)..(29)
<223> OTHER INFORMATION: X12 represents amino acid residues Tyrosine (Y), Threonine (T), Glycine (G), Alanine (A), Serine (S), Valine (V), Asparagine (N), or Phenylalanine (F)
<220> FEATURE:
<221> NAME/KEY: MISC_FEATURE
<222> LOCATION: (30)..(30)
<223> OTHER INFORMATION: X13 represents amino acid residues Asparagine (N), Arginine (R), Proline (P), Threonine (T), Methionine (M), Lysine (K), or Histidine (H)
<220> FEATURE:
<221> NAME/KEY: MISC_FEATURE
<222> LOCATION: (33)..(33)
<223> OTHER INFORMATION: X14 represents amino acid residues Serine (S), Alanine (A), Valine (V), Glycine (G), Threonine (T)
<220> FEATURE:
<221> NAME/KEY: MISC_FEATURE
<222> LOCATION: (34)..(34)
<223> OTHER INFORMATION: X15 represents amino acid residues Leucine (L), Phenylalanine (F), Methionine (M), or Isoleucine (I)
<220> FEATURE:
<221> NAME/KEY: MISC_FEATURE
<222> LOCATION: (36)..(36)
<223> OTHER INFORMATION: [FW8], which represents VH framework region

<400> SEQUENCE: 371

```
Gly Tyr Thr Phe Xaa Xaa Xaa Xaa Met Asn Trp Ile Asn Met Tyr Thr
1               5                   10                  15

Gly Glu Xaa Xaa Tyr Ala Asp Asp Phe Lys Gly Xaa Xaa Xaa Gly Asn
            20                  25                  30

Xaa Xaa Asp Tyr
        35
```

<210> SEQ ID NO 372
<211> LENGTH: 19
<212> TYPE: PRT
<213> ORGANISM: Artificial Sequence
<220> FEATURE:
<223> OTHER INFORMATION: An example leader sequence for signal peptide

<400> SEQUENCE: 372

```
Met Gly Trp Ser Cys Ile Ile Leu Phe Leu Val Ala Thr Ala Thr Gly
1               5                   10                  15

Val His Ser
```

<210> SEQ ID NO 373
<211> LENGTH: 87
<212> TYPE: DNA
<213> ORGANISM: Artificial Sequence
<220> FEATURE:
<223> OTHER INFORMATION: A primer designed to swap the CDR-L1 of 5C9 antibody into pSY1

<400> SEQUENCE: 373

```
agggtcacca tcacctgcaa aagcagtcag agtctgctca acagtggcaa ccagaaaagc     60
tatctgacct ggtatcaaca gaaacca                                         87
```

<210> SEQ ID NO 374

```
<211> LENGTH: 60
<212> TYPE: DNA
<213> ORGANISM: Artificial Sequence
<220> FEATURE:
<223> OTHER INFORMATION: A primer designed to swap the CDR-L2 of 5C9
      antibody into pSY1

<400> SEQUENCE: 374
gctccgaagc ttctgattta ttgggcatct accctcgaaa gcggagtccc ttctcgcttc    60

<210> SEQ ID NO 375
<211> LENGTH: 57
<212> TYPE: DNA
<213> ORGANISM: Artificial Sequence
<220> FEATURE:
<223> OTHER INFORMATION: A primer designed to swap the CDR-L3 of 5C9
      antibody into pSY1

<400> SEQUENCE: 375
gcaacttatt actgtcagaa cgcgtattct tttccgttta cgttcggaca gggtacc       57

<210> SEQ ID NO 376
<211> LENGTH: 63
<212> TYPE: DNA
<213> ORGANISM: Artificial Sequence
<220> FEATURE:
<223> OTHER INFORMATION: A primer designed to swap the CDR-H1 of 5C9
      antibody into pSY1

<400> SEQUENCE: 376
tcctgtgcag cttctggcta cacctttacc aactatggta tgaactgggt gcgtcaggcc    60
ccg                                                                 63

<210> SEQ ID NO 377
<211> LENGTH: 87
<212> TYPE: DNA
<213> ORGANISM: Artificial Sequence
<220> FEATURE:
<223> OTHER INFORMATION: A primer designed to swap the CDR-H2 of 5C9
      antibody into pSY1

<400> SEQUENCE: 377
ggcctggaat gggttgcatg gattaacatg tataccggcg aaccgaccta tgccgatgac    60
ttcaagggcc gtttcactat aagccgt                                       87

<210> SEQ ID NO 378
<211> LENGTH: 57
<212> TYPE: DNA
<213> ORGANISM: Artificial Sequence
<220> FEATURE:
<223> OTHER INFORMATION: A primer designed to swap the CDR-H3 of 5C9
      antibody into pSY1

<400> SEQUENCE: 378
gtctattatt gtgctcgcct gtataacggc aactctctgg actactgggg tcaagga       57

<210> SEQ ID NO 379
<211> LENGTH: 42
<212> TYPE: DNA
<213> ORGANISM: Artificial Sequence
<220> FEATURE:
<223> OTHER INFORMATION: A primer for introducing the degenerate codon
      via Kunkel mutagenesis
<220> FEATURE:
<221> NAME/KEY: misc_feature
<222> LOCATION: (22)..(22)
<223> OTHER INFORMATION: n represents M = A or C
```

<400> SEQUENCE: 379
gcctatgcat ccgatatcca gntgacccag tccccgagct cc    42

<210> SEQ ID NO 380
<211> LENGTH: 78
<212> TYPE: DNA
<213> ORGANISM: Artificial Sequence
<220> FEATURE:
<223> OTHER INFORMATION: A primer for introducing the degenerate codon
      via Kunkel mutagenesis
<220> FEATURE:
<221> NAME/KEY: misc_feature
<222> LOCATION: (23)..(23)
<223> OTHER INFORMATION: n represents W = A or T

<400> SEQUENCE: 380
ggtagcggtt ccgggacgga ttncactctg accatcagca gtctgcagcc ggaagacytc    60
gcaacttatt actgtcag    78

<210> SEQ ID NO 381
<211> LENGTH: 78
<212> TYPE: DNA
<213> ORGANISM: Artificial Sequence
<220> FEATURE:
<223> OTHER INFORMATION: A primer for introducing the degenerate codon
      via Kunkel mutagenesis
<220> FEATURE:
<221> NAME/KEY: misc_feature
<222> LOCATION: (19)..(19)
<223> OTHER INFORMATION: n represents R = A or G
<220> FEATURE:
<221> NAME/KEY: misc_feature
<222> LOCATION: (20)..(20)
<223> OTHER INFORMATION: n represents Y = C or T
<220> FEATURE:
<221> NAME/KEY: misc_feature
<222> LOCATION: (58)..(58)
<223> OTHER INFORMATION: n represents R = A or G

<400> SEQUENCE: 381
ctccgtttgt cctgtgcann ctctggctac acctttacca actatggtat gaactggntc    60
cgtcaggccc cgggtaag    78

<210> SEQ ID NO 382
<211> LENGTH: 72
<212> TYPE: DNA
<213> ORGANISM: Artificial Sequence
<220> FEATURE:
<223> OTHER INFORMATION: A primer for introducing the degenerate codon
      via Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents Y = C or T
<220> FEATURE:
<221> NAME/KEY: misc_feature
<222> LOCATION: (25)..(25)
<223> OTHER INFORMATION: n represents W = A or T
<220> FEATURE:
<221> NAME/KEY: misc_feature
<222> LOCATION: (37)..(37)
<223> OTHER INFORMATION: n represents R = A or G
<220> FEATURE:
<221> NAME/KEY: misc_feature
<222> LOCATION: (38)..(38)
<223> OTHER INFORMATION: n represents M = A or C
<220> FEATURE:
<221> NAME/KEY: misc_feature
<222> LOCATION: (43)..(43)
<223> OTHER INFORMATION: n represents R = A or G
<220> FEATURE:
<221> NAME/KEY: misc_feature
<222> LOCATION: (44)..(44)
<223> OTHER INFORMATION: n represents M = A or C
<220> FEATURE:
<221> NAME/KEY: misc_feature
<222> LOCATION: (47)..(47)
<223> OTHER INFORMATION: n represents R = A or G
<220> FEATURE:
<221> NAME/KEY: misc_feature
<222> LOCATION: (52)..(52)
<223> OTHER INFORMATION: n represents S = G or C
<220> FEATURE:
<221> NAME/KEY: misc_feature
<222> LOCATION: (53)..(53)
<223> OTHER INFORMATION: n represents Y = C or T

<400> SEQUENCE: 382
gatgacttca agggccgtnn cactntcagc ckcgacnnct ccnngancac anngtaccta    60
caaatgaaca gc    72

<210> SEQ ID NO 383
<211> LENGTH: 45
<212> TYPE: DNA
<213> ORGANISM: Artificial Sequence
<220> FEATURE:
<223> OTHER INFORMATION: A primer for introducing the degenerate codon
      via Kunkel mutagenesis
<220> FEATURE:
<221> NAME/KEY: misc_feature
<222> LOCATION: (22)..(22)
<223> OTHER INFORMATION: n represents D = A, G, or T
<220> FEATURE:
<221> NAME/KEY: misc_feature
<222> LOCATION: (23)..(23)
<223> OTHER INFORMATION: n represents Y = C or T
<220> FEATURE:
<221> NAME/KEY: misc_feature
<222> LOCATION: (26)..(26)
<223> OTHER INFORMATION: n represents R = A or G

<400> SEQUENCE: 383
gacactgccg tctattattg tnngangctg tataacggca actct    45

<210> SEQ ID NO 384
<211> LENGTH: 21
<212> TYPE: DNA
<213> ORGANISM: Artificial Sequence
<220> FEATURE:
<223> OTHER INFORMATION: A CDR-H3 sequence

<400> SEQUENCE: 384
taaggccaag acggcctata a    21

<210> SEQ ID NO 385
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (18)..(19)
<223> OTHER INFORMATION: 6 customized codons, XYZ, where X = G (0.45), A
      (0.23), T (0.11), C (0.21), Y = G (0.31), A (0.34), T (0.17), C
      (0.18), Z = G (0.24), C (0.76)
<220> FEATURE:
<221> NAME/KEY: misc_feature

```
<222> LOCATION: (19)..(19)
<223> OTHER INFORMATION: n represents W = A or T
<220> FEATURE:
<221> NAME/KEY: misc_feature
<222> LOCATION: (21)..(21)
<223> OTHER INFORMATION: n represents K = G or T

<400> SEQUENCE: 385
gtctattatt gtgctcgcnt ngactactgg ggtcaagga                            39

<210> SEQ ID NO 386
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (18)..(19)
<223> OTHER INFORMATION: 7 customized codons, XYZ, X = G (0.45), A
      (0.23), T (0.11), C (0.21), Y = G (0.31), A (0.34), T (0.17), C
      (0.18), Z = G (0.24), C (0.76)
<220> FEATURE:
<221> NAME/KEY: misc_feature
<222> LOCATION: (19)..(19)
<223> OTHER INFORMATION: n represents W = A or T
<220> FEATURE:
<221> NAME/KEY: misc_feature
<222> LOCATION: (21)..(21)
<223> OTHER INFORMATION: n represents K = G or T

<400> SEQUENCE: 386
gtctattatt gtgctcgcnt ngactactgg ggtcaagga                            39

<210> SEQ ID NO 387
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (18)..(19)
<223> OTHER INFORMATION: 8 customized codon XYZ, X = G (0.45), A (0.23),
      T (0.11), C (0.21), Y = G (0.31), A (0.34), T (0.17), C (0.18),
      Z = G (0.24), C (0.76)
<220> FEATURE:
<221> NAME/KEY: misc_feature
<222> LOCATION: (19)..(19)
<223> OTHER INFORMATION: n represents W = A or T
<220> FEATURE:
<221> NAME/KEY: misc_feature
<222> LOCATION: (21)..(21)
<223> OTHER INFORMATION: n represents K = G or T

<400> SEQUENCE: 387
gtctattatt gtgctcgcnt ngactactgg ggtcaagga                            39

<210> SEQ ID NO 388
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (18)..(19)
<223> OTHER INFORMATION: 9 customized codons, XYZ, X = G (0.45), A
      (0.23), T (0.11), C (0.21), Y = G (0.31), A (0.34), T (0.17), C
      (0.18), Z = G (0.24), C (0.76)
<220> FEATURE:
<221> NAME/KEY: misc_feature
<222> LOCATION: (19)..(19)
```

<223> OTHER INFORMATION: n represents W = A or T
<220> FEATURE:
<221> NAME/KEY: misc_feature
<222> LOCATION: (21)..(21)
<223> OTHER INFORMATION: n represents K = G or T

<400> SEQUENCE: 388
gtctattatt gtgctcgcnt ngactactgg ggtcaagga    39

<210> SEQ ID NO 389
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T

<400> SEQUENCE: 389
gtctattatt gtgctcgcnn stataacggc aactctctg    39

<210> SEQ ID NO 390
<211> LENGTH: 40
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents N = A, C ,G, or T

<400> SEQUENCE: 390
ctattattgt gctcgcctgn nsaacggcaa ctctctggac    40

<210> SEQ ID NO 391
<211> LENGTH: 43
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (23)..(23)
<223> OTHER INFORMATION: n represents N = A, C ,G, or T
<220> FEATURE:
<221> NAME/KEY: misc_feature
<222> LOCATION: (24)..(24)
<223> OTHER INFORMATION: n represents N = A, C ,G, or T

<400> SEQUENCE: 391
ctattattgt gctcgcctgt atnnsggcaa ctctctggac tac    43

<210> SEQ ID NO 392
<211> LENGTH: 46
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (26)..(26)
<223> OTHER INFORMATION: n represents N = A, C ,G, or T
<220> FEATURE:
<221> NAME/KEY: misc_feature
<222> LOCATION: (27)..(27)
<223> OTHER INFORMATION: n represents N = A, C ,G, or T

<400> SEQUENCE: 392
ctattattgt gctcgcctgt ataacnnsaa ctctctggac tactgg        46

<210> SEQ ID NO 393
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C

<400> SEQUENCE: 393
gctcgcctgt ataacggcnn ntctctggac tactggggt        39

<210> SEQ ID NO 394
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C

<400> SEQUENCE: 394
cgcctgtata acggcaacnn nctggactac tggggtcaa        39

<210> SEQ ID NO 395
<211> LENGTH: 42
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (22)..(22)
<223> OTHER INFORMATION: n represents N = A, C ,G, or T
<220> FEATURE:
<221> NAME/KEY: misc_feature
<222> LOCATION: (23)..(23)
<223> OTHER INFORMATION: n represents N = A, C ,G, or T
<220> FEATURE:
<221> NAME/KEY: misc_feature
<222> LOCATION: (24)..(24)
<223> OTHER INFORMATION: n represents S = G or C

<400> SEQUENCE: 395
gcaacttatt actgtcagaa cnnntattct tttccgttta cg                42

<210> SEQ ID NO 396
<211> LENGTH: 41
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (21)..(21)
<223> OTHER INFORMATION: n represents N = A, C ,G, or T
<220> FEATURE:
<221> NAME/KEY: misc_feature
<222> LOCATION: (22)..(22)
<223> OTHER INFORMATION: n represents N = A, C ,G, or T
<220> FEATURE:
<221> NAME/KEY: misc_feature
<222> LOCATION: (23)..(23)
<223> OTHER INFORMATION: n represents S = G or C

<400> SEQUENCE: 396
cttattactg tcagaacgcg nnntctttc cgtttacgtt c                  41

<210> SEQ ID NO 397
<211> LENGTH: 44
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (24)..(24)
<223> OTHER INFORMATION: n represents N = A, C ,G, or T
<220> FEATURE:
<221> NAME/KEY: misc_feature
<222> LOCATION: (25)..(25)
<223> OTHER INFORMATION: n represents N = A, C ,G, or T
<220> FEATURE:
<221> NAME/KEY: misc_feature
<222> LOCATION: (26)..(26)
<223> OTHER INFORMATION: n represents S = G or C

<400> SEQUENCE: 397
cttattactg tcagaacgcg tatnnnttc cgtttacgtt cgga              44

<210> SEQ ID NO 398
<211> LENGTH: 40
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents N = A, C ,G, or T
<220> FEATURE:
<221> NAME/KEY: misc_feature
<222> LOCATION: (22)..(22)
<223> OTHER INFORMATION: n represents S = G or C

<400> SEQUENCE: 398
ctgtcagaac gcgtattctn nnccgtttac gttcggacag                   40

<210> SEQ ID NO 399
<211> LENGTH: 40

-continued

```
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C
<220> FEATURE:
<221> NAME/KEY: misc_feature
<222> LOCATION: (22)..(22)
<223> OTHER INFORMATION: n is a, c, g, or t

<400> SEQUENCE: 399
cacctgcaaa agcagtcagn nnctgctcaa cagtggcaac                            40

<210> SEQ ID NO 400
<211> LENGTH: 40
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C
<220> FEATURE:
<221> NAME/KEY: misc_feature
<222> LOCATION: (22)..(22)
<223> OTHER INFORMATION: n is a, c, g, or t

<400> SEQUENCE: 400
ctgcaaaagc agtcagagtn nnctcaacag tggcaaccag                            40

<210> SEQ ID NO 401
<211> LENGTH: 40
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C
<220> FEATURE:
<221> NAME/KEY: misc_feature
<222> LOCATION: (22)..(22)
<223> OTHER INFORMATION: n is a, c, g, or t

<400> SEQUENCE: 401
```
caaaagcagt cagagtctgn nnaacagtgg caaccagaaa                                    40

<210> SEQ ID NO 402
<211> LENGTH: 43
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (23)..(23)
<223> OTHER INFORMATION: n represents N = A, C ,G, or T
<220> FEATURE:
<221> NAME/KEY: misc_feature
<222> LOCATION: (24)..(24)
<223> OTHER INFORMATION: n represents N = A, C ,G, or T
<220> FEATURE:
<221> NAME/KEY: misc_feature
<222> LOCATION: (25)..(25)
<223> OTHER INFORMATION: n represents S = G or C

<400> SEQUENCE: 402
caaaagcagt cagagtctgc tcnnnagtgg caaccagaaa agc                                43

<210> SEQ ID NO 403
<211> LENGTH: 40
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents N = A, C ,G, or T
<220> FEATURE:
<221> NAME/KEY: misc_feature
<222> LOCATION: (22)..(22)
<223> OTHER INFORMATION: n represents S = G or C

<400> SEQUENCE: 403
cagtcagagt ctgctcaacn nnggcaacca gaaaagctat                                    40

<210> SEQ ID NO 404
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C

<400> SEQUENCE: 404
cagagtctgc tcaacagtnn naaccagaaa agctatctg                                     39

<210> SEQ ID NO 405
<211> LENGTH: 40
<212> TYPE: DNA
<213> ORGANISM: Artificial Sequence

```
<220> FEATURE:
<223> OTHER INFORMATION: A primer for Kunkel mutagenesis
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents N = A, C ,G, or T
<220> FEATURE:
<221> NAME/KEY: misc_feature
<222> LOCATION: (22)..(22)
<223> OTHER INFORMATION: n represents S = G or C

<400> SEQUENCE: 405
gagtctgctc aacagtggcn nncagaaaag ctatctgacc                40

<210> SEQ ID NO 406
<211> LENGTH: 41
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (21)..(21)
<223> OTHER INFORMATION: n represents N = A, C ,G, or T
<220> FEATURE:
<221> NAME/KEY: misc_feature
<222> LOCATION: (22)..(22)
<223> OTHER INFORMATION: n represents N = A, C ,G, or T
<220> FEATURE:
<221> NAME/KEY: misc_feature
<222> LOCATION: (23)..(23)
<223> OTHER INFORMATION: n represents S = G or C

<400> SEQUENCE: 406
gtctgctcaa cagtggcaac nnnaaaagct atctgacctg g                41

<210> SEQ ID NO 407
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C

<400> SEQUENCE: 407
ctcaacagtg gcaaccagnn nagctatctg acctggtat                39

<210> SEQ ID NO 408
<211> LENGTH: 40
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (20)..(20)
<223> OTHER INFORMATION: n represents N = A, C ,G, or T
<220> FEATURE:
```

```
<221> NAME/KEY: misc_feature
<222> LOCATION: (21)..(21)
<223> OTHER INFORMATION: n represents N = A, C ,G, or T
<220> FEATURE:
<221> NAME/KEY: misc_feature
<222> LOCATION: (22)..(22)
<223> OTHER INFORMATION: n represents S = G or C

<400> SEQUENCE: 408
caacagtggc aaccagaaan nntatctgac ctggtatcaa                40

<210> SEQ ID NO 409
<211> LENGTH: 40
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents N = A, C ,G, or T
<220> FEATURE:
<221> NAME/KEY: misc_feature
<222> LOCATION: (22)..(22)
<223> OTHER INFORMATION: n represents S = G or C

<400> SEQUENCE: 409
cagtggcaac cagaaaagcn nnctgacctg gtatcaacag                40

<210> SEQ ID NO 410
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents S = G or C
<220> FEATURE:
<221> NAME/KEY: misc_feature
<222> LOCATION: (21)..(21)
<223> OTHER INFORMATION: n is a, c, g, or t

<400> SEQUENCE: 410
ggcaaccaga aaagctatnn nacctggtat caacagaaa                39

<210> SEQ ID NO 411
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
```

```
<220> FEATURE:
<221> NAME/KEY: misc_feature
<222> LOCATION: (20)..(20)
<223> OTHER INFORMATION: n represents S = G or C
<220> FEATURE:
<221> NAME/KEY: misc_feature
<222> LOCATION: (21)..(21)
<223> OTHER INFORMATION: n is a, c, g, or t

<400> SEQUENCE: 411
ccgaagcttc tgatttatnn ngcatctacc ctcgaaagc                              39

<210> SEQ ID NO 412
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C

<400> SEQUENCE: 412
ccgaagcttc tgatttatnn ngcatctacc ctcgaaagc                              39

<210> SEQ ID NO 413
<211> LENGTH: 43
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (23)..(23)
<223> OTHER INFORMATION: n represents N = A, C ,G, or T
<220> FEATURE:
<221> NAME/KEY: misc_feature
<222> LOCATION: (24)..(24)
<223> OTHER INFORMATION: n represents N = A, C ,G, or T
<220> FEATURE:
<221> NAME/KEY: misc_feature
<222> LOCATION: (25)..(25)
<223> OTHER INFORMATION: n represents S = G or C

<400> SEQUENCE: 413
gatttattgg gcatctaccc tcnnnagcgg agtcccttct cgc                         43

<210> SEQ ID NO 414
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(21)
<223> OTHER INFORMATION: n is a, c, g, or t

<400> SEQUENCE: 414
ggcctggaat gggttgcann nattaacatg tataccggc                              39
```

```
<210> SEQ ID NO 415
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C

<400> SEQUENCE: 415
gaatgggttg catggattnn natgtatacc ggcgaaccg                          39

<210> SEQ ID NO 416
<211> LENGTH: 42
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (22)..(22)
<223> OTHER INFORMATION: n represents N = A, C ,G, or T
<220> FEATURE:
<221> NAME/KEY: misc_feature
<222> LOCATION: (23)..(23)
<223> OTHER INFORMATION: n represents N = A, C ,G, or T
<220> FEATURE:
<221> NAME/KEY: misc_feature
<222> LOCATION: (24)..(24)
<223> OTHER INFORMATION: n represents S = G or C

<400> SEQUENCE: 416
gaatgggttg catggattaa cnnntatacc ggcgaaccga cc                      42

<210> SEQ ID NO 417
<211> LENGTH: 39
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (19)..(19)
<223> OTHER INFORMATION: n represents N = A, C ,G, or T
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents S = G or C

<400> SEQUENCE: 417
gttgcatgga ttaacatgnn naccggcgaa ccgacctat                          39

<210> SEQ ID NO 418
<211> LENGTH: 39
<212> TYPE: DNA
<213> ORGANISM: Artificial Sequence
```

```
<220> FEATURE:
<223> OTHER INFORMATION: A primer for Kunkel mutagenesis
<220> FEATURE:
<221> NAME/KEY: misc_feature
<222> LOCATION: (19)..(21)
<223> OTHER INFORMATION: n is a, c, g, or t

<400> SEQUENCE: 418
gcatggatta acatgtatnn nggcgaaccg acctatgcc                              39

<210> SEQ ID NO 419
<211> LENGTH: 40
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (20)..(22)
<223> OTHER INFORMATION: n is a, c, g, or t

<400> SEQUENCE: 419
gattaacatg taccggcn nnccgaccta tgccgatgac                               40

<210> SEQ ID NO 420
<211> LENGTH: 43
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (23)..(23)
<223> OTHER INFORMATION: n represents N = A, C ,G, or T
<220> FEATURE:
<221> NAME/KEY: misc_feature
<222> LOCATION: (24)..(24)
<223> OTHER INFORMATION: n represents N = A, C ,G, or T
<220> FEATURE:
<221> NAME/KEY: misc_feature
<222> LOCATION: (25)..(25)
<223> OTHER INFORMATION: n represents S = G or C

<400> SEQUENCE: 420
gattaacatg taccggcg aannnaccta tgccgatgac ttc                           43

<210> SEQ ID NO 421
<211> LENGTH: 40
<212> TYPE: DNA
<213> ORGANISM: Artificial Sequence
<220> FEATURE:
<223> OTHER INFORMATION: A primer for Kunkel mutagenesis
<220> FEATURE:
<221> NAME/KEY: misc_feature
<222> LOCATION: (20)..(20)
<223> OTHER INFORMATION: n represents N = A, C ,G, or T
<220> FEATURE:
<221> NAME/KEY: misc_feature
<222> LOCATION: (21)..(21)
<223> OTHER INFORMATION: n represents N = A, C ,G, or T
<220> FEATURE:
<221> NAME/KEY: misc_feature
<222> LOCATION: (22)..(22)
<223> OTHER INFORMATION: n represents S = G or C

<400> SEQUENCE: 421
catgtatacc ggcgaaccgn nntatgccga tgacttcaag                             40
```

BINDING MOLECULES SPECIFIC FOR CLAUDIN 18.2, COMPOSITIONS AND METHODS THEREOF, FOR THE TREATMENT OF CANCER AND OTHER DISEASES

CROSS-REFERENCE TO RELATED APPLICATIONS

The present patent document claims the benefit of the filing date under 35 U.S.C. § 119(e) of Provisional U.S. Patent Application Ser. No. 62/786,012, filed Dec. 28, 2018, which is hereby incorporated by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "16565_4_Sequence_Listing" created on Dec. 26, 2019, and is 529 KB (542,545 bytes) in size. The sequence listing contained in this .txt file is part of the specification and is hereby incorporated by reference in its entirety.

BACKGROUND

Gastric cancer is one of the most common cancers worldwide; it is the fourth and fifth most common cause of cancer-related deaths in the developed world for men and women, respectively (Rawla P., et al., *Przeglad Gastroenterologiczny*, 2019; 14:26). An estimated 1.22 millions new stomach cancer cases and 885,000 deaths occurred in 2017, rendering it a malignancy with the high unmet medical need (Etemadi A, et al., *The Lancet Gastroenterology & Hepatology*, 2019 Oct. 21(doi.org/10.1016/S2468-1253(19)30328-0)). Gastric cancer is the third leading cause of cancer death worldwide. The incidence of esophageal cancer has been increasing and the histological type and primary tumor location have been shifting with adenocarcinoma of the esophagus being the dominant form. The overall five-year survival rate for metastatic gastric cancer is ~5% despite the fact that several chemotherapies have been approved.

The majority of patients with locally advanced or metastatic disease are treated with chemotherapy regimens based on a backbone of platinum and fluoropyrimidine derivatives often combined with a third compound (e.g., taxane or anthracyclines). The median progression free survival of 5 to 7 months and median overall survival of 9 to 11 months can be expected using these standard-of-care regimens (SOC). Recently, several more targeted therapies emerged. For example, trastuzumab has been approved for HER2-positive gastroesophageal cancers. Pembrolizumab has been approved for PD-L1-positive and microsatellite instability-high (MSI-H) or mismatch repair deficient (dMMR) gastroesophageal cancers. However, only a portion of patients express these targets and the majority of the patients cannot benefit from these narrowly targeted therapies.

The claudin protein family has at least 27 member molecules in mammals (Furuse M. et al., *J Cell Biol.*, 1998, 141, 1539). These tight junction molecules are indispensable for the paracellular barrier in vertebrate epithelial cell sheets. The claudin 18 molecule is an integral transmembrane protein containing four membrane spanning hydrophobic regions and two extracellular loops. Claudin 18 exists in two different splice variants. Isotype 1 (Claudin 18.1 or CLDN 18.1) is selectively expressed on cells of normal lung and isotype 2 (Claudin 18.2 or CLDN 18.2) is considered to be a cancer-associated splice variant (Sanada Y. et al., *J Pathol.*, 2006, 208, 633).

Claudin 18.2 is a CD20-like differentiation protein that is overexpressed in non-small cell lung cancers (NSCLCs; 25%), gastric (70%), pancreatic (50%), and esophageal (30%) cancers. The expression of this protein is affected by the ethnic background, with higher expression levels observed in Japanese patients than in Caucasian patients. Claudin 18.2 was also ectopically expressed in ovarian, breast carcinoma, and head-neck tumors (Sahin U. et al. Clin Cancer Res. 2008, 14, 7624). Claudin 18.2 can be detected in lymph node and distant metastases of gastric cancer. Its expression in normal tissues is strictly confined to the short-lived differentiated epithelial cells of the gastric mucosa.

Claudin 18.2 likely plays a complex role in tumorigenesis and maintaining tumor microenvironment. It was found that EGFR/ERK signaling induced bile duct neoplasia-related Claudin 18 expression, which is involved in cell proliferation, invasion and tumorigenicity in vivo (Kumi, T., *Cancer Lett.*, 2017, 403, 66). It was also reported that claudin-18 suppressed the abnormal proliferation and motility of lung epithelial cells mediated by inhibition of the PI3K/PDK1/AKT signaling pathway (Shun, S. et al. Bio Bioph Acta (BBA)-Mole Cell Res, 2016, 1863, 1170). In Claudin 18.2 knockout mice the paracellular barrier was impaired, resulting in the leakage of $H^+$ ions secreted by parietal cells across the gastric epithelia into the stomach lumen and a subsequent decrease in gastric pH value. Chronic gastritis in the knockout mice led to high levels of inflammatory cells and spasmolytic polypeptide-expressing meta plastic (SPEM) cells. Inflammation from inflammatory cells was characterized by higher expression of various proinflammatory markers, such as IL-1β and TNF-α (Hayashi, D. Gastroenterology, 2012, 142, 292).

Although the biological functions of Claudin 18.2 in tumorigenesis and tumor microenvironment are uncertain, it is clear that Claudin 18.2 expression is retained in gastric cancer transformation and is aberrantly activated in a variety of neoplasms, including esophageal cancer, pancreatic adenocarcinoma, and cholangiocarcinoma (Micke, P. et al., *Intl J Cancer*, 2014, 135, 2206). The exposed extracellular loops of Claudin 18.2 are available for monoclonal antibody binding and an appropriate antibody that binds to Claudin 18.2 on the tumor cell surface may kill tumor cells through antibody-dependent cellular cytotoxicity (ADCC) and complement dependent cytotoxicity (CDC) effects. Anti-Claudin 18.2 compounds can also induce apoptosis and inhibit cell proliferation. When combined with chemotherapies, they may enhance T-cell infiltration and induce pro-inflammatory cytokines.

Claudin 18.2 is thus a valuable target for the prevention and/or treatment of several primary tumors, such as, gastric cancer, esophageal cancer, pancreatic cancer, lung cancers such as non-small cell lung cancer, ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

IMAB362 (Claudiximab, Zolbetuximab) is a chimeric monoclonal antibody of IgG subtype selectively targeting the first extracellular domain of Claudin 18.2 with minimal activity against the closely related splice variant 1 of Claudin 18 (U.S. Pat. No. 8,168,427). In human xenografts expressing Claudin 18.2 survival benefit and tumor regressions have been observed in mice after administration of IMAB362. In a dose finding phase I trial, no dose-limiting toxicity was observed at single doses up to 1000 mg/m². In a phase IIa trial, IMAB362 produced a 10% response rate and 30% disease control rate with all adverse events being grades 1-3. In a subsequent phase IIb trial, IMAB362 in combination with EOX (epirubicin 50 mg/m², oxaliplatin 130 mg/m² d1, and capecitabine 625 mg/m² bid, d1-21, every 21 days) significantly improved progression-free survival (PFS) compared to EOX alone (median 7.9 vs 4.8 months; HR 0.47; p=0.0001), meeting the primary endpoint of the trial. The regimen also improved overall survival (OS, median 13.3 vs 8.4 months; HR 0.51, p<0.001) compared to EOX alone. Subgroup analysis of patients with very high Claudin 18.2 expression (≥2+ intensity in ≥70% tumor cells), outcomes were more pronounced (PFS, 7.2 vs 5.6 months; HR 0.36; p=0.0005; OS, 16.7 months vs 9.0; HR 0.45, p<0.0005). Patients who received IMAB362 also showed a higher objective response rate (ORR) at 39% compared with 25% in the EOX arm (Prabhsimranjot S. et al., *J. Hem. Onc.*, 2017, 105).

A humanized Claudin 18.2 specific hu8E5 and hu8E5-2I single-chain fragment variables (scFv) were incorporated in chimeric antigen receptor T (CAR T) cells by lentiviral vector transduction. These CAR T cells contained a CD28 costimulatory domain and potently suppressed tumor growth in a cancer cell line xenograft mouse model. Partial or complete tumor elimination was observed in Claudin 18.2 positive gastric cancer PDX models treated with the hu8E5-2I-28Z CAR T cells, which persist well in vivo and infiltrate efficiently into the tumor tissues. No obvious deleterious effects on the normal organs including the gastric tissues were observed in mice at efficacious dose (Hua, J. et al., *Natl Cancer Inst.*, 2019, 111).

The pathogenesis of most cancers involves many different genetic mutations, epigenetic alterations, and the dysfunction of molecular signaling pathways. Also, cancer develops resistance to almost all treatments by acquiring alternative mechanisms. Consequently, the combination of two or more therapeutic treatments to specifically target cancer-inducing or cell-sustaining pathways is a cornerstone of cancer therapy. Modern combination of targeted therapies is different from the conventional mono-therapeutic techniques non-selectively targeting actively proliferating cells, which ultimately leads to the destruction of both healthy and cancerous cells. Ideally, a combination works in a synergistic or additive manner at a lower therapeutic dosage than each of the individual drugs used. For example, several targeted therapies targeting various oncogenic pathways have been investigated as therapeutics in gastric cancer, such as inhibitors of human epidermal growth factor receptor type 2 (HER2), vascular endothelial growth factor (VEGF) receptor, epidermal growth factor receptor (EGFR), the insulin-like growth factor receptor, phosphatidylinositol 3-kinase (PI3K)/protein kinase B (AKT)/mammalian target of rapamycin (mTOR) pathway, c-MET, fibroblast growth factor receptor (FGFR), poly [adenosine diphosphate (ADP)]-ribose polymerase (PARP), and immune checkpoints.

Immunotherapy has revolutionized the treatment of metastatic cancers in recent years and several classes of immunotherapies have been approved, including anti-PD-1, anti-PD-L1, anti-CTLA4 antibodies, CAR-T therapy, oncolytic virus, and T cell engagers. These approvals provided clinical validation that cytotoxic T cells are the most potent effector cells of the immune system.

SUMMARY

Accordingly, it is an object of the invention to provide antibodies, or antibody fragments that specifically bind to a membrane protein Claudin 18.2 and are useful as therapeutic agents for treating and/or preventing diseases associated with cells expressing Claudin 18.2, including tumor-related diseases such as gastric cancer, esophageal cancer, pancreatic cancer, lung cancer, ovarian cancer, colon cancer, hepatic cancer, head-neck cancer, and cancer of the gallbladder are described.

One aspect of the invention is to combine an anti-Claudin 18.2 molecule with various oncogenic pathway inhibitors. Another aspect of the invention is to use the said CLDN18.2-binding molecule (e.g. an antibody) or antigen-binding fragment thereof, wherein the subject is undergoing, has undergone, or will undergo an immunotherapy including anti-PD-1, anti-PD-L1, or anti-CTLA4 therapy.

Thus, one embodiment relates to an isolated antibody, or antibody fragment thereof that binds to Claudin 18.2, comprising an antibody light chain variable region (VL) and an antibody heavy chain variable region (VH), wherein the light chain variable region (VL) comprises the amino acid sequence: [FW1]$X_1X_2SX_3X_4X_5X_6X_7X_8X_9X_{10}X_{11}X_{12}X_{13}X_{14}X_{15}X_{16}$[FW2]$X_{17}X_{18}X_{19}X_{20}X_{21}X_{22}X_{23}$[FW3]$X_{24}X_{25}X_{26}X_{27}X_{28}X_{29}PX_{30}$T[FW4] (SEQ ID NO 362:), wherein [FW1], [FW2], [FW3] and [FW4] represent VL framework regions, and wherein

- $X_1$ represents amino acid residues Isoleucine (I), Arginine (R), Serine (S), or Lysine (K), wherein Lysine (K) is the most conservative and preferred residue in some embodiments;
- $X_2$ represents amino acid residues Threonine (T), Alanine (A), or Serine (S), wherein Serine (S) is the most conservative and preferred residue in some embodiments;
- $X_3$ represents amino acid residues Threonine (T), Serine (S), or Glutamine (Q), wherein Glutamine (Q) is the most conservative and preferred residue in some embodiments;
- $X_4$ represents amino acid residues Aspartic acid (D), Serine (S), or Threonine (T), wherein Serine (S) is the most conservative and preferred residue in some embodiments;
- $X_5$ represents amino acid residues Isoleucine (I), Valine (V), or Leucine, wherein Leucine (L) is the most conservative and preferred residue in some embodiments;
- $X_6$ represents a bond or amino acid residues compromised Valine (V), Leucine (L), or Phenylalanine (F), wherein Leucine (L) is the most conservative and preferred residue in some embodiments;
- $X_7$ represents a bond or amino acid residues compromised Histidine (H), Asparagine (N), wherein Asparagine (N) is the most conservative and preferred residue in some embodiments;
- $X_8$ represents a bond or amino acid residues compromised of Serine (S), Tryptophan (W), or Glycine (G), wherein Serine (S) is the most conservative and preferred residue in some embodiments;
- $X_9$ represents a bond or amino acid residues compromised of Glycine (G), wherein Glycine (G) is the most conservative and preferred residue in some embodiments;
- $X_{10}$ represents a bond or amino acid residues compromised of Asparagine (N), wherein Asparagine (N) is the most conservative and preferred residue in some embodiments;
- $X_{11}$ represents a bond or amino acid residues compromised of Glycine (G), Glutamine (Q), or Leucine (L), wherein Glutamine (Q) is the most conservative and preferred residue in some embodiments;

$X_{12}$ represents a bond or amino acid residues compromised of Aspartic acid (D), Asparagine (N), Lysine (K), or Arginine (R), wherein Lysine (K) is the most conservative and preferred residue in some embodiments;

$X_{13}$ represents amino acid residues Aspartic acid (D), Asparagine (N), Serine (S), or Threonine (T), wherein Serine (S) is the most conservative and preferred residue in some embodiments;

$X_{14}$ represents amino acid residues Aspartic acid (D), or Tyrosine (Y), wherein Tyrosine (Y) is the most conservative and preferred residue in some embodiments;

$X_{15}$ represents amino acid residues Methionine (M), or Leucine (L), wherein Leucine (L) is the most conservative and preferred residue in some embodiments;

$X_{16}$ represents amino acid residues Asparagine (N), Tyrosine (Y), Histidine (H), Glutamine (Q), Threonine (T), or Alanine (A), wherein Threonine (T) is the most conservative and preferred residue in some embodiments;

$X_{17}$ represents amino acid residues Glutamic acid (E), Tyrosine (Y), Aspartic acid (D), Glycine (G), Lysine (K), or Tryptophan (W), wherein Tryptophan (W) is the most conservative and preferred residue in some embodiments;

$X_{18}$ represents amino acid residues Glycine (G), Threonine (T), Valine (V), or Alanine (A), wherein Alanine (A) is the most conservative and preferred residue in some embodiments;

$X_{19}$ represents amino acid residues Asparagine (N), or Serine (S), wherein Serine (S) is the most conservative and preferred residue in some embodiments;

$X_{20}$ represents amino acid residues Threonine (T), or Asparagine (N), wherein Threonine (T) is the most conservative and preferred residue in some embodiments;

$X_{21}$ represents amino acid residues Leucine (L), or Arginine (R), wherein Leucine (L) is the most conservative and preferred residue in some embodiments;

$X_{22}$ represents amino acid residues Arginine (R), Alanine (A), Phenylalanine (F), Tryptophan (W), Glutamine (Q), Glutamic acid (E), or Aspartic acid (D), wherein Glutamic acid (E) is the most conservative and preferred residue in some embodiments;

$X_{23}$ represents amino acid residues Proline (P), or Serine (S), wherein Serine (S) is the most conservative and preferred residue in some embodiments;

$X_{24}$ represents amino acid residues Leucine (L), Glutamine (Q), Histidine (H), or Phenylalanine (F), wherein Glutamine (Q) is the most conservative and preferred residue in some embodiments;

$X_{25}$ represents amino acid residues Glutamine (Q), or Asparagine (N), wherein Asparagine (N) is the most conservative and preferred residue in some embodiments;

$X_{26}$ represents amino acid residues Serine (S), Phenylalanine (F), Arginine (R), Tryptophan (W), Glycine (G), Alanine (A), Aspartic acid (D), Asparagine (N), or Valine (V), wherein Alanine (A) is the most conservative and preferred residue in some embodiments;

$X_{27}$ represents amino acid residues Aspartic acid (D), Threonine (T), Serine (S), or Tyrosine (Y), wherein Tyrosine (Y) is the most conservative and preferred residue in some embodiments;

$X_{28}$ represents amino acid residues Asparagine (N), Serine (S), Histidine (H), Arginine (R), Glutamic acid (E), Tyrosine (Y), Tryptophan (W), Phenylalanine (F), Alanine (A), Isoleucine (I), wherein Serine (S) is the most conservative and preferred residue in some embodiments;

$X_{29}$ represents amino acid residues Leucine (L), Serine (S), Tyrosine (Y), Asparagine (N), Valine (V), Phenylalanine (F), wherein Phenylalanine (F) is the most conservative and preferred residue in some embodiments;

$X_{30}$ represents a bond or amino acid residues compromised of Tryptophan (W), Tyrosine (Y), Leucine (L), or Phenylalanine (F), wherein Phenylalanine (F) is the most conservative and preferred residue in some embodiments, and wherein the heavy chain variable region (VH) comprises the amino acid sequence: [FW1]$X_{31}X_{32}X_{33}X_{34}X_{35}X_{36}X_{37}X_{38}X_{39}X_{40}X_{41}$[FW2]$X_{42}IX_{43}X_{44}X_{45}X_{46}X_{47}X_{48}X_{49}X_{50}X_{51}X_{52}X_{53}X_{54}X_{55}X_{56}X_{57}$[FW3]$X_{58}X_{59}X_{60}X_{61}X_{62}X_{63}X_{64}X_{65}X_{66}X_{67}X_{68}$[FW4] (SEQ ID NO 363:), wherein [FW1], [FW2], [FW3] and [FW4] represent VH framework regions, and wherein $X_{31}$ represents amino acid residues Aspartic acid (D), Glycine (G), Lysine (K), or Arginine (R), wherein Glycine (G) is the most conservative and preferred residue in some embodiments;

$X_{32}$ represents amino acid residues Tyrosine (Y), or Phenylalanine (F), wherein Tyrosine (Y) is the most conservative and preferred residue in some embodiments;

$X_{33}$ represents amino acid residues Serine (S), Threonine (T), or Alanine (A), wherein Threonine (T) is the most conservative and preferred residue in some embodiments;

$X_{34}$ represents amino acid residues Isoleucine (I), or Phenylalanine (F), wherein Phenylalanine (F) is the most conservative and preferred residue in some embodiments;

$X_{35}$ represents amino acid residues Threonine (T), or Serine (S), wherein Serine (S) is the most conservative and preferred residue in some embodiments;

$X_{36}$ represents a bond or amino acid residues compromised Arginine (R), wherein a bond is preferred in some embodiments;

$X_{37}$ represents a bond or amino acid residues compromised Glycine (G), Aspartic acid (D), Serine (S), or Asparagine (N), wherein a bond is preferred in some embodiments;

$X_{38}$ represents a bond or amino acid residues compromised Phenylalanine (F), or Tyrosine (Y), wherein a bond is preferred in some embodiments;

$X_{39}$ represents a bond or amino acid residues compromised Asparagine (N), Lysine (K), Tryptophan (W), Leucine (L), Glycine (G), Serine (S), or Alanine (A), wherein a bond is preferred in some embodiments;

$X_{40}$ represents amino acid residues Tryptophan (W), Methionine (M), or Isoleucine (I), wherein Methionine (M) is the most conservative and preferred residue in some embodiments;

$X_{41}$ represents amino acid Histidine (H), Aspartic acid (D), Glutamic acid (E), Alanine (A), Serine (S), or Asparagine (N), wherein Asparagine (N) is the most conservative and preferred residue in some embodiments;

$X_{42}$ represents amino acid residues Tyrosine (Y), Aspartic acid (D), Glutamic acid (E), Methionine (M), Phenylalanine (F), Serine (S), or Tryptophan (W), wherein Tryptophan (W) is the most conservative and preferred residue in some embodiments;

$X_{43}$ represents amino acid residues Histidine (H), Asparagine (N), Leucine (L), or Serine (S), wherein Asparagine (N) is the most conservative and preferred residue in some embodiments;

$X_{44}$ represents a bond or amino acid residues compromised of Proline (P), Asparagine (N), Serine (S), Methionine (M), or Threonine (T), wherein Methionine (M) is the most conservative and preferred residue in some embodiments;

$X_{45}$ represents amino acid residues Tyrosine (Y), Asparagine (N), Glycine (G), or Leucine (L), wherein Tyrosine (Y) is the most conservative and preferred residue in some embodiments;

$X_{46}$ represents a bond or amino acid residues compromised of Serine (S), Asparagine (N), Alanine (A), Glycine (G), or Threonine (T), wherein Threonine (T) is the most conservative and preferred residue in some embodiments;

$X_{47}$ represents amino acid residues Glycine (G), Aspartic acid (D), Tyrosine (Y), or Serine (S), wherein Glycine (G) is the most conservative and preferred residue in some embodiments;

$X_{48}$ represents amino acid residues Serine (S), Glycine (G), Proline (P), Threonine (T), Alanine (A), or Glutamic acid (E), wherein Glutamic acid (E) is the most conservative and preferred residue in some embodiments;

$X_{49}$ represents amino acid residues Threonine (T), Serine (S), Isoleucine (I), Proline (P), Arginine (R), or Glutamine (Q), wherein Proline (P) is the most conservative and preferred residue in some embodiments;

$X_{50}$ represents amino acid residues Asparagine (N), Isoleucine (I), Histidine (H), Lysine (K), Tyrosine (Y), Phenylalanine (F), Threonine (T), wherein Threonine (T) is the most conservative and preferred residue in some embodiments;

$X_{51}$ represents amino acid residues Tyrosine (Y), or Serine, wherein Tyrosine (Y) is the most conservative and preferred residue in some embodiments;

$X_{52}$ represents amino acid residues Asparagine (N), Threonine (T), Alanine (A), or Proline (P), wherein Alanine (A) is the most conservative and preferred residue in some embodiments;

$X_{53}$ represents amino acid residues Proline (P), Glutamine (Q), Glutamic acid (E), or Aspartic acid (D), wherein Aspartic acid (D) is the most conservative and preferred residue in some embodiments;

$X_{54}$ represents amino acid residues Serine (S), Lysine (K), Threonine (T), Aspartic acid (D), or Glutamic acid (E), wherein Aspartic acid (D) is the most conservative and preferred residue in some embodiments;

$X_{55}$ represents amino acid residues Leucine (L), Phenylalanine (F), or Valine (V), wherein Phenylalanine (F) is the most conservative and preferred residue in some embodiments;

$X_{56}$ represents amino acid residues Lysine (K), or Threonine (T), wherein Lysine (K) is the most conservative and preferred residue in some embodiments;

$X_{57}$ represents amino acid residues Serine (S), Glycine (G), or Valine (V), wherein Glycine (G) is the most conservative and preferred residue in some embodiments;

$X_{58}$ represents amino acid residues Aspartic acid (D), Serine (S), Glycine (G), Valine (V), Asparagine (N), Histidine (H), Phenylalanine (F), Leucine (L), Threonine (T), Arginine (R), Alanine (A), or Methionine (M), wherein Leucine (L) is the most conservative and preferred residue in some embodiments;

$X_{59}$ represents amino acid residues Tyrosine (Y), Alanine (A), Glycine (G), Serine (S), Asparagine (N), Phenylalanine (F), Threonine (T), Valine (V), or Methionine (M), wherein Tyrosine (Y) is the most conservative and preferred residue in some embodiments;

$X_{60}$ represents a bond or amino acid residues compromised Tyrosine (Y), or Threonine (T), wherein a bond is preferred in some embodiments;

$X_{61}$ represents amino acid residues Tyrosine (Y), Phenylalanine (F), Asparagine (N), Arginine (R), Threonine (T), Proline (P), Lysine (K), Alanine (A), or Methionine (M), wherein Asparagine (N) is the most conservative and preferred residue in some embodiments;

$X_{62}$ represents amino acid residues Glycine (G), Tyrosine (Y), or Aspartic acid (D), wherein Glycine (G) is the most conservative and preferred residue in some embodiments;

$X_{63}$ represents a bond or amino acid residues compromised Tyrosine (Y), wherein a bond is preferred in some embodiments;

$X_{64}$ represents a bond or amino acid residues compromised of Asparagine (N), Arginine (R), Aspartic acid (D), or Valine (V), wherein Asparagine (N) is the most conservative and preferred residue in some embodiments;

$X_{65}$ represents a bond or amino acid residues compromised of Serine (S), Alanine (A), Threonine (T), Valine (V), or Glycine (G), wherein Serine (S) is the most conservative and preferred residue in some embodiments;

$X_{66}$ represents a bond or amino acid residues compromised of Phenylalanine (F), Leucine (L), Methionine (M), or Isoleucine (I), wherein Leucine (L) is the most conservative and preferred residue in some embodiments;

$X_{67}$ represents a bond or amino acid residues compromised of Alanine (A), or Aspartic acid (D), wherein Aspartic acid (D) is the most conservative and preferred residue in some embodiments;

$X_{68}$ represents amino acid residues Tyrosine (Y), or Aspartic acid (D), wherein Tyrosine (Y) is the most conservative and preferred residue in some embodiments.

Another embodiment relates to an antibody, or antibody fragment that is a) an immunoglobulin (Ig) $G_{1-4}$, IgM, $IgA_{1-2}$, IgD or IgE molecule; or b) a single-chain antibody, a Fab fragment, a F(ab')$_2$ fragment, and a single-chain fragment variable (scFv) wherein the variable regions of the heavy ($V_H$) and light chains ($V_L$) of the immunoglobulins connected with a short linker peptide of ten to about 25 amino acids.

Another embodiment relates to an antibody, or antibody fragment capable of binding to CLDN18.2 and mediating killing of cells expressing CLDN18.2.

Another embodiment relates to an isolated antibody, or antibody fragment thereof, wherein the killing of cells is induced by binding of said isolated antibody or antibody fragment thereof to CLDN18.2 expressed by the cells.

A further embodiment relates to an isolated antibody or antibody fragment thereof, wherein the said antibody or antibody fragment thereof mediates the cell killing by inducing at least one of complement dependent cytotoxicity (CDC) mediated lysis, antibody dependent cellular cytotoxicity (ADCC) mediated lysis, apoptosis, homotypic adhesion, or phagocytosis.

Yet a further embodiment relates to an isolated antibody, or antibody fragment thereof, which specifically binds to CLDN18.2, comprising a VL and a VH comprising VL-CDR1, VL-CRD2, VL-CDR3, VH-CDR1, VH-CDR2, and VH-CDR3 amino acid sequences identical or identical except for three, two, or one amino acid substitutions in one or more CDRs to: SEQ ID NOs: 7, 8, 9, 11, 12, and 13; SEQ ID NOs: 15, 16, 17, 19, 20, and 21; SEQ ID NOs: 23, 16, 24, 26, 27, and 28; SEQ ID NOs: 30, 16, 31, 33, 34, and 35, SEQ ID NOs: 44, 45, 46, 48, 49, and 50, SEQ ID NOs: 52, 45, 53, 55, 56, and 50, SEQ ID NOs: 58, 59, 60, 33, 62, and 63, SEQ ID NOs: 65, 66, 67, 69, 70, and 71, SEQ ID NOs: 73, 74, 75, 48, 77, and 50, SEQ ID NOs: 79, 80, 81, 83, 84, and 85, SEQ ID NOs: 87, 45, 88, 90, 91, and 92, SEQ ID NOs: 94, 45, 95, 97, 98, and 99, SEQ ID NOs: 87, 45, 101, 103, 104, and 105, SEQ ID NOs: 107, 45, 108, 90, 91, and 92, SEQ ID NOs: 111, 45, 112, 114, 115, and 116, SEQ ID NOs: 118, 119, 120, 122, 123, and 124, SEQ ID NOs: 30, 45, 126, 90, 128, and 129, SEQ ID NOs: 30, 132, 133, 33, 34, and 135, SEQ ID NOs: 30, 132, 133, 156, 34, and 135, SEQ ID NOs: 30, 132, 158, 156, 34, and 135, SEQ ID NOs: 30, 132, 161, 156, 34, and 135, SEQ ID NOs: 30, 132, 164, 156, 34, and 135, SEQ ID NOs: 30, 132, 167, 156, 34, and 135, SEQ ID NOs: 30, 132, 170, 156, 34, and 135, SEQ ID NOs: 30, 132, 173, 156, 34, and 135, SEQ ID NOs: 30, 132, 173, 156, 34, and 177, SEQ ID NOs: 30, 132, 158, 156, 34, and 177, SEQ ID NOs: 30, 132, 173, 156, 34, and 182, SEQ ID NOs: 30, 132, 161, 156, 34, and 185, SEQ ID NOs: 30, 132, 133, 156, 34, and 188, SEQ ID NOs: 30, 132, 133, 156, 34, and 190, SEQ ID NOs: 30, 132, 133, 156, 34, and 192, SEQ ID NOs: 30, 132, 133, 156, 34, and 194, SEQ ID NOs: 30, 132, 133, 156, 34, and 196, SEQ ID NOs: 30, 132, 133, 156, 34, and 198, SEQ ID NOs: 30, 132, 133, 156, 34, and 200, SEQ ID NOs: 30, 132, 133, 156, 34, and 202, SEQ ID NOs: 30, 132, 133, 156, 34, and 204, SEQ ID NOs: 30, 132, 133, 156, 34, and 206, SEQ ID NOs: 30, 132, 133, 156, 34, and 208, SEQ ID NOs: 30, 132, 133, 156, 34, and 210, SEQ ID NOs: 30, 132, 133, 156, 34, and 212, SEQ ID NOs: 30, 132, 133, 156, 34, and 214, SEQ ID NOs: 30, 132, 133, 156, 34, and 216, SEQ ID NOs: 30, 132, 133, 156, 34, and 218, SEQ ID NOs: 30, 132, 133, 156, 34, and 220, SEQ ID NOs: 30, 132, 156, 156, 34, and 135, SEQ ID NOs: 30, 132, 156, 156, 34, and 177, SEQ ID NOs: 30, 132, 161, 156, 34, and 177, SEQ ID NOs: 30, 132, 156, 156, 34, and 227, SEQ ID NOs: 30, 132, 133, 156, 34, and 230, SEQ ID NOs: 30, 132, 133, 156, 34, and 233, SEQ ID NOs: 30, 132, 133, 156, 34, and 236, SEQ ID NOs: 238, 239, 133, 156, 241, and 135, SEQ ID NOs: 238, 243, 133, 156, 245, and 135, or SEQ ID NOs: 238, 247, 133, 156, 249, and 135, respectively.

Another embodiment relates to an isolated antibody or fragment thereof that binds to CLDN 18.2, comprising at least one light chain variable region (VL) and at least one heavy chain variable region (VH), wherein the light chain variable region comprises the amino acid sequences of SEQ ID NOS: 6, 14, 22, 29, 43, 51, 57, 64, 72, 78, 86, 93, 100, 106, 110, 117, 125, 130, 131, 136, 138, 140, 142, 144, 146, 148, 150, 152, 154, 157, 160, 163, 166, 169, 172, 175, 178, 180, 183, 186, 221, 224, 228, 231, 234, 237, 242, or 246, and wherein the heavy chain variable region comprises the amino acid sequence selected from the group consisting of SEQ ID NOs: 10, 18, 25, 32, 47, 54, 61, 68, 76, 82, 89, 96, 102, 109, 113, 121, 127, 134, 137, 139, 141, 143, 145, 147, 149, 151, 153, 155, 159, 162, 165, 168, 171, 174, 176, 179, 181, 184, 187, 189, 191, 193, 195, 197, 199, 201, 203, 205, 207, 209, 211, 213, 215, 217, 219, 222, 223, 225, 226, 229, 232, 235, 240, 244, or 248.

Another embodiment relates to an isolated antibody that binds to CLDN 18.2, comprising a light chain and a heavy chain consisting essentially of the amino acid sequences of SEQ ID NOs: 250 and 251, 252 and 253, 254 and 255, 256 and 257, 258 and 259, 260 and 261, 262 and 263, 264 and 265, 266 and 267, 268 and 269, 270 and 271, 272 and 273, 274 and 275, 276 and 277, 278 and 279, 280 and 281, 282 and 283, 284 and 285, 286 and 287, 288 and 289, 290 and 291, 292 and 293, 294 and 295, 296 and 297, 298 and 299, 300 and 301, 302 and 303, 304 and 305, 306 and 307, 308 and 309, 310 and 311, 312 and 313, 314 and 315, 316 and 317, 318 and 319, 320 and 321, 322 and 323, 324 and 325, 326 and 327, 328 and 329, 330 and 331, 332 and 333, 334 and 335, 336 and 337, 338 and 339, 340 and 341, 342 and 343, 344 and 345, 346 and 347, 348 and 349, 350 and 351, 352 and 353, 354 and 355, 356 and 357, 358 and 359, 360 and 361.

In one aspect, an antibody or antibody fragment thereof is described, where the light chain variable domain (VL) of the antibody has an amino acid sequence having at least about 90% to about 100% identity to a reference amino acid sequence selected from SEQ ID NO: 6, 14, 22, 29, 43, 51, 57, 64, 72, 78, 86, 93, 100, 106, 110, 117, 125, 130, 131, 136, 138, 140, 142, 144, 146, 148, 150, 152, 154, 157, 160, 163, 166, 169, 172, 175, 178, 180, 183, 186, 221, 224, 228, 231, 234, 237, 242, or 246.

In other aspect, an isolated binding molecule (e.g., an antibody) or antigen-binding fragment thereof is described, where the heavy chain variable domain (VH) of the antibody has an amino acid sequence having at least about 90% to about 100% identity to a reference amino acid sequence selected from SEQ ID NO:10, 18, 25, 32, 47, 54, 61, 68, 76, 82, 89, 96, 102, 109, 113, 121, 127, 134, 137, 139, 141, 143, 145, 147, 149, 151, 153, 155, 159, 162, 165, 168, 171, 174, 176, 179, 181, 184, 187, 189, 191, 193, 195, 197, 199, 201, 203, 205, 207, 209, 211, 213, 215, 217, 219, 222, 223, 225, 226, 229, 232, 235, 240, 244, or 248.

In another aspect, an isolated antibody or antigen-binding fragment thereof is described, which specifically binds to CLDN 18.2, where the antibody or antigen binding fragment has a light chain variable domain (VL) having a sequence at least about 90% to about 100% identical to a reference amino acid sequence selected from SEQ ID NO:6, 14, 22, 29, 43, 51, 57, 64, 72, 78, 86, 93, 100, 106, 110, 117, 125, 130, 131, 136, 138, 140, 142, 144, 146, 148, 150, 152, 154, 157, 160, 163, 166, 169, 172, 175, 178, 180, 183, 186, 221, 224, 228, 231, 234, 237, 242, or 246, and where the antibody or antigen binding fragment has a heavy chain variable domain (VH) having a sequence at least about 90% to about 100% identical to a reference amino acid sequence selected from SEQ ID NO:10, 18, 25, 32, 47, 54, 61, 68, 76, 82, 89, 96, 102, 109, 113, 121, 127, 134, 137, 139, 141, 143, 145, 147, 149, 151, 153, 155, 159, 162, 165, 168, 171, 174, 176, 179, 181, 184, 187, 189, 191, 193, 195, 197, 199, 201, 203, 205, 207, 209, 211, 213, 215, 217, 219, 222, 223, 225, 226, 229, 232, 235, 240, 244, or 248

In a further aspect, an antibody or antibody fragment thereof is described, which has a light chain variable domain (VL) consisting essentially of SEQ ID NO: 154, and a heavy chain variable domain (VH) consisting essentially of SEQ ID NO:155.

In a further aspect, an antibody or antibody fragment thereof is described, which has a light chain variable domain (VL) consisting essentially of SEQ ID NO: 160, and a heavy chain variable domain (VH) consisting essentially of SEQ ID NO:162.

In a further aspect, an antibody or antibody fragment thereof is described, which has a light chain variable domain (VL) consisting essentially of SEQ ID NO: 231, and a heavy chain variable domain (VH) consisting essentially of SEQ ID NO:232.

In a further aspect, an antibody or antibody fragment thereof is described, which has a light chain variable domain (VL) consisting essentially of SEQ ID NO: 237, and a heavy chain variable domain (VH) consisting essentially of SEQ ID NO:240.

In a further aspect, an antibody or antibody fragment thereof is described, which has a light chain variable domain (VL) consisting essentially of SEQ ID NO: 242, and a heavy chain variable domain (VH) consisting essentially of SEQ ID NO:244.

In another aspect, a composition containing an antibody or antibody fragment thereof described herein, and a carrier is described. In a further aspect, a nucleic acid comprising a sequence encoding the antibody, or antibody fragment thereof described herein, is described.

In another aspect, a composition including a nucleic acid in accordance with the invention is described.

In another aspect, a vector containing a nucleic acid described herein is described.

In another aspect, a host cell comprising a nucleic acid sequence, composition, or the vector is described.

In another aspect, a purified or enriched preparation of CLDN 18.2 antigen and/or nucleic acids and/or cells expressing CLDN 18.2 or a peptide fragment thereof are described herein.

In another aspect, a method of making the antibody or antibody fragment thereof described herein, is described, including culturing a cell containing a nucleic acid sequence, composition, or vector described herein; and an antibody or antibody fragment thereof described herein.

In one aspect, the described antibody or antibody fragment thereof is a monoclonal, chimeric, or humanized antibody, and may be selected from the group consisting of an IgG1, an IgG2, an IgG3, an IgG4, an IgM, an IgA1, an IgA2, a secretory IgA, an IgD, and an IgE antibody.

In other aspect, an isolated antibody or antibody fragment thereof is described, which specifically binds to CLDN 18.2 but not to CLDN18.1.

In one embodiment, the isolated antibodies or antibody fragments thereof described herein that bind to a CLDN 18.2 and are useful as therapeutic agents for treating and/or preventing diseases associated with cells expressing Claudin 18.2, including tumor-related diseases such as gastric cancer, esophageal cancer, pancreatic cancer, lung cancer, ovarian cancer, colon cancer, hepatic cancer, head-neck cancer, and cancer of the gallbladder are described. In particular embodiments, anti-CLDN18.2 antibodies are useful therapeutic agents for treating and/or preventing gastric cancer. In certain further embodiments, therapeutic combinations featuring anti-CLDN18.2 antibodies and other agents targeting the cancer immunity cycle (e.g., anti-PD-1 or anti-PD-L1 antibodies) and methods of using such combinations is useful for treating the said tumor-related diseases, are also provided.

In one aspect, the killing of cells by the described antibody may be induced by binding of the antibody to CLDN 18 expressing cells, or by binding of the antibody to CLDN 18.2 expressing cells. In the other aspect, binding of the described antibody to CLDN 18.1 expressing cells does not induce killing of the said cells. The cells expressing CLDN 18.2 may be cancer cells and may be, in particular, selected from the group consisting of tumorigenic gastric, esophageal, pancreatic, lung, ovarian, colon, hepatic, head-neck, and gallbladder cancer cells.

In another aspect, an antibody, or antibody fragments thereof, is described, which have the ability of binding to CLDN 18.2 and mediating killing of cells expressing CLDN 18.2. Preferably, the antibody binds to CLDN 18.1 and CLDN 18.2, and more preferably, binds to CLDN 18.2 but not to CLDN 18.1. Killing of cells by the antibody described herein is preferably induced by binding of the antibody to CLDN 18.2 expressed by said cells. The cells expressing CLDN 18.2 are preferably cancer cells and are, in certain embodiments, selected from the group consisting of tumorigenic gastric, esophageal, pancreatic, lung, ovarian, colon, hepatic, head-neck, and gallbladder cancer cells.

In certain embodiments, the described antibody mediates killing of cells by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis.

In certain further embodiments, ADCC mediated lysis of cells takes place in the presence of effector cells, which may be selected from the group consisting of monocytes, mononuclear cells, NK cells and PMNs, and phagocytosis is by macrophages.

According to all aspects described herein, CLDN 18.2 is preferably human CLDN 18.2, which preferably has the amino acid sequence of SEQ ID NO: 2.

In certain embodiments, the described antibody binds to native epitopes of CLDN 18.2 present on the surface of living cells. In further embodiments, the described antibody is specific for cancer cells, preferably stomach cancer cells.

In one aspect, the described antibodies may be obtained by a method comprising the step of immunizing an animal with a protein or peptide having an amino acid sequence selected from the group consisting of SEQ ID NO:1, 2, or 3, or an immunogenic fragment thereof, or a nucleic acid or host cell expressing said protein or peptide, or immunogenic fragment thereof. Preferably, the described antibody is specific for the aforementioned proteins, peptides or immunogenic fragments thereof. The described antibodies are designated herein by referring to the clone producing the antibody, e.g., 5C9.

In another aspect, the described antibodies may be obtained by phage display selection from a large pool of antibody libraries. Preferably, the described antibodies may be obtained by a method comprising phage display screening of human recombinant variants of single chain fragment variable (scFv) or antigen-binding fragment (Fab) or F(ab')2 fragments with a protein or peptide having an amino acid sequence selected from the group consisting of SEQ ID NO: 2 or 3.

In a further aspect, a method of inhibiting growth and/or killing of a cell expressing CLDN 18.2 is described, the method comprising contacting the cell with an effective amount of the described antibody. In certain embodiments, CLDN 18.2 is expressed on the surface of the cell.

In a further aspect, a method of treating or preventing a disease or disorder involving cells expressing CLDN 18.2 is described, the method comprising administering to a subject an antibody described herein. Preferably the disease or disorder is a tumor-related disease and, in particular embodiments, is selected from the group consisting of gastric cancer, esophageal cancer, pancreatic cancer, lung cancer, ovarian cancer, colon cancer, hepatic cancer, head-neck cancer, and cancer of the gallbladder. In certain embodiments, CLDN 18.2 is expressed on the surface of the cells.

In a preferred embodiment, the antibodies described herein have the ability to bind to CLDN 18.2 while they do not bind to a CLDN 18.1 variant, or bind to CLDN 18.1 with a lower affinity as compared to the binding affinity to CLDN 18.2.

The term "binding" refers to a specific binding between one molecule or agent to another molecule with specificity. The term 'specific binding" means that a molecule or an agent, such as an antibody, binds stronger to a target, such as an epitope, for which it is specific compared to the binding to another target. An agent binds stronger to a first target compared to a second target if it binds to the first target with a "dissociation constant" or "$K_D$" which is lower than the dissociation constant for the second target. Preferably, the dissociation constant ($K_D$) for the target to which the agent binds specifically is more than 10-fold, preferably more than 20-fold, more preferably more than 50-fold, even more preferably more than 100-fold, 200-fold, 500-fold or 1000-fold lower than the dissociation constant ($K_D$) for the target, to which the agent does not bind specifically.

The antibodies described herein mediate killing of cells expressing CLDN 18.2, preferably expressed on the surface of these cells.

In one embodiment, antibodies described herein induce complement dependent cytotoxicity (CDC), e.g., at least about 20% CDC mediated lysis; alternatively, at least about 20-40% CDC mediated lysis; alternatively about 40-50% CDC mediated lysis; and alternatively, more than 50% CDC mediated lysis of cells expressing CLDN 18.2. Examples of such antibodies include the following antibodies: 15G11, 9A1, 5C9, 5H1, 1D5, 8C5, 9F1, 7A10, 8C12, 14D7, 5H7, 5G7, 4G3, 14B7, 7H1, 5H1, 15B5, or their chimeric or humanized version comprising a light chain and a heavy chain consisting essentially of the amino acid sequences of SEQ ID NOs:250 and 251, 252 and 253, 254 and 255, 256 and 257, 258 and 259, 260 and 261, 262 and 263, 264 and 265, 266 and 267, 268 and 269, 270 and 271, 272 and 273, 274 and 275, 276 and 277, 278 and 279, 280 and 281, 282 and 283, 284 and 285, 286 and 287, 288 and 289, 290 and 291, 292 and 293, 294 and 295, 296 and 297, 298 and 299, 300 and 301, 302 and 303, 304 and 305, 306 and 307, 308 and 309, 310 and 311, 312 and 313, 314 and 315, 316 and 317, 318 and 319, 320 and 321, 322 and 323, 324 and 325, 326 and 327, 328 and 329, 330 and 331, 332 and 333, 334 and 335, 336 and 337, 338 and 339, 340 and 341, 342 and 343, 344 and 345, 346 and 347, 348 and 349, 350 and 351, 352 and 353, 354 and 355, 356 and 357, 358 and 359, 360 and 361.

Alternatively, or in addition to inducing CDC, antibodies described herein may induce antibody dependent cellular cytotoxicity (ADCC) of cells expressing CLDN 18.2 in the presence of effector cells (e.g., monocytes, mononuclear cells, NK cells and PMNs). Examples of such antibodies include the following antibodies: 15G11, 9A1, 5C9, 5H1, 1D5, 8C5, 9F1, 7A10, 8C12, 14D7, 5H7, 5G7, 4G3, 14B7, 7H1, 5H1, 15B5, or their chimeric or humanized version comprising a light chain and a heavy chain consisting essentially of the amino acid sequences of SEQ ID NOs:250 and 251, 252 and 253, 254 and 255, 256 and 257, 258 and 259, 260 and 261, 262 and 263, 264 and 265, 266 and 267, 268 and 269, 270 and 271, 272 and 273, 274 and 275, 276 and 277, 278 and 279, 280 and 281, 282 and 283, 284 and 285, 286 and 287, 288 and 289, 290 and 291, 292 and 293, 294 and 295, 296 and 297, 298 and 299, 300 and 301, 302 and 303, 304 and 305, 306 and 307, 308 and 309, 310 and 311, 312 and 313, 314 and 315, 316 and 317, 318 and 319, 320 and 321, 322 and 323, 324 and 325, 326 and 327, 328 and 329, 330 and 331, 332 and 333, 334 and 335, 336 and 337, 338 and 339, 340 and 341, 342 and 343, 344 and 345, 346 and 347, 348 and 349, 350 and 351, 352 and 353, 354 and 355, 356 and 357, 358 and 359, 360 and 361.

The described antibodies may have the ability to induce apoptosis of cells expressing CLDN 18.2, induce homotypic adhesion of cells expressing CLDN 18.2 and/or induce phagocytosis of cells expressing CLDN 18.2 in the presence of macrophages. The antibodies described herein may have one or more of the above described functional properties. In certain embodiments, preferably, the described antibodies induce CDC mediated lysis and ADCC mediated lysis of cells expressing CLDN 18.2, and more preferably, induce ADCC mediated lysis of cells expressing CLDN 18.2 while they do not induce CDC mediated lysis of said cells. Exemplary target cells for antibodies described herein include, but are not limited to, cancer cells expressing CLDN 18.2, such as tumorigenic gastric, pancreatic, esophageal and lung cancer cells. In a particular preferred embodiment, killing of cells mediated by antibodies described herein is CLDN 18.2 specific, i.e., antibodies described herein mediate killing of cells, preferably CDC and/or ADCC mediated lysis of cells, expressing CLDN 18.2 but do not mediate killing of cells expressing CLDN 18.1 but not expressing CLDN 18.2. The antibodies described herein may be used to mediate killing of tumor cells in the treatment or prevention of cancers, such as gastric cancer, esophageal cancer, pancreatic cancer, lung cancer, ovarian cancer, colon cancer, hepatic cancer, head-neck cancer, and cancer of the gallbladder.

In one aspect, the antibodies described herein may be derived from different species, including but not limited to mouse, rat, rabbit, guinea pig, and human.

In certain embodiments, antibodies described herein also include chimeric molecules, in which an antibody constant region derived from one species, preferably human, is combined with the antigen binding site derived from another species.

Moreover, in certain further embodiments, antibodies described herein include humanized molecules, in which the antigen binding sites of an antibody derived from a non-human species are combined with constant and framework regions of human origin.

Antibodies described herein preferably dissociate from CLDN 18.2 with a dissociation equilibrium constant (KD) of approximately 0.1-1000 nM or less.

Preferably, antibodies described herein do not cross-react with related cell-surface antigens and thus do not inhibit their function.

In still another aspect, compositions, e.g., pharmaceutical and diagnostic compositions/kits are described, comprising a pharmaceutically acceptable carrier formulated along with one or a combination of antibodies described herein. In a particular embodiment, the composition includes a combination of antibodies, which bind to distinct epitopes or which possess distinct functional characteristics, such as inducing CDC and/or ADCC and inducing apoptosis. In this embodiment, antibodies may be used in combination, e.g., as a pharmaceutical composition comprising two or more anti-CLDN 18.2 monoclonal antibodies. For example, anti-CLDN 18.2 antibodies having different but complementary activities can be combined into a single therapy to achieve a desired therapeutic effect. In one embodiment, the composition includes an anti-CLDN 18.2 antibody that mediates CDC in combination with another anti-CLDN 18.2 antibody that induces apoptosis. In another embodiment, the composition includes an anti-CLDN 18.2 antibody that mediates highly effective killing of target cells in the presence of effector cells, in combination with another anti-CLDN 18.2 antibody that inhibits the growth of cells expressing CLDN 18.2.

Also, included are the simultaneous or sequential administration of two or more anti-CLDN 18.2 antibodies described herein, wherein at least one of the antibodies is a chimeric anti-CLDN 18.2 antibody and at least one further antibody is a human anti-CLDN 18.2 antibody, the antibodies binding to the same or different epitopes of CLDN 18.2. Preferably, a chimeric CLDN 18.2 antibody described herein is administered first, followed by the administration of a human anti-CLDN 18.2 antibody described herein, wherein the human anti-CLDN 18.2 antibody is, in certain preferred embodiments administered for an extended period of time, e.g., as maintenance therapy.

Accordingly, antibodies described herein can be used for treatment and/or prevention of a variety of diseases involving cells expressing CLDN 18.2 by administering the antibodies to patients suffering from such diseases. Exemplary diseases that can be treated (e.g., ameliorated) or prevented include, but are not limited to, tumorigenic diseases. Examples of tumorigenic diseases, which can be treated and/or prevented include gastric cancer, pancreatic cancer, esophageal cancer, lung cancer, ovarian cancer, colorectal cancer, hepatic cancer, head-neck cancer, and cancer of the gallbladder.

Certain further embodiments include a combination therapy including an antibody described herein in combination with another treatment protocol. For example, in a particular embodiment, the subject being administered the antibody described herein is additionally treated with a chemotherapeutic agent, radiation, or an agent that modulates, e.g., enhances or inhibits, the expression or activity of an Fc receptor, e.g., an Fc-gamma receptor, such as a cytokine. Typical cytokines for administration during treatment include granulocyte colony-stimulating factor (GCSF), granulocyte-macrophage colony-stimulating factor (GM-CSF), interferon-gama (IFN-gama), and tumor necrosis factor (TNF). Exemplary therapeutic agents include, among others, anti-neoplastic agents such as doxorubicin, cisplatin, taxotere, 5-fluoruracil, methotrexate, gemcitabine and cyclophosphamide.

In yet another aspect, an immunization strategy to immunize non-human animals, such as mice with human CLDN 18.2 or a peptide fragment thereof, preferably CLDN 18.2 or a peptide fragment thereof to obtain antibodies, is described. Exemplary peptides for immunization are those selected from the group consisting of SEQ ID NO:1, 2, or 3. Accordingly, in some preferred embodiments, the antibodies described herein are those obtained by immunization using peptides selected from the group consisting of SEQ ID NO:2 and 3. Analogously, antibodies to CLDN 18.2 can be generated in a transgenic non-human animal, such as a transgenic mouse. The transgenic non-human animal may be a transgenic mouse having a genome comprising a heavy chain transgene and a light chain transgene encoding all or a portion of an antibody.

Wildtype as well as transgenic non-human animals can be immunized with a purified or enriched preparation of CLDN 18.2 antigen and/or nucleic acids and/or cells expressing CLDN 18.2 or a peptide fragment thereof. Preferably, the non-human animal is capable of producing multiple isotypes of human monoclonal antibodies to CLDN 18.2 (e.g., IgG, IgA and/or IgM) by undergoing V-D-J recombination and isotype switching. Isotype switching may occur by e.g., classical or non-classical isotype switching.

Accordingly, in yet another aspect, isolated B cells from a non-human animal as described above, are described. The isolated B cells can be immortalized by fusion to an immortalized cell to provide a source (e.g., a hybridoma) of described antibodies. Methods to do so are known to those skilled in the art. Such hybridomas (i.e., which, produce antibodies described herein) are also included herein.

As exemplified herein, the described antibodies can be obtained directly from hybridomas, which express the antibody, or can be cloned and recombinantly expressed in a host cell (e.g., a CHO cell, or a lymphocytic cell). Further examples of host cells are microorganisms, such as E. coli, and fungi, such as yeast. Alternatively, they can be produced recombinantly in a transgenic non-human animal or plant.

The terms "fragment" or "fragment of an amino acid sequence" as used above relate to a part of an antibody sequence, i.e., a sequence which represents the antibody sequence shortened at the N- and/or C-terminus, which when it replaces said antibody sequence in an antibody retains binding of the antibody to CLDN 18.2 and, preferably, functions of the antibody as described herein, e.g., CDC mediated lysis or ADCC mediated lysis. Preferably, a fragment of an amino acid sequence comprises at least 80%, preferably at least 90%, 95%, 96%, 97%, 98%, or 99% of the amino acid residues from said amino acid sequence or any percentage in-between the provided exemplary percentages. Fragments of amino acid sequences described herein may be encoded by respective fragments of nucleic acid sequences encoding said amino acid sequences.

In certain embodiments, an antibody described herein comprises a combination of light chain variable domain (VL) and heavy chain variable domain (VH), wherein the light chain variable region comprises the amino acid sequences of one of SEQ ID NOS:14, 22, 29, 43, 51, 57, 64, 72, 78, 86, 93, 100, 106, 110, 117, 125, 130, 131, 136, 138, 140, 142, 144, 146, 148, 150, 152, 154, 157, 160, 163, 166, 169, 172, 175, 178, 180, 183, 186, 221, 224, 228, 231, 234, 237, 242, or 246, and wherein said heavy chain variable region comprises the amino acid sequence selected from the group consisting of SEQ ID NOs: 18, 25, 32, 47, 54, 61, 68, 76, 82, 89, 96, 102, 109, 113, 121, 127, 134, 137, 139, 141, 143, 145, 147, 149, 151, 153, 155, 159, 162, 165, 168, 171, 174, 176, 179, 181, 184, 187, 189, 191, 193, 195, 197, 199, 201, 203, 205, 207, 209, 211, 213, 215, 217, 219, 222, 223, 225, 226, 229, 232, 235, 240, 244, or 248.

In a preferred embodiment, an antibody described herein comprises a combination of a light chain variable domain (VL) and a heavy chain variable domain (VH) selected from the following possibilities (i) to (vi):

(i) the VL comprises an amino acid sequence of SEQ ID NO:154 or a fragment thereof, and the VH comprises an amino acid sequence of SEQ ID NO:155 or a fragment thereof, (ii) the VL comprises an amino acid sequence of SEQ ID NO:160 or a fragment thereof, and the VH comprises an amino acid sequence of SEQ ID NO:162 or a fragment thereof, (iii) the VL comprises an amino acid sequence of SEQ ID NO:224 or a fragment thereof, and the VH comprises an amino acid sequence of SEQ ID NO:225 or a fragment thereof, (iv) the VL comprises an amino acid sequence of SEQ ID NO:231 or a fragment thereof, and the VH comprises an amino acid sequence of SEQ ID NO:232 or a fragment thereof, (v) the VL comprises an amino acid sequence of SEQ ID NO:237 or a fragment thereof and the VH comprises an amino acid sequence of SEQ ID NO:240 or a fragment thereof.

(vi) the VL comprises an amino acid sequence of SEQ ID NO:242 or a fragment thereof, and the VH comprises an amino acid sequence of SEQ ID NO:244 or a fragment thereof, In a further embodiment, an antibody described herein comprises resurfaced or humanized versions, wherein surface exposed residues of the antibody or its fragments are replaced in both light and heavy chains to more closely resemble known human antibody surfaces. Such humanized antibodies may have increased utility, compared to murine or chimeric antibodies, as therapeutic or diagnostic agents. Humanized versions of the antibodies are characterized herein with respect to their respective amino acid sequences of both light and heavy chain variable regions, the DNA sequences of the genes for the light and heavy chain variable regions, the identification of the CDRs, the identification of their surface amino acids, and disclosure of a means for their expression in recombinant form.

In a preferred aspect, an antibody or antibody fragment described herein have improved properties. For example, antibodies or antibody fragments having improved affinity for CLDN 18.2 are prepared and described herein.

Reference herein to "an antibody comprising with respect to the heavy chain thereof a particular chain, or a particular region or sequence" preferably relates to the situation wherein all heavy chains of the antibody comprise the particular chain, region or sequence. This applies correspondingly to the light chain of an antibody.

Other embodiments relate to nucleic acids comprising genes or nucleic acid sequences encoding antibodies or parts thereof, e.g., an antibody chain, as described herein. The nucleic acids may be comprised in a vector, e.g., a plasmid, cosmid, virus, bacteriophage or another vector used, e.g., conventionally in genetic engineering. The vector may comprise further genes such as marker genes, which allow for the selection of the vector in a suitable host cell and under suitable conditions. Furthermore, the vector may comprise expression control elements allowing proper expression of the coding regions in suitable hosts. Such control elements are known to the artisan and may include a promoter, a splice cassette, and a translation initiation codon.

In certain embodiments, the described nucleic acid may be operatively attached to expression control sequences allowing expression in eukaryotic or prokaryotic cells. Control elements ensuring expression in eukaryotic or prokaryotic cells are well known to those skilled in the art.

Methods for construction of the described nucleic acid molecules, for construction of vectors comprising the above nucleic acid molecules, for introduction of the vectors into appropriately chosen host cells, for causing or achieving the expression are well-known in the art.

Further embodiments relate to a host cell comprising a nucleic acid or vector as disclosed herein.

Other features and advantages of the embodiments described herein will be apparent from the following detailed description and claims.

DETAILED DESCRIPTION

Figure 1:
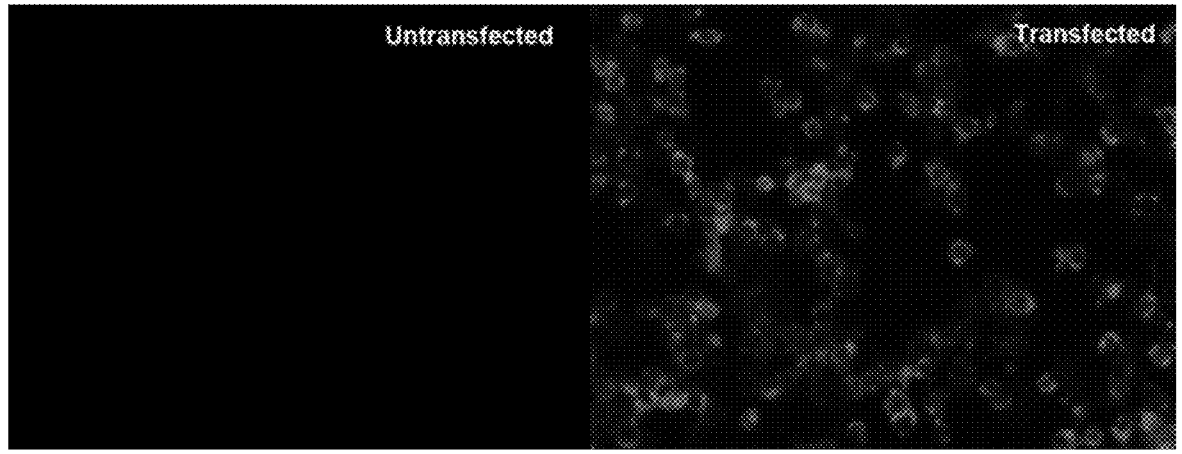
FIG. 1 shows a photograph of fluorescence analysis of HEK293 cells transfected with CLD18.2 coupled to a GFP and demonstrates fusion protein expressing on cell membrane.

The discovery of novel and improved antibodies that specifically bind to the membrane protein Claudin 18.2 on the cell surface is described herein. The binding of the antibody or antibody fragment thereof to the CLDN18.2-expressing cells mediates the killing of cells expressing CLDN18.2 by inducing at least one of complement dependent cytotoxicity (CDC) mediated lysis, antibody dependent cellular cytotoxicity (ADCC) mediated lysis, apoptosis, homotypic adhesion, or phagocytosis. The antibodies or antibody fragments described herein have the improved properties over those previously known anti-Claudin 18.2 antibodies including improved binding affinity to Claudin 18.2, or stability, or pharmacokinetic properties. Related polynucleotides, vectors, pharmaceutical compositions comprising the described anti-CLDN18.2 antibodies or antibody fragments thereof, are also provided. Also, provided are methods of making, as well as methods of using the anti-CLDN18.2 antibodies and antibody fragments disclosed herein, for example, in diagnostic methods and methods of treating cancer in a subject (as direct therapy, adjuvant therapy, and/or in combination therapy). Further, therapeutic combinations featuring antiCLDN18.2 antibodies (e.g., 5C9) and one or more of agents targeting additional aspects of the cancer immunity cycle, such as anti-PD-1 antibodies, anti-PD-L1 antibodies, antiCTLA4 antibodies; and methods of using such combinations for reducing tumor-mediated immunosuppression are also described.

In some aspects, the isolated monoclonal antibodies include IgA, IgG 1-4, IgE, IgM, and IgD antibodies. In one embodiment, the antibody is an IgG1 antibody, more particularly an IgG1, kappa or IgG1, lambda isotype. In another embodiment, the antibody is an IgG3 antibody, more particularly an IgG3, kappa or IgG3, lambda isotype. In yet another embodiment, the antibody is an IgG4 antibody, more particularly an IgG4, kappa or IgG4, lambda isotype. In still another embodiment, the antibody is an IgA1 or IgA2 antibody. In still another embodiment, the antibody is an IgM antibody.

In one embodiment, isolated antibody or antibody fragments thereof are described, which specifically bind to cells expressing CLDN 18, and preferably (i) bind to cells expressing CLDN 18.2, and (ii) do not bind to cells not expressing CLDN 18.2 but expressing CLDN 18.1. The described isolated antibody or antibody fragments thereof preferably (i) mediate killing of cells expressing CLDN 18.2, and (ii) do not mediate killing of cells not expressing CLDN 18.2 but expressing CLDN 18.1.

In another embodiment, isolated antibody or antibody fragments thereof are described, which (i) bind to tumor cells expressing CLDN 18, (ii) do not bind to CLDN 18 expressing cells of normal stomach mucosa, and/or (iii) do not bind to CLDN 18 expressing cells of non-cancer lung tissue. Also included are isolated antibody or antibody fragments thereof, which (i) mediate killing of tumor cells expressing CLDN 18, (ii) do not mediate killing of CLDN 18 expressing cells of normal stomach mucosa, and/or (iii) do not mediate killing of CLDN 18 expressing cells of non-cancer lung tissue.

Binding of the described isolated antibody or antibody fragments thereof to the CLDN 18.2 antigen may mediate the killing of cells expressing CLDN 18.2, for example, by activation of the complement system. Without being bound by the theory, it is contemplated that the killing of cells expressing CLDN 18.2 may occur by one or more of the following mechanisms: complement dependent cytotoxicity (CDC) of cells expressing CLDN 18.2; apoptosis of cells expressing CLDN 18.2; effector cell phagocytosis of cells expressing CLDN 18.2; or effector cell antibody dependent cellular cytotoxicity (ADCC) of cells expressing CLDN 18.2.

In some embodiments, the described isolated antibody or antibody fragments thereof bind to an epitope on CLDN 18.2, which is not present on CLDN 18.1, e.g., SEQ ID NO:1 and 2. In other embodiments, the described isolated antibody or antibody fragments thereof bind to an epitope localized on the CLDN 18.2-loop 1, e.g., SEQ ID NO:1. In preferred embodiments, the isolated antibody or antibody fragments thereof bind to an epitope on CLDN 18.2 which is not present on CLDN 18.1.

In one embodiment, an antibody described herein comprises resurfaced or humanized versions, wherein surface exposed residues of the antibody or its fragments are replaced in both light and heavy chains to more closely resemble known human antibody surfaces. Such humanized antibodies may have increased utility as therapeutic or diagnostic agents, as compared to murine or chimeric antibodies.

The described antibodies include fully human antibodies as well. In some exemplary embodiments, such antibodies may be produced in a non-human transgenic animal, for example a transgenic mouse that is capable of producing multiple isotypes of human monoclonal antibodies to CLDN 18.2 by undergoing V-D-J recombination and isotype switching. Such transgenic animal can also be a transgenic rabbit for producing polyclonal antibodies, such as disclosed in, e.g., U.S. Pub. No. 2003/0017534, which is incorporated herein in its entirety.

I. General Terms (Definitions of Terms)

It is to be understood that this invention is not limited to specific compositions or process steps, as such can vary. As used in this specification and the appended claims, the singular forms 'a,' "an" and "the" include plural referents unless the context clearly dictates otherwise. The terms "a' (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

It is understood that wherever aspects are described herein with the language "comprising," otherwise analogous aspects described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "CLDN 18.2" or "CLDN18.2 polypeptide" as used herein refer to the isoform 2 of the tight junction molecule Claudin-18 protein. The respective sequences of the human and murine forms of CLDN18.2 are available at the Uniprot database. In defining any CLDN18.2 antibody epitopes, the amino acid numbering used represents the amino acid residue of the mature CLDN18.2 protein, which does not contain the signal sequence residues. An exemplary CLDN18.2 polypeptide is provided in SEQ ID No:2.

The term "CLDN18.2" includes post-translationally modified variants, isoforms and species homologs of human CLDN18.2, which are naturally expressed by cells or are expressed on cells transfected with the CLDN18.2 gene.

The term "CLDN18 variant" shall encompass (i) CLDN18 splice variants, (ii) CLDN18-post translationally modified variants, particularly including variants with different N-glycosylation status, (iii) CLDN18 conformation variants, particularly including CLDN18-conformation-1, CLDN18-conformation-2 and CLDN18-conformation-3, (iv) CLDN18 free and homotypically/heterotypically associated variants localized at intercellular tight junctions, (v) CLDN18 cancer related and CLDN18 non-cancer related variants.

The terms "inhibit," "block," "suppress," and grammatical variants thereof are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% (including percentages in-between) in biological activity. Accordingly, when the terms "inhibition" or "suppression" are applied to describe, e.g., an effect on the enzymatic activity of CLDN18.2, the term refers to the ability of an anti-CLDN18.2 antibody or antigen binding fragment thereof to statistically significantly decrease the activity of CLDN18.2, relative to the CLDN18.2-mediated activity in an untreated (control) cell. The cell that expresses CLDN18.2 can be a naturally occurring cell or cell line (e.g., a cancer cell) or can be recombinantly-produced by introducing a nucleic acid encoding CLDN18.2 into a host cell. In some aspects, an anti-CLDN18.2 antibody or antigen binding fragment thereof can statistically significantly decrease the activity of a soluble form of CLDN18.2 in a biological fluid. In one aspect, the anti-CLDN18.2 binding molecule, e.g., an antibody or antigen binding fragment thereof inhibits CLDN18.2-mediated activity by at least 10%, at least 15%, or at least 20%, at least 25%, or at least 30%, at least 35%, or at least 40%, at least 45%, or at least 50%, at least 55%, or at least 60%, at least 65%, or at least 70%, at least 75%, or at least 80%, at least 85%, or at least 90%, at least 95%, or about 100%, as determined, for example, by the methods described in the Examples infra, and/or methods known in the art.

The term "suppress CLDN18.2 activity," as used herein, refers to the ability of anti-CLDN18.2 binding molecule, e.g., an antibody or antigen-binding fragment thereof to statistically significantly decrease CLDN18.2-dependent activity in a cell expressing CLDN18.2 or a sample containing CLDN18.2. In some aspects, the suppression of CLDN18.2 activity can be a decrease of at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or about 100% when cells or a sample are contacted with an anti-CLDN18.2 binding molecule, e.g., an antibody or antigen-binding fragment thereof described herein, relative to the CLDN18.2 activity measured in the absence of the anti-CLDN18.2 binding molecule, e.g., an antibody or antigen-binding fragment thereof (control conditions).

The terms "antibody" or "immunoglobulin," as used interchangeably herein, include whole antibodies and any antigen binding fragment or single chains thereof. A typical antibody comprises at least two heavy chains (abbreviated herein as "HC") and two light chains (abbreviated herein as "LC") interconnected by disulfide bonds. Each heavy chain is comprised of a heavy chain variable region (or heavy chain variable domain, abbreviated herein as "VH" or "$V_H$") and a heavy chain constant region. The heavy chain constant region is comprised of three domains, CH1, CH2, and CH3. Each light chain is comprised of a light chain variable region (or light chain variable domain, abbreviated herein as "VL" or "$V_L$") and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. Exemplary antibodies of the present disclosure include anti-CLDN18.2 antibodies (original and germlined), affinity optimized clones, optimized antibodies lacking ADCC, and other optimized antibodies (e.g., serum half-life-optimized antibodies including, for example, YTE mutations, see Dall'Acqua et al., J. Biol. Chem. 281:23514-24 (2006) and U.S. Pat. No. 7,083,784, which are hereby incorporated by reference in their entireties).

An antibody can be of any the five major classes of immunoglobulins: IgA, IgD, IgE, IgG, and IgM, or subclasses (isotypes) thereof (e.g., IgG1, IgG2, IgG3, IgG4, IgA1, and IgA2), based on the identity of their heavy-chain constant domains referred to as alpha, delta, epsilon, gamma, and mu, respectively. The different classes of immunoglobulins have different and well known subunit structures and three-dimensional configurations.

A "blocking antibody" or an "antagonist antibody" is one which inhibits or reduces biological activity of the antigen it binds, such as CLDN18.2. In a certain aspect, blocking antibodies or antagonist antibodies substantially or completely inhibit the biological activity of the antigen. Desirably, the biological activity is reduced or blocked by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or even 100%.

The terms "CLDN18.2 antibody," "antibody that binds to CLDN18.2" or "anti-CLDN18.2" refer to an antibody or antigen binding fragment thereof that is capable of binding CLDN18.2 with sufficient affinity, such that the molecule is useful as a therapeutic agent or diagnostic reagent in targeting CLDN18.2. The extent of binding of an anti-CLDN18.2 antibody to an unrelated, non-CLDN18.2 protein is less than about 10% of the binding of the antibody to CLDN18.2 as measured, e.g., by a radioimmunoassay (RIA), BIACORE™ (using recombinant CLDN18.2 as the analyte and antibody as the ligand, or vice versa), or other binding assays known in the art. In certain aspects, an antibody that binds to CLDN18.2 has a dissociation constant ($K_D$) of <1 µM, <100 nM, <10 nM, <1 nM, <0.1 nM, <10 pM, <1 pM, or <0.1 pM. The term "anti-CLDN18.2" also broadly encompasses molecules comprising, e.g., the CDRs of the antibodies disclosed herein incorporated into a scaffold. Thus, the phrase "isolated binding molecule or antigen binding fragment thereof which specifically binds to CLDN18.2" would refer not only to antibodies and antigen-binding fragments thereof, but also would refer to a molecule comprising, for example, one or more scaffolds incorporating the CDRs of the antibodies disclosed herein. See, for example, U.S. Patent Publ. No. 20150098955, which is herein incorporated by reference in its entirety.

By "CTLA4 polypeptide" is meant a polypeptide having at least 85% amino acid sequence identity to GenBank AccessionAAL07473.1 or a fragment thereof having T cell inhibitory activity. The sequence of AAL07473.1 is provided below:

CTLA4 polypeptide sequence:
(SEQ ID No: 40)
MACLGFQRHKAQLNLATRTWPCTLLFFLLFIPVFCKAMHVAQPAVVLASS

RGIASFVCEYASPGKATEVRVTVLRQADSQVTEVCAATYMMGNELTFLDD

SICTGTSSGNQVNLTIQGLRAMDTGLYICKVELMYPPPYYLGIGNGTQIY

VIDPEPCPDSDFLLWILAAVSSGLFFYSFLLTAVSLSKMLKKRSPLTTGV

YVKMPPTEPECEKQFQPYFIPIN

By "CTLA4 nucleic acid molecule" is meant a polynucleotide encoding a CTLA4 polypeptide. An exemplary CTLA4 nucleic acid molecule sequence is provided at GenBank Accession No. AAL07473.

By "anti-CTLA4 antibody" is meant an antibody that selectively binds a CTLA4 polypeptide. Exemplary anti-CTLA4 antibodies are described for example at U.S. Pat. Nos. 6,682,736; 7,109,003; 7,123,281; 7,411,057; 7,824,679; 8,143,379; 7,807,797; and 8,491,895 (Tremelimumab is 11.2.1, therein), which are herein incorporated by reference in their entirety. Tremelimumab is an exemplary anti-CTLA4 antibody.

By "PD-1 polypeptide" is meant a polypeptide or fragment thereof having at least about 85% amino acid identity to NCBI Accession No. NP_005009 and having PD-L1 and/or PD-L2 binding activity. The sequence of NP_005009 is provided below.

PD-1 polypeptide sequence (NCBI ACCESSION NO. NP_005009):
(SEQ ID No: 41)
MQIPQAPWPV VWAVLQLGWR PGWFLDSPDR PWNPPTFSPALLVVTE

GDNA TFTCSFSNTSESFVINWYRM SPSNQTDKLA AFPEDRSQPG

QDCRFRVTQL PNGRDFHMSV VRARRNDSGTYLCGAISLAP

KAQIKESLRA ELRVTERRAE VPTAHPSPSP RPAGQFQTIV

VGVVGGLLGSLVLLVWVLAV ICSRAARGTI GARRTGQPLK

EDPSAVPVFS VDYGELDFQW REKTPEPPVP CVPEQTEYAT

IVFPSGMGTS SPARRGSADG PRSAGPLRPE DGHCSWPL

By "PD-1 nucleic acid molecule" is meant a polynucleotide encoding a PD-1 polypeptide. An exemplary PD-1 nucleic acid molecule sequence is provided at NCBI Accession No. NM_005018. By "anti-PD-1 antibody" is meant an antibody or antigen binding fragment thereof that selectively binds a PD-1 polypeptide. Exemplary anti-PD-1 antibodies include for example pembrolizumab (KEYTRUDA®, lambrolizumab, MK-3475), nivolumab (OPDIvA®, BMS-936558, MDX-1106, ONO-4538), or AMP-224.

By "PD-L1 polypeptide" is meant a polypeptide or fragment thereof having at least about 85%, 95% or 100% amino acid identity to NCBI Accession No. NP_001254635 and having PD-1 and CD80 binding activity. The sequence of NP_001254635 is provided below.

PD-L1 polypeptide sequence (NCBI ACCESSION NO. NP_001254635):
(SEQ ID No: 42)
MRIFAVFIFMTWHLLNAPYNKINGRILVVDPVTSEHELTCQLAEGYPKAE

VIWTSSDHQVLSGKTTTTNSKREEKLFNVTSTLRINTTTNEIFYCTFRRL

DPEENHTAELVIPELPLAHPPNERTHLVILGAILLCLGVALTFIFRLRKG

RMMDVKKCGIQDTNSKKGSD THLEET

By "PD-L1 nucleic acid molecule" is meant a polynucleotide encoding a PD-L1 polypeptide. An exemplary PD-L1 nucleic acid molecule sequence is provided at NCBI Accession No. NM_001267706.

By "anti-PD-L1 antibody" is meant an antibody or antigen binding fragment thereof that selectively binds a PD-L1 polypeptide. Exemplary anti-PD-L1 antibodies are described, for example, in U.S. Pat. Pub. Nos. US 2013/0034559 (U.S. Pat. No. 8,779,108) and U.S. 2014/0356353, which are herein incorporated by reference in their entirety.

The term "antigen binding fragment" refers to a molecule comprising a portion of an intact antibody, and in particular refers to a molecule comprising the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

The term "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "monoclonal antibody" encompasses both intact and full-length monoclonal antibodies as well as antibody fragments (such as Fab, Fab', F(ab')2, Fv), single chain variable fragments (scFv), fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals (e.g., expression of a human antibody in a transgenic mouse).

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the CDRs are replaced by residues from the CDR of a non-human species (e.g., mouse, rat, rabbit, or hamster) that have the desired specificity, affinity, and capability (Jones et al., 1986, Nature, 321:522525; Riechmann et al., 1988, Nature, 332:323-327; Verhoeyen et al., 1988, Science, 239:1534-1536). In some instances, the framework (FW) amino acid residues of a human immunoglobulin are replaced with the corresponding residues in an antibody from a non-human species that has the desired specificity, and/or affinity, and/or capability.

The humanized antibody can be further modified by the substitution of additional residues either in the Fv framework region (FW) and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin, whereas all or substantially all of the FW regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641, which are incorporated herein in their entirety.

A "variable region" of an antibody refers to the variable region of the antibody light chain or the variable region of the antibody heavy chain, either alone or in combination. The variable regions of the heavy and light chain each consist of four FW regions connected by three CDR regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al., Sequences of Proteins of Immunological Interest, 5th ed., 1991, National Institutes of Health, Bethesda Md.)); and (2) an approach based on crystallographic studies of antigen-antibody complexes (Al-lazikani et al., (1997) *J. Molec. Biol.*, 273:927-948)). In addition, combinations of these two approaches are sometimes used in the art to determine CDRs.

The Kabat numbering system is generally used when referring to a residue in the variable domain (e.g., Kabat et al., Sequences of Immunological Interest, 5th Ed. Public Health Service, National Institutes of Health, Bethesda, Md. (1991)). For consistency, all antibodies described herein are numbered according to the Kabat system as described in a more recent publication (Mathieu Dondelinger et al Understanding the Significance and Implications of Antibody Numbering and Antigen-Binding Surface/Residue Definition, Frontiers in Immunology 9, 2278 (2018)), However, since Kabat definition of CDRs is flawed, we chose AbM system for CDR definition The phrases "amino acid position numbering as in Kabat," "Kabat position," "Kabat numbering scheme", "Kabat numbering system," and grammatical variants thereof refer to the numbering system used for heavy chain variable domains, light chain variable domains, heavy chain, or light chain of the compilation of antibodies in Mathieu Dondelinger et al Understanding the Significance and Implications of Antibody Numbering and Antigen-Binding Surface/Residue Definition, Frontiers in Immunology 9, 2278 (2018)). Using this numbering system, the actual linear amino acid sequence can contain fewer or additional amino acids corresponding to a shortening of, or insertion into, a FW or CDR of the variable domain, or CH1, CH2, or CH3 of said antibodies described in the invention. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

As used throughout the specification the VH CDRs sequences described correspond to the classical Kabat numbering locations, namely Kabat VH-CDR1 is at positions 26-35B, VH-CDR2 is a positions 50-65, and VH-CDR3 is at positions 95-102. VL-CDR1, VL-CDR2 and VL-CDR3 also correspond to classical Kabat numbering locations, namely positions 24-34, 50-56 and 89-97, respectively.

As used herein the Fc region includes the polypeptides comprising the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc can include the J chain. For IgG, Fc comprises immunoglobulin domains Cgamma2 and Cgamma3 (Cy2 and Cy3) and the hinge between Cgamma 1 (C71) and Cgamma2 (Cy2).

Although the boundaries of the Fc region can vary, the human IgG heavy chain Fc region is usually defined to comprise residues C226 or P230 to its carboxyl-terminus, wherein the numbering is according to the EU numbering (Edelman, G. M. et al., The covalent structure of an entire gammaG immunoglobulin molecule. Proc. Natl. Acad. USA, 63, 78-85 (1969)). Fc can refer to this region in isolation, or this region in the context of an antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art can exist.

The term "human antibody" means an antibody produced by a human or an antibody having an amino acid sequence corresponding to an antibody produced by a human made using any technique known in the art (e.g., recombinant expression in cultures cells, or expression in transgenic animals). Thus, the term human antibody also encompasses an antibody having an amino acid sequence corresponding to an antibody originally produced by a human (or an engineered variant or derivative thereof) but expressed in a non-human system (e.g., produced by chemical synthesis; recombinantly expressed in microbial, mammal, or insect cells; or expressed in an animal subject). Accordingly, an antibody obtained from a human subject or from human cells (e.g., hybridoma or cell line expressing a recombinant antibody or fragment thereof) and subsequently expressed in an animal, e.g., mice, is considered a human antibody. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more animal species. Typically, the variable region of both light and heavy chains corresponds to the variable region of antibodies derived from one species of mammals (e.g., mouse, rat, rabbit, etc.) with the desired specificity, and/or affinity, and/or capability while the constant regions are homologous to the sequences in antibodies derived from another specie (usually human) to avoid eliciting an immune response in that species. The term "epitope" as used herein refers to an antigenic protein determinant capable of binding to a CLDN18.2 antibody or CLDN18.2 binding molecule disclosed herein. Epitopes usually consist of chemically active surface groupings of molecules such as amino acids or sugar side chains and usually have specific three dimensional structural characteristics, as well as specific charge characteristics. The part of an antibody or binding molecule that recognizes the epitope is called a "paratope." The epitopes of protein antigens are divided into two categories, conformational epitopes and linear epitopes, based on their structure and interaction with the paratope. A conformational epitope is composed of discontinuous sections of the antigen's amino acid sequence. These epitopes interact with the paratope based on the 3-D surface features and shape or tertiary structure of the antigen. By contrast, linear epitopes interact with the paratope based on their primary structure. A linear epitope is formed by a continuous sequence of amino acids from the antigen.

The term "antibody binding site" refers to a region in the antigen (e.g., CLDN18.2) comprising a continuous or discontinuous site (i.e., an epitope) to which a complementary antibody specifically binds. Thus, the antibody binding site can contain additional areas in the antigen which are beyond the epitope and which can determine properties such as binding affinity and/or stability, or affect properties such as antigen enzymatic activity or dimerization. Accordingly, even if two antibodies bind to the same epitope within an antigen, if the antibody molecules establish distinct intermolecular contacts with amino acids outside of the epitope, such antibodies are considered to bind to distinct antibody binding sites.

The term "binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

The term "potency" is normally expressed as an $IC_{50}$ value, in nM unless otherwise stated. $IC_{50}$ is the median inhibitory concentration of an antigen-binding molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art. Improvement in potency can be determined by measuring, e.g., against a parent antibody (for example, the parent antibody prior to germlining or the parent antibody prior to affinity optimization).

The term "germlining" means that amino acids at specific positions in an antibody are mutated back to those in the germ line.

The fold improvement in potency for the antibodies or polypeptides of the present disclosure as compared to a parent antibody can be at least about 2-fold, at least about 4-fold, at least about 6-fold, at least about 8-fold, at least about 10-fold, at least about 15-fold, at least about 20-fold, at least about 25-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

The terms "antibody-dependent cell-mediated cytotoxicity" or "ADCC" refer to a form of cytotoxicity in which secreted immunoglobulins bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A polypeptide, antibody, polynucleotide, vector, cell, or composition which is "isolated" is a polypeptide, antibody, polynucleotide, vector, cell, or composition, respectively, which is in a form not found in nature. Isolated polypeptides, antibodies, polynucleotides, vectors, cells or compositions include those, which have been purified to a degree that they are no longer in a form in which they are found in nature. In some aspects, an antibody, polynucleotide, vector, cell, or composition, which is isolated is substantially pure.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical composition" refers to a preparation which is in such form as to permit the biological activity of the active ingredient (e.g., an anti-CLDN18.2 binding molecule disclosed herein) to be effective, and which contains no additional components which are unacceptably toxic to a subject to which the composition would be administered. Such composition can be sterile.

An "effective amount" of an anti-CLDN18.2 binding molecule as disclosed herein is an amount sufficient to carry out a specifically stated purpose. An "effective amount" can be determined empirically and in a routine manner, in relation to the stated purpose.

The term "therapeutically effective amount" refers to an amount of an anti-CLDN18.2 binding molecule disclosed herein or other drug effective to "treat" a disease or disorder in a subject or mammal.

Terms such as "treating," or "treatment," or "to treat," or "alleviating," or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The terms "cancer," "tumor," "cancerous," and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, cholangiocarcinoma (liver) and renal papillary carcinoma. In some aspects, the term cancer as used herein specifically refers to cancer expressing CLDN18.2. In some specific aspects, the term cancer refers to cancers expressing low levels of CLDN18.2. In some aspects, the term cancer as used herein specifically refers to cancer expressing CLDN18.2 (e.g., gastric cancer, esophageal cancer, pancreatic cancer, lung cancer, ovarian cancer, colon cancer, hepatic cancer, head-neck cancer, and cancer of the gallbladder).

The terms "polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the instant disclosure are based upon antibodies, in certain aspects, the polypeptides can occur as single chains or associated chains.

A "recombinant" polypeptide or protein refers to a polypeptide or protein produced via recombinant DNA technology. Recombinantly-produced polypeptides and proteins expressed in engineered host cells are considered isolated, as are native or recombinant polypeptides, which have been separated, fractionated, or partially or substantially purified by any suitable technique. The polypeptides disclosed herein can be recombinantly produced using methods known in the art. Alternatively, the proteins and peptides disclosed herein can be chemically synthesized.

The term "amino acid substitution" refers to replacing an amino acid residue present in a parent sequence with another amino acid residue. An amino acid can be substituted in a parent sequence, for example, via chemical peptide synthesis or through recombinant methods known in the art. Accordingly, references to a "substitution at position X" or "substitution at position X" refer to the substitution of an amino acid present at position X with an alternative amino acid residue. In some aspects, substitution patterns can be described according to the scheme AXY, wherein A is the single letter code corresponding to the amino acid naturally present at position X, and Y is the substituting amino acid residue. In other aspects, substitution patterns can be described according to the schema XY, wherein Y is the single letter code corresponding to the amino acid residue substituting the amino acid naturally present at position X.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

"Non-conservative substitutions" include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala, Ser) or no side chain (e.g., Gly).

Other substitutions can be readily identified by those of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

The term "amino acid insertion" refers to introducing a new amino acid residue between two amino acid residues present in the parent sequence. An amino acid can be inserted in a parent sequence, for example, via chemical peptide synthesis or through recombinant methods known in the art. Accordingly as used herein, the phrases "insertion between positions X and Y" or "insertion between Kabat positions X and Y," wherein X and Y correspond to amino acid positions (e.g., a cysteine amino acid insertion between positions 239 and 240), refers to the insertion of an amino acid between the X and Y positions, and also to the insertion in a nucleic acid sequence of a codon encoding an amino acid between the codons encoding the amino acids at positions X and Y. Insertion patterns can be described according to the schema AXins, wherein A is the single letter code corresponding to the amino acid being inserted, and X is the position preceding the insertion.

The term "percent sequence identity" between two polypeptide or polynucleotide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program is disclosed at the U.S. government's National Center for Biotechnology Information (NCBI) BLAST web site-(blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and, also, available from the European Bioinformatics Institute (EBI) at ebi.ac.uldTools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, see clustal.org. Another suitable program is MUSCLE, available from drive5.com/muscle/. ClustalW2 and MUSCLE are alternatively disclosed, e.g., at the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, disclosed at tcoffee.org, and alternatively available, e.g., from the EBI. It will also be appreciated that the final alignment used to calculate percent sequence identity can be curated either automatically or manually.

The term "consensus sequence," as used herein with respect to light chain (VL) and heavy chain (VH) variable regions, refers to a composite or genericized VL or VH sequence defined based on information as to which amino acid residues within the VL or VH chain are amenable to modification without detriment to antigen binding. Thus, in a "consensus sequence" for a VL or VH chain, certain amino acid positions are occupied by one of multiple possible amino acid residues at that position. For example, if an arginine (R) or a serine (S) occur at a particular position, then that particular position within the consensus sequence can be either arginine or serine (R or S). Consensus sequences for VH and VL chain can be defined, for example, by in vitro affinity maturation (e.g., randomizing every amino acid position in a certain CDR using degenerate coding primers), by scanning mutagenesis (e.g., alanine scanning mutagenesis) of amino acid residues within the antibody CDRs, or any other methods known in the art, followed by evaluation of the binding of the mutants to the antigen to determine whether the mutated amino acid position affects antigen binding. In some aspects, mutations are introduced in the CDR regions. In other aspects, mutations are introduced in framework regions. In some other aspects, mutations are introduced in CDR and framework regions.

II. CLDN18.2-Binding Molecules, and their Mechanisms of Action (i). Mechanisms of Action of CLDN 18.2-Binding Molecules Although the following provides a potential mechanism underlying the therapeutic efficacy of the antibodies or antibody fragments thereof described herein it is not to be considered as limiting in any way.

The isolated antibody or antibody fragment thereof described herein preferably interacts with components of the immune system, preferably through Antibody-dependent cell-mediated cytotoxicity (ADCC) or Complement-dependent cytotoxicity (CDC).

ADCC describes the cell-killing ability of effector cells as described herein, in particular lymphocytes, which preferably requires the target cell being marked by an isolated binding molecule (e.g., an antibody) or antigen-binding fragment thereof. ADCC preferably occurs when the isolated binding molecule (e.g., an antibody) or antigen-binding fragment thereof binds to antigens on tumor cells and the Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

CDC is another cell-killing method that can be directed by antibodies. Preferably, in this cascade, the formation of antigen-antibody complexes results in the uncloaking of multiple C1q binding sites in close proximity on the CH2 domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

(ii). CLDN18.2-Binding Molecules

Certain embodiments provide CLDN18.2 binding molecules, e.g., antibodies and antigen-binding fragments thereof that specifically bind CLDN18.2, for example, human CLDN18.2. The full-length amino acid (aa) and nucleotide (nt) sequences for CLDN18.2 are known in the art. In some aspects, the anti-CLDN18.2 binding molecules are human antibodies. In certain aspects, the CLDN18.2 binding molecules are antibodies or antigen-binding fragments thereof.

In some aspects, CLDN18.2 binding molecules, e.g., antibodies or antigen-binding fragments thereof comprise a Fab, a Fab', a F(ab')$_2$, a Fd, a single chain Fv or scFv, a disulfide linked Fv, a V-NAR domain, an IgNar, an intrabody, an IgG CH2, a minibody, a F(ab)$_3$, a tetrabody, a triabody, a diabody, a single-domain antibody, DVD-Ig, Fcab, mAb$^2$, a (scFv)$_2$, or a scFv-Fc. In some aspects, the antibody is of the IgG type, for example of the IgG type.

In some aspects, the anti-CLDN18.2 antibody or antigen-binding fragment thereof comprises a heavy chain constant region or fragment thereof. In some specific aspects, the heavy chain constant region is an IgG constant region. The IgG constant region can comprise a light chain constant region selected from the group consisting of a kappa constant region and a lambda constant region.

In certain aspects, the mouse antibody is CLDN18.2-15G11, CLDN18.2-5C9, CLDN18.2-9A, CLDN18.2-5H1, CLDN18.2-1D5, CLDN18.2-8C5, CLDN18.2-9F1, CLDN18.2-7A10, CLDN18.2-8C12, CLDN18.2-14D7, CLDN18.2-5H7, CLDN18.2-5G7, CLDN18.2-4G3, CLDN18.2-14B7, CLDN18.2-7H1, CLDN18.2-5H1, CLDN18.2-15B5, and their humanized version such as CLDN18.2-h5C9o, CLDN18.2-h5C9ob, or CLDN18.2-h5C9oap. In other aspects, the anti-CLDN18.2 antibodies or antigen-binding fragments thereof disclosed herein are modified compared to a mouse antibody. The modifications can include mutations in the CDR regions and/or in the FW regions as compared to the mouse antibody.

The phrase "CLDN18.2-15G11 antibody" refers to an IgG comprising two light chain variable domains (VLs) comprising the amino acid sequence of SEQ ID NO:14 and two heavy chain variable domains (VHs) comprising the amino acid sequence of SEQ ID NO:18.

The phrase "CLDN18.2-5C9 antibody" refers to an IgG comprising two light chain variable domains (VLs) comprising the amino acid sequence of SEQ ID NO:29 and two heavy chain variable domains (VHs) comprising the amino acid sequence of SEQ ID NO:32.

The phrase "CLDN18.2-9A1 antibody" refers to an IgG comprising two light chain variable domains (VLs) comprising the amino acid sequence of SEQ ID NO:22 and two heavy chain variable domains (VHs) comprising the amino acid sequence of SEQ ID NO:25.

The phrase "CLDN18.2-5H1 antibody" refers to an IgG comprising two light chain variable domains (VLs) comprising the amino acid sequence of SEQ ID NO:43 and two heavy chain variable domains (VHs) comprising the amino acid sequence of SEQ ID NO:47.

The phrase "CLDN18.2-1D5 antibody" refers to an IgG comprising two light chain variable domains (VLs) comprising the amino acid sequence of SEQ ID NO:51 and two heavy chain variable domains (VHs) comprising the amino acid sequence of SEQ ID NO:54.

The phrase "CLDN18.2-8C5 antibody" refers to an IgG comprising two light chain variable domains (VLs) comprising the amino acid sequence of SEQ ID NO:57 and two heavy chain variable domains (VHs) comprising the amino acid sequence of SEQ ID NO:61.

The phrase "CLDN18.2-9F1 antibody" refers to an IgG comprising two light chain variable domains (VLs) comprising the amino acid sequence of SEQ ID NO:64 and two heavy chain variable domains (VHs) comprising the amino acid sequence of SEQ ID NO:68.

The phrase "CLDN18.2-7A10 antibody" refers to an IgG comprising two light chain variable domains (VLs) comprising the amino acid sequence of SEQ ID NO:72 and two heavy chain variable domains (VHs) comprising the amino acid sequence of SEQ ID NO:76.

The phrase "CLDN18.2-8C12 antibody" refers to an IgG comprising two light chain variable domains (VLs) comprising the amino acid sequence of SEQ ID NO:78 and two heavy chain variable domains (VHs) comprising the amino acid sequence of SEQ ID NO:82.

The phrase "CLDN18.2-14D7 antibody" refers to an IgG comprising two light chain variable domains (VLs) comprising the amino acid sequence of SEQ ID NO:86 and two heavy chain variable domains (VHs) comprising the amino acid sequence of SEQ ID NO:89.

The phrase "CLDN18.2-5H7 antibody" refers to an IgG comprising two light chain variable domains (VLs) comprising the amino acid sequence of SEQ ID NO:93 and two heavy chain variable domains (VHs) comprising the amino acid sequence of SEQ ID NO:96.

The phrase "CLDN18.2-5G7 antibody" refers to an IgG comprising two light chain variable domains (VLs) comprising the amino acid sequence of SEQ ID NO:100 and two heavy chain variable domains (VHs) comprising the amino acid sequence of SEQ ID NO:102.

The phrase "CLDN18.2-4G3 antibody" refers to an IgG comprising two light chain variable domains (VLs) comprising the amino acid sequence of SEQ ID NO:106 and two heavy chain variable domains (VHs) comprising the amino acid sequence of SEQ ID NO:109.

The phrase "CLDN18.2-14B7 antibody" refers to an IgG comprising two light chain variable domains (VLs) comprising the amino acid sequence of SEQ ID NO:110 and two heavy chain variable domains (VHs) comprising the amino acid sequence of SEQ ID NO:113

The phrase "CLDN18.2-7H1 antibody" refers to an IgG comprising two light chain variable domains (VLs) comprising the amino acid sequence of SEQ ID NO:117 and two heavy chain variable domains (VHs) comprising the amino acid sequence of SEQ ID NO:121.

The phrase "CLDN18.2-h5C9o antibody" refers to an IgG comprising two light chain variable domains (VLs) comprising the amino acid sequence of SEQ ID NO:154 and two heavy chain variable domains (VHs) comprising the amino acid sequence of SEQ ID NO: 155.

The phrase "CLDN18.2-h5C9ob antibody" refers to an IgG comprising two light chain variable domains (VLs) comprising the amino acid sequence of SEQ ID NO:160 and two heavy chain variable domains (VHs) comprising the amino acid sequence of SEQ ID NO:162.

The phrase "CLDN18.2-h5C9oap antibody" refers to an IgG comprising two light chain variable domains (VLs) comprising the amino acid sequence of SEQ ID NO:237 and two heavy chain variable domains (VHs) comprising the amino acid sequence of SEQ ID NO:240.

(iii). CLDN18.2-5C9-Derived Anti-CLDN18.2 Antibodies

In certain aspects, an anti-CLDN18.2 antibody comprises modifications to CDR1 and/or CDR2 and/or CDR3 of the light chain variable domain (VL) of the CLDN18.2-5C9 antibody, including, but not limited to: a light chain CDR1 comprising the consensus sequence KSSQSLLNX$_1$GNQKSYLT (SEQ ID NO: 364), wherein X$_1$ represents amino acid residues Serine (S) or Tryptophan (W); and/or, a light chain CDR2 comprising the consensus sequence WASTX$_2$ES (SEQ ID NO:365), wherein X$_2$ represents amino acid residues leucine (L) or Arginine (R); and/or, a light chain CDR3 comprising the consensus sequence QNX$_3$YX$_4$FPFT (SEQ ID NO: 366), wherein X$_3$ represents amino acid residues Asparagine (N), Glycine (G), Serine (S); X$_4$ represents amino acid residues Serine (S), Alanine (A), Phenylalanine (F).

In certain other embodiments, an anti-CLDN18.2 antibody comprises modifications to CDR1 and/or CDR2 and/or CDR3 of the heavy chain variable of the CLDN18.2-5C9 antibody, including, but not limited to:

a heavy chain CDR1 comprising the consensus sequence GYTFX$_5$X$_6$X$_7$X$_8$MN (SEQ ID NO: 367), wherein X$_5$ represents amino acid residues Serine (S) or Threonine (T); X$_6$ represents amino acid residues Asparagine (N) or a bond; X$_7$ represents amino acid residues Tyrosine (Y) or a bond; X$_8$ represents amino acid residues Glycine (G) or a bond; and/or, a heavy chain CDR2 comprising the consensus sequence WINMYTGEX$_9$X$_{10}$YADDFKG (SEQ ID NO: 368), wherein X$_9$ represents amino acid residues Proline (P), Arginine (R) or Glutamine (Q); X$_{10}$ represents amino acid residues Threonine (T) or Asparagine (N); and/or, a heavy chain CDR3 comprising the consensus sequence X$_{11}$X$_{12}$X$_{13}$GNX$_{14}$X$_{15}$DY (SEQ ID NO: 369), wherein X$_{11}$ represents amino acid residues Leucine (L), Methionine (M), Threonine (T), Serine (S), or Alanine (A); X$_{12}$ represents amino acid residues Tyrosine (Y), Threonine (T), Glycine (G), Alanine (A), Serine (S), Valine (V), Asparagine (N), or Phenylalanine (F); X$_{13}$ represents amino acid residues Asparagine (N), Arginine (R), Proline (P), Threonine (T), Methionine (M), Lysine (K), or Histidine (H); X$_{14}$ represents amino acid residues Serine (S), Alanine (A), Valine (V), Glycine (G), Threonine (T); X$_{15}$ represents amino acid residues Leucine (L), Phenylalanine (F), Methionine (M), or Isoleucine (I), In another embodiment, the anti-CLDN18.2 antibody or antigen binding fragment thereof comprises a VL region comprising the consensus amino acid sequence: [FW1] KSSQSLLNX$_1$GNQKSYLT[FW2] WASTX$_2$ES[FW3] QNX$_3$YX$_4$FPFT[FW4] (SEQ ID NO: 370), wherein [FW1], [FW2], [FW3] and [FW4] represent VL framework regions, and wherein:

X$_1$ represents amino acid residues Serine (S) or Tryptophan (W);

X$_2$ represents amino acid residues leucine (L) or Arginine (R);

X$_3$ represents amino acid residues Asparagine (N), Glycine (G), Serine (S);

X$_4$ represents amino acid residues Serine (S), Alanine (A), Phenylalanine (F), Tryptophan (W), Arginine (R), Glutamic Acid (E), and Tyrosine (Y);

In another embodiment, the anti-CLDN18.2 antibody or antigen binding fragment thereof comprises a VH region which comprises the consensus amino acid sequence: [FW5] GYTFX$_5$X$_6$X$_7$X$_8$MN[FW6] WINMYTGEX$_9$X$_{10}$YADDFKG[FW7] X$_{11}$X$_{12}$X$_{13}$GNX$_{14}$X$_{15}$DY[FW8] (SEQ ID NO: 371) wherein [FW5], [FW6], [FW7] and [FW8] represent VH framework regions, and wherein:

X$_5$ represents amino acid residues Serine (S) or Threonine (T);

X$_6$ represents amino acid residues Asparagine (N) or a bond;

X$_7$ represents amino acid residues Tyrosine (Y) or a bond;

X$_8$ represents amino acid residues Glycine (G) or a bond;

X$_9$ represents amino acid residues Proline (P), Arginine (R) or Glutamine (Q);

X$_{10}$ represents amino acid residues Threonine (T) or Asparagine (N);

X$_{11}$ represents amino acid residues Leucine (L), Methionine (M), Threonine (T), Serine (S), or Alanine (A), X$_{12}$ represents amino acid residues Tyrosine (Y), Threonine (T), Glycine (G), Alanine (A), Serine (S), Valine (V), Asparagine (N), or Phenylalanine (F), X$_{13}$ represents amino acid residues Asparagine (N), Arginine (R), Proline (P), Threonine (T), Methionine (M), Lysine (K), or Histidine (H), X$_{14}$ represents amino acid residues Serine (S), Alanine (A), Valine (V), Glycine (G), Threonine (T), X$_{15}$ represents amino acid residues Leucine (L), Phenylalanine (F), Methionine (M), or Isoleucine (I), In a further embodiment, the anti-CLDN18.2 antibody or antigen binding fragment thereof comprises an antibody light chain variable region (VL) and an antibody heavy chain variable region (VH), wherein the VL region comprising the consensus amino acid sequence: [FW1] KSSQSLLNX$_1$GNQKSYLT[FW2] WASTX$_2$ES[FW3] QNX$_3$YX$_4$FPFT[FW4] (SEQ ID NO: 370), wherein [FW1], [FW2], [FW3] and [FW4] represent VL framework regions, and wherein:

X$_1$ represents amino acid residues Serine (S) or Tryptophan (W);

X$_2$ represents amino acid residues leucine (L) or Arginine (R);

X$_3$ represents amino acid residues Asparagine (N), Glycine (G), Serine (S);

X$_4$ represents amino acid residues Serine (S), Alanine (A), Phenylalanine (F), Tryptophan (W), Arginine (R), Glutamic Acid (E), and Tyrosine (Y);

and the VH region comprising the consensus amino acid sequence: [FW5] GYTFX$_5$X$_6$X$_7$X$_8$MN[FW6] WINMYTGEX$_9$X$_{10}$YADDFKG[FW7] X$_{11}$X$_{12}$X$_{13}$GNX$_{14}$X$_{15}$DY[FW8] (SEQ ID NO: 371) wherein [FW5], [FW6], [FW7] and [FW8] represent VH framework regions, and wherein:

$X_5$ represents amino acid residues Serine (S) or Threonine (T);

$X_6$ represents amino acid residues Asparagine (N) or a bond;

$X_7$ represents amino acid residues Tyrosine (Y) or a bond;

$X_8$ represents amino acid residues Glycine (G) or a bond;

$X_9$ represents amino acid residues Proline (P), Arginine (R) or Glutamine (Q);

$X_{10}$ represents amino acid residues Threonine (T) or Asparagine (N);

$X_{11}$ represents amino acid residues Leucine (L), Methionine (M), Threonine (T), Serine (S), or Alanine (A), $X_{12}$ represents amino acid residues Tyrosine (Y), Threonine (T), Glycine (G), Alanine (A), Serine (S), Valine (V), Asparagine (N), or Phenylalanine (F), $X_{13}$ represents amino acid residues Asparagine (N), Arginine (R), Proline (P), Threonine (T), Methionine (M), Lysine (K), or Histidine (H), $X_{14}$ represents amino acid residues Serine (S), Alanine (A), Valine (V), Glycine (G), Threonine (T), $X_{15}$ represents amino acid residues Leucine (L), Phenylalanine (F), Methionine (M), or Isoleucine (I), (iv). Mutant anti-CLDN18.2 Antibodies In certain embodiments, an anti-CLDN18.2 antibody (for example, CLDN18.2-15G11, CLDN18.2-5C9, or CLDN18.2-9A1 CLDN18.2-5H1, CLDN18.2-1D5, CLDN18.2-8C5, CLDN18.2-9F1, CLDN18.2-7A10, CLDN18.2-8C12, CLDN18.2-14D7, CLDN18.2-5H7, CLDN18.2-5G7, CLDN18.2-4G3, CLDN18.2-14B7, CLDN18.2-7H1, CLDN18.2-5H1, CLDN18.2-15B5, and their humanized version such as CLDN18.2-h5C9o, CLDN18.2-h5C9ob, or CLDN18.2-h5C9oap antibody) or antigen-binding fragment thereof disclosed herein comprises mutations that improve the binding to human FcRn, improve the immunogenicity of said antibodies, and improve the half-life of the anti-CLDN18.2 antibody or antigen-binding fragment thereof.

For example, in some embodiment, such mutations are a methionine (M) to tyrosine (Y) mutation in position 252, a serine (S) to threonine (T) mutation in position 254, and a threonine (T) to glutamic acid (E) mutation in position 256, according to the EU numbering scheme, introduced into the constant domain of an IgG1. See, e.g., U.S. Pat. No. 7,658,921, which is incorporated by reference herein. This type of mutant IgG, referred to as a "YTE mutant" has been shown display approximately four-times increased half-life as compared to wild-type versions of the same antibody (Dall'Acqua et al., *J. Biol. Chem.*, 281:23514-24 (2006)). In some embodiments, an anti-CLDN18.2 antibody or antigen-binding fragment thereof comprising an IgG constant domain comprises one or more amino acid substitutions of amino acid residues at positions 251-257, 285-290, 308-314, 385-389, and 428-436, according to the EU numbering scheme, wherein such mutations increase the serum half-life of the anti-CLDN18.2 antibody or antigen-binding fragment thereof.

In additional embodiments, a YTE mutant further comprises a substitution at position 434 of the IgG constant domain, according to the EU numbering scheme, with an amino acid selected from the group consisting of tryptophan (W), methionine (M), tyrosine (Y), and serine (S).

In an alternative embodiment, a YTE mutant further comprises a substitution at position 434 of the IgG constant domain, numbered according to the EU system, with an amino acid selected from the group consisting of tryptophan (W), methionine (M), tyrosine (Y), and serine (S), and substitution at position 428 of the IgG constant domain, numbered according to the EU scheme, with an amino acid selected from the group consisting of threonine (T), leucine (L), phenylalanine (F), and serine (S).

In yet further embodiment, a YTE mutant further comprises a substitution at position 434 of the IgG constant domain, numbered according to the EU scheme, with tyrosine (Y), and a substitution at position 257 of the IgG constant domain, numbered according to the EU scheme, with leucine (L). In some aspects, a YTE mutant further comprises a substitution at position 434 of the IgG constant domain, according to the EU numbering scheme, with serine (S), and a substitution at position 428 of the IgG constant domain, numbered according to the EU scheme, with leucine (L).

Still in a further embodiment, invention YTE mutant comprises a substitution of Lysine (K) at position 214 of the CH1 domain, numbered according to the EU scheme, with Arginine (R) (K214R), and a substitution of Aspartic acid (D) at position 356 with Glutamic acid (E) (D356E) and Leucine (L) at position of 358 with Methionine (M) (L358M) of the Fc domain, numbered according to the EU scheme. The mutation of K214R of CH1 domain and mutations of D356E and L358M on the Fc domain is believed to improve immunogenicity of said antibody or its fragment.

In one embodiment, the anti-CLDN18.2 antibody (for example, CLDN18.2-15G11, CLDN18.2-5C9, or CLDN18.2-9A1 CLDN18.2-5H1, CLDN18.2-1D5, CLDN18.2-8C5, CLDN18.2-9F1, CLDN18.2-7A10, CLDN18.2-8C12, CLDN18.2-14D7, CLDN18.2-5H7, CLDN18.2-5G7, CLDN18.2-4G3, CLDN18.2-14B7, CLDN18.2-7H1, CLDN18.2-5H1, CLDN18.2-15B5, and their humanized version such as CLDN18.2-h5C9o, CLDN18.2-h5C9ob, or CLDN18.2-h5C9oap antibody) or antigen-binding fragment thereof disclosed herein comprises an IgG1 constant domain comprising a methionine (M) to tyrosine (Y) mutation in position 252, a serine (S) to threonine (T) mutation in position 254, and a threonine (T) to glutamic acid (E) mutation in position 256 of the IgG1 constant domain, according to the EU numbering scheme.

In certain further embodiments, the anti-CLDN18.2 antibody (for example, CLDN18.2-15G11, CLDN18.2-5C9, or CLDN18.2-9A1 CLDN18.2-5H1, CLDN18.2-1D5, CLDN18.2-8C5, CLDN18.2-9F1, CLDN18.2-7A10, CLDN18.2-8C12, CLDN18.2-14D7, CLDN18.2-5H7, CLDN18.2-5G7, CLDN18.2-4G3, CLDN18.2-14B7, CLDN18.2-7H1, CLDN18.2-5H1, CLDN18.2-15B5, and their humanized version such as CLDN18.2-h5C9o, CLDN18.2-h5C9ob, or CLDN18.2-h5C9oap antibody) or antigen-binding fragment thereof disclosed herein comprises at least one IgG constant domain amino acid substitution selected from the group consisting of:

(a) substitution of the amino acid at position 252 with tyrosine (Y), phenylalanine (F), tryptophan (W), or threonine (T);

(b) substitution of the amino acid at position 254 with threonine (T);

(c) substitution of the amino acid at position 256 with serine (S), arginine (R), glutamine (Q), glutamic acid (E), aspartic acid (D), or threonine (T);

(d) substitution of the amino acid at position 257 with leucine (L);

(e) substitution of the amino acid at position 309 with proline (P);

(f) substitution of the amino acid at position 311 with serine (S);

(g) substitution of the amino acid at position 428 with threonine (T), leucine (L), phenylalanine (F), or serine (S);

(h) substitution of the amino acid at position 433 with arginine (R), serine (S), isoleucine (I), proline (P), or glutamine (Q);

(i) substitution of the amino acid at position 434 with tryptophan (W), methionine (M), serine (S), histidine (H), phenylalanine (F), or tyrosine; and, (j) a combination of two or more of said substitutions, wherein the positions are numbered according to the EU numbering scheme, and wherein the modified IgG has an increased serum half-life compared to the serum half-life of an IgG having the wild-type IgG constant domain.

In some embodiments, the VH and/or VL amino acid sequence of an anti-CLDN18.2 antibody (for example, CLDN18.2-15G11, CLDN18.2-5C9, or CLDN18.2-9A1 CLDN18.2-5H1, CLDN18.2-1D5, CLDN18.2-8C5, CLDN18.2-9F1, CLDN18.2-7A10, CLDN18.2-8C12, CLDN18.2-14D7, CLDN18.2-5H7, CLDN18.2-5G7, CLDN18.2-4G3, CLDN18.2-14B7, CLDN18.2-7H1, CLDN18.2-5H1, CLDN18.2-15B5 antibody) or antigen-binding fragment thereof disclosed herein can be at least about 90%, at least about 95%, at least about 96%, at least about 97%, at least about 98% or at least about 99% similar to the VH and VL sequences set forth above, and comprise 1, 2, 3, 4 or more conservative substitutions. A CLDN18.2 antibody having VH and VL regions having high (i.e., 90% or greater) sequence similarity or sequence identity to the VH regions of SEQ ID NOs: 18, 25, 32, 47, 54, 61, 68, 76, 82, 89, 96, 102, 109, 113, 121, 127, 134, 137, 139, 141, 143, 145, 147, 149, 151, 153, 155, 159, 162, 165, 168, 171, 174, 176, 179, 181, 184, 187, 189, 191, 193, 195, 197, 199, 201, 203, 205, 207, 209, 211, 213, 215, 217, 219, 222, 223, 225, 226, 229, 232, 235, 240, 244, or 248, and/or VL regions of SEQ ID NOs:14, 22, 29, 43, 51, 57, 64, 72, 78, 86, 93, 100, 106, 110, 117, 125, 130, 131, 136, 138, 140, 142, 144, 146, 148, 150, 152, 154, 157, 160, 163, 166, 169, 172, 175, 178, 180, 183, 186, 221, 224, 228, 231, 234, 237, 242, or 246, respectively, can be obtained by mutagenesis (e.g., site-directed or PCR-mediated mutagenesis) of nucleic acid molecules encoding the said antibodies, followed by testing of the encoded altered antibody for retained function using the functional assays described herein.

In some embodiments, the Fc domain of an anti-CLDN18.2 antibody disclosed herein or the Fc domain of a fusion protein comprising a CLDN18.2-binding fragment of an antibody disclosed herein can have reduced binding to an Fc receptor to reduce cytotoxicity, e.g., via ADCC. Alternatively, in some aspects, the Fc domain of the antibody or Fc fusion protein cab have increased binding to an Fc receptor to increase cytotoxicity, e.g., via ADCC. In some aspects, the Fc domain of the antibody or Fc fusion protein comprises a non-naturally occurring ADCC reducing amino acid residue at one or more positions.

Numerous specific mutations capable of reducing the ADCC activity of an antibody are known in the art. For example, exemplary mutations were previously described in U.S. Pat. Nos. 5,624,821, 5,648,260, 7,597,889, 8,961,967, 7,371,826, 7,785,791, 7,790,858, U.S. Patent Publication Nos. 2014/0378663, 2013/0071390, 2011/0212087, 2015/0118227, 2006/0194290, 2006/0194291, 2008/0274105, 2008/0274506, 2013/0089541, and 2013/0108623, which are herein incorporated by reference in their entireties. Antibodies with reduced ADCC effector function also include those with substitution of one or more of Fc region residues 238, 265, 269, 270, 297, 327, and 329 according to the EU numbering system (see, e.g., U.S. Pat. No. 6,737,056, which is incorporated herein in its entirety). Such Fc mutants also include Fc mutants with substitutions at two or more amino acid positions 265, 269, 270, 297 and 327, including Fc mutant with substitution of residues 265 and 297 to alanine (see, e.g., U.S. Pat. No. 7,332,581, which is incorporated herein in its entirety). Optionally, mutations which reduce both ADCC and CDC can be incorporated.

In one aspect, an anti-CLDN18.2 antibody is described, wherein the antibody is an IgG1, IgG2 or IgG3 and comprises at least one modification at one or more positions selected from the group consisting of 234, 235, and 331 as numbered by the EU numbering scheme. In still another specific aspect, the Fc region is an IgG1, IgG2 or IgG3 Fc region and the non-naturally occurring amino acids are selected from the group consisting of 234F, 235E, 235F, 235Q (or 235Y), 239A, 332Q, 331S, 332Q as numbered by the EU numbering scheme.

In another embodiment, an anti-CLDN18.2 antibody is described herein, wherein the antibody is an IgG4 and comprises at least one modification at one or more positions selected from the group consisting of 228 and 235 as numbered by the EU numbering scheme. In still another specific aspect, the Fc region is an IgG4 Fc region and the non-naturally occurring amino acids are selected from the group consisting of 228P, 235E and 235Y as numbered by the EU numbering scheme. In specific aspects, an anti-CLDN18.2 antibody is described herein, wherein the antibody is an IgG1, IgG2, or IgG3 and comprises modifications at positions (i) 234F, 235E, and 331S; (ii) 234F, 235F, and 331S; (iii) 234F, 235Q, and 322Q. In another specific aspect, an anti-CLDN18.2 antibody is described herein, wherein the antibody is an IgG4 and comprises modifications 228P and 235E.

III. Functional Characteristics of Anti-CLDN18.2 Antibodies

The affinity or avidity of an antibody for an antigen can be determined experimentally using any suitable method well known in the art, e.g., flow cytometry, enzyme-linked immunosorbent assay (ELISA), or radioimmunoassay (RIA), or kinetics (e.g., BIACORE™ analysis). Direct binding assays as well as competitive binding assay formats can be readily employed. (See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein). The measured affinity of a particular antibody-antigen interaction can vary if measured under different conditions (e.g., salt concentration, pH, temperature). Thus, measurements of affinity and other antigen-binding parameters (e.g., KD or Kd, $K_{off}/K_{on}$) are made with standardized solutions of antibody and antigen, and a standardized buffer, as known in the art and such as the buffer described herein.

It also known in the art that affinities measured using surface plasmon resonance analysis (e.g., BIACORE™) can vary depending on which one of the reactants is bound to the chip. In this respect, affinity can be measured using a format in which the targeting antibody (e.g., a clone 5C9 antibody) is immobilized onto the chip (referred to as an 'IgG down" format) or using a format in which the target protein (e.g., CLDN18.2) is immobilized onto the chip (referred to as, e.g., a "CLDN18.2 down" format).

In one embodiment, the anti-CLDN18.2 antibody (for example, a clone 5C9 antibody) or an antibody fragment thereof specifically binds CLDN18.2 and/or antigenic fragments thereof with a dissociation constant or $k_d$ ($k_{off}/k_{on}$) of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M.

In another embodiment, the anti-CLDN18.2 antibody (for example, anti-CLDN18.2-5C9, or a clone 5C9 antibody) or an antibody fragment thereof binds to CLDN18.2 and/or antigenic fragments thereof with a $K_{off}$ of less than $1\times10^{-3}$ $s^{-1}$, or less than $2\times10^{-3}$ $s^{-1}$. In other aspects, an anti-CLDN18.2 antibody or an antigen-binding fragment thereof binds to CLDN18.2 and antigenic fragments thereof with a $K_{off}$ of less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$. In another aspect, the anti-CLDN18.2 antibody (for example, anti-CLDN18.2 or a clone 5C9 antibody) or an antigen-binding fragment thereof binds to CLDN18.2 and/or antigenic fragments thereof with an association rate constant or $k_{on}$ rate of at least $10^5$ $M^{-1}$ $s^{-1}$, at least $5\times10^5$ $M^{-1}$ $s^{-1}$, at least $10^6$ $M^{-1}$ $s^{-1}$, at least $5\times10^6$ $M^{-1}$ $s^{-1}$, at least $10^7$ $M^{-1}$ $s^{-1}$, at least $5\times10^7$ $M^{-1}$ $s^{-1}$, or at least $10^8$ $M^{-1}$ $s^{-1}$, or at least $10^9$ $M^{-1}$ $s^{-1}$.

In some embodiments, the anti-CLDN18.2 antibody (for example, anti-CLDN18.2 or a clone 5C9 antibody) or an antigen-binding fragment thereof binds to CLDN18.2 on the surface of NUGC-4 cells with a $K_D$ of at least about 1 nM, at least about 10 nM, at least about 50 nM, at least about 80 nM, at least about 90 nM, at least about 100 nM, at least about 110 nM, at least about 120 nM, at least about 130 nM, at least about 140 nM, at least about 150 nM, at least about 160 nM, or at least about 170 nm, as measured by flow cytometry.

In certain further embodiments, the anti-CLDN18.2 antibody (for example, anti-CLDN18.2 or a clone 5C9 antibody) or an antibody fragment thereof binds to CLDN18.2 on the surface of CLDN 18.2 overexpressed cells such as CLDN18.2-293T cell (H4) with a $K_D$ of at least about 1 nM, at least about 10 nM, at least about 50 nM, at least about 80 nM, at least about 90 nM, at least about 100 nM, at least about 110 nM, at least about 120 nM, at least about 130 nM, at least about 140 nM, at least about 150 nM, at least about 160 nM, or at least about 170 nm, as measured by flow cytometry.

IV. Preparation of Anti-CLDN18.2 Antibodies and Antigen-Binding Fragments

Monoclonal anti-CLDN18.2 antibodies (for example, CLDN18.2-15G11, CLDN18.2-5C9, CLDN18.2-9A, CLDN18.2-5H1, CLDN18.2-1D5, CLDN18.2-8C5, CLDN18.2-9F1, CLDN18.2-7A10, CLDN18.2-8C12, CLDN18.2-14D7, CLDN18.2-5H7, CLDN18.2-5G7, CLDN18.2-4G3, CLDN18.2-14B7, CLDN18.2-7H1, CLDN18.2-5H1, CLDN18.2-15B5 antibody) and antigen-binding fragments thereof can be prepared using hybridoma methods, such as those described by Kohler and Milstein (1975) Nature 256:495. Using the hybridoma method, a mouse, hamster, or other appropriate host animal, is immunized as described above Kohler reference to elicit the production by lymphocytes of antibodies that will specifically bind to an immunizing antigen.

Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively, anti-CLDN18.2 monoclonal antibodies (for example, CLDN18.2-15G11, CLDN18.2-5C9, CLDN18.2-9A, CLDN18.2-5H1, CLDN18.2-1D5, CLDN18.2-8C5, CLDN18.2-9F1, CLDN18.2-7A10, CLDN18.2-8C12, CLDN18.2-14D7, CLDN18.2-5H7, CLDN18.2-5G7, CLDN18.2-4G3, CLDN18.2-14B7, CLDN18.2-7H1, CLDN18.2-5H1, CLDN18.2-15B5 antibody) and antigen-binding fragments thereof can also be made using recombinant DNA methods as described, for example, in U.S. Pat. No. 4,816,567, which is incorporated herein in its entirety. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells.

The polynucleotide(s) encoding an anti-CLDN18.2 antibody (for example, anti-CLDN 18.2-5C9 or a clone of 5C9) or antigen-binding fragment thereof can further be modified in a number of different manners using recombinant DNA technology to generate alternative antibodies. In some aspects, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some aspects, the constant regions are truncated or removed to generate the desired antibody fragment of a monoclonal antibody. Site-directed or high-density mutagenesis of the variable region can be used to optimize specificity, affinity, etc. of a monoclonal antibody.

In certain aspects, the anti-CLDN18.2 antibody (for example, anti-CLDN 18.2-5C9 or a clone of 5C9) or antigen-binding fragment thereof is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373, which are incorporated herein in their entirety).

Also, the anti-CLDN18.2 human antibody (for example, anti-CLDN 18.2-5C9 or a clone of 5C9) or antigen-binding fragment thereof can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-

6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Antibody phage display approach has emerged as a powerful alternative to hybridoma technology for the generation of monoclonal antibodies (A. S. Kang et al (1991) Proc. Nail. Acad. Sci. USA, 88, 4363; Sidhu, S. S., and Fellouse, F. A. (2006) *Nat. Chem. Biol.* 2, 682; Winter, G. (1998) *FEBS Lett.* 430, 92-94; Lerner, R. A. (2006) *Angew. Chem. Int. Ed. Engl.* 48, 8106-8125). It is now possible to select high-affinity antibodies against practically any antigen from phage libraries that bear tailored diversity elements encoded by synthetic DNA and/or libraries containing natural antibody genes from non-immunized human donors (Fellouse, F. A. et al. (2007) *J. Mol. Biol.* 373, 924-940; Fellouse, F. A. et al (2005) *J. Mol. Biol.* 348, 1153-1162; Liu, Y. et al (2011) *Biochem. Biophys. Res. Commun.* 413, 611-615; Ye, J. D. et al (2008) *Proc. Natl. Acad. Sci. USA* 105, 82-87; Gao, J., Sidhu, S. S., and Wells, J. A. (2009) *Proc. Natl. Acad. Sci. USA* 106, 3071-3076; Lerner, R. A. (2006) *Angew. Chem. Int. Ed. Engl.* 48, 8106-8125). This approach avoids the requirement for human or animal immunization, greatly reducing the labor and cost of antibody production. Selective enrichment of high-affinity binders from phage antibody libraries under controlled conditions enhances the reliability of output antibodies, and permits selection of binding with user-specified stringency (Gao, J., Sidhu, S. S., and Wells, J. A. (2009) *Proc. Natl. Acad. Sci. USA* 106, 3071-3076).

Affinity maturation strategies and chain shuffling strategies (Marks et al., 1992, Bio/Technology 10:779-783, incorporated by reference in its entirety) are known in the art and can be employed to generate high affinity human antibodies or antigen-binding fragments thereof described herein.

In some aspects, the anti-CLDN18.2 monoclonal antibody (for example, anti-CLDN 18.2-5C9 or a clone of 5C9) can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing CLDN18.2 binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the CLDN18.2 antigen and other favorable biological properties. To achieve this goal, humanized (or human) or engineered anti-CLDN18.2 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as CLDN18.2. In this way, framework (FW) residues can be selected and combined from the consensus and import sequences so that the desired antibody characteristic, such as increased affinity for the target antigen(s), is achieved.

Humanization, resurfacing or engineering of anti-CLDN18.2 antibodies (for example, anti-CLDN 18.2-5C9 or a clone of 5C9) or antigen-binding fragments thereof can be performed using any known method, such as but not limited to those described in, Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol; each of which is entirely incorporated herein by reference, including the references cited therein.

In certain embodiments, anti-CLDN18.2 humanized antibodies and antigen-binding fragments thereof can also be made in transgenic mice containing human immunoglobulin loci that are capable upon immunization of producing the full repertoire of human antibodies in the absence of endogenous immunoglobulin production. This approach wa previously described in U.S. Pat. Nos. 5,545,807; 5,545,806; 5,569,825; 5,625,126; 5,633,425; and 5,661,016, which are incorporated herein in their entirety.

In certain embodiments, an anti-CLDN18.2 antibody fragment (for example, a fragment from anti-CLDN 18.2-5C9 or a clone of 5C9) is provided. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain aspects, antiCLDN18.2 antibody fragments are produced recombinantly. Fab, Fv, and scFv antibody fragments can all be expressed in and secreted from *E. coli* or other host cells, thus allowing the production of large amounts of these fragments. Such anti-CLDN18.2 antibody fragments can also be isolated from the antibody phage libraries discussed above. The anti-CLDN18.2 antibody fragments can also be linear antibodies as described in U.S. Pat. No. 5,641,870, which is incorporated herein in its entirety. Other techniques for the production of antibody fragments, e.g., chemical synthesis, will be apparent to the skilled practitioner.

According to the present disclosure, techniques can be adapted for the production of single-chain antibodies specific to CLDN18.2 (see, e.g., U.S. Pat. No. 4,946,778, which is incorporated herein in its entirety). In addition, methods can be adapted for the construction of Fab expression libraries (see, e.g., Huse et al., Science 246:1275-1281 (1989)) to allow rapid and effective identification of monoclonal Fab fragments with the desired specificity for CLDN18.2, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

An anti-CLDN18.2 antibody (for example, anti-CLDN 18.2-5C9 or a clone of 5C9) or an antigen-binding fragment thereof disclosed herein can be modified in order to increase its serum half-life. This can be achieved, for example, by incorporation of a salvage receptor binding epitope into the antibody or antibody fragment by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule such as PEG are known in the art.

For the purposes of the present disclosure, it should be appreciated that modified anti-CLDN18.2 antibodies or antigen-binding fragments thereof can comprise any type of variable region that provides for the association of the antibody or polypeptide with CLDN18.2. In this regard, the variable region can comprise or be derived from any type of mammal that can be induced to mount a humoral response and generate immunoglobulins against the desired tumor associated antigen. As such, the variable region of the modified anti-CLDN18.2 antibodies or antigen-binding fragments thereof can be, for example, of human, murine, non-human primate (e.g., cynomolgus monkeys, macaques, etc.) or lupine origin. In some embodiments, both the variable and constant regions of the modified anti-CLDN18.2 antibodies or antigen-binding fragments thereof are human. In other embodiments, the variable regions of compatible antibodies (usually derived from a non-human source) can be engineered or specifically tailored to improve the binding properties or reduce the immunogenicity of the molecule. In this respect, variable regions can be humanized or otherwise altered through the inclusion of imported amino acid sequences.

In certain aspects, the variable domains in both the heavy and light chains of an anti-CLDN18.2 antibody (for example, anti-CLDN 18.2-5C9 or a clone of 5C9) or antigen-binding fragment thereof described herein may be altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain aspects from an antibody from a different species. It is not necessary to replace all of the CDRs with the complete CDRs from the donor variable region to transfer the antigen binding capacity of one variable domain to another. Rather, it is only necessary to transfer those residues that are necessary to maintain the activity of the antigen binding site. Given the explanations set forth in U.S. Pat. Nos. 5,585,089, 5,693,761 and 5,693,762 (which are incorporated herein in their entirety), it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified anti-CLDN18.2 antibodies (for example, anti-CLDN 18.2-5C9 or a clone of 5C9) or antigen-binding fragments thereof will comprise antibodies (e.g., full-length antibodies or immunoreactive fragments thereof), in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this the anti-CLDN18.2 molecules disclosed herein comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some aspects, modified constant regions wherein one or more domains are partially or entirely deleted are contemplated. In some embodiments, the modified antibodies will comprise domain deleted constructs or variants wherein the entire CH2 domain has been removed (ACH2 constructs). In some aspects, the omitted constant region domain will be replaced by a short amino acid spacer (e.g., 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the anti-CLDN18.2 antibody (for example, anti-CLDN 18.2-5C9 or a clone of 5C9) or an antigen-binding fragment thereof provides for altered effector functions that, in turn, affect the biological profile of the administered antibody or antigen-binding fragment thereof. For example, the deletion or inactivation (through point mutations or other means) of a constant region domain can reduce Fc receptor binding of the circulating modified antibody thereby increasing tumor localization. In other cases it can be that constant region modifications, consistent with this disclosure, moderate complement binding and thus reduce the serum half-life. Yet other modifications of the constant region can be used to eliminate disulfide linkages or oligosaccharide moieties that allow for enhanced localization due to increased antigen specificity or antibody flexibility. Similarly, modifications to the constant region in accordance with this disclosure can easily be made using well known biochemical or molecular engineering techniques well within the purview of the skilled artisan.

In certain embodiments, a CLDN18.2-binding molecule disclosed herein that is an antibody (for example, anti-CLDN18.2-5C9 or a clone of 5C9) or antigen-binding fragment thereof does not have one or more effector functions. For instance, in some aspects, the antibody or antigen-binding fragment thereof has no antibody-dependent cellular cytotoxicity (ADCC) activity and/or no complement-dependent cytotoxicity (CDC) activity. In certain aspects, the anti-CLDN18.2 antibody or antigen binding fragment thereof does not bind to an Fc receptor and/or complement factors. In certain aspects, the antibody or antigen-binding fragment thereof has no effector function.

It will be noted that in certain embodiments, the anti-CLDN18.2 modified antibodies or antigen-binding fragments thereof can be engineered to fuse the CH3 domain directly to the hinge region of the respective modified antibodies or fragments thereof. In other constructs, it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain aspects, any spacer added to the construct will be relatively non-immunogenic, or even omitted altogether, so as to maintain the desired biochemical qualities of the modified antibodies.

Besides the deletion of whole constant region domains, it will be appreciated that the anti-CLDN18.2 antibodies and antigen-binding fragments thereof of the present disclosure can be provided by the partial deletion or substitution of a few or even a single amino acid. For example, the mutation of a single amino acid in selected areas of the CH2 domain can be enough to substantially reduce Fc binding and thereby increase tumor localization. Similarly, it can be desirable to simply delete that part of one or more constant region domains that control the effector function to be modulated. Such partial deletions of the constant regions can improve selected characteristics of the antibody or antigen-binding fragment thereof (e.g., serum half-life) while leaving other desirable functions associated with the subject constant region domain intact. Moreover, as alluded to above, the constant regions of the disclosed anti-CLDN18.2 antibodies and antigen-binding fragments thereof can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified antibody or antigen-binding fragment thereof. Certain embodiments can comprise the addition of one or more amino acids to the constant region to enhance desirable characteristics such as decreasing or increasing effector function or provide for more cytotoxin or carbohydrate attachment. In such aspects, it can be desirable to insert or replicate specific sequences derived from selected constant region domains.

Variants and equivalents are also described herein, which are substantially homologous to the chimeric, humanized and human anti-CLDN18.2 antibodies, or antigen-binding fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

V. Polynucleotides Encoding CLDN18.2-Binding Molecules

In certain aspects, encompassed herein are polynucleotides comprising nucleic acid sequences that encode a polypeptide that specifically binds CLDN18.2 or an antigen-binding fragment thereof. For example, provided is a polynucleotide comprising a nucleic acid sequence that encodes an anti-CLDN18.2 antibody (e.g., anti-CLDN 18.2-5C9 or a clone of 5C9) or encodes an antigen-binding fragment of such an antibody. The described polynucleotides can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides are isolated. In certain aspects, the polynucleotides are substantially pure. In certain aspects, the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a CLDN18.2-binding proprotein, which is the mature protein plus additional 5' amino acid residues.

In certain embodiments, the polynucleotides comprise the coding sequence for the mature CLDN18.2-binding polypeptide, e.g., an anti-CLDN18.2 antibody (e.g., anti-CLDN 18.2-5C9 or a clone of 5C9) or an antigen-binding fragment thereof fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

In certain further embodiments, described are variants of the described polynucleotides encoding, for example, CLDN18.2-binding fragments, analogs, and derivatives of the CLDN18.2-binding molecules disclosed herein (e.g., anti-CLDN 18.2-5C9 or a clone of 5C9).

The polynucleotide variants can contain alterations in the coding regions, non-coding regions, or both. In some aspects, the polynucleotide variants contain alterations which produce silent substitutions, additions, or deletions, but do not alter the properties or activities of the encoded polypeptide. In some aspects, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*). Vectors and cells comprising the polynucleotides described herein are also provided.

In some aspects, a DNA sequence encoding a CLDN18.2-binding molecule, e.g., an anti-CLDN18.2 antibody (e.g., anti-CLDN 18.2-5C9 or a clone of 5C9) or an antigen-binding fragment thereof can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain aspects, recombinant expression vectors are used to amplify and express DNA encoding anti-CLDN18.2 antibodies (e.g., anti-CLDN 18.2-5C9 or a clone of 5C9) or antigen-binding fragments thereof. Recombinant expression vectors are replicable DNA constructs which have synthetic or cDNA-derived DNA fragments encoding a polypeptide chain of an anti-CLDN18.2 antibody or and antigen-binding fragment thereof, operatively linked to suitable transcriptional or translational regulatory elements derived from mammalian, microbial, viral or insect genes.

A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

Suitable host cells for expression of a CLDN18.2-binding molecule, e.g., an anti-CLDN18.2 antibody (e.g., anti-CLDN 18.2-5C9 or a clone of 5C9) or antigen-binding fragment thereof include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Pub. No. 2008/0187954, U.S. Pat. Nos. 6,413,746, 6,660,501, and 7,932,087, each of which is hereby incorporated by reference herein in its entirety.

Various mammalian or insect cell culture systems can also be advantageously employed to express recombinant CLDN18.2-binding molecules, e.g., anti-CLDN18.2 antibodies (e.g., anti-CLDN 18.2-5C9 or a clone of 5C9) or antigen-binding fragments thereof. Expression of recombinant proteins in mammalian cells can be performed because such proteins are generally correctly folded, appropriately modified and completely functional.

Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), NSO, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio-Technology 6:47 (1988).

CLDN18.2-binding molecules, e.g., anti-CLDN18.2 antibodies (e.g., anti-CLDN 18.2-5C9 or a clone of 5C9) or antigen-binding fragments thereof produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an AMICON® or Millipore PELLICON® ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an CLDN18.2-binding molecule (e.g., anti-CLDN 18.2-5C9 or a clone of 5C9). Some or all of the foregoing purification steps, in various combinations, can also be employed to provide a homogeneous recombinant protein.

A recombinant CLDN18.2-binding protein, e.g., an anti-CLDN18.2 antibody (e.g., anti-CLDN 18.2-5C9 or a clone of 5C9) or antigen-binding fragment thereof produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Pub. Nos. 2008/0312425, 2008/0177048, and 2009/0187005, each of which is hereby incorporated by reference herein in its entirety.

In certain aspects, the CLDN18.2-binding molecule is a polypeptide that is not an antibody. A variety of methods for identifying and producing non-antibody polypeptides that bind with high affinity to a protein target are known in the art. See, e.g., Skerra, Curr. Opin. Biotechnol., 18:295304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275: 2677-83 (2008), each of which is incorporated by reference herein in its entirety. In certain aspects, phage display technology can been used to identify/produce an CLDN18.2-binding polypeptide.

VI. Treatment Methods Using Therapeutic Anti-CLDN18.2 Antibodies

Also, provided are methods directed to the use of anti-CLDN18.2 binding molecules, e.g., antibodies, including antigen-binding fragments, variants, and derivatives thereof (for example, anti-CLDN18.2-5C9, or a clone of 5C9 antibody), to treat patients having a disease associated with CLDN18.2 expression or CLDN18.2-expressing cells, e.g., cancer. In some specific aspects, such cancer is gastric cancer, esophageal cancer, pancreatic cancer, lung cancer, ovarian cancer, colon cancer, hepatic cancer, head-neck cancer, and cancer of the gallbladder. Other cancer types are also contemplated.

By "CLDN18.2-expressing cell" is meant a cell expressing CLDN18.2. CLDN18.2 can be membrane-bound via glycosyl phosphatidylinositol-anchoring and also be present as a soluble protein. Methods for detecting CLDN18.2 expression in cells and other suitable samples are well known in the art and include, but are not limited to immunohistochemistry, flow cytometry, Western blot, ELISA, and the like.

Though the following discussion refers to diagnostic methods and treatment of various diseases and disorders with an CLDN18.2-binding molecule of the present disclosure (for example, anti-CLDN18.2-5C9, or a clone of 5C9 antibody), the methods described herein are also applicable to any other anti-CLDN18.2 antibodies, and the antigen-binding fragments, and variants of these anti-CLDN18.2 antibodies that retain the desired properties of the anti-CLDN18.2 antibodies disclosed herein, e.g., being capable of specifically binding CLDN18.2. In some aspects, CLDN18.2-binding molecules are human or humanized antibodies that do not mediate human ADCC, or are anti-CLDN18.2 antibodies that are engineered such that they do not mediate ADCC.

In some embodiments, the CLDN18.2-binding molecule is for example, an anti-CLDN18.2-5C9 or an antigen-binding fragment thereof, or an anti-CLDN18.2-9A1 or an antigen-binding fragment thereof. In other embodiments, the CLDN18.2-binding molecule is a clone mutant antibody. In some aspects, the CLDN18.2-binding molecule is a clone monoclonal antibody. In some aspects, the CLDN18.2-binding molecule is a clone monoclonal antibody engineered to extend serum half-life. In other aspects, the CLDN18.2-binding molecule is a clone YTE mutant antibody.

In one embodiment, treatment includes the application or administration of an anti-CLDN18.2 binding molecule, for example, an anti-CLDN18.2-5C9 antibody or antigen binding fragment, variant, or derivative thereof of the current disclosure to a subject or patient, or application or administration of the anti-CLDN18.2 binding molecule to an isolated tissue or cell line from a subject or patient, where the subject or patient has a disease, a symptom of a disease, or a predisposition toward a disease. In another embodiment, treatment is also intended to include the application or administration of a pharmaceutical composition comprising the antiCLDN18.2 binding molecule, e.g., an antibody or antigen binding fragment, variant, or derivative thereof described herein to a subject or patient, or application or administration of a pharmaceutical composition comprising the anti-CLDN18.2 binding molecule to an isolated tissue or cell line from a subject or patient, who has a disease, a symptom of a disease, or a predisposition toward a disease.

The anti-CLDN18.2 binding molecules, for example, an anti-CLDN18.2-5C9 antibody or antigen-binding fragments, variants, or derivatives thereof of the present disclosure are useful for the treatment of various cancers. In one aspect, anti-CLDN18.2 binding molecules are described, for example an anti-CLDN18.2-5C9 antibody or antigen-binding fragments, variants, or derivatives thereof for use as a medicament, in particular for use in the treatment or prophylaxis of cancer including gastric cancer, esophageal cancer, pancreatic cancer, lung cancer, ovarian cancer, colon cancer, hepatic cancer, head-neck cancer, and cancer of the gallbladder.

In accordance with the described methods, at least one anti-CLDN18.2 binding molecule, for example anti-CLDN18.2-5C9, or antigen binding fragment, variant, or derivative thereof as defined elsewhere herein is used to promote a positive therapeutic response with respect to cancer. The term "positive therapeutic response" with respect to cancer treatment refers to an improvement in the disease in association with the activity of these anti-CLDN18.2 binding molecules, e.g., antibodies or antigen-binding fragments, variants, or derivatives thereof, and/or an improvement in the symptoms associated with the disease. Thus, for example, an improvement in the disease can be characterized as a complete response. By "complete response" is intended an absence of clinically detectable disease with normalization of any previously test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of an anti-CLDN18.2 binding molecule disclosed herein.

In specific aspects, such terms refer to one, two or three or more results following the administration of anti-CLDN18.2 binding molecules disclosed herein: (1) a stabilization, reduction or elimination of the cancer cell population; (2) a stabilization or reduction in cancer growth; (3) an impairment in the formation of cancer; (4) eradication, removal, or control of primary, regional and/or metastatic cancer; (5) a reduction in mortality; (6) an increase in disease-free, relapse-free, progression-free, and/or overall survival, duration, or rate; (7) an increase in the response rate, the durability of response, or number of patients who respond or are in remission; (8) a decrease in hospitalization rate, (9) a decrease in hospitalization lengths, (10) the size of the cancer is maintained and does not increase or increases by less than 10%, preferably less than 5%, preferably less than 4%, preferably less than 2%, and (12) an increase in the number of patients in remission.

Clinical response can be assessed using screening techniques such as magnetic resonance imaging (MRI) scan, x-radiographic imaging, computed tomography (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-CLDN18.2 binding molecule, e.g., an antibody or antigen-binding fragment, variant, or derivative thereof, can experience the beneficial effect of an improvement in the symptoms associated with the disease.

In certain embodiments, the anti-CLDN18.2 binding molecules, for example anti-CLDN18.2-5C9 or antigen-binding fragments, variants, or derivatives thereof disclosed herein can be used in combination with any known therapies for cancer, including any agent or combination of agents that are known to be useful, or which have been used or are currently in use, for treatment of cancer, for example gastric cancer, esophageal cancer, pancreatic cancer, lung cancer, ovarian cancer, colon cancer, hepatic cancer, head-neck cancer, and cancer of the gallbladder. The second agent or combination of agents of the pharmaceutical combination formulation or dosing regimen, In certain embodiments, has complementary activities to the antibody or polypeptide described herein, such that they do not adversely affect each other.

Anticancer agents include drugs used to treat malignancies, such as cancerous growths. Drug therapy can be used alone, or in combination with other treatments such as surgery or radiation therapy. Several classes of drugs can be used in cancer treatment, depending on the nature of the organ involved. In specific aspects, the CLDN18.2-binding molecules disclosed herein, for example anti-CLDN18.2-5C9 or antigen-binding fragments thereof, can be administered in combination with antibodies or antibody fragments targeting, for example, PD-1 (programmed death 1 protein), its two ligands PD-L1 (programmed death ligand 1) and/or PD-L2, or CTLA-4 (cytotoxic T lymphocyte antigen 4 protein). See, e.g., Stagg et al. PNAS 107:15471552 (2010); Jin et al. Cancer Res. 70(6): (2010); Allard et al. Clin. Cancer Res. 19:5626 (2013) which are herein incorporated by reference in their entireties. In some aspects, the anti-CTLA-4 antibody is ipilimumab or an antigen binding fragment thereof. In other aspects, the anti-CTLA-4 antibody is tremelimumab (ticilimumab, CP-675,206) or an antigen binding fragment thereof. In some aspects, the anti-PD-1 antibody is pembrolizumab (KEYTRUDA®, formerly lambrolizumab, also known as MK-3475) or an antigen-binding fragment thereof. In some aspects, the anti-PD-1 antibody is nivolumab (BMS-936558, MDX-1106, ONO-4538, OPDivA0) or an antigen-binding fragment thereof. In some aspects, the anti-PD-L1 antibody is BMS-936559 or an antigen binding fragment thereof. In other aspects, the anti-PD-L1 antibody is MPDL3280A. In other aspects, the anti-PD-1 antibody is AMP-224 (anti-PD-1 Fc fusion protein) or an antigen binding fragment thereof.

In some embodiments, the CLDN18.2-binding molecules disclosed herein (for example, anti-CLDN18.2-5C9) can be administered in combination with an anti-PD-1 or antiPD-1 antibody. In various embodiments, the anti-CLDN18.2 antibody is administered at a concentration of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg. Other concentrations are also contemplated.

In some embodiments, the CLDN18.2-binding molecules disclosed herein (for example, anti-CLDN18.2-5C9) can be administered in combination with an anti-PD-1, anti-PD-L1, or anti-CTLA4 antibody, wherein the anti-PD-1, anti-PD-L1, or anti-CTLA4 antibody is administered at a concentration of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg. Other concentrations are also contemplated.

In some other embodiments, the anti-CLDN18.2 antibody and the anti-PD-1 antibody, anti-PD-L1, or anti-CTLA4 may be administered at a ratio of about 1:1, 1:2, 1:3 or 1:4. Other ratios are also contemplated. For example, in some embodiments, the anti-CLDN18.2 antibody and the anti-PD-1, anti-PD-L1, or anti-CTLA4 antibody are administered at a ratio of about 1:2. In one exemplary embodiment, the concentration of anti-CLDN18.2 antibody (for example, anti-CLDN18.2-5C9) is about 10 mg/kg, and the concentration of the anti-PD-1 antibody is about 20 mg/kg.

In an alternative embodiment, the CLDN18.2-binding molecules disclosed herein (for example, anti-CLDN18.2-5C9) can be administered in combination with an anti-PD-1 antibody.

In some aspects, the administration of a combination treatment comprising an CLDN18.2-binding molecule disclosed herein (for example, anti-CLDN18.2-5C9) in combination with an anti-PD-1, anti-PD-L1, or anti-CTLA4 antibody, can increase survival by at least about 10%, about 20%, about 30%, about 40%, about 50%, about 60%, about 70%, about 80%, about 90%, or about 100% compared to untreated subjects or subjects treated with a monotherapy (e.g., an anti-PD-1, anti-PD-L1, or anti-CTLA4 antibody without an anti-CLDN18.2 antibody).

In some embodiments, the administration of a combination treatment comprising an CLDN8.2-binding molecule disclosed herein (for example, anti-CLDN18.2-5C9) in combination with an anti-PD-1, anti-PD-L1, or anti-CTLA4 antibody, can increase survival at least by about 2-fold, about 3-fold, about 4-fold, about 5-fold, about 6-fold, about 7-fold, about 8-fold, about 9-fold, or about 10-fold compared to untreated subjects or subjects treated with a monotherapy (e.g., an anti-PD-1, anti-PD-L1, or antiCTLA4 antibody without an anti-CLDN18.2 antibody).

Where the combined therapies comprise administration of an anti-CLDN18.2 binding molecule in combination with administration of another therapeutic agent (e.g., an anti-PD-1, anti-PD-L1, or anti-CTLA4 antibody), the methods disclosed herein encompass co-administration, using separate formulations or a single pharmaceutical formulation, and consecutive administration in either order. In some aspects, the anti-CLDN18.2 antibodies described herein (for example anti-CLDN18.2-5C9) are administered in combination with other drugs, wherein the antibody or antigen binding fragment, variant, or derivative thereof and the therapeutic agent(s) can be administered sequentially, in either order, or simultaneously (i.e., concurrently or within the same time frame).

The combination therapy can provide "synergy" and prove "synergistic," i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In other aspects, the CLDN18.2-binding molecules disclosed herein (for example anti-CLDN18.2-5C9) can be administered in combination with tyrosine kinase inhibitors. In some other specific aspects, the CLDN18.2-binding molecules disclosed herein can be administered in combination with inhibitors of the tyrosine kinase activity associated with EGFR and/or HER2/neu, e.g., lapatinib. In some aspects, the CLDN18.2-binding molecules disclosed herein can be administered in combination with antimitotic agents. In some specific aspects, the CLDN18.2binding molecules disclosed herein can be administered in combination with agents that stabilize the mitotic spindle microtubule assembly, e.g, paclitaxel or docetaxel.

A further embodiment relates to the use of anti-CLDN18.2 binding molecules, e.g., antibodies or antigen-binding fragments, variants, or derivatives thereof (for example anti-CLDN18.2-5C9), for diagnostic monitoring of protein levels in tissue as part of a clinical testing procedure, e.g., to determine the efficacy of a given treatment regimen. For example, detection can be facilitated by coupling the antibody to a detectable substance.

Examples of detectable substances include various enzymes, prosthetic groups, fluorescent materials, luminescent materials, bioluminescent materials, and radioactive materials. Examples of suitable enzymes include horseradish peroxidase, alkaline phosphatase, 13-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 1251, 131-, 1 $^{35}$S, or $^3$H.

VII. Anti-CLDN18.2 Antibody Therapeutic Combinations and Co-Therapy

Certain further embodiments relate to methods directed to the use of therapeutic combinations comprising anti-CLDN18.2 binding molecules, e.g., antibodies, including antigen binding fragments, variants, and derivatives thereof (for example anti-CLDN18.2-5C9 antibody), to treat patients having cancer including gastric cancer, esophageal cancer, pancreatic cancer, lung cancer, ovarian cancer, colon cancer, hepatic cancer, head-neck cancer, and cancer of the gallbladder. Though the following discussion refers to therapeutic combinations featuring a CLDN18.2-binding molecule described herein (for example, anti-CLDN18.2-5C9 antibody), the methods described herein are also applicable to any other anti-CLDN18.2 antibodies, and the antigen binding fragments, variants, and derivatives (e.g., fusion proteins or conjugates) of these anti-CLDN18.2 antibodies that retain the desired properties of the anti-CLDN18.2 antibodies disclosed herein. In some aspects, CLDN18.2-binding molecules are human or humanized antibodies that do not mediate human ADCC, or are anti-CLDN18.2 antibodies that are engineered, such that they do not mediate ADCC.

Treatment of a patient with a solid tumor using a combination therapy described herein, such as an anti-CLDN18.2 antibody, or antigen binding fragment thereof, in combination with an anti-PD-1, antiPD-L1, or anti-CTLA4 antibody, or antigen binding fragments thereof, can result in an additive or synergistic effect. As used herein, the term ""synergistic" refers to a combination of therapies (e.g., a combination of an anti-CLDN18.2 antibody for example anti-CLDN18.2-5C9 antibody) and an anti-PD-1, anti-PD-L1, or anti-CTLA4 antibody, which is more effective than the additive effects of the single therapies.

A synergistic effect of a combination of therapies (e.g., a combination of an anti-CLDN18.2 antibody and an anti-PD-1, anti-PD-L1, or anti-CTLA4 antibody permits the use of lower dosages of one or more of the therapeutic agents and/or less frequent administration of said therapeutic agents to a patient with a solid tumor. The ability to utilize lower dosages of therapeutic agents and/or to administer said therapies less frequently reduces the toxicity associated with the administration of said therapies to a subject without reducing the efficacy of said therapies in the treatment of a solid tumor. In addition, a synergistic effect can result in improved efficacy of therapeutic agents in the management, treatment, or amelioration of a solid tumor. The synergistic effect of a combination of therapeutic agents can avoid or reduce adverse or unwanted side effects associated with the use of either single therapy.

In co-therapy, a combination of an anti-CLDN18.2 antibody (for example anti-CLDN18.2-5C9 antibody) or antigen binding fragment thereof and anti-PD-1, anti-PD-L1, or anti-CTLA4 antibody, or antigen binding fragments thereof, can be optionally included in the same pharmaceutical composition, or may be included in a separate pharmaceutical composition. In this latter case, the pharmaceutical composition comprising an anti-CLDN18.2 antibody (for example anti-CLDN18.2-5C9 antibody) or antigen binding fragment thereof is suitable for administration prior to, simultaneously with, or following administration of the pharmaceutical composition comprising an anti-PD-1, anti-PD-L1, or anti-CTLA4 antibody, or antigen binding fragment thereof. In certain instances, the anti-CLDN18.2 antibody (for example anti-CLDN18.2-5C9 antibody) or antigen binding fragment thereof and an anti-PD-1, anti-PD-L1, or anti-CTLA4 antibody is administered at overlapping times in a separate composition.

An anti-CLDN18.2 antibody (for example anti-CLDN18.2-5C9 antibody) or antigen binding fragment thereof and an anti-PD-1, anti-PD-L1, or anti-CTLA4 antibody, or antigen binding fragment thereof, can be administered only once or infrequently while still providing benefit to the patient. In further embodiments, the patient may be administered additional follow-on doses. Follow-on doses can be administered at various time intervals depending on the patient's age, weight, clinical assessment, tumor burden, and/or other factors, including the judgment of the attending physician. For example, follow up doses can be administered one week, two weeks, three weeks, etc., 1 month, 2 months, 3 months, 6 months, etc., 1 year, 2 years, 3 years, etc. after the initial dose has been administered to the patient.

The methods provided herein can decrease or retard tumor growth. In some aspects, the reduction or retardation can be statistically significant. A reduction in tumor growth can be measured by comparison to the growth of patient's tumor at baseline, against an expected tumor growth, against an expected tumor growth based on a large patient population, or against the tumor growth of a control population. In other embodiments, the described methods result in increased survival.

VIII. Pharmaceutical Compositions and Methods of Administration

Methods of preparing and administering anti-CLDN18.2 binding molecules, e.g., antibodies, or antigen-binding fragments, variants, or derivatives thereof (for example anti-CLDN18.2-5C9 antibody) to a subject in need thereof are well known to or are readily determined by those skilled in the art. The route of administration of the anti-CLDN18.2 binding molecule, e.g., an antibody, or antigen-binding fragment, variant, or derivative thereof can be, for example, oral, parenteral, by inhalation or topical. The term parenteral as used herein includes, e.g., intravenous, intraarterial, intraperitoneal, intramuscular, subcutaneous, rectal, or vaginal administration. However, in other methods compatible with the teachings herein, anti-CLDN18.2 binding molecules, e.g., antibodies, or antigen-binding fragments, variants, or derivatives thereof, of the present disclosure can be delivered directly to the site of the adverse cellular population thereby increasing the exposure of the diseased tissue to the therapeutic agent.

As discussed herein, anti-CLDN18.2 binding molecules, e.g., antibodies, or antigen-binding fragments, variants, or derivatives thereof of the present disclosure (for example anti-CLDN18.2-5C9 antibody) can be administered in a pharmaceutically effective amount for the in vivo treatment of CLDN18.2-expressing cell-mediated diseases such as certain types of cancers.

Methods of preparing and administering therapeutic combinations comprising anti-CLDN18.2 binding molecules, e.g., antibodies, or antigen binding fragments, variants, or derivatives thereof (for example anti-CLDN18.2-5C9 antibody) in combination with an anti-PD-1, anti-PDL1, and/or anti-CTLA4 antibody, or antigen binding fragments thereof to a subject in need thereof are well known to or are readily determined by those skilled in the art. The route of administration of the combination thereof can be, for example, oral, parenteral, by inhalation or topical. The term parenteral as used herein includes, e.g., intravenous, intraarterial, intraperitoneal, intramuscular, subcutaneous, rectal, or vaginal administration. However, in other methods compatible with the teachings herein, the combination described herein can be delivered directly to the site of the adverse cellular population thereby increasing the exposure of the diseased tissue to the therapeutic agent. As discussed herein, a combination of an anti-CLDN18.2 antibody (for example, anti-CLDN18.2-5C9 antibody) and an anti-PD-1, anti-PD-L1, and/or anti-CTLA4 antibody can be administered in a pharmaceutically effective amount for the in vivo treatment of CLDN18.2-expressing cell-mediated diseases, such as certain types of cancers (e.g., gastric caner).

In certain embodiments, the pharmaceutical compositions described herein can also comprise pharmaceutically acceptable carriers, including, e.g., water, ion exchangers, proteins, buffer substances, and salts. Preservatives and other additives can also be present in some alternative embodiments. The carrier can be a solvent or dispersion medium. Suitable formulations for use in therapeutic methods disclosed herein were previously described in Remington's Pharmaceutical Sciences (Mack Publishing Co.) 16th ed. (1980)).

According to any embodiment described herein, sterile injectable solutions can be prepared by incorporating the described therapeutic combination of an active compound (e.g., an anti-CLDN18.2 antibody, or antigen-binding fragment, variant, or derivative thereof, for example anti-CLDN18.2-5C9 antibody, by itself or in combination with other active agents) in the required amount in an appropriate solvent followed by filtered sterilization. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

The composition can be administered as a single dose, multiple doses or over an established period of time in an infusion. Dosage regimens also can be adjusted to provide the optimum desired response (e.g., a therapeutic or prophylactic response).

Therapeutically effective doses of the compositions described herein, for treatment of CLDN18.2-expressing cell-mediated diseases, such as certain types of cancers, including gastric cancer, esophageal cancer, pancreatic cancer, lung cancer, ovarian cancer, colon cancer, hepatic cancer, head-neck cancer, and cancer of the gallbladder, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The amount of at least one anti-CLDN18.2 binding molecule, e.g., antibody or binding fragment, variant, or derivative thereof (for example anti-CLDN18.2-5C9 antibody) or therapeutic combination of the invention to be administered is readily determined by one of ordinary skill in the art without undue experimentation given the present disclosure. Factors influencing the mode of administration and the respective amount of at least one anti-CLDN18.2 binding molecule, e.g., antibody, antigen binding fragment, variant or derivative thereof, or therapeutic combination of the invention, include, but are not limited to, the severity of the disease, the history of the disease, and the age, height, weight, health, and physical condition of the individual undergoing therapy. Similarly, the amount of anti-CLDN18.2 binding molecule, e.g., antibody, or fragment, variant, or derivative thereof, or therapeutic combination described herein, to be administered will be dependent upon the mode of administration and whether the subject will undergo a single dose or multiple doses of this agent.

Further embodiments relate to the use of an anti-CLDN18.2 binding molecule, e.g., an antibody or antigen binding fragment, variant, or derivative thereof (for example anti-CLDN18.2-5C9 antibody), or therapeutic combination described herein, in the manufacture of a medicament for treating a type of cancer, including, e.g. gastric cancer, esophageal cancer, pancreatic cancer, lung cancer, colon cancer, head and neck cancers, and the cancer of the gallbladder. Other cancer types are also contemplated.

Yet further embodiments relate to the use of an anti-CLDN18.2 binding molecule, e.g., antibody, or antigen-binding fragment, variant, or derivative thereof (for example anti-CLDN18.2-5C9 antibody), in the manufacture of a medicament for treating a subject for treating a type of cancer. In certain aspects, the medicament is used in a subject that has been pretreated with at least one other therapy.

The terms "pretreated" or "pretreatment" mean that the subject has received one or more other therapies (e.g., the subject has been treated with at least one other anti-cancer therapy) prior to receiving the medicament comprising the anti-CLDN18.2 binding molecule, e.g., antibody or antigen-binding fragment, variant, or derivative thereof (for example anti-CLDN18.2-5C9 antibody). It is not necessary that the subject was a responder to pretreatment with the prior therapy or therapies. Thus, the subject that receives the medicament comprising the anti-CLDN18.2 binding molecule, e.g., an antibody or antigen-binding fragment, variant, or derivative thereof could have responded, or could have failed to respond to pretreatment with the prior therapy, or to one or more of the prior therapies where pretreatment comprised multiple therapies.

Yet further embodiments relates to the co-administration of an anti-CLDN18.2 binding molecule, e.g., antibody, or antigen-binding fragment, variant, or derivative thereof (for example anti-CLDN18.2-5C9 antibody) and at least one other therapy. The anti-CLDN18.2 antibody and the at least one other therapy can be co-administered together in a single composition or can be co-administered together at the same time or overlapping times in separate compositions. In some aspects, the anti-CLDN18.2 antibody can be co-administered with, for example, an antibody that targets PD-1 (programmed death 1 protein). An additional embodiment relates to the use of an anti-CLDN18.2 binding molecule, e.g., antibody, or antigen-binding fragment, variant, or derivative thereof (for example, anti-CLDN18.2-5C9 antibody), in the manufacture of a medicament for treating a subject for treating cancer, wherein the anti-CLDN18.2 binding molecule is administered before a subject has been treated with at least one other therapy.

IX. Diagnostics

Yet another embodiment relates to diagnostic methods useful during diagnosis of CLDN18.2-expressing cell-mediated diseases such as certain types of cancer, which involves measuring the expression level of CLDN18.2 protein in tissue or other cells or body fluid from an individual and comparing the measured expression level with a standard CLDN18.2 expression level in normal tissue or body fluid, whereby an increase in the expression level compared to the standard is indicative of a disorder.

The anti-CLDN18.2 antibodies disclosed herein and antigen-binding fragments, variants, and derivatives thereof (for example anti-CLDN18.2-5C9 antibody, or anti-CLDN18.2-1D5 antibody), can be used to assay CLDN18.2 protein levels in a biological sample using classical immunohistological methods known to those of skill in the art (see, e.g., Jalkanen, et al., *J. Cell. Biol.* 101:976-985 (1985); Jalkanen et al., *J. Cell Biol.* 105:3087-3096 (1987)). Other antibody-based methods useful for detecting CLDN18.2 protein expression include immunoassays, such as the enzyme linked immunosorbent assay (ELISA), immunoprecipitation, or Western blotting. Suitable assays are described in more detail elsewhere herein.

The phrase "assaying the expression level of CLDN18.2 polypeptide" means qualitatively or quantitatively measuring or estimating the level of CLDN18.2 polypeptide in a first biological sample either directly (e.g., by determining or estimating absolute protein level) or relatively (e.g., by comparing to the disease associated polypeptide level in a second biological sample). CLDN18.2 polypeptide expression level in the first biological sample can be measured or estimated and compared to a standard CLDN18.2 polypeptide level, the standard being taken from a second biological sample obtained from an individual not having the disorder or being determined by averaging levels from a population of individuals not having the disorder. As will be appreciated in the art, once the "standard" CLDN18.2 polypeptide level is known, it can be used repeatedly as a standard for comparison.

The term "biological sample" means any biological sample obtained from an individual, cell line, tissue culture, or other source of cells potentially expressing CLDN18.2. Methods for obtaining tissue biopsies and body fluids from mammals are well known in the art.

X. Kits Comprising CLDN18.2-Binding Molecules

Further embodiments relate to kits that comprise at least one of the CLDN18.2-binding molecules described herein, e.g., anti-CLDN18.2 antibodies or antigen-binding fragment thereof, variants, or derivatives of the molecules disclosed herein (for example anti-CLDN18.2-5C9 antibody or anti-CLDN18.2-1 D5 antibody), that can be used to perform the methods described herein. In certain embodiments, a kit comprises at least one purified anti-CLDN18.2 antibody or an antigen-binding fragment thereof in one or more containers. In some other embodiments, the kits contain all of the components necessary and/or sufficient to perform a detection assay, including all controls, directions for performing assays, and any necessary software for analysis and presentation of results. One skilled in the art will readily recognize that the disclosed CLDN18.2-binding molecule, e.g., an anti-CLDN18.2 antibody or antigen binding fragment thereof as described herein (for example, anti-CLDN18.2-5C9 antibody or anti-CLDN18.2-5C9 antibody) can be readily incorporated into one of the established kit formats, which are well known in the art.

XI. Immunoassays

Anti-CLDN18.2 binding molecules described herein, e.g., anti-CLDN18.2 antibodies or antigen-binding fragments thereof, variants, or derivatives of the molecules disclosed herein (for example anti-CLDN18.2-5C9 antibody), can be assayed for immunospecific binding by any method known in the art. Exemplary immunoassays that can be used include, but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety).

In certain embodiments, CLDN18.2-binding molecules, e.g., anti-CLDN18.2 antibodies or antigen-binding fragments thereof, and their variants or derivatives (for example anti-CLDN18.2-5C9 antibody), can be employed histologically, as in immunofluorescence, immunoelectron microscopy or non-immunological assays, for in situ detection of CLDN18.2 or conserved variants or peptide fragments thereof. In situ detection can be accomplished by removing a histological specimen from a patient, and applying thereto a labeled CLDN18.2-binding molecule, e.g., an anti-CLDN18.2 antibody or antigen-binding fragment thereof, variant, or derivative thereof, preferably applied by overlaying the labeled CLDN18.2-binding molecule onto a biological sample. Through the use of such a procedure, it is possible to determine not only the presence of CLDN18.2, or conserved variants or peptide fragments, but also its distribution in the examined tissue. Using the present disclosure, those of ordinary skill will readily perceive that any of a wide variety of histological methods (such as staining procedures) can be modified in order to achieve such in situ detection.

The binding activity of a given lot of CLDN18.2-binding molecule, e.g., anti-CLDN18.2 antibody (for example anti-CLDN18.2-5C9 antibody) or antigen-binding fragment thereof, variant, or derivative thereof can be determined according to well-known methods. Those skilled in the art will be able to determine operative and optimal assay conditions for each determination by employing routine experimentation.

Methods and reagents suitable for determination of binding characteristics of an isolated CLDN18.2-binding molecule, e.g., anti-CLDN18.2 antibody (for example anti-CLDN18.2-5C9 antibody) or antigen-binding fragment thereof, variant, or an altered/mutant derivative thereof, are known in the art and/or are commercially available. Equipment and software designed for such kinetic analyses are commercially available (e.g., BIAcore, BIAevaluation software, GE Healthcare; KinExa Software, Sapidyne Instruments).

Unless otherwise indicated, conventional techniques of cell biology, cell culture, molecular biology, transgenic biology, microbiology, recombinant DNA, and immunology, which are within the skill of the art will be employed. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hal 12003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

The following non-limiting examples describe in detail preparation of certain antibodies described herein and methods for using the antibodies. It will be apparent to those skilled in the art that many modifications, both to materials and methods, can be practiced without departing from the scope of the present disclosure.

EXAMPLES

Claudins are a family of proteins, first described in 1998, which form the important components of the tight cell junctions. The Claudins establish a paracellular barrier, which controls the flow of molecules between the cells. Different Claudins are expressed on different tissues, their altered function has linked to formation of cancers of respective tissues. Claudin-1 expression has been shown to have prognostic value in colon cancer, claudin-18 in gastric cancer, and claudin-10 in hepatocellular carcinoma. Claudins, being surface proteins, represent a useful target for various therapeutic strategies. Ugur Sahin et al. identified isoform 2 of the tight junction molecule claudin-18 (CLDN 18.2) as a highly selective cell lineage marker. They observed its expression in normal tissues is strictly confined to differentiated epithelial cells of the gastric mucosa, but it was absent from the gastric stem cell zone. Claudin 18.2 was retained on malignant transformation and was expressed in a significant proportion of primary gastric cancers and its metastases. Frequently ectopic activation of claudin 18.2 was also found in pancreatic, esophageal, ovarian, and lung tumors. The study suggested that CLDN18.2 has highly restricted expression pattern in normal tissues, with frequent ectopic activation in a diversity of human cancers.

The Claudin 18 (CLDN 18) molecule (Genbank accession number: splice variant 1 (CLDN 18.1): NP_057453, NM_016369, and splice variant 2 (CLDN 18.2): NM_001002026, NP 001002026) has a molecular weight of approximately 27.9/27.72 kD. The molecular weight of the protein differs in some cancers and adjacent normal tissue. The higher molecular weight protein observed in healthy tissue can be transferred into the same molecular weight as observed in cancer by treating tissue lysates with the deglycosylating compound PNGase F. This suggests that CLDN 18 is less N-glycosylated in cancer as compared to its normal tissue counterpart. This structural difference is likely to give rise to an altered epitope. CLDN 18.1 is selectively expressed on normal lung and stomach epithelia, whereas CLDN 18.2 is expressed only on gastric cells (Niimi, Mol. Cell. Biol. 21:7380-90, 2001). Most importantly, CLDN 18.2 is restricted to the differentiated short-lived cells of stomach epithelium but is devoid from the gastric stem cell region. Claudin 18.2 is involved in tumor development and progression and located in the outer cell membrane. It has exposed extracellular loops and is available for monoclonal antibody binding. These biological characteristics suggested that it is an ideal molecule for targeted therapy and led to the further development of CLDN18.2-binding molecules, e.g., anti-CLDN18.2 antibodies or antigen-binding fragments thereof, and their variants or derivatives (for example anti-CLDN18.2-5C9 antibody).

The antibodies described herein may be isolated monoclonal antibodies, which specifically bind to an epitope present on CLDN 18. Isolated monoclonal antibodies encompassed by the present invention include IgA, IgG1-4, IgE, IgM, and IgD antibodies.

The isolated binding molecule (e.g., an antibody) or antigen-binding fragment thereof described herein can be produced by a variety of techniques, including the conventional hybridoma technology of Kohler and Milstein (Nature 256: 495 (1975). Although the hybridoma procedures are preferred in this invention, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

In yet another preferred embodiment, human monoclonal antibodies directed against CLDN 18.2 can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined strategy e.g. see J S Babcock et al. Proc. Natl. Acad. Sci. USA 93 (15), 7843 (1996). For details of recombinant antibody engineering see also Welschof and Kraus, Recombinant antibodies for cancer therapy ISBN-0-89603-918-8 and Benny K. C. Lo Antibody Engineering ISBN 1-58829-092-1.

General Methods

Immunization

To generate antibodies against CLDN 18.2, female Balb/C mice were immunized with proteins or cells expressing CLDN18.2 as antigens, or with plasmid carrying cDNA encoding full-length CLDN18.2. Antigens are prepared as peptides coupled to carrier proteins or as proteins expressed in prokaryotic or eukaryotic expression system. For example, peptide of SEQ ID No:1 is synthesized and chemically coupled to the keyhole limpet hemocyanin (KLH) protein. Peptides having SEQ ID No:36, SEQ ID No:37, SEQ ID No:38, and SEQ ID No:39 are synthesized and coupled to the bovine serum albumin (BSA). Extracellular loop 1 (ECL1) of CLDN 18.2 (SEQ ID No:1) is also expressed in the *E. coli.* as a fusion protein with thioredoxin (Trx). Full-length CLDN18.2 (SEQ ID No:2) is expressed and purified from HEK293T cells. The 3T3 cell line or HEK293T cell line that express full length of CLDN 18.2 is also used as antigen.

For DNA immunization, plasmid encoding full-length CLDN18.2 (SEQ ID No:2) with adjuvant is injected intravenously to mice. Three injections separated by a 3-week interval are given. At the final DNA injection, or during the injections, three to five million 293T cells or 3T3 cells that express the full-length CLDN 18.2 are also injected intravenously to the mice. Three or four days after this boost, the mice are euthanized and their spleens are harvested for fusion. The protocols of immunization are listed in Table 1 below.

TABLE 1

Immunization schedules for production of antibody against CLDN 18.2

| Protocol | Prime immunization | Boost | Serum monitoring | Splenectomy |
|---|---|---|---|---|
| 1 | SEQ ID NO: 36 or SEQ ID NO: 37, or SEQ ID NO: 38, or SEQ ID NO: 39 coupled with BSA 100 µg | none | none | day 9 |
| 2 | SEQ ID NO: 1, coupled with KLH 50 µg, with Freund's Complete Adjuvant | same antigen at day 21, day 42, with Freund's incomplete Adjuvant | Day 31, Day 52 | |
| 3 | SEQ ID NO: 2 transfected 3T3 cells, 3-5 × $10^6$, with mouse IL1 | same antigen at day 7, day 14 | none | |
| 4 | SEQ ID NO: 2 transfected 293T cells, 3-5 × $10^6$ | SEQ ID NO: 2 transfected 293 cells, 3-5 × $10^6$ | none | |
| 5 | SEQ ID NO: 2 cDNA in vector, 2 µg | SEQ ID NO: 2 cDNA in vector, 50 µg at day 21, SEQ ID NO: 2 cDNA in vector, 50 µg, plus SEQ ID NO: 2 transfected 3T3 cells, 3-5 × $10^6$ at day 42 | Day 31, Day 52 | none |
| 6 | SEQ ID NO: 2 cDNA in vector, 2 µg with PEI | SEQ ID NO: 2 cDNA in vector, 50 µg with PEI at day 21, SEQ ID NO: 2 cDNA in vector, 50 µg with PEI, plus SEQ ID NO: 2 transfected 293T cells, 3-5 × $10^6$ at day 42 | Day 31 | Day 45 |

Hybridoma Production

To produce monoclonal hybridomas, mouse myeloma cell Sp2/0 were grown to a logarithmic growth phase and fused with immunized mouse spleen cells at a ratio of 1:2 or 1:3 in the presence of polyethylene glycol/Dimethyl sulfoxide (PEG/DMSO; 45%/5%) solution (Hybri-max, Sigma, P7181, D2650). The hybridoma cells were selected in hypoxanthine-aminopterin-thymidine (HAT) (Sigma, H0262) media for 7 days. Media containing HT was added and the hybridoma cells were incubated for additional 7-10 days. Hybrids were initially screened for antibody production after 2-3 weeks of fusion and again after additional 2 weeks. Hybridomas were further cloned three times and picked from a plating density of 0.5 cells/well.

Selection of Positive Clones

The clones that secret antibodies against CLDN 18.2 were screened by ELISA assays using HEK293T cells that express full-length CLDN 18.2. The native HEK293T cells were used as control. The clones that secret antibodies bound to HEK293T-CLDN 18.2 but not to HEK293T were selected. Then, the selected clones were subjected to second screen using HEK293-CLDN 18.2 cells and HEK293-CLDN 18.1 cells. The clones that secret antibodies bound to HEK293T-CLDN 18.2 but not HEK293T-CLDN 18.1 were selected for subcloning until all sub single clone was positive for HEK293T-CLDN 18.2 specifically.

Preparation of Mouse Antibodies

To produce monoclonal antibody for characterization, the selected monoclonal hybridoma cells were injected into the peritoneal cavity of a Balb/C mouse to produce monoclonal antibody in the ascitic fluid. The antibody was purified using Protein A/G affinity chromatography.

Production of Recombinant Antibodies Against CLDN 18.2 for In Vitro and In Vivo Characterization The cDNAs encoding the variable domains of the heavy chain and light chain were amplified from phagemid selected from the phage display screening for antibody humanization and maturation using PCR technology. An extra sequence encoding a signal peptide, for example, the leader sequence MGWSCIILFLVATATGVHS (SEQ ID NO: 372), was added to the 5' end of these nucleotides by PCR. To construct a plasmid to express the whole IgG, the above fragments can be ligated in reading frame with a cDNA fragment encoding human IgG 1 constant domain of heavy chain or light chain, and inserted into a mammalian expression vector like pCDNA3.4 to construct the pCDNA3.4-HC and pCDNA3.4-LC.

To transiently express an antibody, 1 µg of plasmids of pCDNA3.4-HC and pCDNA3.4-LC mixture can be used to transfect Expi293F cells. The expressed IgG can be purified from the medium using affinity chromatography with protein A-resin. Eluted IgG can be checked by gel electrophoresis and high-performance liquid chromatography to ensure purity. The buffer solution can be exchanged into PBS, and the concentration can be determined by OD280 using 1.4 extinction coefficient. The monoclonal antibodies can be aliquoted and stored at −80° C.

Antibody Phage Display Selection

Library sorting was carried out according to a procedure modified from the published protocols (Miller et al. *PLOS one*, 7: e43746 (2012); Fellouse F. A. et al *J. Mol. Biol.* 373, 924 (2007); Sherman et al *J. Mol. Biol.* 426, 2145 (2014)).

In a typical procedure in the first round, 0.1-0.5 nmol of the biotinylated CLDN 18.2 was immobilized on the streptavidin-coated magnetic beads, blocked with biotin, and incubated with phage library for 15 min in 1 mL Binding Buffer (PBS Buffer supplemented with 0.05% Tween 20, 0.5% BSA). The beads were then separated from the solution with a magnet, washed twice with the binding buffer, and directly used to transduce the XL1-blue cells to amplify the phages. In the subsequent rounds, purified phages were first incubated with streptavidin beads in the binding buffer for 30 min to remove the bead binders and the supernatant was used then incubated for 15 min with 50 nM biotinylated CLDN 18.2 in 100 µL binding buffer, supplemented with 0.5 µM CLDN 18.1. Streptavidin magnetic beads were then added to the solution for 15 min to allow the capture of the RNA target complex together with the bound phages. The beads were then eluted with 100 mM DTT or 0.1 M Gly-HCl (pH 2.1) buffer followed by neutralization with 1M Tris-Cl buffer (pH 8).

Phage ELISA Screening

After 3-5 rounds of selection, individual clones were analyzed by phage ELISA. Forty-eight or more individual colonies were picked from a fresh LB/Amp plate, inoculated in 400 µL of 2YT medium containing 100 µg/mL ampicillin and $10^{10}$ PFU/mL M13KO7 helper phage in a 96-well deep-well plate, and grown at 37° C. overnight with shaking at 300 rpm. The deep-well plate was then centrifuged for 15 min at 3500 rpm to pellet the cells. The supernatant was diluted 3-fold to prepare a phage solution in Binding Buffer. A 96-well Maxisorp plate was coated with 100 µL of 2 µg/mL neutravidin in 100 mM sodium bicarbonate coating buffer (pH 9.6) overnight at 4° C. The coating solution was removed and the Maxisorp plate was blocked for 1 h with 200 µL/well of 1% (w/v) BSA in PBS. After the blocking solution was removed, the Maxisorp plate was washed with PBS with 0.05% (v/v) Tween 20 and incubated with 100 µL/well of 25 nM CLDN 18.2 in Binding Buffer for 30 min at room temperature. For each well containing CLDN 18.2 target, a control well with CLDN 18.1 was prepared in parallel. The Maxisorp plate was then washed with Binding Buffer, incubated with 100 µL/well phage solution at room temperature for 30 min. After washing with Binding Buffer, the Maxisorp plate was incubated with 100 µL/well anti-M 13/horseradish peroxidase conjugate (diluted 5000× in Binding Buffer) at room temperature for 30 min. After another washing step with Binding Buffer, the Maxisorp plate was incubated with 100 µL/well Ultra TMB-ELISA Substrates for 5-10 min, quenched with 100 µL/well of 1 M phosphoric acid, and read spectrophotometrically at 450 nm in a microplate reader.

Flow Cytometric Analysis

Flow cytometry was used to determine the binding of monoclonal antibodies to living cells expressing CLDN 18.2. Cell lines expressing naturally or after transfection CLDN 18.2 and negative controls lacking CLDN 18.2 expression (grown under standard growth conditions) were mixed with various concentrations of monoclonal antibodies in PBS containing 3% BSA, and incubated at 4° C. for 60 min in the dark. After 3 times washing, the DyLight 650-labeled secondary anti-IgG antibody bound to CLDN 18.2-bound monoclonal antibody under the same conditions as the primary antibody staining. The samples were analyzed by flow cytometry with a FACS instrument (BD, Accuri™ C6 Plus) using light and side scatter properties to gate on single living cells. In order to distinguish CLDN 18.2-specific monoclonal antibodies from non-specific binders in a single measurement, the method of co-transfection was employed. Cells transiently transfected with plasmids encoding CLDN 18.2 and a fluorescent marker were stained as described above. Binding was assessed by flow cytometry using a BD Accuri C6 Plus, transfected cells were detected in a different fluorescence channel than antibody stained cells. Fluorescence marker expression was plotted on the horizontal axis against antibody binding on the vertical axis. As the majority of transfected cells expressed both transgenes, CLDN 18-specific monoclonal antibodies bound preferentially to fluorescence marker expressing cells.

An alternative assay using fluorescence microscopy may be used in addition to or instead of the flow cytometry assay. Cells may be stained exactly as described above and examined by fluorescence microscopy. Tight junction proteins tend to be internalized, if cell contact to neighboring cells of particularly adherent cells is lost by e.g. detachment of cells. Cell surface expression of CLDN 18 can be optimized by a) adjusting culture conditions, e.g., culturing in higher cell density in a standardized manner, using mild detachment (e.g., 2 mM EDTA/PBS or accutase), processing at room temperature, and adding inhibitors of endocytosis (e.g. sodium azide) or activators of CLDN 18 transcription or translation, and by b) selecting and cloning of cells maintaining CLDN 18 in high levels at the cell surface, e.g., by selection with antibiotics in terms of transfected cells, by immunomagnetic or FACS cell sorting, and by limited dilution cloning.

Comparison of Antibody Binding to Human CLDN 18.2 Versus CLDN 18.1 Transfection Cells by Flow Cytometry Binding specificity of the identified monoclonal antibodies to CLDN 18.2 isoform was analyzed by flow cytometry. HEK293 cells transiently expressing human CLDN 18.2 (HEK293-CLDN 18.2 from Origene) and HEK293 cells transiently expressing human CLDN 18.1 (HEK293-CLDN 18.1 from Origene) were incubated for 60 min at 4° C. with monoclonal antibodies, followed by incubation with Dylight 650-conjugated anti-mouse IgG secondary antibody. Binding was assessed by flow cytometry using a BD Accuri™ C6 Plus.

Enzyme-Linked Immunosorbent Assay (ELISA)

Recombinant Protein Claudin 18.2 was Diluted to a Final Concentration of 10 µg/mL in carbonate buffer and coated to Elisa plate overnight at 4° C. The coating solution was then removed and the plate was washed three times by filling the wells with 200 µL TBST. An additional blocking step (30 min, 5% BSA-PBS) may be applied, if needed. The diluted monoclonal anti-CLDN 18.2 antibodies were added to each well and incubated at room temperature for 2 hours. The negative control should be species- and isotype-matched, non-specific immunoglobulin diluted in TBST. Washing the plate three times by filling the wells with 200 µLTBST, the enzyme-conjugated secondary antibody was added and incubated at room temperature for 2 hours. The plate was then washed three times and TMB substrate solution was added to each well. The plate was incubated for 15-30 min, equal volume of stopping solution (2 M $H_2SO_4$, option) was added, and the optical density was read at 370 or 450 nm.

Immunofluorescence Microscopy

Cell lines expressing either spontaneously or after transfection CLDN 18.2 and negative controls lacking CLDN 18 expression were grown in chamber slides under standard growth conditions in DMEM medium, supplemented with 10% fetal calf serum (FCS), 2 mM L-glutamine, 100 IU/mL penicillin and 100 pg/mL streptomycin. Cells were then fixed with methanol or 4% paraformaldehyde or left untreated. Cells were next reacted with monoclonal antibodies against CLDN 18 for 2 hours at 25° C. After washing, cells were reacted with an Alexa Fluor 488 Anti-Mouse IgG antibody-labelled anti-mouse IgG secondary antibody (Thermo scientific) under the same conditions. Cells were then examined by fluorescence microscopy. Total CLDN 18 levels in cells was observed when cells were 4% paraformaldehyde fixed and permeabilized with Triton X-100. In living cells and non-permeabilized, 4% paraformaldehyde fixed cells surface localization of CLDN 18 was examined.

Immunoprecipitation (IP)/Western Blot

The binding specificity of the isolated monoclonal antibodies to CLDN18.2 isoforms can be analyzed by Immunoprecipitation (IP)/Western blot.

HEK293T cells stably expressing human CLDN18.2 and human CLDN18.1 were harvested and total proteins were extracted by a lysing procedure. Briefly, the cell culture dishes were placed on ice and washed the cells with ice-cold PBS. Draining the PBS and then ice-cold lysis buffer was added, scraping adherent cells off the dish using a cold plastic cell scraper then the cell suspension was gently transferred into a pre-cooled microcentrifuge tube. Centrifuging in a microcentrifuge at 4° C., the supernatant was aspirated and placed in a fresh tube kept on ice, the total proteins were used for antibody immunoprecipitation. 10-50 µg cell lysate plus hybridoma supernatant with detected antibody were mixed in a microcentrifuge tube on ice, incubating the sample with the antibody for 1-12 h at 4° C. under gentle rotation. The protein G-coupled Sepharose beads were added to samples, the lysate beads mixture then was incubated at 4° C. under rotary agitation for 4 h. Centrifuging the tubes, the supernatant was removed from the beads and discard. The proteins of interest were specifically bound to the antibody coating the beads. Washing the beads and eluting 50 µL of beads by heating in 50 µL of 2×SDS loading buffer without DTT for 10 min at 50° C. was executed. Boiling the eluted samples for 5 min and the samples were analyzed by Western blot. Briefly, samples from IP were subjected to sodium dodecyl sulfate (SDS) polyacrylamide gel electrophoresis. After electrophoresis, the separated proteins were transferred to nitrocellulose membranes, blocked, and probed with a commercial CLDN18 antibody. Specific binding was detected using a secondary antibody against CLDN18 antibody and developed with ECL substrate.

Antibody Dependent Cell-Mediated Cytotoxicity (ADCC)

Effector cells, peripheral blood mononuclear cells (PBMC) including lymphocytes (T cells, B cells, NK cells) and monocytes from healthy donors were purified by Ficoll Hypaque density centrifugation, followed by lysis of contaminating erythrocytes. Washed effector cells were suspended in RPMI supplemented with 10% heat-inactivated fetal calf serum or, alternatively with 5% heat-inactivated human serum and mixed with target cells expressing CLDN 18.2, at various ratios of effector cells to target cells. ADCC was detected by MultiTox-Glo Multiplex Cytotoxicity Assay (Promega).

Alternatively, the target cells may be labeled with a fluorescence enhancing ligand (BATDA). A highly fluorescent chelate of Europium with the enhancing ligand which is released from dead cells is measured by a fluorometer.

Another alternative assay may utilize ADCC Reporter Bioassay (Promega). Purified anti-CLDN 18.2 IgGs are then added at various concentrations. Irrelevant human IgG is used as negative control. Assays is carried out for 4 to 20 hours at 37° C. depending on the effector cell type used. Samples are assayed for cytolysis by measuring dead-cell protease release or the presence of the EuTDA chelate in the culture supernatant. For ADCC Reporter Bioassay (Promega), luminescence signal resulting from NFAF (nueclear factor of activated T-cells) response element driving expression of luciferase. Anti-CLDN 18.2 monoclonal antibodies can also be tested in various combinations to determine whether cytolysis is enhanced with multiple monoclonal antibodies.

Complement Dependent Cytotoxicity (CDC)

Monoclonal anti-CLDN 18.2 antibodies were tested for their ability to mediate CDC using a variety of known techniques. To determine the CDC activity of mAbs, different methods may be used.

A stable "glow-type" luminescent signal can, for example, be measured by a CytoTox-Glo Cytotoxicity Assay (Promega) or elevated membrane permeability may be assessed using an ethidium bromide assay. Transfected HEK293 cells (expressing human CLDN 18.2), NUGC-4 and KATO III cells may be harvested by trypsinization and washed, 1-5× $10^5$/ml is incubated with various concentrations of mAb for 60 min at room temperature or at 37° C. Human Serum or plasma with complements can then be added to a final concentration of 25% (v/v) and the cells may be incubated at 37° C. for 3-4 hours. The Cyto-Glo cytotoxicity assay reagent may be added and luminescence signal can be measured.

In an alternative assay, cells can be seeded 24 h before the assay with a density of $3\times10^4$/well in tissue-culture flat-bottom microtiter plates. The next day growth medium is removed and the cells can be incubated in triplicates with antibodies. Control cells may be incubated with growth medium or growth medium containing 0.2% saponin for the determination of background lysis and maximal lysis, respectively. After incubation for 60 min at room temperature supernatant may be removed and 25% (v/v) human plasma or serum in DMEM (prewarmed to 37° C.) may be added to the cells and incubated for another 3-4 hours at 37° C. Then, supernatants may be replaced by PBS containing 2.5 pg/ml ethidium bromide and fluorescence emission upon excitation at 520 nm may be measured at 600 nm using a Bio-Tek plate reader. The percentage specific lysis may be calculated as follows: % specific lysis=(fluorescence sample fluorescence background)/(fluorescence maximal lysis-fluorescence background)×100.

Inhibition of Cell Proliferation by Monoclonal Antibodies

To test for the ability to initiate apoptosis, monoclonal anti-CLDN 18.2 antibodies are, for example, incubated with CLDN 18.2 positive tumor cells, e.g., NUGC-4, KATO-III or CLDN 18.2 transfected HEK293 cells at 37° C. for about 20-96 hours. A general inhibition of cell-proliferation by monoclonal antibodies may be detected with CellTiter-Glo Luminescent Cell Viability kit (Promega). The assay is based on quantitation of the ATP present, an indicator of metabolically active cells. A direct relationship exists between luminescence measured with the CellTiter-Glo Assay and the number of cells in culture.

Briefly, the test monoclonal anti-CLDN 18.2 antibodies may be added to experimental wells, and incubated according to culture protocol. After incubation the plate and its contents may be equilibrated at room temperature for approximately 30 minutes, then a volume of CellTiter-Glo Reagent equal to the volume of cell culture medium present in each well may be added. The plate may be incubated at room temperature for 10 minutes to stabilize luminescent signal, and luminescence may be recorded.

In an alternative assay, the cells under treatment may be harvested, washed in Annexin-V binding buffer (BD biosciences), and incubated with Annexin V conjugated with FITC or APC (BD biosciences) for 15 min in the dark. All cells from each sample may be added to PI solution (10 pg/ml in PBS) in a FACS tube and assessed immediately by flow cytometry (as above).

Example 1: Anti-CLDN 18.2-3B8

The antibody described in Example 1 was generated according to the above general method. The antibody described in Example 1 comprises two light chain variable domains (VLs) comprising the amino acid sequence of SEQ ID NO:6 and two heavy chain variable domains (VHs) comprising the amino acid sequence of SEQ ID NO:10.

Binding Characteristics of Example 1 i) Generation of CLDN 18.2 Expressing Cells and Binding Characteristics to Example 1.

Figure 2:
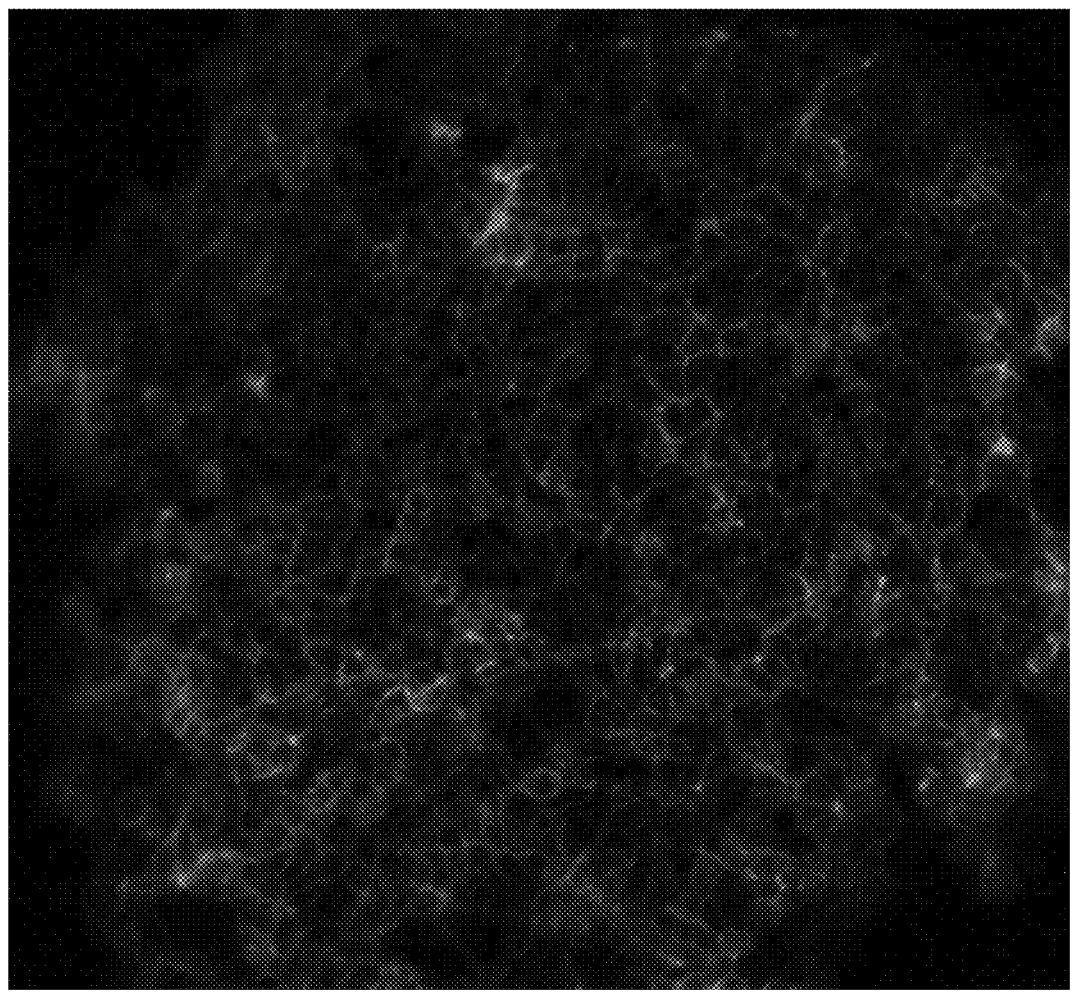
FIG. 2 shows a photograph of an immunofluorescence analysis of HEK293 cells transfected with CLD18.2 and reacted with monoclonal antibody 3B8 on the cell membrane.
Figure 3:
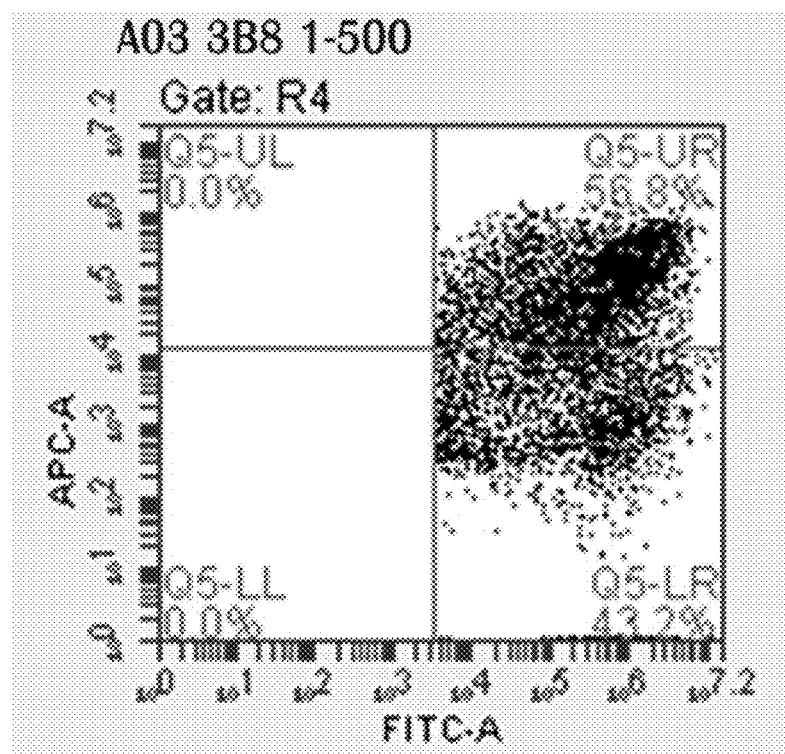
FIG. 3 shows binding of monoclonal antibody 3B8 to HEK293 cells transiently transfected with a GFP and human CLD18.2 as analyzed by flow cytometry.
Figure 4:
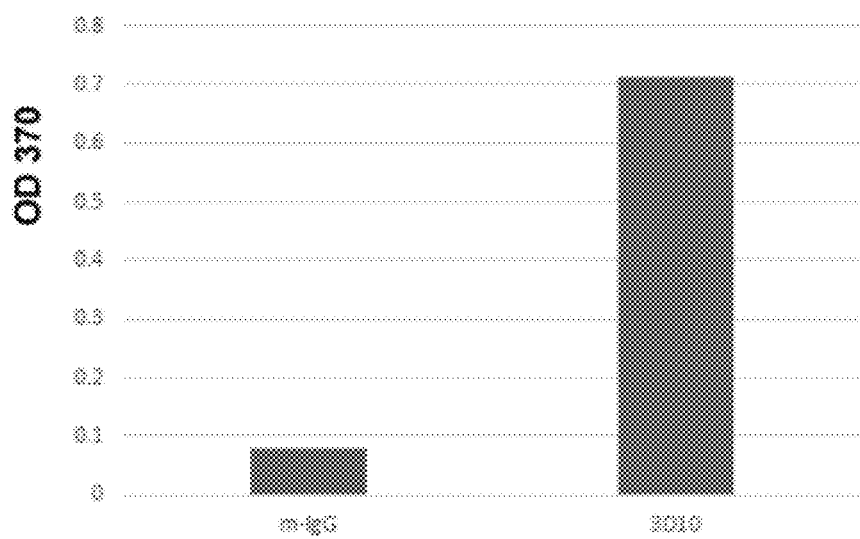
FIG. 4 shows a bar graph depicting binding of monoclonal antibody 3B8 to HEK293 cells transiently transfected with a GFP and human CLD18.2 by an ELISA based assay.
Figure 5:
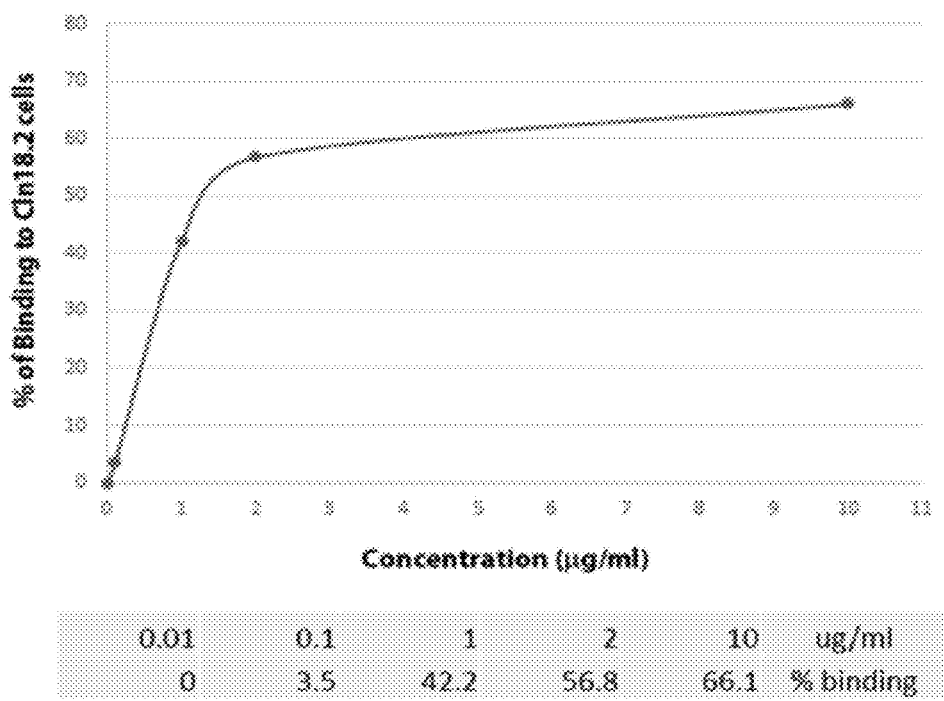
FIG. 5 shows a graph of binding affinity assessment of monoclonal antibody 3B8 to HEK293 cells transiently transfected with a GFP and human CLD18.2 as analyzed by flow cytometry. Various concentrations of monoclonal antibodies (0.01, 0.1, 1, 2, 10 µg/ml) were used, the binding EC50 of antibody 3B8 is between 1-2 µg/ml.

To generate CLDN 18.2 expressing cells, HEK293 cells were transfected with nucleic acids encoding CLDN 18.2 alone and fusion protein CLDN 18.2-GFP reporter. HEK293 cells were transfected and grown on chamber slides for 48 hours. FIG. 1 shows transfected HEK293 cells, expressing CLDN 18.2 and GFP on the cell membrane as well as untransfected cells. HEK293 cells encoding CLDN 18.2 alone were fixed with 4% paraformaldehyde and stained with a monoclonal antibody 3B8 against CLDN 18.2 for 60 min at 25° C. After washing, cells were stained with an Alexa Fluor 488 labelled anti-mouse IgG secondary antibody (Thermo scientific) and evaluated by fluorescence microscopy. FIG. 2 shows monoclonal antibody 3B8 binding to CLDN 18.2 transfected HEK293 cells on the cell membrane. These heterologous CLDN 18.2 expressing cells were used for the following assays to test the specificity of antibody binding.

ii) Monoclonal Antibody 3B8 Binding to CLDN 18.2 was Analyzed by Flow Cytometry:

HEK293 cells were co-transfected with expression vectors encoding human CLDN 18.2 and a fluorescing reporter protein GFP 48 h prior to the assay or alternatively HEK293 cells stably expressing human CLDN 18.2 (HEK293-CLD18.2) were used. After cell detachment using 2 mM EDTA/PBS cells were washed with complete growth medium and plated at approximately $1-5\times10^5$ cells/well in U-bottom microtiter plates. Cells were incubated for 1 min. at 4° C. with monoclonal antibody 3B8 followed by three washing steps with ice cold PBS and finally incubation with Dylight 650-conjugated secondary anti-IgG antibody. Binding was assessed by flow cytometry using a BD, Accuri™ C6 Plus. Fluorescence marker expression was plotted on the horizontal axis against antibody binding on the vertical axis. Mouse antibodies 3B8 were detected to bind specifically to the surface of fluorescence marker expressing HEK293 cells (FIG. 3, cells in Q5-UR).

iii) Monoclonal Antibodies 3B8 Binding to CLDN18.2 were Analyzed by ELISA Assay:

Recombinant protein Claudin 18.2 (or Claudin 18.1) was diluted to a final concentration of 4.5 µg/mL in carbonate buffer. An Elisa plate was coated overnight at 4° C. The coating solution was then removed and the plate was washed three times by filling the wells with 200 µl TBST. An additional blocking step (30 min, 5% BSA-PBS) may be applied. The diluted monoclonal antibody 3B8 was added to each well and incubated at room temperature for 2 hours. The non-specific negative control mouse IgG was diluted in TBST. The plate was washed three times by filling the wells with 200 µl TBST, the HRP-conjugated secondary antibody was added and incubated at room temperature for 2 hours. The plate was washed again three times and TMB substrate solution was added to each well, incubated for 15-30 min, equal volume of stopping solution (2 M $H_2SO_4$, option) as added, and the optical density was read at 370 or 450 nm (FIG. 4).

iv) Monoclonal Antibodies 3B8 Binding Affinity Assessment by Flow Cytometry:

Various concentrations (0.01, 0.1, 1, 2, 10 µg/mL) of monoclonal antibody 3B8 were mixed with transfected cells expressing human CLDN 18.2 and GFP, the operations were as same as general description. Fluorescence marker expression was plotted on the horizontal axis against antibody binding on the vertical axis. The binding characteristics of antibody 3B8 is shown in FIG. 5.

Example 2: Anti-CLDN 18.2-15G11

The antibody described in Example 2 was generated according to the above general method. The antibody described in Example 2 comprises two light chain variable domains (VLs) comprising the amino acid sequence of SEQ ID NO:14 and two heavy chain variable domains (VHs) comprising the amino acid sequence of SEQ ID NO:18.

Figure 6:
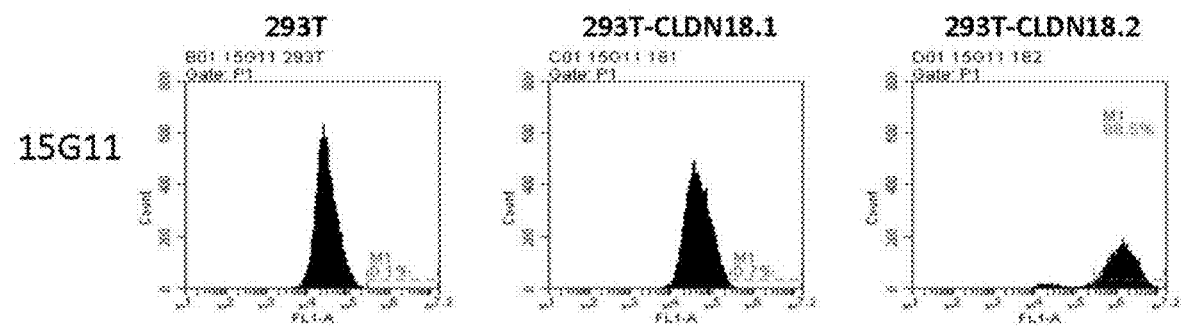
FIG. 6 depicts Flow Cytometry Analysis of anti-CLDN 18.2-15G11 to HEK293-T, HEK293-CLDN 18.2 and HEK293-CLDN 18.1 Cells. The data show that monoclonal antibody 15G11 binds to CLDN 18.2 but not to CLDN 18.1.
Figure 9:
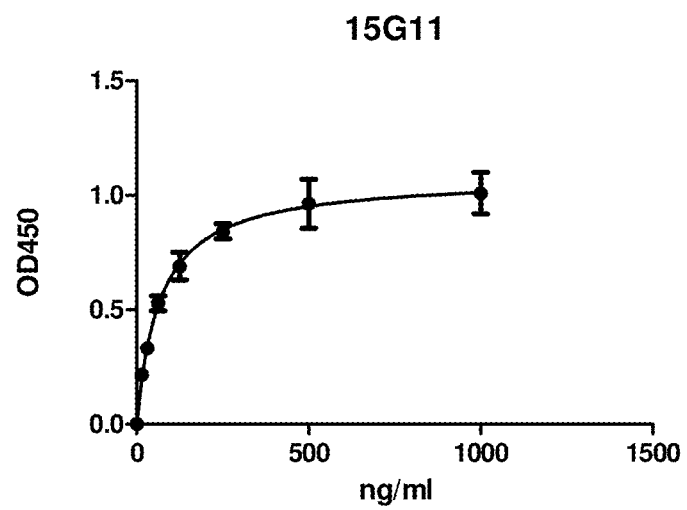
FIG. 9 depicts a graph of binding affinity of anti-CLDN 18.2-15G11 to Claudin18.2 by Elisa based analysis.

The studies of Binding Characteristics of the antibody described in Example 2 were performed as in Example 1. The results are shown in FIG. 6 and FIG. 9.

Example 3: Anti-CLDN 18.2-9A1

The antibody described in Example 3 was generated according to the above general method. The antibody described in Example 3 comprises two light chain variable domains (VLs) comprising the amino acid sequence of SEQ ID NO:22 and two heavy chain variable domains (VHs) comprising the amino acid sequence of SEQ ID NO:25.

Figure 7:
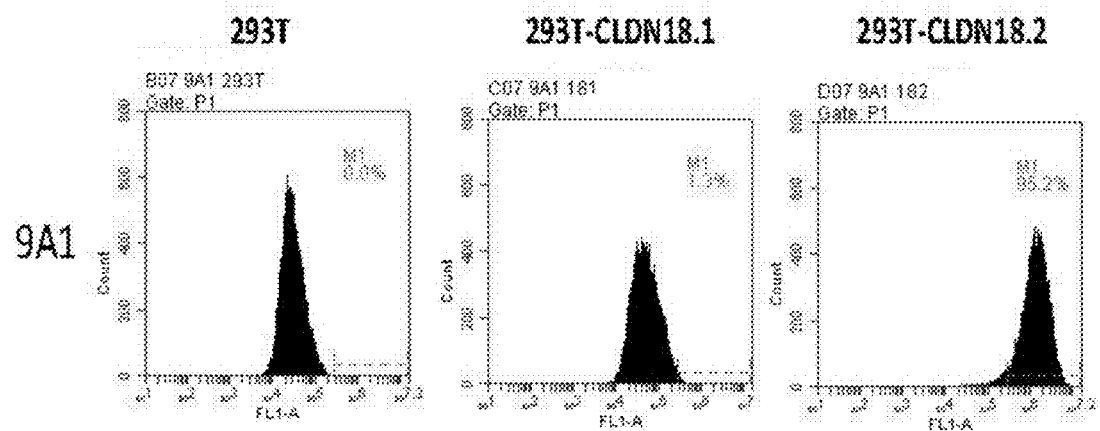
FIG. 7 depicts Flow Cytometry Analysis of anti-CLDN 18.2-9A1 to HEK293-T, HEK293-CLDN 18.2 and HEK293-CLDN 18.1 Cells. The data show that monoclonal antibody 9A1 binds to CLDN 18.2 but not to CLDN 18.1.
Figure 10:
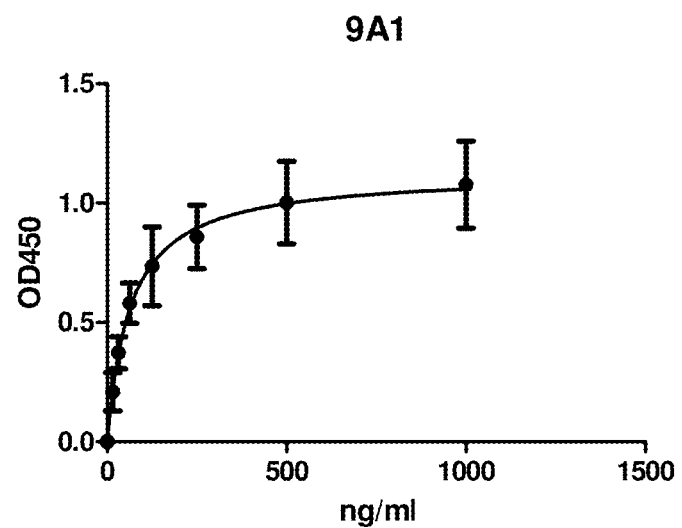
FIG. 10 depicts a graph of binding affinity of anti-CLDN 18.2-9A1 to Claudin18.2 by Elisa based analysis.

The studies of Binding Characteristics of the antibody described in Example 3 were performed as in Example 1. The results are shown in FIG. 7 and FIG. 10.

Example 4: Anti-CLDN 18.2-5C9

The antibody described in Example 4 was generated according to the above general method. The antibody described in Example 4 comprises two light chain variable domains (VLs) comprising the amino acid sequence of SEQ ID NO:29 and two heavy chain variable domains (VHs) comprising the amino acid sequence of SEQ ID NO:32.

Figure 8:
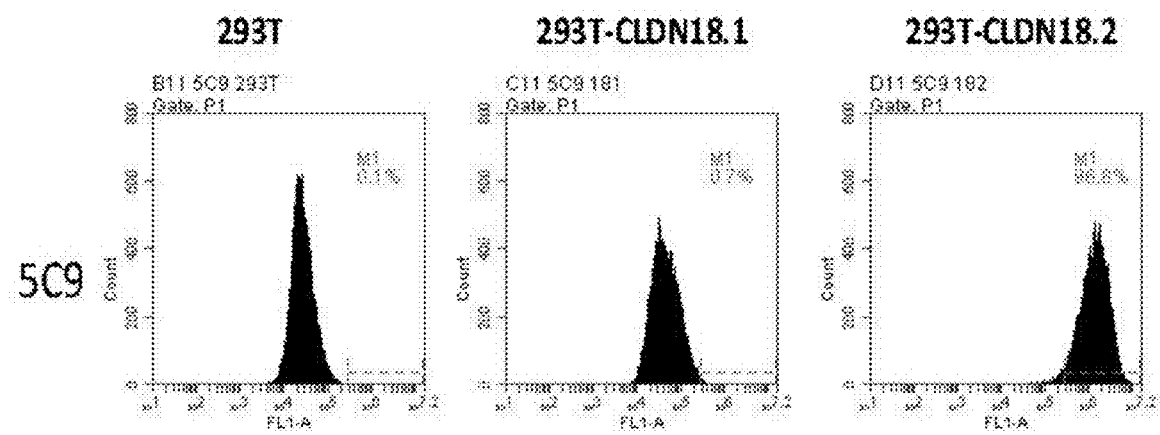
FIG. 8 depicts Flow Cytometry Analysis of anti-CLDN 18.2-5C9 to HEK293-T, HEK293-CLDN 18.2 and HEK293-CLDN 18.1 Cells. The data show that monoclonal antibody 5C9 binds to CLDN 18.2 but not to CLDN 18.1.
Figure 11:
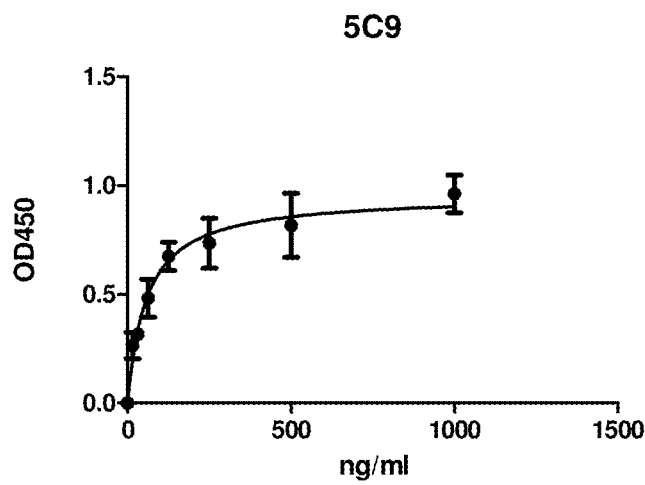
FIG. 11 depicts a graph of binding affinity of anti-CLDN 18.2-5C9 to Claudin18.2 by Elisa based analysis.
Figure 12:
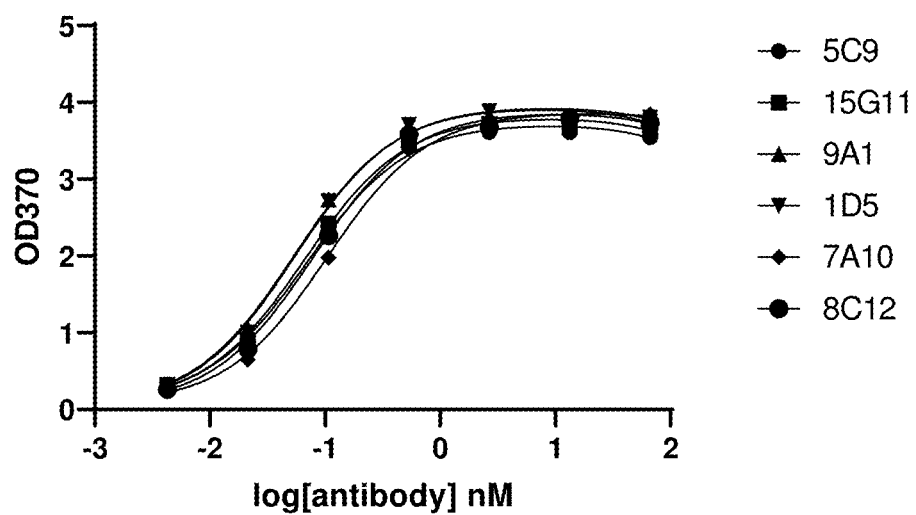
FIG. 12 depicts a graph of binding affinity measurements of mouse monoclonal anti-CLDN 18.2 antibodies 5C9, 15G11, 9A1, 1D5, 7A10 and 8C12 by Elisa based analysis.

The studies of Binding Characteristics of the antibody described in Example 4 were performed as for Example 1. The results are shown in FIG. 8, FIG. 11 and FIG. 12.

Example 5: Anti-CLDN 18.2-5H1

The antibody described in Example 5 was generated according to the above general method. The antibody described in Example 5 comprises two light chain variable domains (VLs) comprising the amino acid sequence of SEQ ID NO:43 and two heavy chain variable domains (VHs) comprising the amino acid sequence of SEQ ID NO:47.

The studies of the Binding Characteristics of the antibody described in Example 5 were performed as in Example 1 with a Kd of 0.32 nM.

Example 6: Anti-CLDN 18.2-1D5

The antibody described in Example 6 was generated according to the above general method. The antibody described in Example 6 comprises two light chain variable domains (VLs) comprising the amino acid sequence of SEQ ID NO:51 and two heavy chain variable domains (VHs) comprising the amino acid sequence of SEQ ID NO:54.

The studies of the Binding Characteristics of the antibody described in Example 6 were performed as in Example 1. The results are shown in FIG. 12.

Example 7: Anti-CLDN 18.2-8C5

The antibody described in Example 7 was generated according to the above general method. The antibody described in Example 7 comprises two light chain variable domains (VLs) comprising the amino acid sequence of SEQ ID NO:57 and two heavy chain variable domains (VHs) comprising the amino acid sequence of SEQ ID NO:61.

The studies of the Binding Characteristics of the antibody described in Example 7 were performed as in Example 1. The anti-CLDN 18.2-8C5 antibody binds to both CLDN18.1 and 18.2 (results not shown).

Example 8: Anti-CLDN 18.2-9F1

The antibody described in Example 8 was generated according to the above general method. The antibody described in Example 8 comprises two light chain variable domains (VLs) comprising the amino acid sequence of SEQ ID NO:64 and two heavy chain variable domains (VHs) comprising the amino acid sequence of SEQ ID NO:68.

The studies of the Binding Characteristics of the antibody described in Example 8 were performed as in Example 1. The anti-CLDN 18.2-9F1 antibody binds to both CLDN18.1 and 18.2 (results not shown).

Example 9: Anti-CLDN 18.2-7A10

The antibody described in Example 9 was generated according to the above general method. The antibody described in Example 9 comprises two light chain variable domains (VLs) comprising the amino acid sequence of SEQ ID NO:72 and two heavy chain variable domains (VHs) comprising the amino acid sequence of SEQ ID NO:76.

The studies of the Binding Characteristics of the antibody described in Example 9 were performed as in Example 1. The results are shown in FIG. 12.

Example 10: Anti-CLDN 18.2-8C12

The antibody described in Example 10 was generated according to the above general method. The antibody described in Example 10 comprises two light chain variable domains (VLs) comprising the amino acid sequence of SEQ ID NO:78 and two heavy chain variable domains (VHs) comprising the amino acid sequence of SEQ ID NO:82.

The studies of the Binding Characteristics of the antibody described in Example 10 were performed as in Example 1. The results are shown in FIG. 12.

Example 11: Anti-CLDN 18.2-14D7

The antibody described in Example 11 was generated according to the above general method. The antibody described in Example 11 comprises two light chain variable domains (VLs) comprising the amino acid sequence of SEQ ID NO:86 and two heavy chain variable domains (VHs) comprising the amino acid sequence of SEQ ID NO:89.

Figure 13:
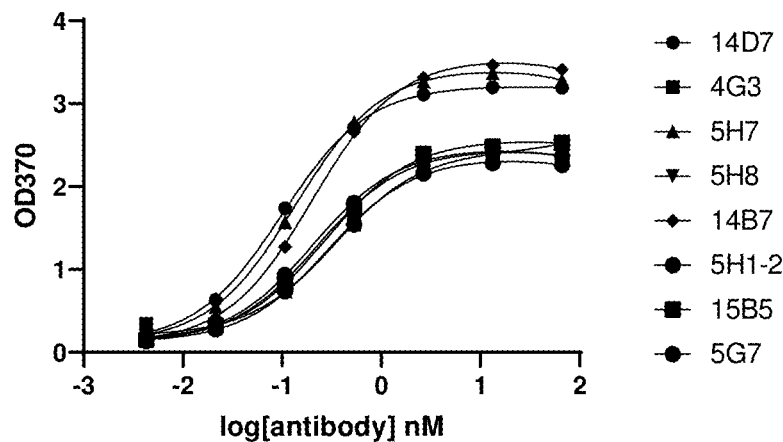
FIG. 13 depicts a graph of binding affinity measurements of mouse monoclonal anti-CLDN 18.2 antibodies 14D7, 4G3, 5H7, 5H8, 14B7, 5H1-2, 15B5, 5G7 by Elisa based analysis.

The studies of the Binding Characteristics of the antibody described in Example 11 were performed as in Example 1. The results are shown in FIG. 13.

Example 12: Anti-CLDN 18.2-5H7

The antibody described in Example 12 was generated according to the above general method. The antibody described in Example 12 comprises two light chain variable domains (VLs) comprising the amino acid sequence of SEQ ID NO:93 and two heavy chain variable domains (VHs) comprising the amino acid sequence of SEQ ID NO:96.

The studies of the Binding Characteristics of the antibody described in Example 12 were performed as for Example 1. The results are shown in FIG. 13.

Example 13: Anti-CLDN 18.2-5G7

The antibody described in Example 13 was generated according to the above general method. The antibody described in Example 13 comprises two light chain variable domains (VLs) comprising the amino acid sequence of SEQ ID NO:100 and two heavy chain variable domains (VHs) comprising the amino acid sequence of SEQ ID NO:102.

The studies of the Binding Characteristics of the antibody described in Example 13 were performed as in Example 1. The results are shown in FIG. 13.

Example 14: Anti-CLDN 18.2-4G3

The antibody described in Example 14 was generated according to the above general method. The antibody described in Example 14 comprises two light chain variable domains (VLs) comprising the amino acid sequence of SEQ ID NO:106 and two heavy chain variable domains (VHs) comprising the amino acid sequence of SEQ ID NO:109.

The studies of the Binding Characteristics of the antibody described in Example 14 were performed as in Example 1. The results are shown in FIG. 13.

Example 15: Anti-CLDN 18.2-14B7

The antibody described in Example 15 was generated according to the above general method. The antibody described in Example 15 comprises two light chain variable domains (VLs) comprising the amino acid sequence of SEQ ID NO:110 and two heavy chain variable domains (VHs) comprising the amino acid sequence of SEQ ID NO:113.

The studies of the Binding Characteristics of the antibody described in Example 15 were performed as in Example 1. The results are shown in FIG. 13.

Example 16: Anti-CLDN 18.2-7H1

The antibody described in Example 16 was generated according to the above general method. The antibody described in Example 16 comprises two light chain variable domains (VLs) comprising the amino acid sequence of SEQ ID NO:117 and two heavy chain variable domains (VHs) comprising the amino acid sequence of SEQ ID NO: 121.

The studies of the Binding Characteristics of the antibody described in Example 16 were performed as in Example 1, showing a Kd of 0.267 nM.

Example 17: Anti-CLDN 18.2-5H12

The antibody described in Example 17 was generated according to the above general method. The antibody described in Example 17 comprises two light chain variable domains (VLs) comprising the amino acid sequence of SEQ ID NO:125 and two heavy chain variable domains (VHs) comprising the amino acid sequence of SEQ ID NO:127.

The studies of the Binding Characteristics of the antibody described in Example 17 were performed as in Example 1. The results are shown in FIG. 13.

Example 18: Anti-CLDN 18.2-5C9a

General Method for Humanization of Anti-CLDN 18.2 Antibodies

Example 18A: Framework

The framework of human consensus sequences of heavy chain subgroup lll (humlll) and light chain κ subgroup I (hum κI) was chosen based on the success of the blockbuster antibody therapeutic drugs, Herceptin (trastuzumab) and Humira (adalimumab) (Carter P, Presta et al *Proc. Natl. Acad. Sci. USA* 89, 4285-4289 (1992); Presta L G, et al *J. Immunol* 151, 2623-2632 (1993); Kabat, E. A., et al Sequences of Proteins of Immunological Interest. 5th ed. Public Health Service, National Institutes of Health, Bethesda, Md. (1991) for the humanization of the anti-CLDN 18.2 antibodies.

To generate a template pSY1 for future CDR swap, the humIII and humκI genes were inserted into a phagemid designed to display human Fab on the surface of M13 bacteriophage. Two open reading frames were used to encode for two Fab chains separately under the control of phoA promoters. The first open reading frame encoded for the light chain and second one encoded for the heavy chain fused to the C-terminal domain of the M13 minor coat protein P3. Both peptide chains were directed for secretion by N-terminal stII signal sequences.

Example 18B: Single Stranded DNA (ssDNA) Template pSY1 was then electroporated into CJ236 cells (uracil deglycosidase deficient) on a micropulser electroporator (Bio-Rad). Single colony was used to inoculate 1 mL 2YT starting culture with 100 μg/mL ampicillin and 10 μg/mL chloramphenicol and the resulting culture was shaken at 37° C. for 6 h. M13KO7 helper phage (~$10^{10}$ pfu) was added and after 10 min shaking at 37° C., 300 μL of the mixture was transferred to 30 μL 2YT with 100 μg/mL ampicillin and 0.25 mg/mL uridine. After 18 h growth at 37° C., phages were purified and the uracil-containing ssDNA was isolated with the E.Z.N.A.® M13 DNA Mini Kit (Omega Biotek Inc).

Example 18C: CDR Swap to Generate the Humanized h5C9a

Kunkel mutagenesis (Kunkel T. A. *Proc Natl Acad Sci USA* 82, 488-92 (1985); Sidhu S. S et al *Methods Enzymol* 328, 333-63 (2000)) was employed to construct the CDR swap version of the humanized anti CLDN 18.2 antibody h5C9a. The following primers were designed to swap the CDRs of 5C9 antibody into pSY1:

(SEQ ID NO: 373)
AGGGTCACCATCACCTGC<u>AAAAGCAGTCAGAGTCTGCTCAACAGTGGCAA</u>

<u>CCAGAAAAGCTATCTGACC</u>TGGTATCAACAGAAACCA,
(for CDR-L1)

(SEQ ID NO: 374)
GCTCCGAAGCTTCTGATTTAT<u>TGGGCATCTACCCTCGAAAGC</u>GGAGTCCC

TTCTCGCTTC,
(for CDR-L2)

(SEQ ID NO: 375)
GCAACTTATTACTGT<u>CAGAACGCGTATTCTTTTCCGTTTACGTTCGGACA</u>

GGGTACC,
(for CDR-L3)

(SEQ ID NO: 376)
TCCTGTGCAGCTTCT<u>GGCTACACCTTTACCAACTATGGTATGAAC</u>TGGGT

GCGTCAGGCCCCG,
(for CDR-H1)

(SEQ ID NO: 377)
GGCCTGGAATGGGTTGCA<u>TGGATTAACATGTATACCGGCGAACCGACCTA</u>

<u>TGCCGATGACTTCAAGGGC</u>CGTTTCACTATAAGCCGT,
(for CDR-H2)

(SEQ ID NO: 378)
GTCTATTATTGTGCTCGC<u>CTGTATAACGGCAACTCTCTGGACTAC</u>TGGGG

TCAAGGA.
(for CDR-H3)

Underlined are CDR regions.

The six primers were phosphorylated individually using T4 Polynucleotide kinase (NEB) at 37° C. for 1 h. The phosphorylated primers were annealed to the uracil-containing ssDNA template at 90° C. for 1 min, 50° C. for 3 min and placed on ice. The oligonucleotides were extended with T7 DNA polymerase and ligated with T4 DNA ligase at 37° C. for 1.5 h to form covalently closed circular DNA. The DNA was desalted and affinity purified with Qiagen QIAquick DNA purification kit and transformed into XL-1 blue cells (uracil glycosidase containing strain) by heat shock transformation. Small scale DNA was purified using Qiagen miniprep kit and sent for sequencing to confirm the sequence. Plasmid h5C9a was then used to prepare uracil-containing ssDNA for humanization library construction.

Example 18D: Humanization Library Construction

Based on the published work (Baca M, et al *J. Biol. Chem.* 272, 10678-10684 (1997)) and referenced by some marketed therapeutic antibodies such trastuzumab, a library was designed to include the mouse and frequent human amino acid compositions at the following sites, VL: M4 (MTG), F71 (TWC), F83 (YTC); VH: A24 (RYC), V37 (RTC), F67 (NYC), 169 (WTC), R71 (CKC), D73 (RMC), K75 (RMG), N76 (ARC), L78 (SYG), A93 (DYG), R94 (ARG). Degenerate codons used for each site are shown in the parentheses. M=A or C, W=A or T, R=A or G, Y=C or T, N=A, C, G, or T, K=G or T, S=G or C, and D=A, G, or T. The following primers were designed to introduce these degenerate codons in the desired sites via Kunkel mutagenesis:

(SEQ ID NO: 379)
GCCTATGCATCCGATATCCAG<u>MTG</u>ACCCAGTCCCCGAGCTCC,
(hLibL1)

(SEQ ID NO: 380)
GGTAGCGGTTCCGGGACGGATT<u>W</u>CACTCTGACCATCAGCAGTCTGCAGCC

GGAAGAC<u>Y</u>TCGCAACTTATTACTGTCAG,
(hLibL2)

```
                                                    (SEQ ID NO: 381)
CTCCGTTTGTCCTGTGCARYCTCTGGCTACACCTTTACCAACTATGGTAT

GAACTGGRTCCGTCAGGCCCCGGGTAAG,
(hLibH1)

(SEQ ID NO: 382)
GATGACTTCAAGGGCCGTNYCACTWTCAGCCKCGACRMCTCCRMGARCAC

ASYGTACCTACAAATGAACAGC,
(hLibH2)

(SEQ ID NO: 383)
GACACTGCCGTCTATTATTGTDYGARGCTGTATAACGGCAACTCT.
(hLibH3)
```

Underlined are degenerate codons.

Phosphorylation of the primers and Kunkel mutagenesis were carried out as described (Sidhu S. S et al *Methods Enzymol* 328, 333-63 (2000)). Covalently closed circular DNA obtained was electroporated into electrocompetent SS320 cells to prepare h5C9 humanization Fab library as described (Sidhu et al. 2000). The tittered apparent diversity was $1.9 \times 10^9$, larger than $3.2 \times 10^6$, the designed theoretical diversity.

Example 18E: Selection of the Humanized h5C9 Clones

Selection was carried out similar to that have been described previously (Ye J. D., et al *Proc Natl Acad Sci USA* 105, 82-87 (2008)). Biotinylated full-length CLDN 18.2 was used as the antigen. In the first round, 0.5 nmol of biotinylated CLDN 18.2 was immobilized on magnetic beads (Promega) and incubated with $10^{12-13}$ cfu of phages for 15 min in 1 ml of PD (1×PBS with 0.1% DDM), supplemented with 0.4% BSA and 0.2 mg/mL streptavidin. The solution was then removed, and the beads were washed twice with PD and amplified for later rounds of selection. In the subsequent rounds, purified phage pools were first incubated with streptavidin beads for 15 min, and the supernatant was used in the subsequent selection on a KingFisher magnetic particle processor (Thermo Fisher). Phages ($10^{10-11}$ cfu) were incubated for 15 min with decreasing concentrations of biotinylated CLDN 18.2 (20-0.1 nM) and increasing concentrations of CLDN 18.1 (400-800 nM). Streptavidin magnetic beads were then added to the solution for 15 min to allow the capture of the biotinylated CLDN 18.2 together with the bound phages. The beads were washed five times with PD, and eluted in 100 mM DTT for 15 min. After each round of selection, recovered phages were amplified as described (Sidhu S. S et al *Methods Enzymol* 328, 333-63 (2000)). After five rounds of selection, phage ELISA were performed to identify positive clones and sequenced.

The antibody described in Example 18 was generated and comprises two light chain variable domains (VLs) comprising the amino acid sequence of SEQ ID NO:131 and two heavy chain variable domains (VHs) comprising the amino acid sequence of SEQ ID NO:134.

Figure 14:
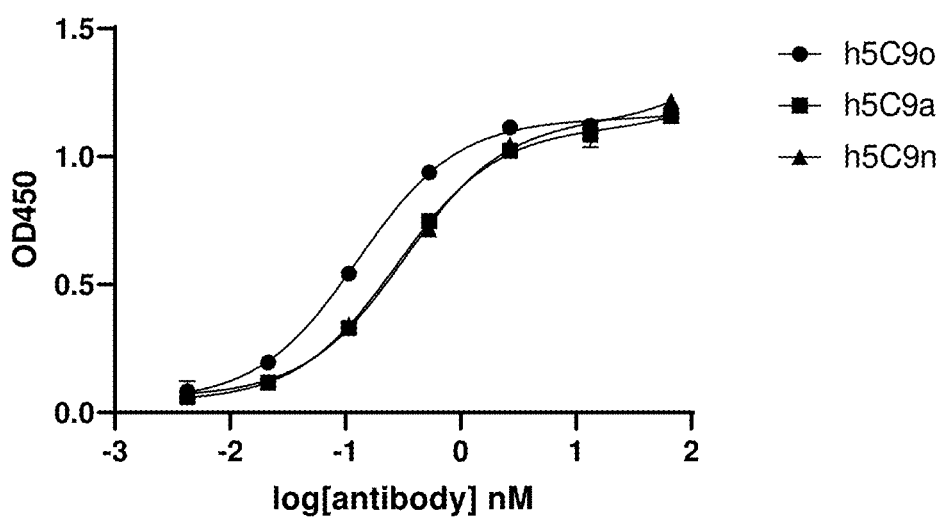
FIG. 14 depicts a graph of binding affinity measurements of humanized monoclonal anti-CLDN 18.2 antibodies h5C9o, h5C9a, h5C9n by Elisa based analysis.

The studies of the Binding Characteristics of the antibody described in Example 18 were performed as in Example 1. The results are shown in FIG. 14.

Example 19: Anti-CLDN 18.2-5C9b

The antibody described in Example 19 was generated according to the above general method as described in Example 18. The antibody described in Example 19 comprises two light chain variable domains (VLs) comprising the amino acid sequence of SEQ ID NO:136 and two heavy chain variable domains (VHs) comprising the amino acid sequence of SEQ ID NO:137.

Example 20: Anti-CLDN 18.2-5C9c

The antibody described in Example 20 was generated according to the above general method as described in Example 18. The antibody described in Example 20 comprises two light chain variable domains (VLs) comprising the amino acid sequence of SEQ ID NO:138 and two heavy chain variable domains (VHs) comprising the amino acid sequence of SEQ ID NO:139.

Example 21: Anti-CLDN 18.2-5C9f

The antibody described in Example 21 was generated according to the above general method as described in Example 18. The antibody described in Example 21 comprises two light chain variable domains (VLs) comprising the amino acid sequence of SEQ ID NO:140 and two heavy chain variable domains (VHs) comprising the amino acid sequence of SEQ ID NO:141.

Example 22: Anti-CLDN 18.2-5C9g

The antibody described in Example 22 was generated according to the above general method as described in Example 18. The antibody described in Example 22 comprises two light chain variable domains (VLs) comprising the amino acid sequence of SEQ ID NO:142 and two heavy chain variable domains (VHs) comprising the amino acid sequence of SEQ ID NO:143.

Example 23: Anti-CLDN 18.2-5C9i

The antibody described in Example 23 was generated according to the above general method as described in Example 18. The antibody described in Example 23 comprises two light chain variable domains (VLs) comprising the amino acid sequence of SEQ ID NO:144 and two heavy chain variable domains (VHs) comprising the amino acid sequence of SEQ ID NO:145.

Example 24: Anti-CLDN 18.2-5C9j

The antibody described in Example 24 was generated according to the above general method as described in Example 18. The antibody described in Example 24 comprises two light chain variable domains (VLs) comprising the amino acid sequence of SEQ ID NO:146 and two heavy chain variable domains (VHs) comprising the amino acid sequence of SEQ ID NO:147.

Example 25: Anti-CLDN 18.2-5C9l

The antibody described in Example 25 was generated according to the above general method as described in Example 18. The antibody described in Example 25 comprises two light chain variable domains (VLs) comprising the amino acid sequence of SEQ ID NO:148 and two heavy chain variable domains (VHs) comprising the amino acid sequence of SEQ ID NO:149.

Example 26: Anti-CLDN 18.2-5C9m

The antibody described in Example 26 was generated according to the above general method as described in Example 18. The antibody described in Example 26 comprises two light chain variable domains (VLs) comprising the amino acid sequence of SEQ ID NO:150 and two heavy chain variable domains (VHs) comprising the amino acid sequence of SEQ ID NO:151.

Example 27: Anti-CLDN 18.2-5C9n

The antibody described in Example 27 was generated according to the above general method as described in Example 18. The antibody described in Example 27 comprises two light chain variable domains (VLs) comprising the amino acid sequence of SEQ ID NO:152 and two heavy chain variable domains (VHs) comprising the amino acid sequence of SEQ ID NO:153.

The studies of the Binding Characteristics of the antibody described in Example 27 were performed as in Example 1. The results are shown in FIG. 14.

Example 28: Anti-CLDN 18.2-5C9o

The antibody described in Example 28 was generated according to the above general method as described in Example 18. The antibody described in Example 28 comprises two light chain variable domains (VLs) comprising the amino acid sequence of SEQ ID NO:154 and two heavy chain variable domains (VHs) comprising the amino acid sequence of SEQ ID NO:155.

Figure 15:
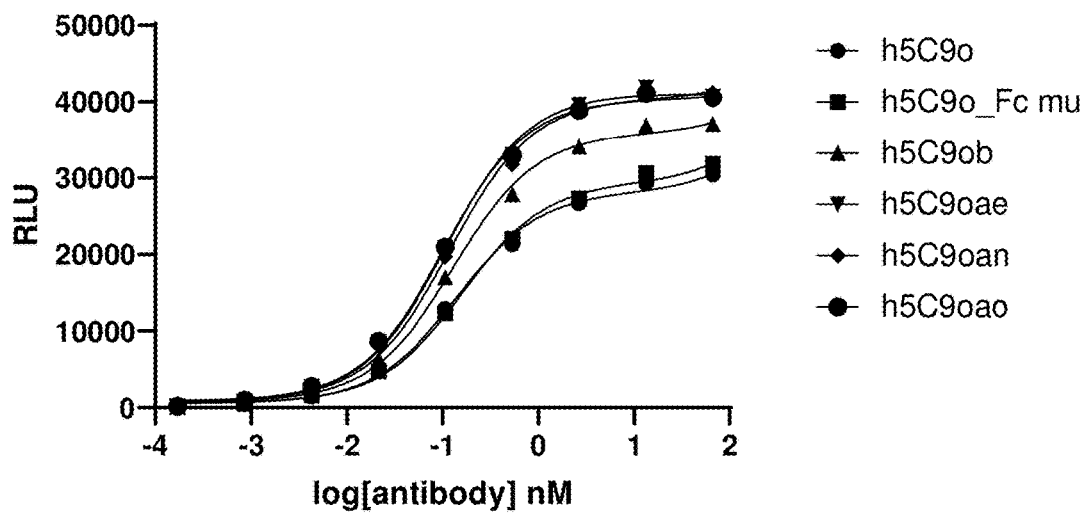
FIG. 15 depicts a graph of binding affinity measurements of humanized monoclonal anti-CLDN 18.2 antibodies h5C9o, h5C9o Fc mu, h5C9ob, h5C9oae, h5C9oan, h5C9oao by Elisa based analysis.
Figure 16:
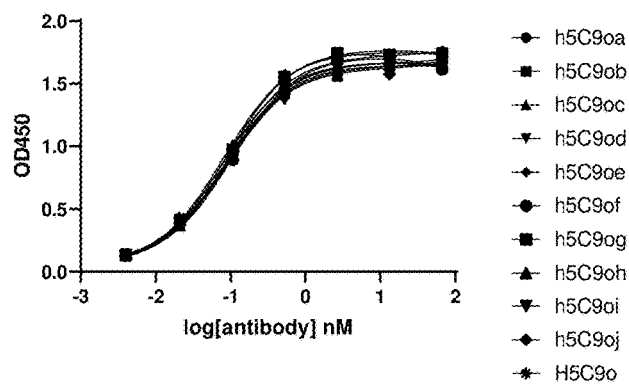
FIG. 16 depicts a graph of binding affinity measurements of humanized monoclonal anti-CLDN 18.2 antibodies h5C9oa, h5C9ob, h5C9oc, h5C9od, h5C9oe, h5C9of, h5C9og, h5C9oh, h5C9oi, h5C9oj, h5C9o by Elisa based analysis.

The studies of the Binding Characteristics of the antibody described in Example 28 were performed as in Example 1. The results are shown in FIG. 14, FIG. 15 and FIG. 16.

Example 29: Anti-CLDN 18.2-5C9oa

General Method for Affinity Maturation of Anti-CLDN 18.2 Antibodies

Example 29A: Construction of the h5C9oAMH9_12 Library

The first library focused on CDR-H3. Within the nine CDR residues, position 101 and 102 according to the Kabat numbering system, are often viewed to play important structural roles therefore not randomized here. Position right upstream of 101 (100a in the current CDR) was given a diversity of the frequent four amino acids: FILM. Position 95-100 were randomized with a customized codon XYZ, X=G (0.45), A (0.23), T (0.11), C (0.21), Y=G (0.31), A (0.34), T (0.17), C (0.18), Z=G (0.24), C (0.76). This codon is similar to the one that mimics the natural AA composition in CDR H3 at position 95-100a_z (Lee C. V., et al *J. Mol. Biol.* 340, 1073-1093 (2004)) with reduced representation in cysteine and stop codon. The length of the CDR-H3 was allowed to vary between 9 and 12 residues with each additional residue encoded by XYZ codon. The theoretical size of the library is $1.5 \times 10^{14}$. Given the large size, therefore diluted binding clones in the library, the position 95-100a of CDR-H3 sequence was replaced with TAAGGCCAA-GACGGCCTATAA (SEQ ID NO: 384) and used this new construct to prepare the template for library construction. This allowed for the effective removal of the parent h5C9o from the affinity maturation library. The following primers were used in Kunkel mutagenesis to construct this library:

(SEQ ID NO: 385)
GTCTATTATTGTGCTCGCXYZXYZXYZXYZXYZXYZWTKGACTACTGGGG

TCAAGGA, (SEQ ID NO: 386)
GTCTATTATTGTGCTCGCXYZXYZXYZXYZXYZXYZXYZWTKGACTACTG

GGGTCAAGGA, (SEQ ID NO: 387)
GTCTATTATTGTGCTCGCXYZXYZXYZXYZXYZXYZXYZXYZWTKGACTA

CTGGGGTCAAGGA, (SEQ ID NO: 388)
GTCTATTATTGTGCTCGCXYZXYZXYZXYZXYZXYZXYZXYZXYZWTKGA

CTACTGGGGTCAAGGA.

Library construction was carried out as described above and the apparent diversity was $1.5 \times 10^{10}$.

Antigen binding requires a concerted action from the direct binding of contact residues and structural support from framework residues in all CDR regions. Therefore, if possible, it is beneficial to be able to screen residues on multiple CDRs at the same time. In addition to the potential improvement in antigen binding affinity and specificity, being able to sample multiple CDR sequence spaces at the same time may have a better chance to obtain antibodies with more compact and stable structures. Our capability of making large sized synthetic antibody libraries with minimal effort allows us to screen multiple CDR sequences within the same library. Two libraries were constructed in this endeavor.

Example 29B: Construction of the h5C9oAM_CDRW_L3_H3 Library

In this library, we aimed to screen CDRs L3 and H3 at the same time. A single amino acid CDR walking (Yang W. P., et al *J. Mol. Biol.* 254, 392-403 (1995)) was adopted to randomize positions 95-100 in CDR-H3 and positions 91-94 in CDR-L3, according to the Kabat numbering system. Each position was randomized individually at a given CDR with the degenerate codon NNS to encode all 20 amino acids. The following primers were used in Kunkel mutagenesis to construct this library:

| Primer sequence | SEQ ID NO: |
|---|---|
| GTCTATTATTGTGCTCGCNNSTATAACGGCAACTCTCTG (HC) | 389 |
| CTATTATTGTGCTCGCCTGNNSAACGGCAACTCTCTGGAC (HC) | 390 |
| CTATTATTGTGCTCGCCTGTATNNSGGCAACTCTCTGGACTAC (HC) | 391 |
| CTATTATTGTGCTCGCCTGTATAACNNSAACTCTCTGGACTACTGG (HC) | 392 |
| GCTCGCCTGTATAACGGCNNSTCTCTGGACTACTGGGGT (HC) | 393 |
| CGCCTGTATAACGGCAACNNSCTGGACTACTGGGGTCAA (HC) | 394 |
| GCAACTTATTACTGTCAGAACNNSTATTCTTTTCCGTTTACG (LC) | 395 |
| CTTATTACTGTCAGAACGCGNNSTCTTTTCCGTTTACGTTC (LC) | 396 |
| CTTATTACTGTCAGAACGCGTATNNSTTTCCGTTTACGTTCGGA (LC) | 397 |
| CTGTCAGAACGCGTATTCTNNSCCGTTTACGTTCGGACAG (LC) | 398 |

83

Library construction was carried out as described above and the apparent diversity was 1.0×10⁹, which is larger than 2.5×10⁴, the designed diversity.

Example 29C: Construction of the h5C9AM_CDRW_L1_L2_H2 Library

In this library, we screened CDRs L1, L2 and H2 at the same time. Similar to the previous library, a single amino acid CDR walking strategy (Yang W. P., et al *J. Mol. Biol.* 254, 392-403 (1995)) was adopted. The randomized positions included 27-33 in CDR-L1, positions 50, 53 and 55 in CDR-L2, and positions 50, 52-54, 56-58 in CDR-H2. Each position was also randomized individually at a given CDR with the degenerate codon NNS to encode all 20 amino acids. The following primers were used in Kunkel mutagenesis to construct this library:

| Primer sequence | SEQ ID NO: |
|---|---|
| CACCTGCAAAAGCAGTCAGNNSCTGCTCAACAGTGGCAAC (L1) | 399 |
| CTGCAAAAGCAGTCAGAGTNNSCTCAACAGTGGCAACCAG (L1) | 400 |
| CAAAAGCAGTCAGAGTCTGNNSAACAGTGGCAACCAGAAA (L1) | 401 |
| CAAAAGCAGTCAGAGTCTGCTCNNSAGTGGCAACCAGAAAAGC (L1) | 402 |
| CAGTCAGAGTCTGCTCAACNNSGGCAACCAGAAAAGCTAT (L1) | 403 |
| CAGAGTCTGCTCAACAGTNNSAACCAGAAAAGCTATCTG (L1) | 404 |
| GAGTCTGCTCAACAGTGGCNNSCAGAAAAGCTATCTGACC (L1) | 405 |
| GTCTGCTCAACAGTGGCAACNNSAAAAGCTATCTGACCTGG (L1) | 406 |
| CTCAACAGTGGCAACCAGNNSAGCTATCTGACCTGGTAT (L1) | 407 |
| CAACAGTGGCAACCAGAAANNSTATCTGACCTGGTATCAA (L1) | 408 |
| CAGTGGCAACCAGAAAAGCNNSCTGACCTGGTATCAACAG (L1) | 409 |
| GGCAACCAGAAAAGCTATNNSACCTGGTATCAACAGAAA (L1) | 410 |
| CCGAAGCTTCTGATTTATNNSGCATCTACCCTCGAAAGC (L2) | 411 |
| CTGATTTATTGGGCATCTNNSCTCGAAAGCGGAGTCCCT (L2) | 412 |
| GATTTATTGGGCATCTACCCTCNNSAGCGGAGTCCCTTCTCGC (L2) | 413 |
| GGCCTGGAATGGGTTGCANNSATTAACATGTATACCGGC (H2) | 414 |
| GAATGGGTTGCATGGATTNNSATGTATACCGGCGAACCG (H2) | 415 |
| GAATGGGTTGCATGGATTAACNNSTATACCGGCGAACCGACC (H2) | 416 |
| GTTGCATGGATTAACATGNNSACCGGCGAACCGACCTAT (H2) | 417 |
| GCATGGATTAACATGTATNNSGGCGAACCGACCTATGCC (H2) | 418 |
| GATTAACATGTATACCGGCNNSCCGACCTATGCCGATGAC (H2) | 419 |
| GATTAACATGTATACCGGCGAANNSACCTATGCCGATGACTTC (H2) | 420 |
| CATGTATACCGGCGAACCGNNSTATGCCGATGACTTCAAG (H2) | 421 |

Library construction was carried out as described above and the apparent diversity was 1.1×10¹⁰, which is larger than 9.4×10⁶, the designed diversity.

84

Example 29D: Selection of the Affinity Maturated Antibodies

The above three affinity maturation libraries were used separately when selected against CLDN 18.2. The basic procedure is similar to that described above with the following modification. The biotinylated antigen concentration used in the selection ranged from 1 nM to 10 pM. With 10 pM biotinylation antigen concentration, after capture of the antigen/antibody complex on the beads, the beads were washed with PD and >1000 fold of non-biotinylated antigen was incubated with the beads for 0.5-1 hour at RT. Then washed and eluted as described above. This off-rate selection allows the selection of antibodies with slower off-rate, potentially beneficial to its in vivo activity.

The antibody described in Example 29 was generated according to the above general method. The antibody described in Example 29 comprises two light chain variable domains (VLs) comprising the amino acid sequence of SEQ ID NO:157 and two heavy chain variable domains (VHs) comprising the amino acid sequence of SEQ ID NO:159.

The studies of the Binding Characteristics of the antibody described in Example 29 were performed as for Example 1. The results are shown in FIG. 16.

Example 30: Anti-CLDN 18.2-5C9ob

The antibody described in Example 30 was generated according to the above general method as described in Example 29. The antibody described in Example 30 comprises two light chain variable domains (VLs) comprising the amino acid sequence of SEQ ID NO:160 and two heavy chain variable domains (VHs) comprising the amino acid sequence of SEQ ID NO:162.

The studies of the Binding Characteristics of the antibody described in Example 30 were performed as in Example 1. The results are shown in FIG. 16.

Example 31: Anti-CLDN 18.2-5C9oc

The antibody described in Example 31 was generated according to the above general method as described in Example 29. The antibody described in Example 31 comprises two light chain variable domains (VLs) comprising the amino acid sequence of SEQ ID NO:163 and two heavy chain variable domains (VHs) comprising the amino acid sequence of SEQ ID NO:165.

The studies of the Binding Characteristics of the antibody described in Example 31 were performed as in Example 1. The results are shown in FIG. 16.

Example 32: Anti-CLDN 18.2-5C9od

The antibody described in Example 32 was generated according to the above general method as described in Example 29. The antibody described in Example 32 comprises two light chain variable domains (VLs) comprising the amino acid sequence of SEQ ID NO:166 and two heavy chain variable domains (VHs) comprising the amino acid sequence of SEQ ID NO:168.

The studies of the Binding Characteristics of the antibody described in Example 32 were performed as in Example 1. The results are shown in FIG. 16.

Example 33: Anti-CLDN 18.2-5C9oe

The antibody described in Example 33 was generated according to the above general method as described in Example 29. The antibody described in Example 33 comprises two light chain variable domains (VLs) comprising the amino acid sequence of SEQ ID NO:169 and two heavy chain variable domains (VHs) comprising the amino acid sequence of SEQ ID NO:171.

The studies of the Binding Characteristics of the antibody described in Example 33 were performed as for Example 1. The results are shown in FIG. 16.

Example 34: Anti-CLDN 18.2-5C9of

The antibody described in Example 34 was generated according to the above general method as described in Example 29. The antibody described in Example 34 comprises two light chain variable domains (VLs) comprising the amino acid sequence of SEQ ID NO:172 and two heavy chain variable domains (VHs) comprising the amino acid sequence of SEQ ID NO:174.

The studies of the Binding Characteristics of the antibody described in Example 34 were performed as in Example 1. The results are shown in FIG. 16.

Example 35: Anti-CLDN 18.2-5C9og

The antibody described in Example 35 was generated according to the above general method as described in Example 29. The antibody described in Example 35 comprises two light chain variable domains (VLs) comprising the amino acid sequence of SEQ ID NO:175 and two heavy chain variable domains (VHs) comprising the amino acid sequence of SEQ ID NO:176.

The studies of the Binding Characteristics of the antibody described in Example 35 were performed as in Example 1. The results are shown in FIG. 16.

Example 36: Anti-CLDN 18.2-5C9oh

The antibody described in Example 36 was generated according to the above general method as described in Example 29. The antibody described in Example 36 comprises two light chain variable domains (VLs) comprising the amino acid sequence of SEQ ID NO:178 and two heavy chain variable domains (VHs) comprising the amino acid sequence of SEQ ID NO:179.

The studies of the Binding Characteristics of the antibody described in Example 36 were performed as in Example 1. The results are shown in FIG. 16.

Example 37: Anti-CLDN 18.2-5C9oi

The antibody described in Example 37 was generated according to the above general method as described in Example 29. The antibody described in Example 37 comprises two light chain variable domains (VLs) comprising the amino acid sequence of SEQ ID NO:180 and two heavy chain variable domains (VHs) comprising the amino acid sequence of SEQ ID NO:181.

The studies of the Binding Characteristics of the antibody described in Example 37 were performed as in Example 1. The results are shown in FIG. 16.

Example 38: Anti-CLDN 18.2-5C9oj

The antibody described in Example 38 was generated according to the above general method as described in Example 29. The antibody described in Example 38 comprises two light chain variable domains (VLs) comprising the amino acid sequence of SEQ ID NO:183 and two heavy chain variable domains (VHs) comprising the amino acid sequence of SEQ ID NO:184.

The studies of the Binding Characteristics of the antibody described in Example 38 were performed as in Example 1. The results are shown in FIG. 16.

Example 39: Anti-CLDN 18.2-5C9ok

The antibody described in Example 39 was generated according to the above general method as described in Example 29. The antibody described in Example 39 comprises two light chain variable domains (VLs) comprising the amino acid sequence of SEQ ID NO:186 and two heavy chain variable domains (VHs) comprising the amino acid sequence of SEQ ID NO:187.

Figure 17:
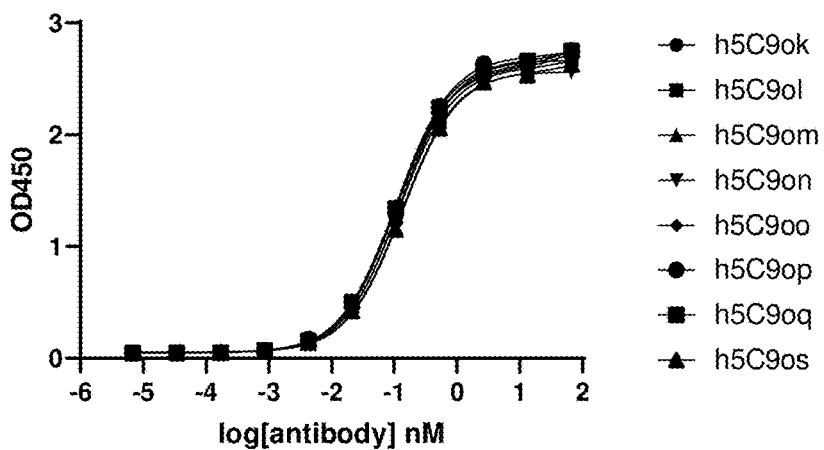
FIG. 17 depicts a graph of binding affinity measurements of humanized monoclonal anti-CLDN 18.2 antibodies h5C9ok, h5C9ol, h5C9om, h5C9on, h5C9oo, h5C9op, h5C9oq, h5C9os by Elisa based analysis.

The studies of the Binding Characteristics of the antibody described in Example 39 were performed as in Example 1. The results are shown in FIG. 17.

Example 40: Anti-CLDN 18.2-5C9ol

The antibody described in Example 40 was generated according to the above general method as described in Example 29. The antibody described in Example 40 comprises two light chain variable domains (VLs) comprising the amino acid sequence of SEQ ID NO:186 and two heavy chain variable domains (VHs) comprising the amino acid sequence of SEQ ID NO:189.

The studies of the Binding Characteristics of the antibody described in Example 40 were performed as in Example 1. The results are shown in FIG. 17.

Example 41: Anti-CLDN 18.2-5C9om

The antibody described in Example 41 was generated according to the above general method as described in Example 29. The antibody described in Example 41 comprises two light chain variable domains (VLs) comprising the amino acid sequence of SEQ ID NO:186 and two heavy chain variable domains (VHs) comprising the amino acid sequence of SEQ ID NO:191.

The studies of the Binding Characteristics of the antibody described in Example 41 were performed as in Example 1. The results are shown in FIG. 17.

Example 42: Anti-CLDN 18.2-5C9on

The antibody described in Example 42 was generated according to the above general method as described in Example 29. The antibody described in Example 42 comprises two light chain variable domains (VLs) comprising the amino acid sequence of SEQ ID NO:186 and two heavy chain variable domains (VHs) comprising the amino acid sequence of SEQ ID NO:193.

The studies of the Binding Characteristics of the antibody described in Example 42 were performed as in Example 1. The results are shown in FIG. 17.

Example 43: Anti-CLDN 18.2-5C9oo

The antibody described in Example 43 was generated according to the above general method as described in Example 29. The antibody described in Example 43 comprises two light chain variable domains (VLs) comprising the amino acid sequence of SEQ ID NO:186 and two heavy chain variable domains (VHs) comprising the amino acid sequence of SEQ ID NO:195.

The studies of the Binding Characteristics of the antibody described in Example 43 were performed as in Example 1. The results are shown in FIG. 17.

Example 44: Anti-CLDN 18.2-5C9op

The antibody described in Example 44 was generated according to the above general method as described in Example 29. The antibody described in Example 44 comprises two light chain variable domains (VLs) comprising the amino acid sequence of SEQ ID NO:186 and two heavy chain variable domains (VHs) comprising the amino acid sequence of SEQ ID NO:197.

The studies of the Binding Characteristics of the antibody described in Example 44 were performed as in Example 1. The results are shown in FIG. 17.

Example 45: Anti-CLDN 18.2-5C9oq

The antibody described in Example 45 was generated according to the above general method as described in Example 29. The antibody described in Example 45 comprises two light chain variable domains (VLs) comprising the amino acid sequence of SEQ ID NO:186 and two heavy chain variable domains (VHs) comprising the amino acid sequence of SEQ ID NO:199.

The studies of the Binding Characteristics of the antibody described in Example 45 were performed as in Example 1. The results are shown in FIG. 17.

Example 46: Anti-CLDN 18.2-5C9or

The antibody described in Example 46 was generated according to the above general method as described in Example 29. The antibody described in Example 46 comprises two light chain variable domains (VLs) comprising the amino acid sequence of SEQ ID NO:186 and two heavy chain variable domains (VHs) comprising the amino acid sequence of SEQ ID NO:201.

Figure 18:
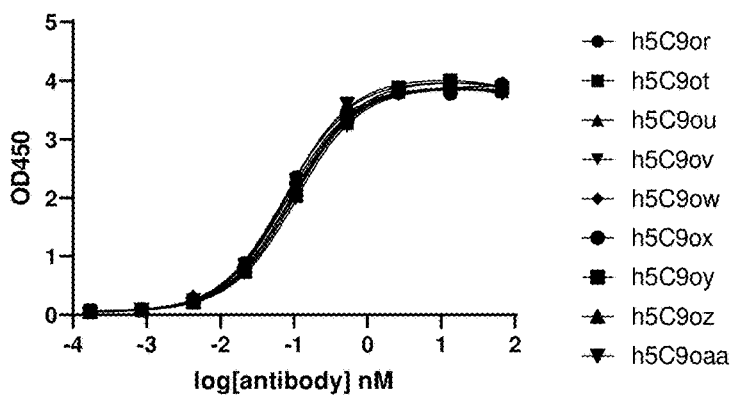
FIG. 18 depicts a graph of binding affinity measurements of humanized monoclonal anti-CLDN 18.2 antibodies h5C9or, h5C9ot, h5C9ou, h5C9ov, h5C9ow, h5C9ox, h5C9oy, h5C9 oz, h5C9oaa by Elisa based analysis.

The studies of the Binding Characteristics of the antibody described in Example 46 were performed as in Example 1. The results are shown in FIG. 18.

Example 47: Anti-CLDN 18.2-5C9os

The antibody described in Example 47 was generated according to the above general method as described in Example 29. The antibody described in Example 47 comprises two light chain variable domains (VLs) comprising the amino acid sequence of SEQ ID NO:186 and two heavy chain variable domains (VHs) comprising the amino acid sequence of SEQ ID NO:203.

The studies of the Binding Characteristics of the antibody described in Example 47 were performed as in Example 1. The results are shown in FIG. 17.

Example 48: Anti-CLDN 18.2-5C9ot

The antibody described in Example 48 was generated according to the above general method as described in Example 29. The antibody described in Example 48 comprises two light chain variable domains (VLs) comprising the amino acid sequence of SEQ ID NO:186 and two heavy chain variable domains (VHs) comprising the amino acid sequence of SEQ ID NO:205.

The studies of the Binding Characteristics of the antibody described in Example 48 were performed as in Example 1. The results are shown in FIG. 18.

Example 49: Anti-CLDN 18.2-5C9ou

The antibody described in Example 49 was generated according to the above general method as described in Example 29. The antibody described in Example 49 comprises two light chain variable domains (VLs) comprising the amino acid sequence of SEQ ID NO:186 and two heavy chain variable domains (VHs) comprising the amino acid sequence of SEQ ID NO:207.

The studies of the Binding Characteristics of the antibody described in Example 49 were performed as in Example 1. The results are shown in FIG. 18.

Example 50: Anti-CLDN 18.2-5C9ov

The antibody described in Example 50 was generated according to the above general method as described in Example 29. The antibody described in Example 50 comprises two light chain variable domains (VLs) comprising the amino acid sequence of SEQ ID NO:186 and two heavy chain variable domains (VHs) comprising the amino acid sequence of SEQ ID NO:209.

The studies of the Binding Characteristics of the antibody described in Example 50 were performed as in Example 1. The results are shown in FIG. 18.

Example 51: Anti-CLDN 18.2-5C9ow

The antibody described in Example 51 was generated according to the above general method as described in Example 29. The antibody described in Example 51 comprises two light chain variable domains (VLs) comprising the amino acid sequence of SEQ ID NO:186 and two heavy chain variable domains (VHs) comprising the amino acid sequence of SEQ ID NO:211.

The studies of the Binding Characteristics of the antibody described in Example 51 were performed as in Example 1. The results are shown in FIG. 18.

Example 52: Anti-CLDN 18.2-5C9ox

The antibody described in Example 52 was generated according to the above general method as described in Example 29. The antibody described in Example 52 comprises two light chain variable domains (VLs) comprising the amino acid sequence of SEQ ID NO:186 and two heavy chain variable domains (VHs) comprising the amino acid sequence of SEQ ID NO:213.

The studies of the Binding Characteristics of the antibody described in Example 52 were performed as in Example 1. The results are shown in FIG. 18.

Example 53: Anti-CLDN 18.2-5C9oy

The antibody described in Example 53 was generated according to the above general method as described in Example 29. The antibody described in Example 53 comprises two light chain variable domains (VLs) comprising the amino acid sequence of SEQ ID NO:186 and two heavy chain variable domains (VHs) comprising the amino acid sequence of SEQ ID NO:215.

Example 54: Anti-CLDN 18.2-5C9 oz

The antibody described in Example 54 was generated according to the above general method as described in Example 29. The antibody described in Example 54 comprises two light chain variable domains (VLs) comprising the amino acid sequence of SEQ ID NO:186 and two heavy chain variable domains (VHs) comprising the amino acid sequence of SEQ ID NO:217.

The studies of the Binding Characteristics of the antibody described in Example 54 were performed as in Example 1. The results are shown in FIG. 18.

Example 55: Anti-CLDN 18.2-5C9oaa

The antibody described in Example 55 was generated according to the above general method as described in Example 29. The antibody described in Example 55 comprises two light chain variable domains (VLs) comprising the amino acid sequence of SEQ ID NO:186 and two heavy chain variable domains (VHs) comprising the amino acid sequence of SEQ ID NO:219.

The studies of the Binding Characteristics of the antibody described in Example 55 were performed as in Example 1. The results are shown in FIG. 18.

Example 56: Anti-CLDN 18.2-5C9oab

The antibody described in Example 56 was generated according to the above general method as described in Example 29. The antibody described in Example 56 comprises two light chain variable domains (VLs) comprising the amino acid sequence of SEQ ID NO:221 and two heavy chain variable domains (VHs) comprising the amino acid sequence of SEQ ID NO:222.

Figure 19:
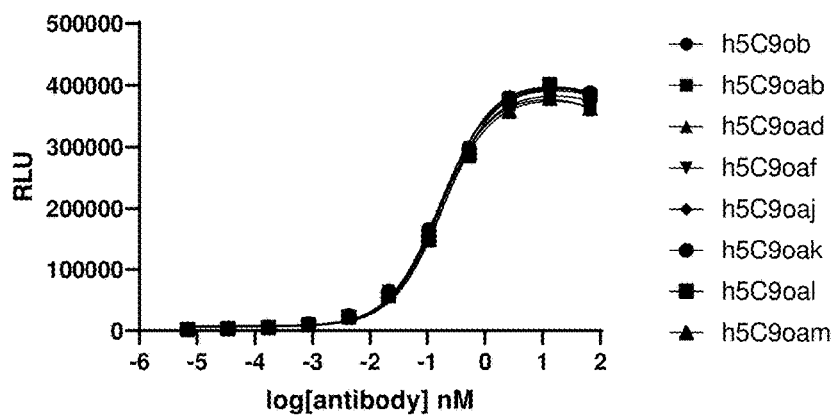
FIG. 19 depicts a graph of binding affinity measurements of humanized monoclonal anti-CLDN 18.2 h5C9ob, h5C9oab, h5C9oad, h5C9oaf, h5C9oaj, h5C9oak, h5C9oal, h5C9oam antibodies by Elisa based analysis.

The studies of the Binding Characteristics of the antibody described in Example 56 were performed as in Example 1. The results are shown in FIG. 19.

Example 57: Anti-CLDN 18.2-5C9oad

The antibody described in Example 57 was generated according to the above general method as described in Example 29. The antibody described in Example 57 comprises two light chain variable domains (VLs) comprising the amino acid sequence of SEQ ID NO:221 and two heavy chain variable domains (VHs) comprising the amino acid sequence of SEQ ID NO:223.

The studies of the Binding Characteristics of the antibody described in Example 57 were performed as in Example 1. The results are shown in FIG. 19.

Example 58: Anti-CLDN 18.2-5C9oae

The antibody described in Example 58 was generated according to the above general method as described in Example 29. The antibody described in Example 58 comprises two light chain variable domains (VLs) comprising the amino acid sequence of SEQ ID NO:224 and two heavy chain variable domains (VHs) comprising the amino acid sequence of SEQ ID NO:225.

Figure 20:
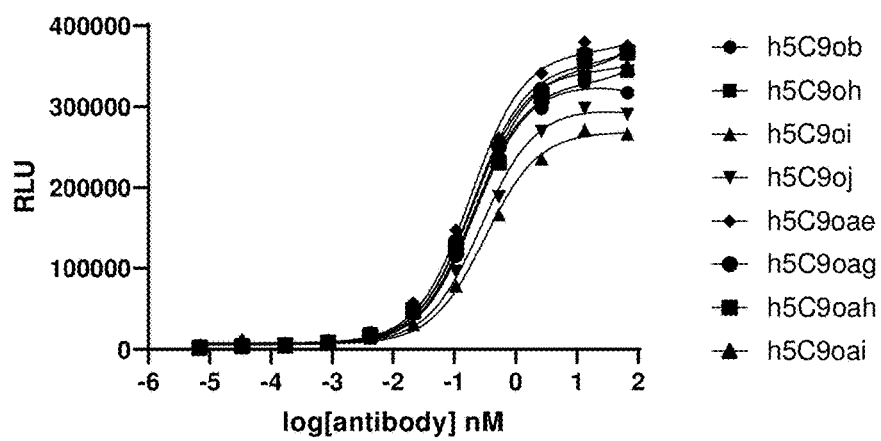
FIG. 20 depicts a graph of binding affinity measurements of humanized monoclonal anti-CLDN 18.2 antibodies h5C9ob, h5C9oh, h5C9oi, h5C9oj, h5C9oae, h5C9oag, h5C9oah, h5C9oai by Elisa based analysis.

The studies of the Binding Characteristics of the antibody described in Example 58 were performed as in Example 1. The results are shown in FIG. 20.

Example 59: Anti-CLDN 18.2-5C9oaf

The antibody described in Example 59 was generated according to the above general method as described in Example 29. The antibody described in Example 59 comprises two light chain variable domains (VLs) comprising the amino acid sequence of SEQ ID NO:221 and two heavy chain variable domains (VHs) comprising the amino acid sequence of SEQ ID NO:226.

The studies of the Binding Characteristics of the antibody described in Example 59 were performed as in Example 1. The results are shown in FIG. 19.

Example 60: Anti-CLDN 18.2-5C9oag

The antibody described in Example 60 was generated according to the above general method as described in Example 29. The antibody described in Example 60 comprises two light chain variable domains (VLs) comprising the amino acid sequence of SEQ ID NO:228 and two heavy chain variable domains (VHs) comprising the amino acid sequence of SEQ ID NO:229.

The studies of the Binding Characteristics of the antibody described in Example 60 were performed as in Example 1. The results are shown in FIG. 20.

Example 61: Anti-CLDN 18.2-5C9oah

The antibody described in Example 61 was generated according to the above general method as described in Example 29. The antibody described in Example 61 comprises two light chain variable domains (VLs) comprising the amino acid sequence of SEQ ID NO:231 and two heavy chain variable domains (VHs) comprising the amino acid sequence of SEQ ID NO:232.

The studies of the Binding Characteristics of the antibody described in Example 61 were performed as in Example 1. The results are shown in FIG. 20.

Example 62: Anti-CLDN 18.2-5C9oai

The antibody described in Example 62 was generated according to the above general method as described in Example 29. The antibody described in Example 62 comprises two light chain variable domains (VLs) comprising the amino acid sequence of SEQ ID NO:234 and two heavy chain variable domains (VHs) comprising the amino acid sequence of SEQ ID NO:235.

The studies of the Binding Characteristics of the antibody described in Example 62 were performed as in Example 1. The results are shown in FIG. 20.

Example 63: Anti-CLDN 18.2-5C9oap

The antibody described in Example 63 was generated according to the above general method as described in Example 29. The antibody described in Example 63 comprises two light chain variable domains (VLs) comprising the amino acid sequence of SEQ ID NO:237 and two heavy chain variable domains (VHs) comprising the amino acid sequence of SEQ ID NO:240.

Figure 21:
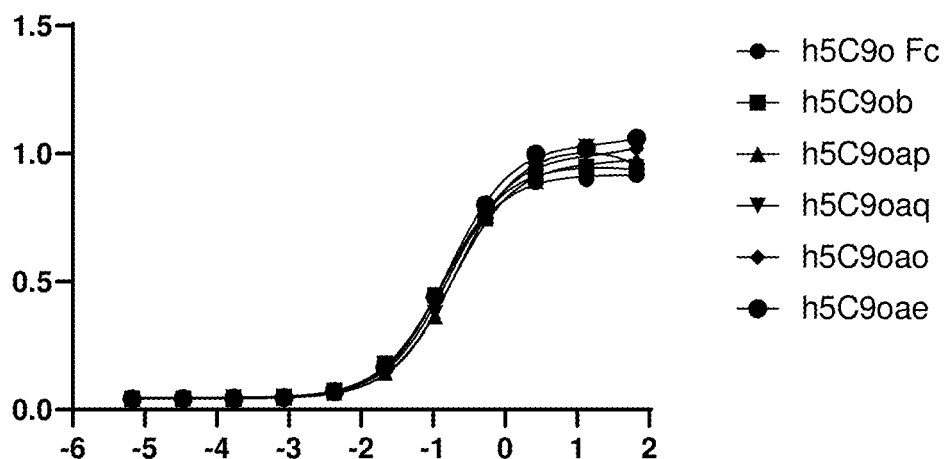
FIG. 21 depicts a graph of binding affinity measurements of humanized monoclonal anti-CLDN 18.2 antibodies h5C9o Fc mu, h5C9ob, h5C9oap, h5C9oaq, h5C9oao, h5C9oae by Elisa based analysis.
Figure 22:
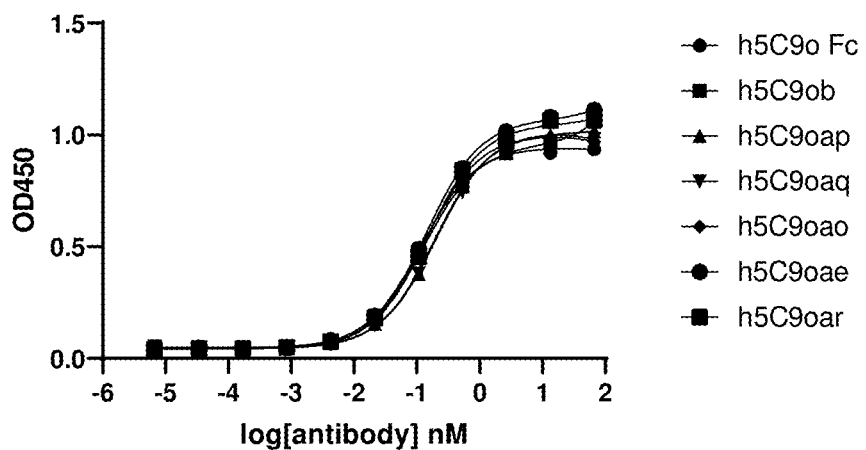
FIG. 22 depicts a graph of binding affinity measurements of humanized monoclonal anti-CLDN 18.2 antibodies h5C9o Fc mu, h5C9ob, h5C9oap, h5C9oaq, h5C9oao, h5C9oae, h5C9oar by Elisa based analysis.

The studies of the Binding Characteristics of the antibody described in Example 63 were performed as in Example 1. The results are shown in FIG. 21 and FIG. 22.

Example 64: Anti-CLDN 18.2-5C9oaq

The antibody described in Example 64 was generated according to the above general method as described in Example 29. The antibody described in Example 64 comprises two light chain variable domains (VLs) comprising the amino acid sequence of SEQ ID NO:242 and two heavy chain variable domains (VHs) comprising the amino acid sequence of SEQ ID NO:244.

The studies of the Binding Characteristics of the antibody described in Example 64 were performed as in Example 1. The results are shown in FIG. 21 and FIG. 22.

Example 65: Anti-CLDN 18.2-5C9oar

The antibody described in Example 65 was generated according to the above general method as described in Example 29. The antibody described in Example 65 comprises two light chain variable domains (VLs) comprising the amino acid sequence of SEQ ID NO:246 and two heavy chain variable domains (VHs) comprising the amino acid sequence of SEQ ID NO:248.

The studies of the Binding Characteristics of the antibody described in Example 65 were performed as in Example 1. The results are shown in FIG. 22.

Example 66: The Purity of Monoclonal Antibodies

Figure 23:
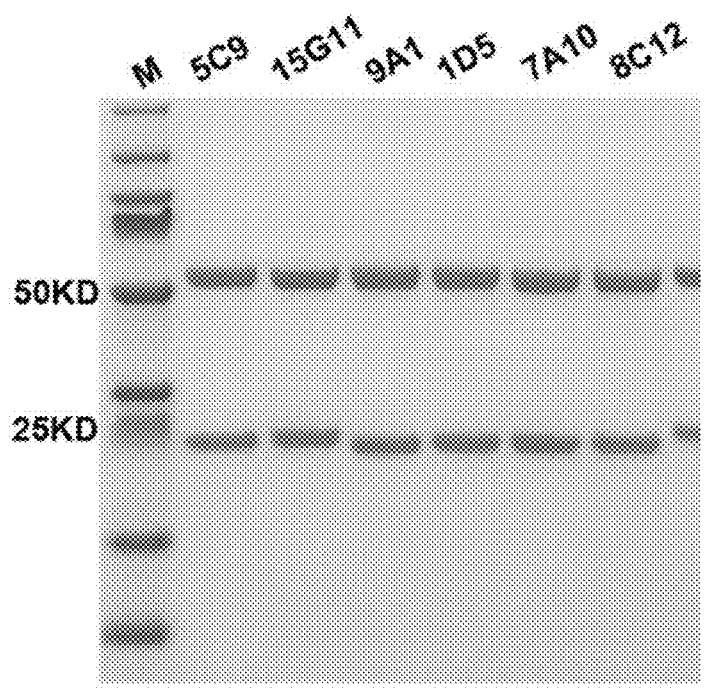
FIG. 23 depicts a photograph of purity analysis of mouse monoclonal anti-CLDN 18.2 antibodies 5C9, 15G 11, 9A1, 1D5, 7A10 and 8C12 by SDS-PAGE electrophoresis.
Figure 24:
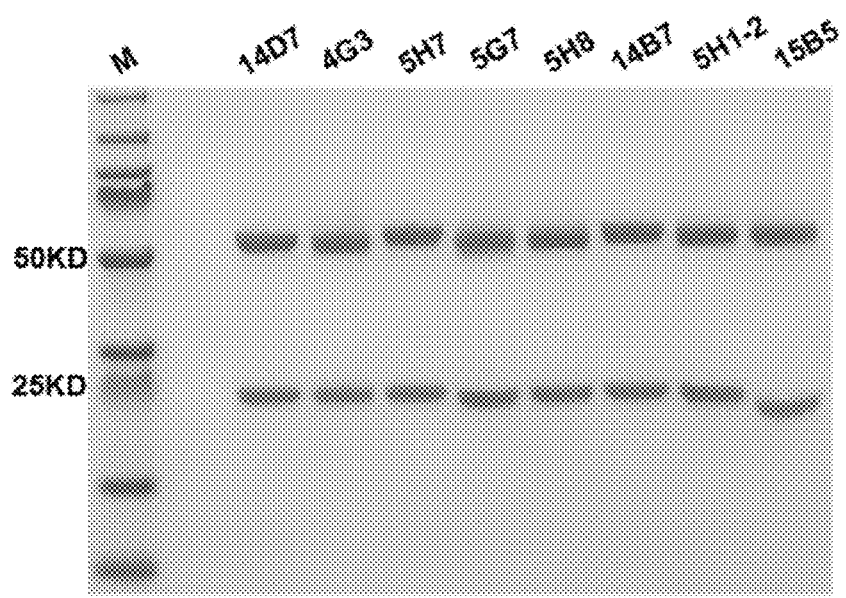
FIG. 24 depicts a photograph of purity analysis of mouse monoclonal anti-CLDN 18.2 antibodies 14D7, 4G3, 5H7, 5G7, 5H8, 14B7, 5H1-1, 15B5 by SDS-PAGE electrophoresis.

The purity of mouse monoclonal antibodies was evaluated by SDS-PAGE electrophoresis as follows. All micro centrifuge tubes containing samples for SDS-PAGE were placed into a heating block (set to 95° C.) or boiling water. The samples were heated for 5 minutes. 5 μg antibody samples were loaded into gel lanes starting with the MW standards. The chamber was covered and the anode and the cathode were connected. The voltage was set on the electrophoresis power supply to a constant voltage of 100 V. The gel was allowed to electrophorese for 45-90 minutes. The power was turned OFF immediately after the dye front migrated out from the bottom of the gel. The electrodes were disconnected and the gel removed from its plates. InstantBlue staining followed (See, FIG. 23 and FIG. 24).

Example 67: Selectivity Assay of Mouse, Chimeric and Humanized Antibodies

Figure 25:
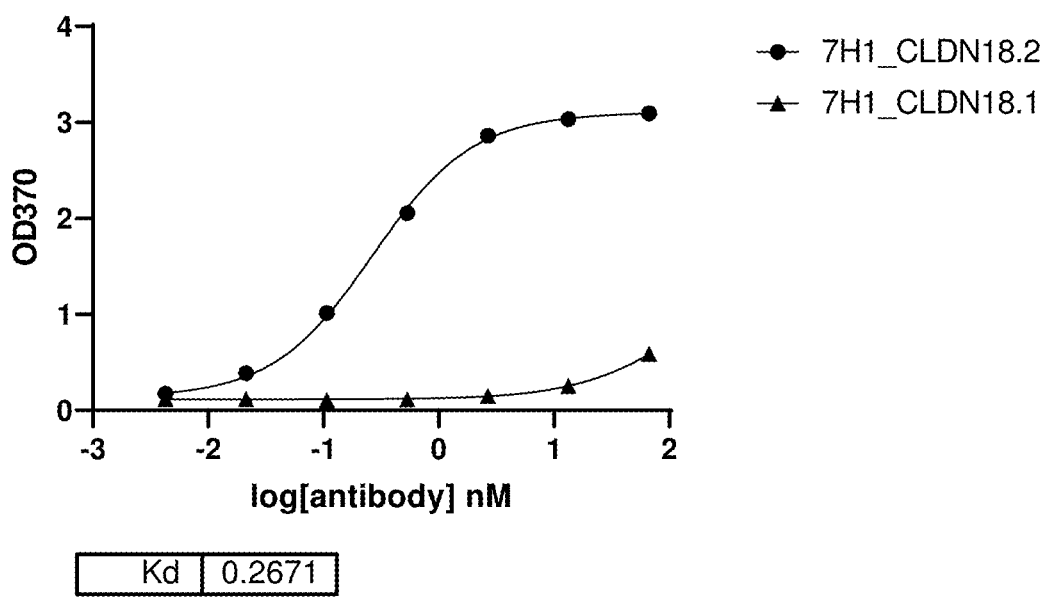
FIG. 25 depicts a graph of binding affinity and selectivity analysis of a mouse monoclonal anti-CLDN 18.2 antibody 7H1 to Claudin18.2 and Claudin18.1.
Figure 26:
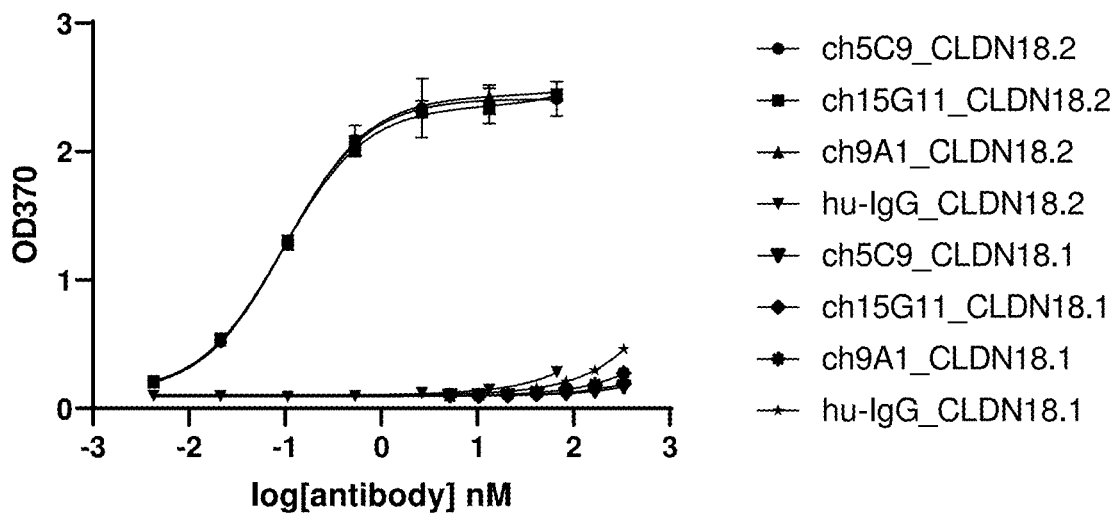
FIG. 26 depicts a graph of binding affinity and selectivity analysis of chimeric anti-CLDN 18.2 antibodies ch5C9, ch15G11 and ch9A1 to Claudin18.2 and Claudin18.1, human IgG as control.
Figure 27:
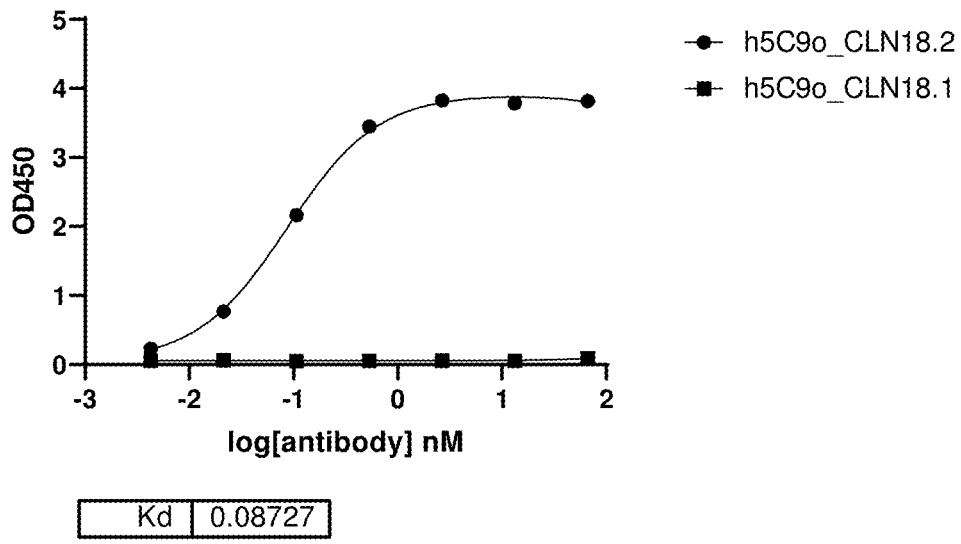
FIG. 27 depicts a graph of binding affinity and selectivity analysis of a humanized anti-CLDN 18.2 antibody ch5C9o to Claudin18.2 and Claudin18.1.

Recombinant protein Claudin 18.2 and Claudin 18.1 were diluted to a final concentration of 4.5 μg/mL in carbonate buffer. The Elisa plates were coated overnight at 4° C. The coating solution was removed and the plates washed three times by filling the wells with 200 μL TBST, an additional blocking step (30 min, 5% BSA-PBS) may be applied. The diluted mouse monoclonal antibody 7H1, chimeric antibody ch5C9, ch05G11, ch9A1, and humanized antibody h5C9o were added to each well and incubated at room temperature for 2 hours. The non-specific negative control mouse IgG was diluted in TBST. The plates were washed three times by filling the wells with 200 μL TBST, the HRP-conjugated secondary antibody was added and incubated at room temperature for 2 hours. The plate was washed again three times and TMB substrate solution was added to each well, the plates incubated for 15-30 min, added equal volume of stopping solution (2 M $H_2SO_4$, option). The optical density was read at 370 or 450 nm. The analysis was executed by GraphPad Prism 8.0.1. All tested antibodies demonstrated high selectivity to Claudin 18.2 but not Claudin 18.1 (FIG. 25, FIG. 26 and FIG. 27).

Figure 28:
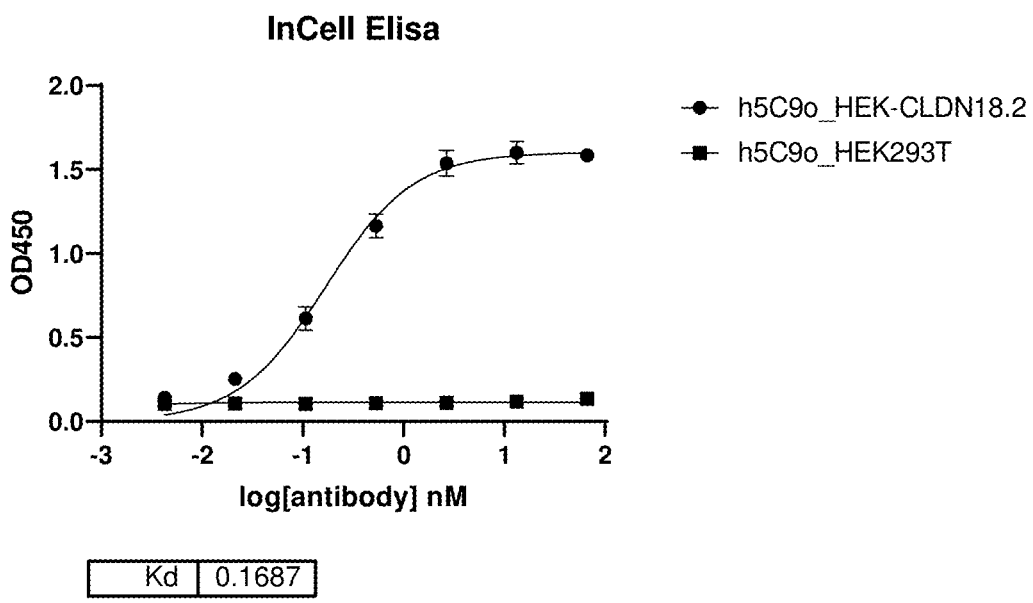
FIG. 28 depicts a humanized anti-Claudin 18.2 antibody h5C9o binding to Claudin 18.2 epitope on HEK_CLDN 18.2 cells but not HEK293T cells by cell-based Elisa analysis.
Figure 29:
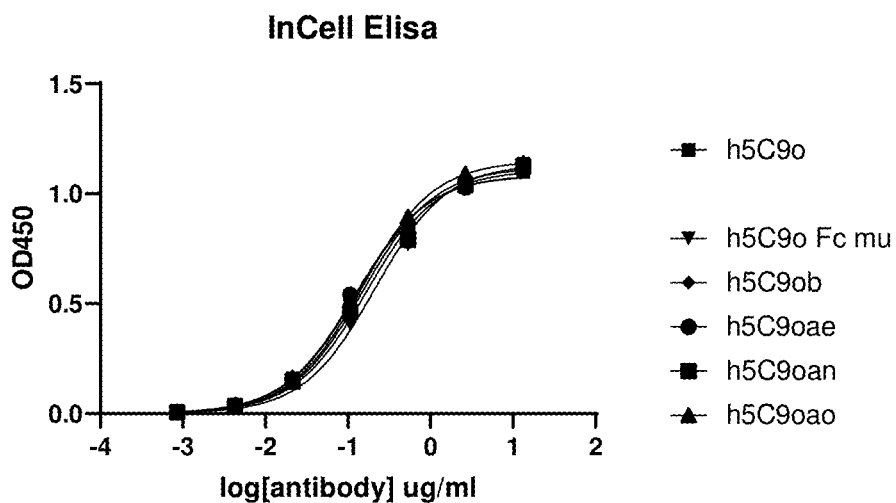
FIG. 29 depicts humanized anti-Claudin 18.2 antibodies h5C9o, h5C9o Fc mu, h5C9ob, h5C9oae, h5C9oan, h5C9oao binding to Claudin 18.2 epitope on HEK_CLDN 18.2 cells by cell-based Elisa analysis.
Figure 30:
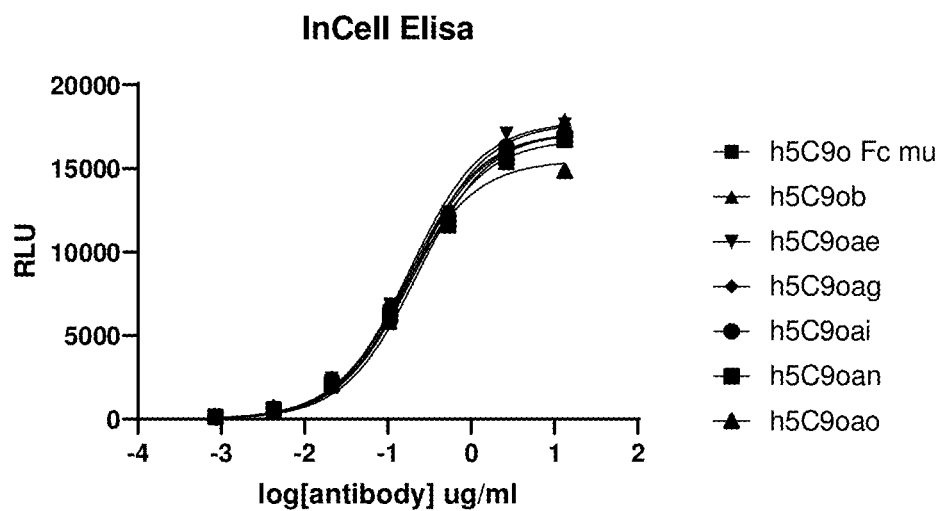
FIG. 30 depicts humanized anti-Claudin 18.2 antibodies h5C9o Fc mu, h5C9ob, h5C9oae, h5C9oag, h5C9oai, h5C9oan, h5C9oao binding to Claudin 18.2 epitope on HEK_CLDN18.2 cells by cell-based Elisa analysis.

Example 68: Humanized Antibodies Binding to Claudin18.2 Stably Expressed HEK293 Cells Humanized anti-Claudin 18.2 antibodies were investigated for their binding to Claudin 18.2 epitope on cells. $1\times10^5$/well HEK293T, HEK293_CLDN18.2 cells were seeded in 96 well plate overnight. Cells were fixed by 10% Formalin at room temperature for 15 min, followed by a 2 hour blocking step. After wash a series of antibody dilution were added to plate wells, the plate was incubated 2 hours at room temperature. After 3× wash, an goat anti-human IgG was added and incubated for another hour, then the binding was demonstrated by adding TMB solution. Results showing all tested antibodies—h5C9o, h5C9o Fc mutation, h5C9ob, h5C9oae, h5C9oag, h5C9oai, h5C9oan and h5C9oao bind to HEK293_CLDN18.2 cells but not HEK293T cells (FIG. 28, FIG. 29 and FIG. 30).

Example 69: Humanized Antibodies Internalization Assay

Figure 31:
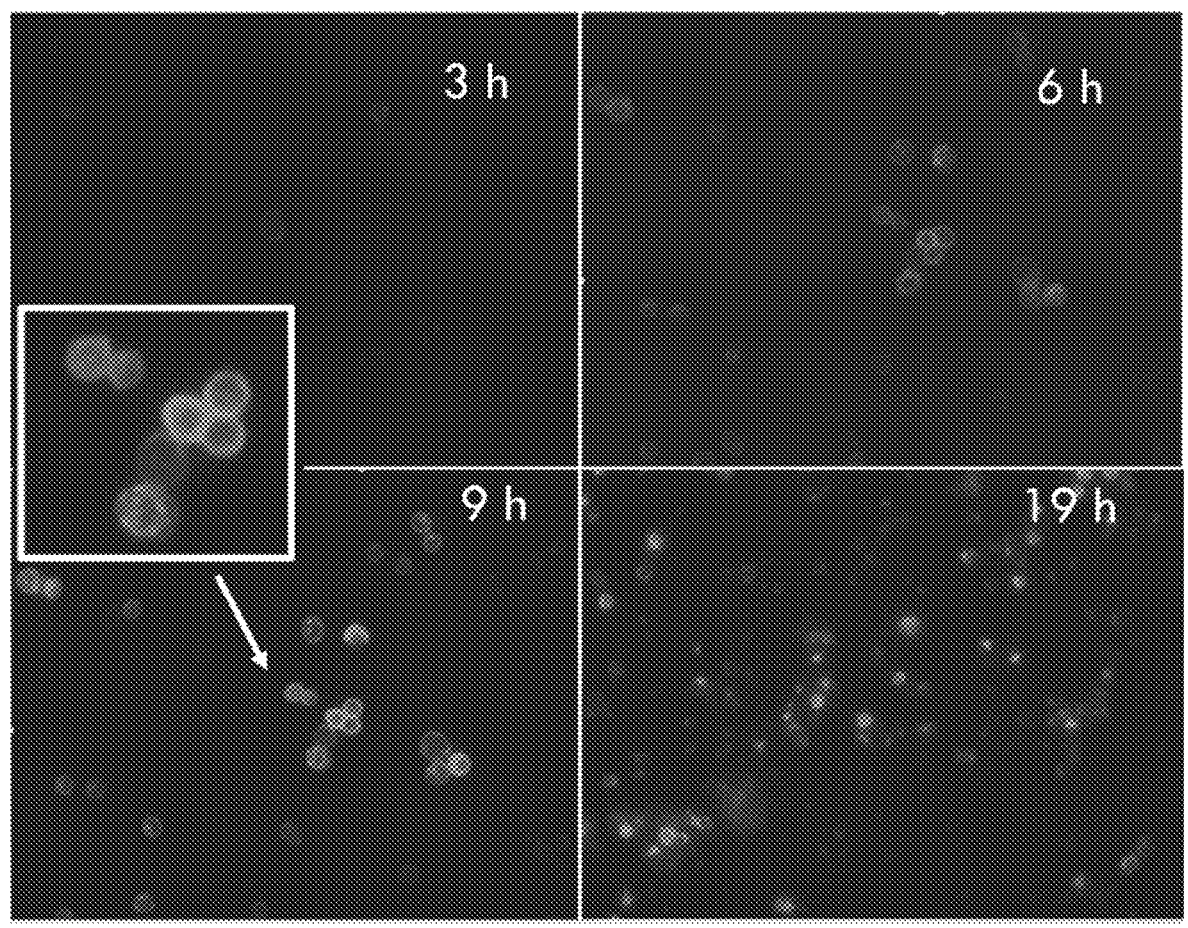
FIG. 31 is a photograph of humanized antibodies h5C9o internalization assay by Alexa Fluor 488 labeling assay.

To investigate humanized anti-Claudin18.2 antibody h5C9o binding to Claudin 18.2 naturally expressed gastric tumor cells NUGC4, a green fluorescent Alexa Fluor® 488 probe (Invitrogen) was used to label h5C9o antibody following the manufacture's protocol. Labeled h5C9o was added to NUGC4 cultures in 96 well plate, pictures were taken along with incubation time. The internalization of h5C9o into NUGC4 cells was monitored using fluorescence microscopy, Alexa Fluor® 488 dye with an excitation and emission maximum of 494/519 nm (FIG. 31).

Figure 32:
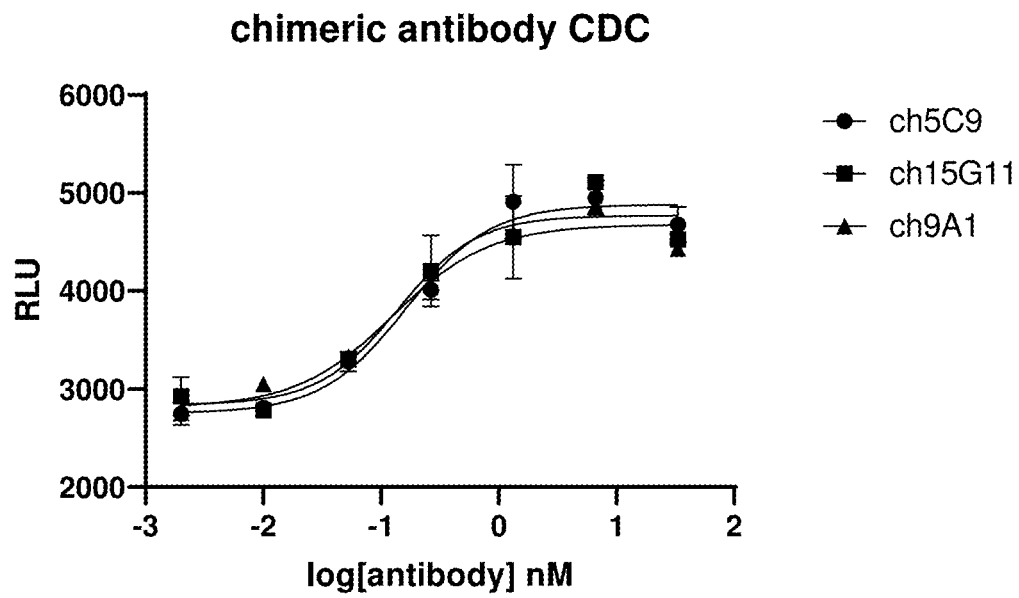
FIG. 32 depicts a graph comparing chimeric anti-Claudin18.2 antibodies ch5C9, ch15G11 and ch9A1 mediated complement dependent cytotoxicity (CDC).

Example 70: Complement Dependent Cytotoxicity (CDC) Assay of ch5C9, ch15G11 and ch9A1 in CLDN 18.2 Transiently Expressed HEK293T Cells $2.5\times10^4$/well 24 hour transiently expressed Claudin 18.2 HEK293T cells were seeded in tissue-culture flat-bottom microtiter plates. The next day growth medium was removed and the cells were incubated with 1:5 series dilution chimeric antibodies ch5C9, ch15G11 and ch9A1 for 2 hour at 37° C., 5% $CO_2$, 90% humidity. Human serum or plasma with complements was then added to a final concentration of 25% (v/v) and the cells incubated at 37° C. for 3.5 hours. Cyto-Glo cytotoxicity assay reagent was added to each well. The plate was mixed and incubated at RT for 15 min. The luminescence signal was measured using a Bio-Tek plate reader synergy 4. EC50 was calculated through Prism Graphpad 8.0.1, nonlinear regression agonist vs response variable slope (four parameters). Results are shown in FIG. 32.

Figure 33:
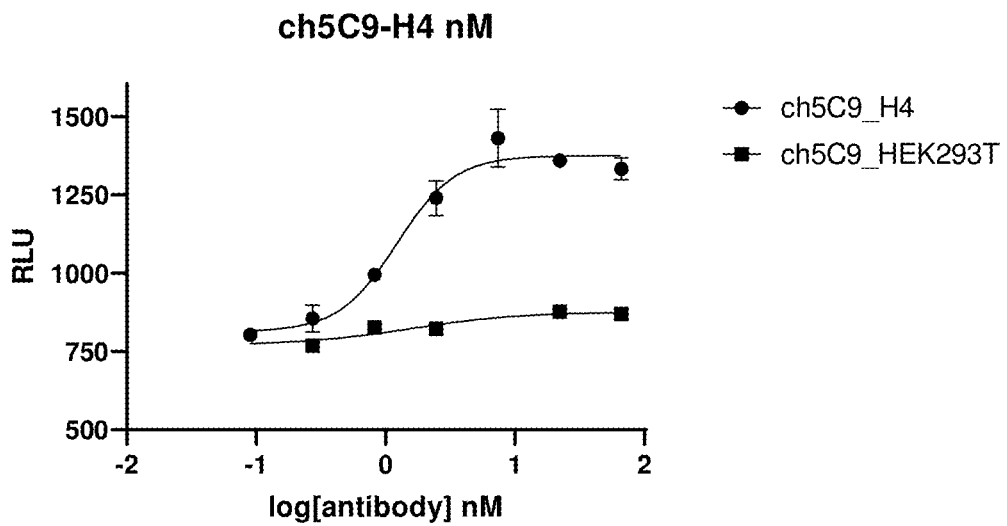
FIG. 33 Shows a graph depicting chimeric anti-Claudin18.2 antibodies ch5C9 mediated CDC effects on Claudin18.2 expressed HEK293 cells but not HEK293T cells.
Figure 34:
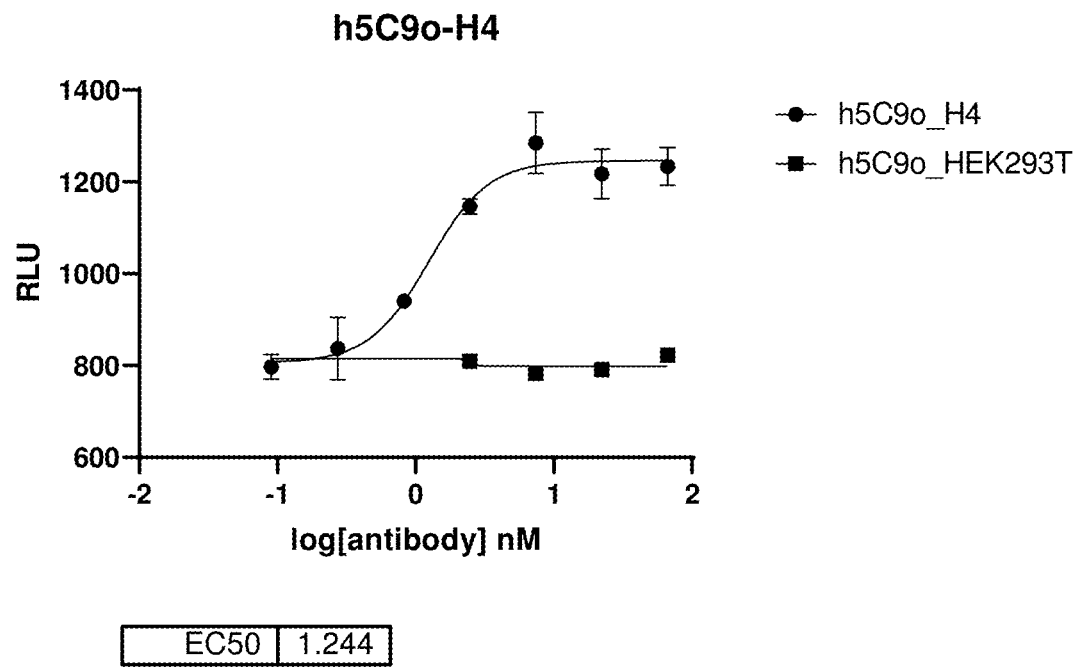
FIG. 34 shows a graph showing humanized anti-Claudin18.2 antibodies h5C9o mediated CDC effects on Claudin18.2 expressed HEK293 cells but not HEK293T cells.

Example 71: Complement Dependent Cytotoxicity (CDC) Assay of ch5C9 and h5C9o in CLDN 18.2 Stably Expressed HEK293T Cells $5\times10^4$/well stably expressed Claudin 18.2 HEK293T cells and control HEK293T cells were seeded in tissue-culture flat-bottom microtiter plates. The next day growth medium was removed and the cells were incubated with 1:3 series dilution chimeric and humanized antibodies ch5C9 and h5C9o for 2 hours at 37° C., 5% $CO_2$, 90% humidity. Human serum or plasma with complements was then added to a final concentration of 25% (v/v) and the cells were incubated at 37° C. for 3 hours. Cyto-Glo cytotoxicity assay reagent was added to each well, mixed and incubated at RT for 15 min. The luminescence signal was measured using a Bio-Tek plate reader synergy 4. EC50 was calculated through Prism Graphpad 8.0.1, nonlinear regression agonist vs response variable slope (four parameters). Results are shown in FIG. 33 and FIG. 34.

Figure 35:
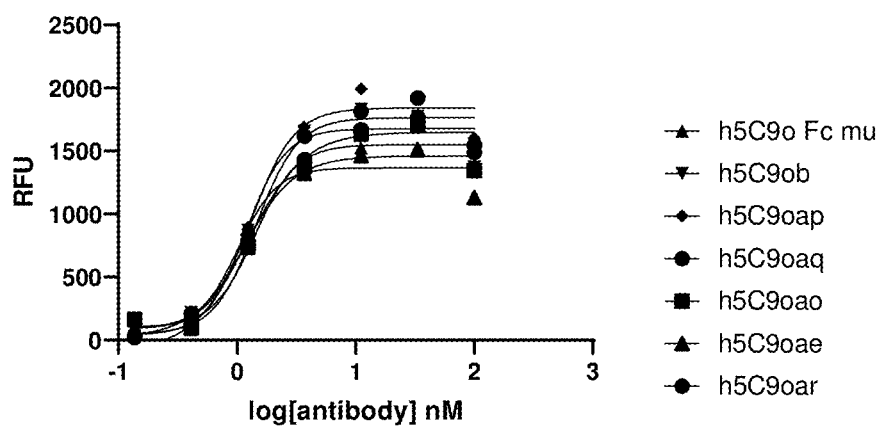
FIG. 35 Shows humanized anti-Claudin18.2 antibodies h5C9o Fc mu, h5C9ob, h5C9oap, h5C9oaq, h5C9oao, h5C9oae, h5C9oar mediated CDC effects on Claudin18.2 expressed HEK293 cells.
Figure 36:
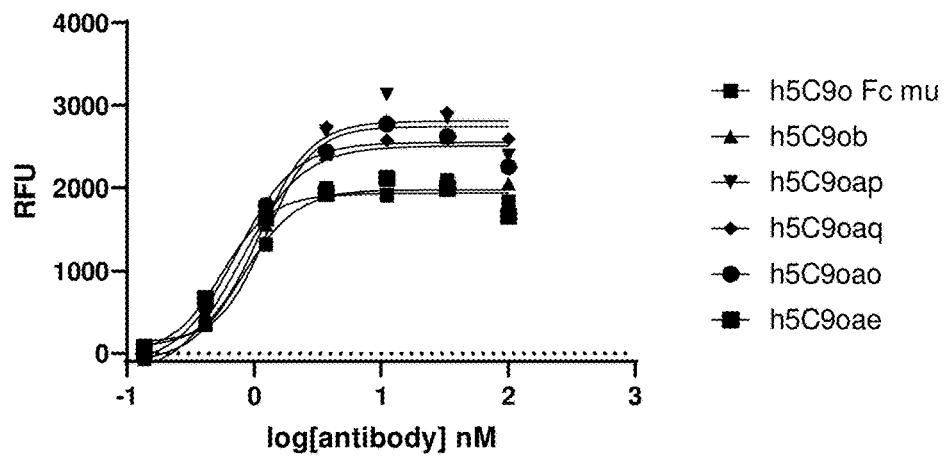
FIG. 36 depicts a graph showing humanized anti-Claudin18.2 antibodies h5C9o Fc mu, h5C9ob, h5C9oap, h5C9oaq, h5C9oao, h5C9oae mediated CDC effects on Claudin18.2 expressed HEK293 cells.

Example 72: Complement Dependent Cytotoxicity (CDC) Assay of h5C9o, h5C9ob, h5C9oap, h5C9oaq, h5C9oae, and h5C9oar in CLDN 18.2 Stably Expressed HEK293T Cells $2 \times 10^4$/well stably expressed Claudin 18.2 HEK293T cells were seeded in tissue-culture flat-bottom microtiter plates. The next day growth medium was removed and the cells were incubated with 1:3 series dilution humanized antibodies h5C9o, h5C9ob, h5C9oap, h5C9oaq, h5C9oae, and h5C9oar for 2 hours at 37° C., 5% $CO_2$, 90% humidity. Human serum or plasma with complements was then added to a final concentration of 25% (v/v) and the cells were incubated at 37° C. for 3 hours. Cyto-Glo cytotoxicity assay reagent was added to each well, mixed and incubated at RT for 15 min. The luminescence signal was measured using a Bio-Tek plate reader synergy 4. EC50 was calculated through Prism Graphpad 8.0.1, nonlinear regression agonist vs response variable slope (four parameters). Results are shown in FIG. 35 and FIG. 36.

Example 73: Antibody Dependent Cellular Cytotoxicity (ADCC) of Chimeric Antibodies ch5C9, ch15G11, and ch9A1

Figure 37:
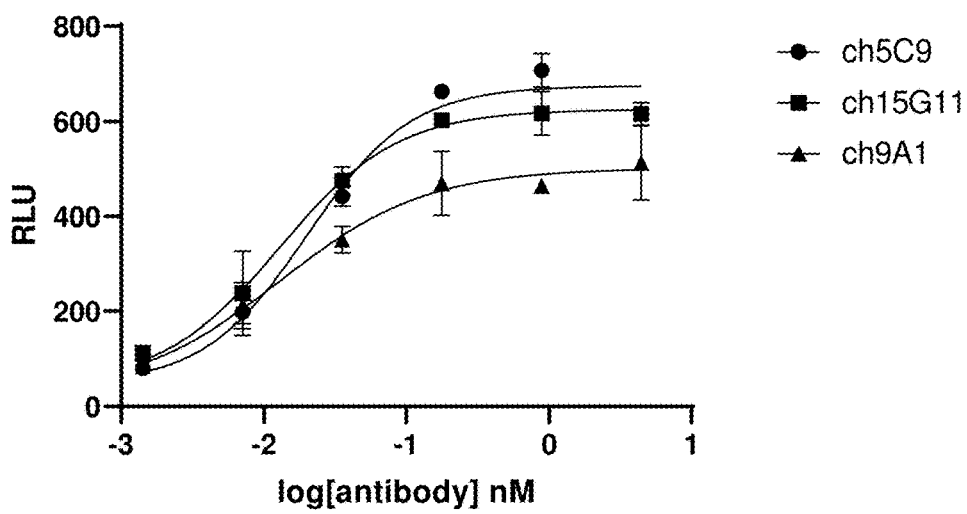
FIG. 37 depicts a graph showing chimeric anti-Claudin18.2 antibodies ch5C9, ch15G11 and ch9A1mediated ADCC effects 18.2 transiently expressed HEK_CLDN18.2 cells.

ADCC assay of three chimeric antibodies ch5C9, ch15G11, and ch9A 1 was executed by utilizing ADCC Reporter Bioassay (Promega). $2.5 \times 10^4$/well CLDN 18.2 transiently expressed cells were seeded in a 96 well culture plate overnight. The culture medium was removed at second day and replaced with 50 µL 4% FBS RPMI medium with a series diluted chimeric anti-CLDN 18.2 antibody-ch5C9, ch15G 11 and ch9A 1. The engineered Jurkat cells 25 µL was added to each well at a ratio E:T=6:1, the cell mixture was incubated for 6 hours at 37° C., 5% $CO_2$, 90% humidity. The luminescence signal resulting from NFAF (nueclear factor of activated T-cells) response element driving expression of luciferase was recorded by Bio-tek synergy 4. EC50 was calculated through Prism Graphpad 8.0.1, nonlinear regression agonist vs response variable slope (4 parameters). The results are shown in FIG. 37.

Example 74: Antibody Dependent Cell-Mediated Cytotoxicity (ADCC) of Chimeric Antibodies ch5C9 and ch7H1

Figure 38:
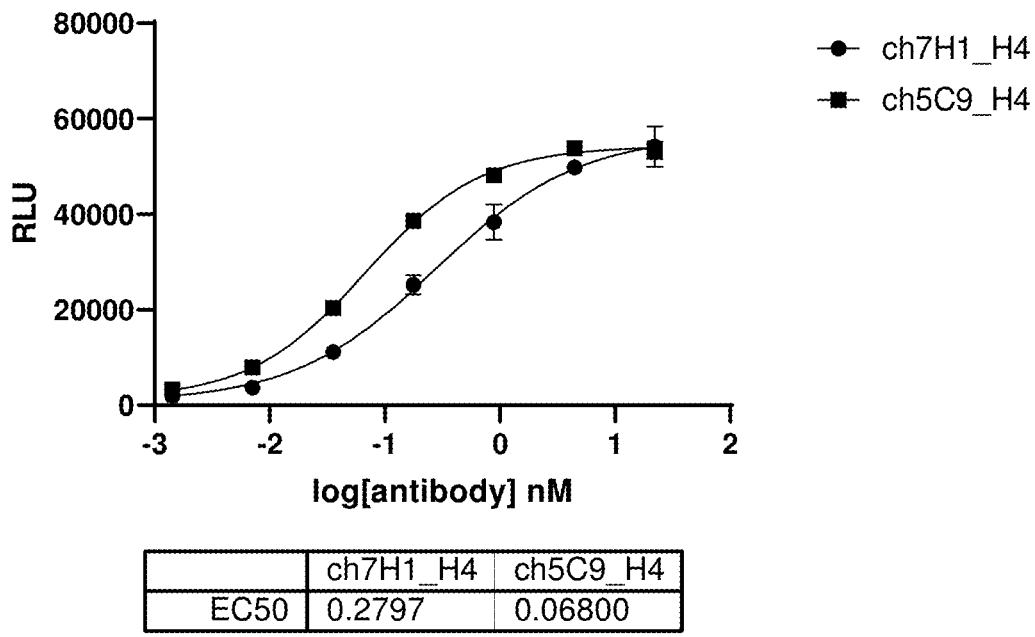
FIG. 38 depicts a graph showing chimeric anti-Claudin18.2 antibodies ch5C9, ch7H1 mediated ADCC effects on CLDN18.2 stably expressed HEK_CLDN18.2 cells.

ADCC assay was executed by utilizing ADCC Reporter Bioassay (Promega). $2.2 \times 10^4$/well CLDN18.2 stably expressed cells HEK293_CLDN18.2 were seeded in a 96 well culture plate overnight. The culture medium was removed at second day and replaced with 50 µL 4% FBS RPMI medium with 1:5 series diluted chimeric anti-CLDN 18.2 antibody-ch5C9 and ch7H1. The engineered Jurkat cells 25 µL was added to each well at a ratio E:T=6:1, the cell mixture was incubated for 6 hours at 37° C., 5% $CO_2$, 90% humidity. The luminescence signal resulting from NFAF (nueclear factor of activated T-cells) response element driving expression of luciferase was recorded by Bio-tek synergy 4. EC50 was calculated through Prism Graphpad 8.0.1, nonlinear regression agonist vs response variable slope (4 parameters). The results are shown in FIG. 38.

Example 75: Antibody Dependent Cell-Mediated Cytotoxicity (ADCC) of Chimeric Antibody ch7H1 in NUGC4

Figure 39:
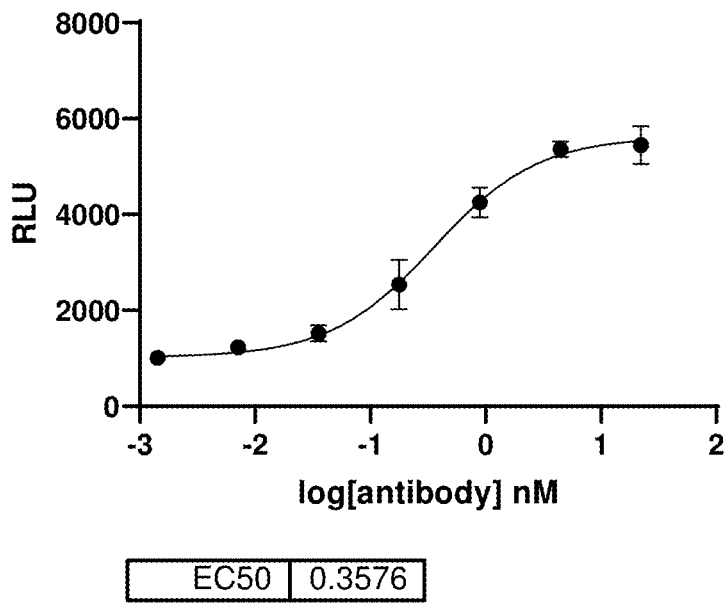
FIG. 39 depicts a graph showing a chimeric anti-Claudin18.2 antibody ch7H1 mediated ADCC effects on CLDN18.2 expressed NUGC4 cells

ADCC assay was executed by utilizing ADCC Reporter Bioassay (Promega). $2.2 \times 10^4$/well gastric tumor cells NUGC4 were seeded in a 96 well culture plate overnight. The culture medium was removed at second day and replaced with 50 ul 4% FBS RPMI medium with 1:5 series diluted chimeric anti-CLDN 18.2 antibody ch7H1. The engineered Jurkat cells 25 ul was added to each well at a ratio E:T=6:1, the cell mixture was incubated for 6 hours at 37° C., 5% $CO_2$, 90% humidity. The luminescence signal resulting from NFAF (nuclear factor of activated T-cells) response element driving expression of luciferase was recorded by Bio-tek synergy 4. EC50 was calculated through Prism Graphpad 8.0.1, nonlinear regression agonist vs response variable slope (4 parameters). The result is shown in FIG. 39.

Figure 40:
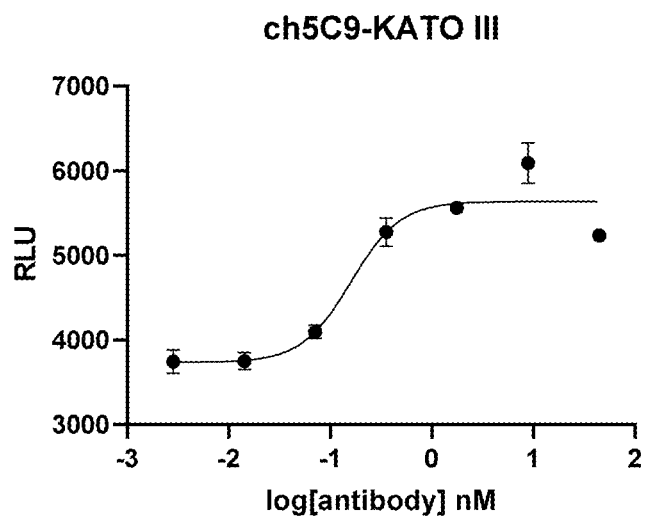
FIG. 40 depicts a graph showing a chimeric anti-Claudin18.2 antibody ch5C9 mediated ADCC effects on CLDN18.2 expressed KATO III cells
Figure 41:
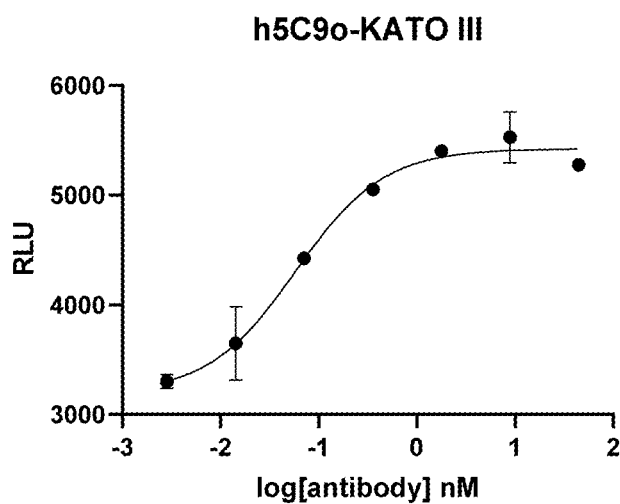
FIG. 41 depicts a graph showing a humanized anti-Claudin18.2 antibody h5C9o mediated ADCC effects on CLDN18.2 expressed KATO III cells

Example 76: ADCC Effects of Chimeric and Humanized Antibodies ch5C9 and h5C9o in Gastric Tumor Cell KATO III ADCC assay was executed by utilizing ADCC Reporter Bioassay (Promega). $2.2 \times 10^4$/well CLDN 18.2 expressed gastric tumor cells KATO III were seeded in a 96 well culture plate overnight. The culture medium was removed at second day and replaced with 50 µL 4% FBS RPMI medium with 1:5 series diluted chimeric anti-CLDN 18.2 antibody-ch5C9 and ch7H1. The engineered Jurkat cells 25 µL was added to each well at a ratio E:T=6:1, the cell mixture was incubated for 6 hours at 37° C., 5% $CO_2$, 90% humidity. The luminescence signal resulting from NFAF (nuclear factor of activated T-cells) response element driving expression of luciferase was recorded by Bio-tek synergy 4. EC50 was calculated through Prism Graphpad 8.0.1, nonlinear regression agonist vs response variable slope (4 parameters). The results are shown in FIG. 40 and FIG. 41.

Figure 42:
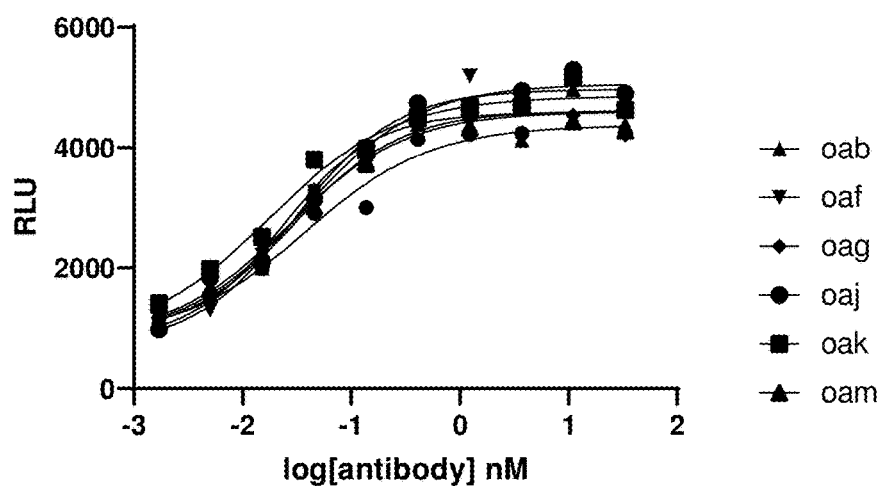
FIG. 42 depicts a graph showing humanized anti-Claudin18.2 antibodies h5C9oab, h5C9oaf, h5C9oag, h5C9oaj, h5C9oak, h5C9oam mediated ADCC effects on CLDN18.2 stably expressed HEK_CLDN18.2 cells.
Figure 43:
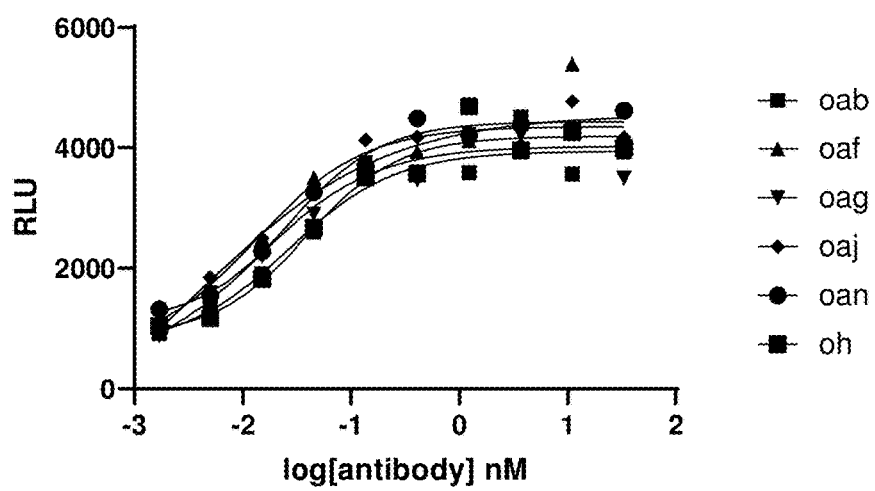
FIG. 43 depicts a graph showing humanized anti-Claudin18.2 antibodies h5C9oab, h5C9oaf, h5C9oag, h5C9oaj, h5C9oan and h5C9oh mediated ADCC effects on CLDN18.2 stably expressed HEK_CLDN18.2 cells.

Example 77: ADCC Effects of h5C9oab, h5C9oaf, h5C9oag, h5C9oaj, h5C9oak, h5C9oam, h5C9oan and h5C9oh in HEK293_CLDN18.2 Cells ADCC assay was executed by utilizing ADCC Reporter Bioassay (Promega). $1 \times 10^4$/well CLDN 18.2 stably expressed cells HEK293_CLDN18.2 were seeded in a 96 well culture plate overnight. The culture medium was removed at second day and replaced with 50 µL 4% FBS RPMI medium with 1:3 series diluted anti-CLDN 18.2 antibodies h5C9oab, h5C9oaf, h5C9oag, h5C9oaj, h5C9oak, h5C9oam, h5C9oan and h5C9oh. The engineered Jurkat cells 25 µL was added to each well at a ratio E:T=10:1, the cell mixture was incubated for 6 hours at 37° C., 5% $CO_2$, 90% humidity. The luminescence signal resulting from NFAF (nueclear factor of activated T-cells) response element driving expression of luciferase was recorded by Bio-tek synergy 4. EC50 was calculated through Prism Graphpad 8.0.1, nonlinear regression agonist vs response variable slope (4 parameters). The results are shown in FIG. 42 and FIG. 43.

Figure 44:
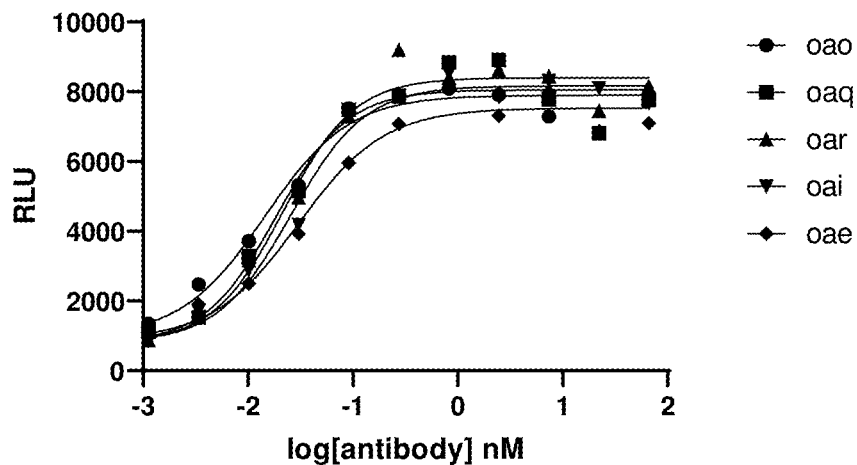
FIG. 44 depicts a graph showing humanized anti-Claudin18.2 antibodies h5C9oao, h5C9oaq, h5C9oar, h5C9oai, h5C9oae mediated ADCC effects on CLDN18.2 stably expressed HEK_CLDN18.2 cells.

Example 78: ADCC of h5C9oao, h5C9oaq, h5C9oar, h5C9oai, h5C9oae in HEK293_CLDN18.2 Cells ADCC assay was executed by utilizing ADCC Reporter Bioassay (Promega). $1 \times 10^4$/well CLDN18.2 stably expressed cells HEK293_CLDN 18.2 were seeded in a 96 well culture plate overnight. The culture medium was removed at second day and replaced with 50 μL 4% FBS RPMI medium with 1:3 series diluted anti-CLDN 18.2 antibodies h5C9oao, h5C9oaq, h5C9oar, h5C9oai, h5C9oae. The engineered Jurkat cells 25 μL was added to each well at a ratio E:T=10:1, the cell mixture was incubated for 6 hours at 37° C., 5% $CO_2$, 90% humidity. The luminescence signal resulting from NFAF (nueclear factor of activated T-cells) response element driving expression of luciferase was recorded by Bio-tek synergy 4. EC50 was calculated through Prism Graphpad 8.0.1, nonlinear regression agonist vs response variable slope (4 parameters). The results are shown in FIG. 44.

Figure 45:
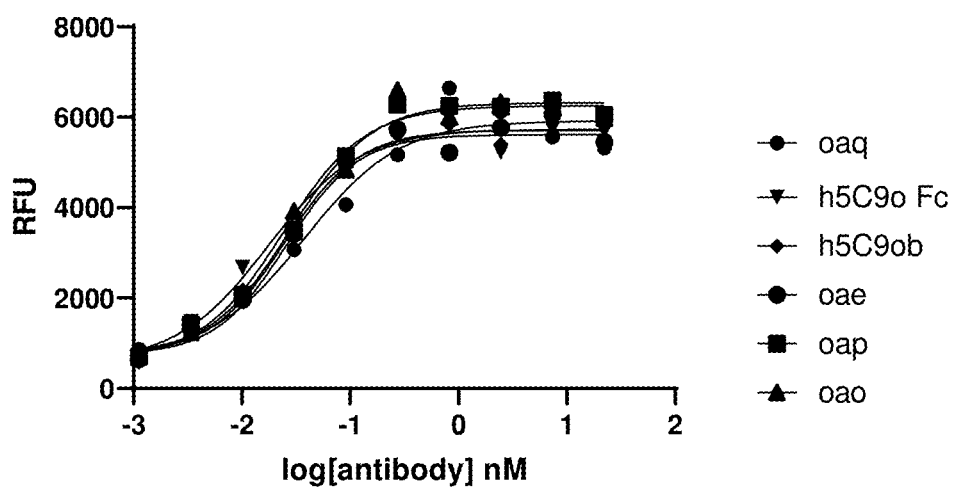
FIG. 45 depicts a graph showing humanized anti-Claudin18.2 antibodies h5C9o Fc, h5C9oao, h5C9oae, h5C9ob, h5C9oap, h5C9oaq mediated ADCC effects on CLDN18.2 stably expressed HEK_CLDN18.2 cells.

Example 79: ADCC of h5C9o Fc, h5C9oao, h5C9oaq, h5C9ob, h5C9oap, and h5C9oae in HEK293_CLDN18.2 Cells ADCC assay was executed by utilizing ADCC Reporter Bioassay (Promega). $1\times10^4$/well CLDN18.2 stably expressed cells HEK293_CLDN 18.2 were seeded in a 96 well culture plate overnight. The culture medium was removed at second day and replaced with 50 μL 4% FBS RPMI medium with 1:3 series diluted anti-CLDN 18.2 antibodies h5C9o Fc, h5C9oao, h5C9oaq, h5C9ob, h5C9oap, h5C9oae. The engineered Jurkat cells 25 μL was added to each well at a ratio E:T=10:1, the cell mixture was incubated for 6 hours at 37° C., 5% $CO_2$, 90% humidity. The luminescence signal resulting from NFAF (nueclear factor of activated T-cells) response element driving expression of luciferase was recorded by Bio-tek synergy 4. EC50 is calculated through Prism Graphpad 8.0.1, nonlinear regression agonist vs response variable slope (4 parameters). The results are shown in FIG. 45.

Figure 46:
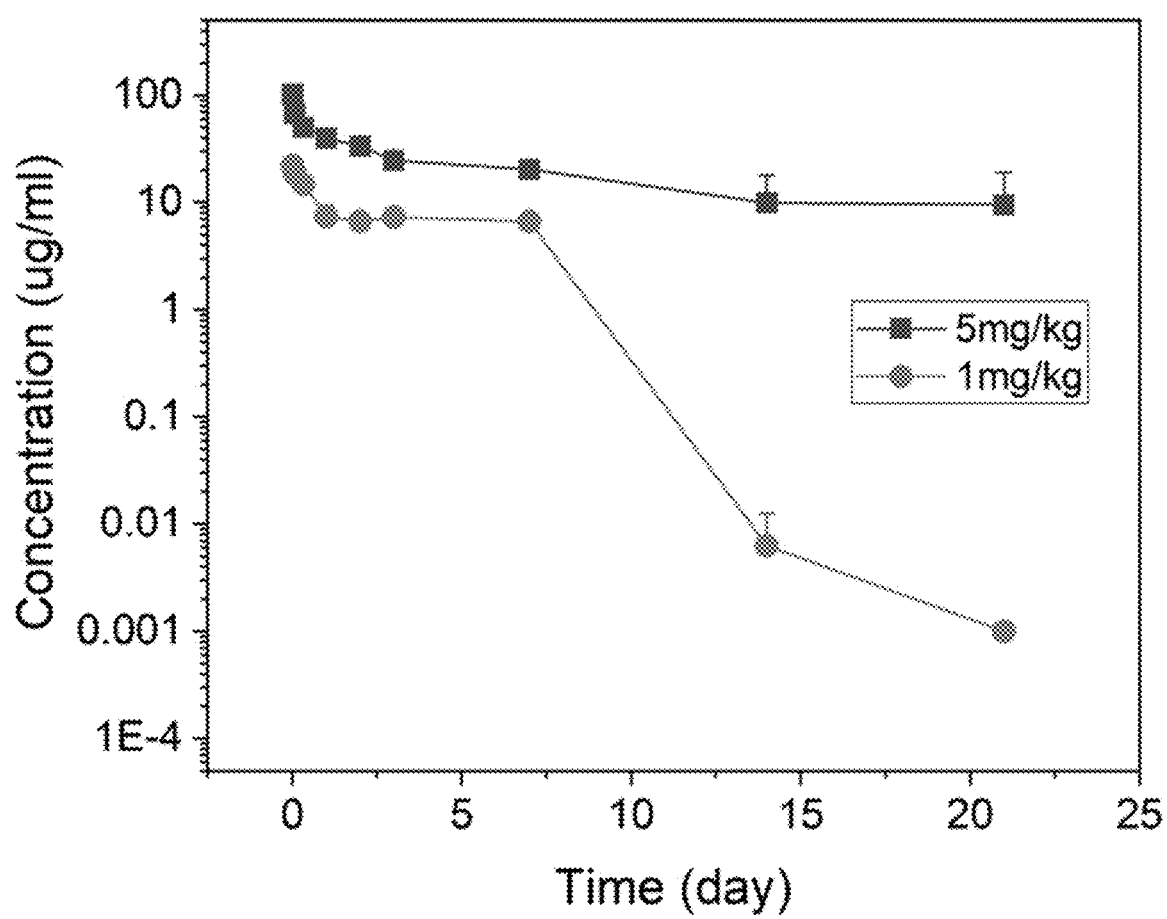
FIG. 46 depicts a graph showing the results of pharmacokinetic study of a humanized anti-Claudin 18.2 antibody h5C9o in CD1 mouse.

Example 80: Pharmacokinetic Studies of Humanized Anti-Claudin 18.2 Antibody h5C9o in CD1 Mice All mice were maintained under specific pathogen-free conditions and all animal procedures were performed in accordance with the animal experimental guidelines set by the Institutional Animal Care and Use Committee of Sparx Therapeutics, Inc. The CD1 mice received a single IV dose of 1 mg/kg and 5 mg/kg of h5C9o via the tail vein in the PK study. The terminal blood sample was collected via cardiac puncture from each animal in each dosing group at the following time points (n=2/group): 15 min, 2 h, 8 h, day 1, 2, 3, 7, 14, and 21, and processed for serum for the PK analysis through Elisa analysis. The results are shown in FIG. 46.

Figure 47:
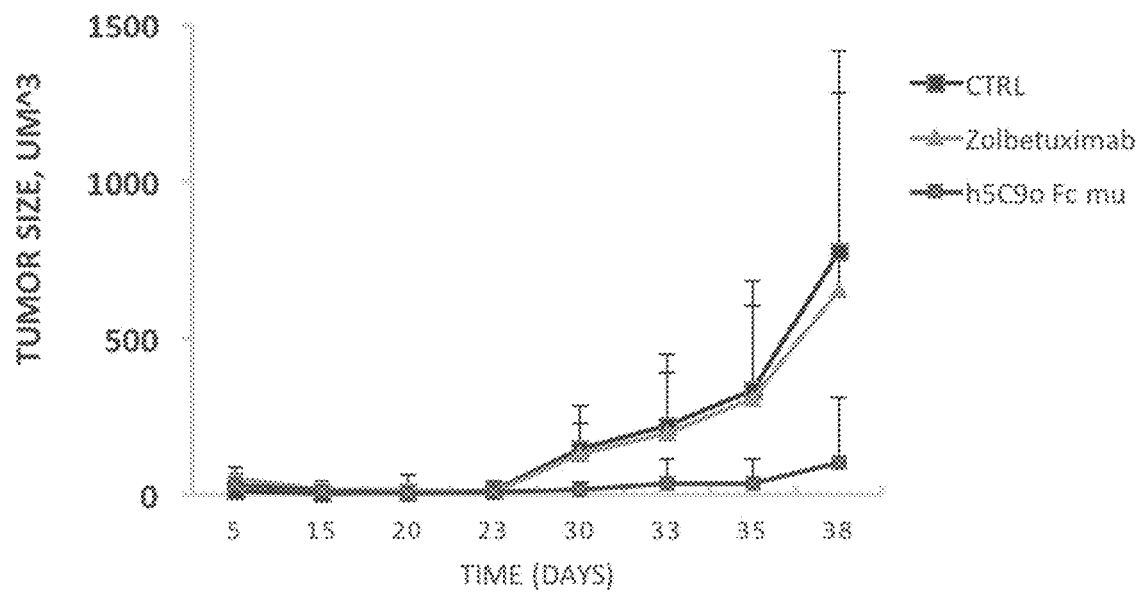
FIG. 47 depicts a graph showing the inhibition of tumor formation and growth by targeting of h5C9o to CLDN18.2-positive tumors on tumor cell xenografts in nude mice.
Figure 48:
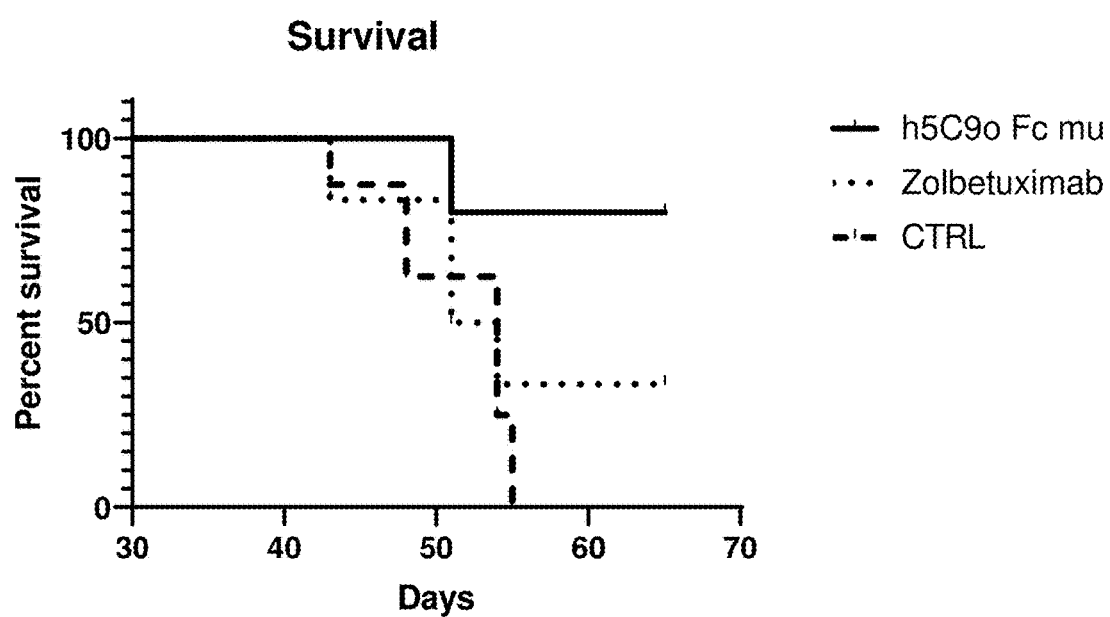
FIG. 48 depicts a graph showing the survival benefit of h5C9o treated mice with tumor xenografts in vivo.

Example 81: In Vivo Efficacy of h5C9o in a CLDN18.2-Positive Tumor Cell Xenograft in Nude Mice All mice were maintained under specific pathogen-free conditions and all animal procedures were performed in accordance with the animal experimental guidelines set by the Institutional Animal Care and Use Committee of Sparx Therapeutics, Inc. Nude mice were subcutaneously inoculated with $1\times10^6$ (1:1 Matrigel) HEK293_CLDN 18.2 cells. Treatment of 8-10 mice per group started 5 days after tumor inoculation. Mice were treated with 200 μg h5C9o, Zolbetuximab, and PBS twice per week for 6 weeks by intravenous routes of application. Whereas all mice in the groups treated with PBS died within 55 days, animals treated with h5C9o not only had significantly inhibition on tumor formation and growth (FIG. 47), but also had better survival benefit than Zolbetuximab (FIG. 48).

Throughout this specification various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, are intended to define the spirit and scope of this invention.

What is claimed is:

1. An isolated antibody or antibody fragment thereof, comprising:
    a light chain variable region (VL) and a heavy chain variable region (VH),
    wherein the VL comprises a light chain complementarity determining region (CDR) 1, a light chain CDR2, and a light chain CDR3 that are the same as those contained in SEQ ID NO: 354; and
    wherein the VH comprises a heavy chain CDR1, a heavy chain CDR2, and heavy chain CDR3 that are the same as those contained in SEQ ID NO: 355.

2. The isolated antibody or antibody fragment thereof of claim 1, wherein the antibody or antibody fragment is:
    a) an immunoglobulin IgG1, IgG2, IgG3, IgG4, IgM, IgA1, IgA2, IgD or IgE molecule; or
    b) a single-chain antibody, a Fab fragment, a F(ab')$_2$ fragment, or a single-chain fragment variable (scFv), wherein the scFv comprises the $V_H$ and the $V_L$, which are connected with a linker peptide of 10 to 25 amino acids.

3. The isolated antibody or antibody fragment thereof of claim 1, comprising:
    a light chain variable region (VL) and a heavy chain variable region (VH),
    wherein said light chain variable region comprises the amino acid sequence of SEQ ID NO: 160, and wherein said heavy chain variable region comprises the amino acid sequence of SEQ ID NO: 162.

4. The isolated antibody or antibody fragment thereof of claim 3, comprising a light chain consisting essentially of SEQ ID NO: 354, and a heavy chain consisting essentially of SEQ ID NO: 355.

5. The isolated antibody or antibody fragment thereof of claim 3, wherein the antibody is an IgG molecule.

6. The isolated antibody or antibody fragment thereof of claim 5, wherein the IgG molecule comprises a heavy chain constant region that contains the amino acid substitution from Aspartic acid (D) to Glutamic acid (E) and the amino acid substitution of Leucine (L) to Methionine (M) at positions 356 and 358, respectively, according to the EU numbering scheme.

7. A pharmaceutical composition, comprising the antibody or antibody fragment thereof of claim 3 and a pharmaceutically acceptable carrier.

8. The isolated antibody or antibody fragment thereof of claim 1, wherein the antibody is an IgG molecule.

9. The isolated antibody or antibody fragment thereof of claim 8, wherein the IgG molecule comprises a heavy chain constant region that contains the amino acid substitution from Aspartic acid (D) to Glutamic acid (E) and the amino acid substitution of Leucine (L) to Methionine (M) at positions 356 and 358, respectively, according to the EU numbering scheme.

10. A pharmaceutical formulation comprising an effective amount of the antibody or antibody fragment thereof of claim 1 and a pharmaceutically acceptable carrier.

* * * * *